United States Patent [19]
Say et al.

[11] Patent Number: 6,134,461
[45] Date of Patent: Oct. 17, 2000

[54] ELECTROCHEMICAL ANALYTE

[75] Inventors: James Say, Alameda; Michael F. Tomasco, Cupertino, both of Calif.; Adam Heller, Austin, Tex.; Yoram Gal, Kibbutz Yagur, Israel; Behrad Aria, Alameda, Calif.; Ephraim Heller, Oakland, Calif.; Phillip John Plante, Sunnyvale, Calif.; Mark S. Vreeke, Alameda, Calif.

[73] Assignee: E. Heller & Company, Alameda, Calif.

[21] Appl. No.: 09/034,372

[22] Filed: Mar. 4, 1998

[51] Int. Cl.⁷ .................................................. A61B 5/05
[52] U.S. Cl. .................................... 600/345; 600/309
[58] Field of Search ................................ 600/306, 308, 600/309, 345, 346, 347, 348, 352, 354, 357, 358, 365, 372, 382, 384, 395, 396, 397, 393

[56] References Cited

U.S. PATENT DOCUMENTS

| | | |
|---|---|---|
| Re. 32,947 | 6/1989 | Dormer et al. . |
| 3,260,656 | 7/1966 | Ross, Jr. . |
| 3,653,841 | 4/1972 | Klein . |
| 3,719,564 | 3/1973 | Lilly, Jr. et al. . |
| 3,776,832 | 12/1973 | Oswin et al. . |
| 3,837,339 | 9/1974 | Aisenberg et al. . |
| 3,926,760 | 12/1975 | Allen et al. . |

(List continued on next page.)

FOREIGN PATENT DOCUMENTS

| | | |
|---|---|---|
| 0 010 375 A1 | 4/1980 | European Pat. Off. . |
| 0 026 995 A1 | 4/1981 | European Pat. Off. . |
| 0 048 090 A2 | 3/1982 | European Pat. Off. . |
| 0 096 288 A1 | 12/1983 | European Pat. Off. . |
| 0 125 139 A2 | 11/1984 | European Pat. Off. . |
| 0 127 958 A2 | 12/1984 | European Pat. Off. . |
| 0 136 362 A1 | 4/1985 | European Pat. Off. . |

(List continued on next page.)

OTHER PUBLICATIONS

Abruña, H. D. et al., "Rectifying Interfaces Using Two–Layer Films of Electrochemically Polymerized Vinylpyridine and Vinylbipyridine Complexes of Ruthenium and Iron on Electrodes," *J. Am. Chem. Soc.*, 103(1):1–5 (Jan. 14, 1981).

Albery, W. J. et al., "Amperometric enzyme electrodes. Part II. Conducting salts as electrode materials for the oxidation of glucose oxidase," *J. Electroanal. Chem. Interfacial Electrochem.*, 194(2) (1 page—Abstract only) (1985).

Albery, W. J. et al., "Amperometric Enzyme Electrodes," *Phil. Trans. R. Soc. Lond.* B316:107–119 (1987).

Alcock, S. J. et al., "Continuous Analyte Monitoring to Aid Clinical Practice," *IEEE Engineering in Medicine and Biology*, 319–325 (1994).

Anderson, L. B. et al., "Thin–Layer Electrochemistry: Steady–State Methods of Studying Rate Processes," *J. Electroanal. Chem.*, 10:295–395 (1965).

(List continued on next page.)

*Primary Examiner*—Cary O'Connor
*Assistant Examiner*—Navin Natnithithadha
*Attorney, Agent, or Firm*—Merchant & Gould P.C.

[57] ABSTRACT

An electrochemical analyte sensor formed using conductive traces on a substrate can be used for determining and/or monitoring a level of analyte in in vitro or in vivo analyte-containing fluids. For example, an implantable sensor may be used for the continuous or automatic monitoring of a level of an analyte, such as glucose, lactate, or oxygen, in a patient. The electrochemical analyte sensor includes a substrate and conductive material disposed on the substrate, the conductive material forming a working electrode. In some sensors, the conductive material is disposed in recessed channels formed in a surface of the sensor. An electron transfer agent and/or catalyst may be provided to facilitate the electrolysis of the analyte or of a second compound whose level depends on the level of the analyte. A potential is formed between the working electrode and a reference electrode or counter/reference electrode and the resulting current is a function of the concentration of the analyte in the body fluid.

29 Claims, 8 Drawing Sheets

U.S. PATENT DOCUMENTS

| | | |
|---|---|---|
| 3,972,320 | 8/1976 | Kalman . |
| 3,979,274 | 9/1976 | Newman . |
| 4,008,717 | 2/1977 | Kowarski . |
| 4,016,866 | 4/1977 | Lawton . |
| 4,055,175 | 10/1977 | Clemens et al. . |
| 4,059,406 | 11/1977 | Fleet . |
| 4,076,596 | 2/1978 | Connery et al. . |
| 4,098,574 | 7/1978 | Dappen . |
| 4,100,048 | 7/1978 | Pompei et al. . |
| 4,151,845 | 5/1979 | Clemens . |
| 4,168,205 | 9/1979 | Danninger et al. . |
| 4,172,770 | 10/1979 | Semersky et al. . |
| 4,178,916 | 12/1979 | McNamara . |
| 4,206,755 | 6/1980 | Klein . |
| 4,224,125 | 9/1980 | Nakamura et al. . |
| 4,240,438 | 12/1980 | Updike et al. . |
| 4,247,297 | 1/1981 | Berti et al. . |
| 4,340,458 | 7/1982 | Lerner et al. . |
| 4,352,960 | 10/1982 | Dormer et al. . |
| 4,356,074 | 10/1982 | Johnson . |
| 4,365,637 | 12/1982 | Johnson . |
| 4,366,033 | 12/1982 | Richter et al. . |
| 4,375,399 | 3/1983 | Havas et al. . |
| 4,384,586 | 5/1983 | Christiansen . |
| 4,390,621 | 6/1983 | Bauer . |
| 4,401,122 | 8/1983 | Clark, Jr. . |
| 4,404,066 | 9/1983 | Johnson . |
| 4,418,148 | 11/1983 | Oberhardt . |
| 4,427,770 | 1/1984 | Chen et al. . |
| 4,431,004 | 2/1984 | Bessman et al. . |
| 4,436,094 | 3/1984 | Cerami . |
| 4,440,175 | 4/1984 | Wilkins . |
| 4,450,842 | 5/1984 | Zick et al. . |
| 4,458,686 | 7/1984 | Clark, Jr. . |
| 4,461,691 | 7/1984 | Frank . |
| 4,469,110 | 9/1984 | Slama . |
| 4,477,314 | 10/1984 | Richter et al. . |
| 4,484,987 | 11/1984 | Gough . |
| 4,522,690 | 6/1985 | Venkatasetty . |
| 4,524,114 | 6/1985 | Samuels et al. . |
| 4,526,661 | 7/1985 | Steckhan et al. . |
| 4,534,356 | 8/1985 | Papadakis . |
| 4,538,616 | 9/1985 | Rogoff . |
| 4,543,955 | 10/1985 | Schroeppel . |
| 4,545,382 | 10/1985 | Higgins et al. . |
| 4,552,840 | 11/1985 | Riffer . |
| 4,560,534 | 12/1985 | Kung et al. . |
| 4,571,292 | 2/1986 | Liu et al. . |
| 4,573,994 | 3/1986 | Fischell et al. . |
| 4,581,336 | 4/1986 | Malloy et al. . |
| 4,595,011 | 6/1986 | Phillips . |
| 4,619,754 | 10/1986 | Niki et al. . |
| 4,627,445 | 12/1986 | Garcia et al. . |
| 4,627,908 | 12/1986 | Miller . |
| 4,633,878 | 1/1987 | Bombardieri . |
| 4,637,403 | 1/1987 | Garcia et al. . |
| 4,650,547 | 3/1987 | Gough . |
| 4,654,197 | 3/1987 | Lilja et al. . |
| 4,655,880 | 4/1987 | Liu . |
| 4,655,885 | 4/1987 | Hill et al. . |
| 4,671,288 | 6/1987 | Gough . |
| 4,679,562 | 7/1987 | Luksha . |
| 4,680,268 | 7/1987 | Clark, Jr. . |
| 4,682,602 | 7/1987 | Prohaska . |
| 4,684,537 | 8/1987 | Graetzel et al. . |
| 4,685,463 | 8/1987 | Williams . |
| 4,703,756 | 11/1987 | Gough et al. . |
| 4,711,245 | 12/1987 | Higgins et al. . |
| 4,717,673 | 1/1988 | Wrighton et al. . |
| 4,721,601 | 1/1988 | Wrighton et al. . |
| 4,721,677 | 1/1988 | Clark, Jr. . |
| 4,726,378 | 2/1988 | Kaplan . |
| 4,726,716 | 2/1988 | McGuire . |
| 4,757,022 | 7/1988 | Shults et al. . |
| 4,758,323 | 7/1988 | Davis et al. . |
| 4,759,371 | 7/1988 | Franetzki . |
| 4,759,828 | 7/1988 | Young et al. . |
| 4,764,416 | 8/1988 | Ueyama et al. . |
| 4,776,944 | 10/1988 | Janata et al. . |
| 4,781,798 | 11/1988 | Gough . |
| 4,784,736 | 11/1988 | Lonsdale et al. . |
| 4,795,707 | 1/1989 | Niiyama et al. . |
| 4,796,634 | 1/1989 | Huntsman et al. . |
| 4,805,624 | 2/1989 | Yao et al. . |
| 4,813,424 | 3/1989 | Wilkins . |
| 4,815,469 | 3/1989 | Cohen et al. . |
| 4,820,399 | 4/1989 | Senda et al. . |
| 4,822,337 | 4/1989 | Newhouse et al. . |
| 4,830,959 | 5/1989 | McNeil et al. . |
| 4,832,797 | 5/1989 | Vadgama et al. . |
| 4,840,893 | 6/1989 | Hill et al. . |
| 4,848,351 | 7/1989 | Finch . |
| 4,871,351 | 10/1989 | Feingold . |
| 4,871,440 | 10/1989 | Nagata et al. . |
| 4,874,500 | 10/1989 | Madou et al. . |
| 4,890,620 | 1/1990 | Gough . |
| 4,894,137 | 1/1990 | Takizawa et al. . |
| 4,897,162 | 1/1990 | Lewandowski et al. . |
| 4,897,173 | 1/1990 | Nankai et al. . |
| 4,909,908 | 3/1990 | Ross et al. . |
| 4,911,794 | 3/1990 | Parce et al. . |
| 4,917,800 | 4/1990 | Lonsdale et al. . |
| 4,919,141 | 4/1990 | Zier et al. . |
| 4,919,767 | 4/1990 | Vadgama et al. . |
| 4,923,586 | 5/1990 | Katayama et al. . |
| 4,927,516 | 5/1990 | Yamaguchi et al. . |
| 4,934,369 | 6/1990 | Maxwell . |
| 4,935,105 | 6/1990 | Churchouse . |
| 4,935,345 | 6/1990 | Guibeau et al. ........................ 435/14 |
| 4,938,860 | 7/1990 | Wogoman . |
| 4,944,299 | 7/1990 | Silvian . |
| 4,950,378 | 8/1990 | Nagata . |
| 4,953,552 | 9/1990 | DeMarzo . |
| 4,954,129 | 9/1990 | Giuliani et al. . |
| 4,969,468 | 11/1990 | Byers et al. . |
| 4,970,145 | 11/1990 | Bennetto et al. . |
| 4,974,929 | 12/1990 | Curry . |
| 4,986,271 | 1/1991 | Wilkins . |
| 4,994,167 | 2/1991 | Shults et al. . |
| 5,001,054 | 3/1991 | Wagner . |
| 5,058,592 | 10/1991 | Whisler . |
| 5,070,535 | 12/1991 | Hochmair et al. . |
| 5,082,550 | 1/1992 | Rishpon et al. . |
| 5,082,786 | 1/1992 | Nakamoto . |
| 5,089,112 | 2/1992 | Skotheim et al. . |
| 5,095,904 | 3/1992 | Seligman et al. . |
| 5,101,814 | 4/1992 | Palti . |
| 5,108,564 | 4/1992 | Szuminsky et al. . |
| 5,109,850 | 5/1992 | Blanco et al. . |
| 5,120,420 | 6/1992 | Nankai et al. . |
| 5,126,034 | 6/1992 | Carter et al. . |
| 5,133,856 | 7/1992 | Yamaguchi et al. . |
| 5,135,003 | 8/1992 | Souma . |
| 5,141,868 | 8/1992 | Shanks et al. . |
| 5,161,532 | 11/1992 | Joseph . |
| 5,165,407 | 11/1992 | Wilson et al. . |
| 5,174,291 | 12/1992 | Schoonen et al. . |
| 5,190,041 | 3/1993 | Palti . |
| 5,192,416 | 3/1993 | Wang et al. . |
| 5,198,367 | 3/1993 | Aizawa et al. . |
| 5,202,261 | 4/1993 | Musho et al. . |
| 5,205,920 | 4/1993 | Oyama et al. . |

| | | |
|---|---|---|
| 5,208,154 | 5/1993 | Weaver et al. . |
| 5,209,229 | 5/1993 | Gilli . |
| 5,217,595 | 6/1993 | Smith et al. . |
| 5,229,282 | 7/1993 | Yoshioka et al. . |
| 5,250,439 | 10/1993 | Musho et al. . |
| 5,262,035 | 11/1993 | Gregg et al. . |
| 5,262,305 | 11/1993 | Heller et al. . |
| 5,264,103 | 11/1993 | Yoshioka et al. . |
| 5,264,104 | 11/1993 | Gregg et al. . |
| 5,264,106 | 11/1993 | McAleer et al. . |
| 5,271,815 | 12/1993 | Wong . |
| 5,279,294 | 1/1994 | Anderson et al. . |
| 5,286,362 | 2/1994 | Hoenes et al. . |
| 5,286,364 | 2/1994 | Yacynych et al. . |
| 5,288,636 | 2/1994 | Pollmann et al. . |
| 5,293,546 | 3/1994 | Tadros et al. . |
| 5,320,098 | 6/1994 | Davidson . |
| 5,320,725 | 6/1994 | Gregg et al. . |
| 5,322,063 | 6/1994 | Allen et al. . |
| 5,336,388 | 8/1994 | Leader et al. . |
| 5,337,747 | 8/1994 | Neftel . |
| 5,352,348 | 10/1994 | Young et al. . |
| 5,356,786 | 10/1994 | Heller et al. . |
| 5,368,028 | 11/1994 | Palti . |
| 5,372,133 | 12/1994 | Hogen Esch . |
| 5,376,251 | 12/1994 | Kaneko et al. . |
| 5,378,628 | 1/1995 | Grätzel et al. . |
| 5,387,327 | 2/1995 | Khan . |
| 5,390,671 | 2/1995 | Lord et al. . |
| 5,391,250 | 2/1995 | Cheney, II et al. . |
| 5,395,504 | 3/1995 | Saurer et al. . |
| 5,403,462 | 4/1995 | Lev et al. . |
| 5,411,647 | 5/1995 | Johnson et al. . |
| 5,437,999 | 8/1995 | Diebold et al. . |
| 5,469,846 | 11/1995 | Khan . |
| 5,494,562 | 2/1996 | Maley et al. . |
| 5,496,453 | 3/1996 | Uenoyama et al. . |
| 5,497,772 | 3/1996 | Schulman et al. . |
| 5,509,410 | 4/1996 | Hill et al. ................................. 600/345 |
| 5,531,878 | 7/1996 | Vadgama et al. . |
| 5,545,191 | 8/1996 | Mann et al. . |
| 5,560,357 | 10/1996 | Faupel et al. . |
| 5,565,085 | 10/1996 | Ikeda et al. . |
| 5,567,302 | 10/1996 | Song et al. . |
| 5,568,806 | 10/1996 | Cheney, II et al. . |
| 5,569,186 | 10/1996 | Lord et al. . |
| 5,582,184 | 12/1996 | Erickson et al. . |
| 5,582,697 | 12/1996 | Ikeda et al. . |
| 5,582,698 | 12/1996 | Flaherty et al. . |
| 5,586,553 | 12/1996 | Halili et al. . |
| 5,589,326 | 12/1996 | Deng et al. . |
| 5,593,852 | 1/1997 | Heller et al. . |
| 5,596,150 | 1/1997 | Arndt et al. . |
| 5,617,851 | 4/1997 | Lipkovker . |
| 5,628,890 | 5/1997 | Carter et al. . |
| 5,651,869 | 7/1997 | Yoshioka et al. . |
| 5,660,163 | 8/1997 | Schulman et al. . |
| 5,670,031 | 9/1997 | Hintsche et al. . |
| 5,680,858 | 10/1997 | Hansen et al. . |
| 5,682,233 | 10/1997 | Brinda . |
| 5,695,623 | 12/1997 | Michel et al. . |
| 5,708,247 | 1/1998 | McAleer et al. . |
| 5,711,861 | 1/1998 | Ward et al. ............................... 204/403 |
| 5,711,862 | 1/1998 | Sakoda et al. . |
| 5,727,548 | 3/1998 | Hill et al. ................................. 600/345 |
| 5,741,211 | 4/1998 | Renirie et al. . |
| 5,807,375 | 9/1998 | Gross et al. . |
| 5,820,551 | 9/1998 | Hill et al. ................................. 600/345 |
| 5,822,715 | 10/1998 | Worthington et al. . |
| 5,840,020 | 11/1998 | Heinonen et al. . |
| 5,842,983 | 12/1998 | Abel et al. ............................... 600/345 |
| 5,954,685 | 9/1999 | Tierney ..................................... 604/20 |

FOREIGN PATENT DOCUMENTS

| | | |
|---|---|---|
| 0 170 375 A2 | 2/1986 | European Pat. Off. . |
| 0 177 743 A2 | 4/1986 | European Pat. Off. . |
| 0 080 304 B1 | 5/1986 | European Pat. Off. . |
| 0 184 909 A2 | 6/1986 | European Pat. Off. . |
| 0 206 218 A2 | 12/1986 | European Pat. Off. . |
| 0 230 472 A1 | 8/1987 | European Pat. Off. . |
| 0 241 309 A3 | 10/1987 | European Pat. Off. . |
| 0 245 073 A2 | 11/1987 | European Pat. Off. . |
| 0 278 647 A2 | 8/1988 | European Pat. Off. . |
| 0 359 831 A1 | 3/1990 | European Pat. Off. . |
| 0 368 209 A1 | 5/1990 | European Pat. Off. . |
| 0 390 390 A1 | 10/1990 | European Pat. Off. . |
| 0 400 918 A1 | 12/1990 | European Pat. Off. . |
| 0 453 283 A1 | 10/1991 | European Pat. Off. . |
| 0 470 290 A1 | 2/1992 | European Pat. Off. . |
| 0 127 958 B2 | 3/1992 | European Pat. Off. . |
| 0 255 291 B1 | 6/1992 | European Pat. Off. . |
| 0 078 636 A1 | 5/1993 | European Pat. Off. . |
| 227 029 A3 | 9/1985 | German Dem. Rep. . |
| 29 03 216 | 8/1979 | Germany . |
| 3934299 | 10/1990 | Germany . |
| 54-41191 | 4/1979 | Japan . |
| 55-10581 | 1/1980 | Japan . |
| 55-10583 | 1/1980 | Japan . |
| 55-10584 | 1/1980 | Japan . |
| 55-12406 | 1/1980 | Japan . |
| 56-163447 | 12/1981 | Japan . |
| 57-70448 | 4/1982 | Japan . |
| 58-194748 | 11/1983 | Japan . |
| 60-173457 | 9/1985 | Japan . |
| 60-173458 | 9/1985 | Japan . |
| 60-173459 | 9/1985 | Japan . |
| 61-90050 | 5/1986 | Japan . |
| 62-85855 | 4/1987 | Japan . |
| 62-114747 | 5/1987 | Japan . |
| 63-58149 | 3/1988 | Japan . |
| 63-139246 | 6/1988 | Japan . |
| 63-294799 | 12/1988 | Japan . |
| 63-317757 | 12/1988 | Japan . |
| 63-317758 | 12/1988 | Japan . |
| 1-114746 | 5/1989 | Japan . |
| 1-114747 | 5/1989 | Japan . |
| 1-124060 | 5/1989 | Japan . |
| 1-134244 | 5/1989 | Japan . |
| 1-156658 | 6/1989 | Japan . |
| 2-62958 | 3/1990 | Japan . |
| 2-120655 | 5/1990 | Japan . |
| 2-287145 | 11/1990 | Japan . |
| 2-310457 | 12/1990 | Japan . |
| 3-26956 | 2/1991 | Japan . |
| 3-28752 | 2/1991 | Japan . |
| 3-202764 | 9/1991 | Japan . |
| 5-72171 | 3/1993 | Japan . |
| 5-196595 | 8/1993 | Japan . |
| 6-190050 | 7/1994 | Japan . |
| 7-55757 | 3/1995 | Japan . |
| 7-72585 | 3/1995 | Japan . |
| 8-285814 | 11/1996 | Japan . |
| 8-285815 | 11/1996 | Japan . |
| 9-21778 | 1/1997 | Japan . |
| 9-101280 | 4/1997 | Japan . |
| 9-285459 | 11/1997 | Japan . |
| 63-128252 | 5/1998 | Japan . |
| 10-170471 | 6/1998 | Japan . |
| 1281988 A1 | 1/1987 | U.S.S.R. . |
| 1394171 | 5/1975 | United Kingdom . |
| 1599241 | 9/1981 | United Kingdom . |
| 2 073 891 | 10/1981 | United Kingdom . |
| 2 154 003 | 2/1988 | United Kingdom . |
| 2 204 408 | 11/1988 | United Kingdom . |

| | | |
|---|---|---|
| 2 254 436 | 10/1992 | United Kingdom . |
| WO 85/05119 | 11/1985 | WIPO . |
| WO 89/08713 | 9/1989 | WIPO . |
| WO 90/05300 | 5/1990 | WIPO . |
| WO 90/05910 | 5/1990 | WIPO . |
| WO 91/01680 | 2/1991 | WIPO . |
| WO 91/04704 | 4/1991 | WIPO . |
| WO 91/15993 | 10/1991 | WIPO . |
| WO 92/13271 | 8/1992 | WIPO . |
| WO 94/20602 | 9/1994 | WIPO . |
| WO 94/27140 | 11/1994 | WIPO . |
| WO 96/30431 | 10/1996 | WIPO . |
| WO 97/02847 | 1/1997 | WIPO . |
| WO 97/19344 | 5/1997 | WIPO . |
| WO 97/42882 | 11/1997 | WIPO . |
| WO 97/42883 | 11/1997 | WIPO . |
| WO 97/42886 | 11/1997 | WIPO . |
| WO 97/42888 | 11/1997 | WIPO . |
| WO 97/43962 | 11/1997 | WIPO . |

OTHER PUBLICATIONS

Bartlett, P. N. et al., "Covalent Binding of Electron Relays to Glucose Oxidation," *J. Chem. Soc. Chem. Commun.*, 1603–1604 (1987).

Bartlett, P. N. et al., "Modification of glucose oxidase by tetrathiafulvalene," *J. Chem. Soc., Chem. Commun.*, 16 (1 page—Abstract only) (1990).

Bartlett, P. N. et al., "Strategies for the Development of Amperometric Enzyme Electrodes," *Biosensors*, 3:359–379 (1987/88).

Bindra, D.S. et al., "Design and in Vitro Studies of a Needle–Type Glucose Sensor for Subcutaneous Monitoring", *Anal. Chem.*, 63(17):1692–1696 (Sep. 1, 1991).

Bobbioni–Harsch, E. et al., "Lifespan of subcutaneous glucose sensors and their performances during dynamic glycaemia changes in rats," *J. Biomed. Eng.* 15:457–463 (1993).

Brandt, J. et al., "Covalent attachment of proteins to polysaccharide carriers by means of benzoquinone," *Biochim. Biophys. Acta*, 386(1) (1 page Abstract only) (1975).

Brownlee, M. et al., "A Glucose–Controlled Insulin–Delivery System: Semisynthetic Insulin Bound to Lectin", *Science*, 206(4423):1190–1191 (Dec. 7, 1979).

Cass, A.E.G. et al., "Ferricinum Ion As An Electron Acceptor for Oxido–Reductases," *J. Electroanal. Chem.*, 190:117–127 (1985).

Cass, A.E.G. et al., "Ferrocene–Mediated Enzyme Electrode for Amperometric Determination of Glucose", *Anal. Chem.*, 56(4):667–671 (Apr. 1984).

Castner, J. F. et al., "Mass Transport and Reaction Kinetic Parameters Determined Electrochemically for Immobilized Glucose Oxidase," *Biochemistry*, 23(10):2203–2210 (1984).

Claremont, D.J. et al., "Biosensors for Continuous In Vivo Glucose Monitoring", *IEEE Engineering in Medicine and Biology Society 10th Annual International Conference*, New Orleans, Louisiana, 3 pgs. (Nov. 4–7, 1988).

Clark, L.C. et al., "Differential Anodic Enzyme Polarography for the Measurement of Glucose", *Oxygen Transport to Tissue: Instrumentation, Methods, and Physiology*, 127–132 (1973).

Clark, L.C., Jr. et al., "Electrode Systems for Continuous Monitoring in Cardiovascular Surgery," *Annals New York Academy of Sciences*, pp. 29–45 (1962).

Clark, L.C. et al., "Long–term Stability of Electroenzymatic Glucose Sensors Implanted in Mice," *Trans. Am. Soc. Artif. Inter. Organs*, XXXIV:259–265 (1988).

Clarke, W. L., et al., "Evaluating Clinical Accuracy of Systems for Self–Monitoring of Blood Glucose," *Diabetes Care*, 10(5):622–628 (Sep.–Oct. 1987).

Csöregi, E. et al., "Design, Characterization, and One–Point in Vivo Calibration of a Subcutaneously Implanted Glucose Electrode," *Anal. Chem.* 66(19):3131–3138 (Oct. 1, 1994).

Csöregi, E. et al., "Design and Optimization of a Selective Subcutaneously Implantable Glucose Electrode Based on "Wired" Glucose Oxidase," *Anal. Chem.* 67(7):1240–1244 (Apr. 1, 1995).

Csöregi, E. et al., "On–Line Glucose Monitoring by Using Microdialysis Sampling and Amperometric Detection Based on "Wired" Glucose Oxidase in Carbon Paste," *Mikrochim. Acta.* 121:31–40 (1995).

Davis, G., "Electrochemical Techniques for the Development of Amperometric Biosensors", *Biosensors*, 1:161–178 (1985).

Degani, Y. et al., "Direct Electrical Communication between Chemically Modified Enzymes and Metal Electrodes. 1. Electron Transfer from Glucose Oxidase to Metal Electrodes via Electron Relays, Bound Covalently to the Enzyme," *J. Phys. Chem.*, 91(6):1285–1289 (1987).

Degani, Y. et al., "Direct Electrical Communication between Chemically Modified Enzymes and Metal Electrodes. 2. Methods for Bonding Electron–Transfer Relays to Glucose Oxidase and D–Amino–Acid Oxidase," *J. Am. Chem. Soc.*, 110(8):2615–2620 (1988).

Degani, Y. et al., "Electrical Communication between Redox Centers of Glucose Oxidase and Electrodes via Electrostatically and Covalently Bound Redox Polymers," *J. Am. Chem. Soc.*, 111:2357–2358 (1989).

Denisevich, P. et al., "Unidirectional Current Flow and Charge State Trapping at Redox Polymer Interfaces on Bilayer Electrodes: Principles, Experimental Demonstration, and Theory," *J. Am. Chem. Soc.*, 103(16):4727–4737 (1981).

Dicks, J. M., "Ferrocene modified polypyrrole with immobilised glucose oxidase and its application in amperometric glucose microbiosenors," *Ann. Biol. clin.*, 47:607–619 (1989).

Engstrom, R. C., "Electrochemical Pretreatment of Glassy Carbon Electrodes", *Anal. Chem.*, 54(13):2310–2314 (Nov. 1982).

Engstrom, R.C. et al., "Characterization of Electrochemically Pretreated Glassy Carbon Electrodes", *Anal. Chem.*, 56(2):136–141 (Feb. 1984).

Ellis, C. D., "Selectivity and Directed Charge Transfer through an Electroactive Metallopolymer Film," *J. Am. Chem. Soc.*, 103(25):7480–7483 (1981).

Feldman, B.J. et al., "Electron Transfer Kinetics at Redox Polymer/Solution Interfaces Using Microelectrodes and Twin Electrode Thin Layer Cells", *J. Electroanal. Chem.*, 194(1):63–81 (Oct. 10, 1985).

Fischer, H. et al., "Intramolecular Electron Transfer Mediated by 4,4'–Bipyridine and Related Bridging Groups", *J. Am. Chem. Soc.*, 98(18):5512–5517 (Sep. 1, 1976).

Foulds, N.C. et al., "Enzyme Entrapment in Electrically Conducting Polymers," *J. Chem. Soc., Faraday Trans 1.*, 82:1259–1264 (1986).

Foulds, N.C. et al., "Immobilization of Glucose Oxidase in Ferrocene–Modified Pyrrole Polymers," *Anal. Chem.*, 60(22):2473–2478 (Nov. 15, 1988).

Frew, J.E. et al., "Electron–Transfer Biosensors", *Phil. Trans. R. Soc. Lond.*, B316:95–106 (1987).

Gorton, L. et al., "Selective detection in flow analysis based on the combination of immobilized enzymes and chemically modified electrodes," *Analytica Chimica Acta.*, 250:203–248 (1991).

Gregg, B. A. et al., "Cross–Linked Redox Gels Containing Glucose Oxidase for Amperometric Biosensor Applications," *Analytical Chemistry*, 62(3):258–263 (Feb. 1, 1990).

Gregg, B. A. et al., "Redox Polymer Films Containing Enzymes. 1. A Redox–Conducting Epoxy Cement: Synthesis, Characterization, and Electrocatalytic Oxidation of Hydroquinone," *J. Phys. Chem.*, 95(15):5970–5975 (1991).

Hale, P.D. et al., "A New Class of Amperometric Biosensor Incorporating a Polymeric Electron–Transfer Mediator," *J. Am. Chem. Soc.*, 11(9):3482–3482 (1989).

Harrison, D.J. et al., "Characterization of Perfluorosulfonic Acid Polymer Coated Enzyme Electrodes and a Miniaturized Integrated Potentiostat for Glucose Analysis in Whole Blood", *Anal. Chem.*, 60(19):2002–2007 (Oct. 1, 1988).

Hawkridge, F. M. et al., "Indirect Coulometric Titration of Biological Electron Transport Components," *Analytical Chemistry*, 45(7):1021–1027 (Jun. 1973).

Heller, A., "Amperometric biosensors based on three–dimensional hydrogel–forming epoxy networks," *Sensors and Actuators B*, 13–14:180–183 (1993).

Heller, A., "Electrical Connection of Enzyme Redox Centers to Electrodes," *J. Phys. Chem.*, 96(9):3579–3587 (1992).

Heller, A., "Electrical Wiring of Redox Enzymes," *Acc. Chem. Res.*, 23(5):129–134 (1990).

Ianniello, R.M. et al. "Immobilized Enzyme Chemically Modified Electrode as an Amperometric Sensor", *Anal. Chem.*, 53(13):2090–2095 (Nov. 1981).

Ianniello, R.M. et al., "Differential Pulse Voltammetric Study of Direct Electron Transfer in Glucose Oxidase Chemically Modified Graphite Electrodes", *Anal. Chem.*, 54:(7):1098–1101 (Jun. 1981).

Ikeda, T. et al., "Glucose oxidase–immobilized benzoquinone–carbon past electrode as a glucose sensor," *Agric. Biol. Chem.*, 49(2) (1 page—Abstract only) (1985).

Ikeda, T. et al., "Kinetics of Outer–Sphere Electron Transfers Between Metal Complexes in Solutions and Polymeric Films on Modified Electrodes", *J. Am. Chem. Soc.*, 103(25):7422–7425 (Dec. 16, 1981).

Johnson, J. M. et al., "Potential–Dependent Enzymatic Activity in an Enzyme Thin–Layer Cell," *Anal. Chem.* 54:1377–1383 (1982).

Johnson, K.W., "Reproducible Electrodeposition of Biomolecules for the Fabrication of Miniature Electroenzymatic Biosensors", *Sensors and Atuators B Chemical*, B5:85–89 (1991).

Jönsson, G. et al., "An Amperometric Glucose Sensor Made by Modification of a Graphite Electrode Surface With Immobilized Glucose Oxidase and Adsorbed Mediator", *Biosensors*, 1:355–368 (1985).

Josowicz, M. et al., "Electrochemical Pretreatment of Thin Film Platinum Electrodes", *J. Elecrochem. Soc.*, 135(1):112–115 (Jan. 1988).

Katakis, I. et al., "Electrostatic Control of the Electron Transfer Enabling Binding of Recombinant Glucose Oxidase and Redox Polyelectrolytes," *J. Am. Chem. Soc.*, 116(8):3617–3618 (1994).

Katakis, I. et al., "L–α–Glycerophosphate and L–Lactate Electrodes Based on the Electrochemical "Wiring" of Oxidases," *Analytical Chemistry*, 64(9):1008–1013 (May 1, 1992).

Kenausis, G. et al., "'Wiring' of glucose oxidase and lactate oxidase within a hydrogel made with poly(vinyl pyridine) complexed with [Os(4,4'–dimethoxy–2,2'–bipyridine)$_2$Cl]$^{+/2+}$," *J. Chem. Soc., Faraday Trans.*, 92(20):4131–4136 (1996).

Koudelka, M. et al., "In–Vivo Behaviour of Hypodermically Implanted Microfabricated Glucose Sensors", *Biosensors & Bioelectronics*, 6(1):31–36 (1991).

Kulys, J. et al., "Mediatorless peroxidase electrode and preparation of bienzyme sensors," *Bioelectrochemistry and Bioenergetics*, 24:305–311 (1990).

Lager, W. et al., "Implantable Electrocatalytic Glucose Sensor," *Horm. Metab. Res.*, 26:526–530 (Nov. 1994).

Lindner, E. et al. "Flexible (Kapton–Based) Microsensor Arrays of High Stability for Cardiovascular Applications", *J. Chem. Soc.Faraday Trans.*, 89(2):361–367 (Jan. 21, 1993).

Maidan, R. et al., "Elimination of Electrooxidizable Interferant–Produced Currents in Amperometric Biosensors," *Analytical Chemistry*, 64(23):2889–2896 (Dec. 1, 1992).

Mastrototaro, J.J. et al., "An Electroenzymatic Glucose Sensor Fabricated on a Flexible Substrate", *Sensors and Biosensors B Chemical*, B5:139–144 (1991).

McNeil, C. J. et al., "Thermostable Reduced Nicotinamide Adenine Dinucleotide Oxidase: Application to Amperometric Enzyme Assay," *Anal. Chem.*, 61(1):25–29 (Jan. 1, 1989).

Miyawaki, O. et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, 838:60–68 (1985).

Moatti–Sirat, D. et al., "Evaluating in vitro and in vivo the interference of ascorbate and acetaminophen on glucose detection by a needle–type glucose sensor," *Biosensors & Bioelectronics*, 7(5):345–352 (1992).

Moatti–Sirat, D. et al., "Reduction of acetaminophen interference in glucose sensors by a composite Nafion membrane: demonstration in rats and man," *Diabetologia*, 37(6) (1 page—Abstract only) (Jun. 1994).

Moatti–Sirat, D. et al., "Towards continuous glucose monitoring: in vivo evaluation of a miniaturized glucose sensor implanted for several days in rat subcutaneous tissue," *Diabetologia*, 35(3) (1 page—Abstract only) (Mar. 1992).

Nagy, G. et al., "A New Type of Enzyme Electrode: The Ascorbic Acid Eliminator Electrode," *Life Sciences*, 31(23):2611–2616 (1982).

Nakamura, S. et al., "Effect of Periodate Oxidation on the Structure and Properties of Glucose Oxidase," *Biochimica et Biophysica Acta.*, 445:294–308 (1976).

Narazimhan, K. et al., "p–Benzoquinone activation of metal oxide electrodes for attachment of enzymes," *Enzyme Microb. Technol.*, 7(6) (1 page—Abstract only) (1985).

Ohara, T. J. et al., "Glucose Electrodes Based on Cross–Linked [Os(bpy)$_2$Cl]$^{+/2+}$ Complexed Poly(1–vinylimadazole) Films," *Analytical Chemistry*, 65(23):3512–3516 (Dec.1, 1993).

Ohara, T. J., "Osmium Bipyridyl Redox Polymers Used in Enzyme Electrodes," *Platinum Metals Rev.*, 39(2):54–62 (Apr. 1995).

Ohara, T. J. et al., ""Wired" Enzyme Electrodes for Amperometric Determination of Glucose or Lactate in the Presence of Interfering Substances," *Analytical Chemistry*, 66(15):2451–2457 (Aug. 1, 1994).

Olievier, C. N. et al., "In vivo Measurement of Carbon Dioxide Tension with a Miniature Electrode," *PflugersArch.* 373:269–272 (1978).

Paddock, R. et al., "Electrocatalytic reduction of hydrogen peroxide via direct electron transfer from pyrolytic graphite electrodes to irreversible adsorbed cytochrome c peroxidase," *J. Electroanal. Chem.*, 260:487–494 (1989).

Palleschi, G. et al., "A Study of Interferences in Glucose Measurements in Blood by Hydrogen Peroxide Based Glucose Probes", *Anal. Biochem.*, 159:114–121 (1986).

Pankratov, I. et al., "Sol–gel derived renewable–surface biosensors," *Journal of Electroanalytical Chemistry*, 393:35–41 (1995).

Pathak, C. P. et al., "Rapid Photopolymerization of Immunoprotective Gels in Contact with Cells and Tissue," *J. Am. Chem. Soc.*, 114(21):8311–8312 (1992).

Pickup, J., "Developing glucose sensors for in vivo use," *Tibtech*, 11:285–289 (Jul. 1993).

Pickup, J. C. et al., "In vivo molecular sensing in diabetes mellitus: an implantable glucose sensor with direct electron transfer," *Diabetologia*, 32(3):213–217 (1989).

Pickup, J. et al., "Potentially–implantable, amperometric glucose sensors with mediated electron transfer improving the operating stability," *Biosensors*, 4(2) (1 page—Abstract only) (1989).

Pishko, M.V. et al., "Amperometric Glucose Microelectrodes Prepared Through Immobilization of Glucose Oxidase in Redox Hydrogels", *Anal. Chem.*, 63(20):2268–2272 (Oct. 15, 1991).

Poitout, V. et al., "A glucose monitoring system for on line estimation in man blood glucose concentration using a miniaturized glucose sensor implanted in the subcutaneous tissue and a wearable control unit," *Biabetolgia*, 36(7) (1 page—Abstract only) (Jul. 1993).

Poitout, V. et al., "Calibration in dogs of a subcutaneous miniaturized glucose sensor using a glucose meter for blood glucose determination," *Biosensors & Bioelectronics*, 7:587–592 (1992).

Poitout, V. et al., "In vitro and in vivo evaluation in dogs of a miniaturized glucose sensor," *ASAIO Transactions*, 37(3) (1 page—Abstract only) (Jul.–Sep. 1991).

Pollak, A. et al., "Enzyme Immobilization by Condensation Copolymerization into Cross–Linked Polyacrylamide Gels," *J. Am. Chem. Soc.*, 102(20):6324–6336 (1980).

Reach, G. et al., "Can Continuous Glucose Monitoring Be Used for the Treatment of Diabetes?" *Analytical Chemistry*, 64(6):381–386 (Mar. 15, 1992).

Rebrin, K. et al., "Automated Feedback Control of Subcutaneous Glucose Concentration in Diabetic Dogs", *Diabetologia*, 32(8):573–576 (Aug. 1989).

Sakakida, M. et al., "Ferrocene–mediate needle–type glucose sensor covered with newly designed biocompatible membrane," *Sensors and Actuators B*, 13–14:319–322 (1993).

Samuels, G. J. et al., "An Electrode–Supported Oxidation Catalyst Based on Ruthenium (IV). pH "Encapsulation" in a Polymer Film," *J. Am. Chem. Soc.*, 103(2):307–312 (1981).

Sasso, S. V. et al., "Electropolymerized 1,2–Diaminobenzene as a Means to Prevent Interferences and Fouling and to Stabilize Immobilized Enzyme in Electrochemical Biosensors", *Anal. Chem.*, 62(11):1111–1117 (Jun. 1, 1990).

Scheller, F. et al., "Enzyme electrodes and their application," *Phil. Trans. R. Soc. Lond.*, B 316:85–94 (1987).

Schmehl, R.H. et al., "The Effect of Redox Site Concentration on the Rate of Mediated Oxidation of Solution Substrates by a Redox Copolymer Film", *J. Electroanal. Chem.*, 152:97–109 (Aug. 25, 1983).

Shichiri, M. et al., "Glycaemic Control in Pancreatetomized Dogs with a Wearable Artificial Endocrine Pancreas", *Diabetologia*, 24(3):179–184 (Mar. 1983).

Sittampalam, G. et al., "Surface–Modified Electrochemical Detector for Liquid Chromatography", *Anal. Chem.*, 55(9):1608–1610 (Aug. 1983).

Soegijoko, S. et al., *Horm. Metabl. Res., Suppl. Ser*, 12 (1 page—Abstract only) (1982).

Sprules, S. D. et al., "Evaluation of a New Disposable Screen–Printed Sensor Strip for the Measurement of NADH and Its Modification to Produce a Lactate Biosensor Employing Microliter Volumes," *Electroanalysis*, 8(6):539–543 (1996).

Sternberg, F. et al., "Calibration Problems of Subcutaneous Glucosensors when Applied "In–Situ" in Man," *Horm. metabl. Res*, 26:524–525 (1994).

Sternberg, R. et al., "Covalent Enzyme Coupling on Cellulose Acetate Membranes for Glucose Sensor Development," *Analytical Chemistry*, 60(24):2781–2786 (Dec. 15, 1988).

Sternberg, R. et al., "Study and Development of Multilayer Needle–type Enzyme–based Glucose Microsensors," *Biosensors*, 4:27–40 (1988).

Suekane, M., "Immobilization of glucose isomerase," *Zeitschrift für Allgemeine Mikrobiologie*, 22(8):565–576 (1982).

Tajima, S. et al., "Simultaneous Determination of Glucose and 1,5–Anydroglucitol", *Chemical Abstracts*, 111(25):394 111:228556g (Dec. 18, 1989).

Tarasevich, M.R. "Bioelectrocatalysis", *Comprehensive Treatise of Electrochemistry*, 10 (Ch. 4):231–295 (1985).

Tatsuma, T. et al., "Enzyme Monolayer– and Bilayer–Modified Tin Oxide ELectrodes for the Determination of Hydrogen Peroxide and Glucose," *Anal. Chem.*, 61(21):2352–2355 (Nov. 1, 1989).

Taylor, C. et al., "'Wiring' of glucose oxidase within a hydrogel made with polyvinyl imidazole complexed with $[(Os-4,4'-dimethoxy-2,2'-bipyridine)Cl]^{+/2+}$," *Journal of Electroanalytical Chemistry*, 396:511–515 (1995).

Trojanowicz, M. et al., "Enzyme Entrapped Polypyrrole Modified Electrode for Flow–Injection Determination of Glucose," *Biosensors & Bioelectronics*, 5:149–156 (1990).

Turner, A.P.F. et al., "Diabetes Mellitus: Biosensors for Research and Management", *Biosensors*, 1:85–115 (1985).

Turner, R. F. B. et al., "A Biocompatible Enzyme Electrode for Continuous in vivo Glucose Monitoring in Whole Blood," *Sensors and Actuators*, B1(1–6):561–564 (Jan. 1990).

Tuzhi, P. et al., "Constant Potential Pretreatment of Carbon Fiber Electrodes for In Vivo Electrochemistry", *Analytical Letters*, 24(6):935–945 (1991).

Umaha, M., "Protein–Modifeid Electrochemically Active Biomaterial Surface," *U.S. Army Research Office Report*, (12 pages) (Dec. 1988).

Urban, G. et al., "Miniaturized Thin–Film Biosensors Using Covalently Immobilized Glucose Oxidase", *Biosensors & Bioelectronics*, 6(7):555–562 (1991).

Velho, G. et al., "In Vitro and In Vivo Stability of Electrode Potentials in Needle–Type Glucose Sensors", *Diabetes*, 38(2):164–171 (Feb. 1989).

Velho, G. et al., "Strategies for calibrating a subcutaneous glucose sensor," *Biomed. Biochin. Acta*, 48(11/12):957–964 (1989).

Von Woedtke, T. et al., "In Situ Calibration of Implanted Electrochemical Glucose Sensors," *Biomed. Biochim. Acta*, 48(11/12):943–952 (1989).

Vreeke, M. S. et al., "Chapter 15: Hydrogen Peroxide Electrodes Based on Electrical Connection of Redox Centers of Various Peroxidases to Electrodes through a Three–Dimensional Electron–Relaying Polymer Network," *Diagnostic Biosensor Polymers*, 7 pgs. (Jul. 26, 1993).

Vreeke, M. et al., "Hydrogen Peroxide and β–Nicotinamide Adenine Dinucleotide Sensing Amperometric Electrodes Based on Electrical Connection of Horseradish Peroxidase Redox Centers to Electrodes through a Three–Dimensional Electron Relaying Polymer Network," *Analytical Chemistry*, 64(24):3084–3090 (Dec. 15, 1992).

Wang, J. et al., "Activation of Glassy Carbon Electrodes by Alternating Current Electrochemical Treatment", *Analytica Chimica Acta*, 167:325–334 (Jan. 1985).

Wang, J. et al., "Amperometric biosensing of organic peroxides with peroxidase–modified electrodes," *Analytica Chimica Acta*. 254:81–88 (1991).

Wang, D. L. et al., "Miniaturized Flexible Amperometric Lactate Probe," *Analytical Chemistry*, 65(8):1069–1073 (Apr. 15, 1993).

Wang, J. et al. "Screen–Printable Sol–Gel Enzyme–Containing Carbon Inks," *Analytical Chemistry*, 68(15):2705–2708 (Aug. 1, 1996).

Wang, J. et al., "Sol–Gel–Derived Metal–Dispersed Carbon Composite Amperometric Biosensors," *Electroanalysis*, 9(1):52–55 (1997).

Williams, D.L. et al., "Electrochemical–Enzymatic Analysis of Blood Glucose and Lactate", *Anal. Chem.*, 42(1):118–121 (Jan. 1970).

Wilson, G. S. et al., "Progress toward the Development of an Implantable Sensor for Glucose," *Clinical Chemistry*, 38(9):1613–1617 (1992).

Yabuki, S. et al., "Electro–conductive Enzyme Membrane," *J. Chem. Soc. Chem. Commun*, 945–946 (1989).

Yang, L. et al., "Determination of Oxidase Enzyme Substrates Using Cross–Flow Thin–Layer Amperometry," *Electroanalysis*, 8(8–9):716–721 (1996).

Yao, S.J. et al., "The Interference of Ascorbate and Urea in Low–Potential Electrochemical Glucose Sensing", *Proceedings of the Twelfth Annual International Conference of the IEEE Engineering in Medicine and Biology Society*, 12(2):487–489 (Nov. 1–4, 1990).

Yao, T. et al., "A Chemically–Modified Enzyme Membrane Electrode As An Amperometric Glucose Sensor," *Analytica Chimica Acta.*, 148:27–33 (1983).

Ye, L. et al., "High Current Density "Wired" Quinoprotein Glucose Dehydrogenase Electrode," *Anal. Chem.*, 65(3):238–241 (Feb. 1, 1993).

Yildiz, A. et al., "Eavluation of an Improved Thin–Layer Electrode," *Analytical Chemistry*, 40(70):1018–1024 (Jun. 1968).

Zamzow, K. et al., New Wearable Continuous Blood Glucose Monitor (BGM) and Artificial Pancreas (AP), *Diabetes*, 39:5A(20) (May 1990).

Zhang, Y. et al., "Application of cell culture toxicity tests to the development of implantable biosensors," *Biosensors & Bioelectronics*, 6:653–661 (1991).

Zhang, Y. et al., "Elimination of the Acetaminophen Interference in an Implantable Glucose Sensor," *Anal. Chem.* 66:1183–1188 (1994).

ABSTRACT NOT APPLICABLE

ELECTROCHEMICAL ANALYTE

FIELD OF THE INVENTION

The present invention is, in general, directed to an analyte sensor. More particularly, the present invention relates to an electrochemical sensor for determining a level of an analyte, such as glucose, lactate, or oxygen, in vivo and/or in vitro.

BACKGROUND OF THE INVENTION

The monitoring of the level of glucose or other analytes, such as lactate or oxygen, in certain individuals is vitally important to their health. High or low levels of glucose or other analytes may have detrimental effects. The monitoring of glucose is particularly important to individuals with diabetes, as they must determine when insulin is needed to reduce glucose levels in their bodies or when additional glucose is needed to raise the level of glucose in their bodies.

A conventional technique used by many diabetics for personally monitoring their blood glucose level includes the periodic drawing of blood, the application of that blood to a test strip, and the determination of the blood glucose level using colorimetric, electrochemical, or photometric detection. This technique does not permit continuous or automatic monitoring of glucose levels in the body, but typically must be performed manually on a periodic basis. Unfortunately, the consistency with which the level of glucose is checked varies widely among individuals. Many diabetics find the periodic testing inconvenient and they sometimes forget to test their glucose level or do not have time for a proper test. In addition, some individuals may wish to avoid the pain associated with the test. These situations may result in hyperglycemic or hypoglycemic episodes. An in vivo glucose sensor that continuously or automatically monitors the individual's glucose level would enable individuals to more easily monitor their glucose, or other analyte, levels.

A variety of devices have been developed for continuous or automatic monitoring of analytes, such as glucose, in the blood stream or interstitial fluid. Many of these devices use electrochemical sensors which are directly implanted into a blood vessel or in the subcutaneous tissue of a patient. However, these devices are often difficult to reproducibly and inexpensively manufacture in large numbers. In addition, these devices are typically large, bulky, and/or inflexible, and many can not be used effectively outside of a controlled medical facility, such as a hospital or a doctor's office, unless the patient is restricted in his activities.

The patient's comfort and the range of activities that can be performed while the sensor is implanted are important considerations in designing extended-use sensors for continuous or automatic in vivo monitoring of the level of an analyte, such as glucose. There is a need for a small, comfortable device which can continuously monitor the level of an analyte, such as glucose, while still permitting the patient to engage in normal activities. Continuous and/or automatic monitoring of the analyte can provide a warning to the patient when the level of the analyte is at or near a threshold level. For example, if glucose is the analyte, then the monitoring device might be configured to warn the patient of current or impending hyperglycemia or hypoglycemia. The patient can then take appropriate actions.

In addition to in vivo monitoring of analyte levels, it is often important to determine the level of an analyte in a sample taken from a subject. For many individuals and for many analytes, continuous monitoring of analyte level is not necessary, convenient, and/or desirable. In vitro measurements are often useful in making periodic determinations of analyte level when an in vivo sensor is not being used. Such measurements may also be useful for calibrating an in vivo sensor. In these cases, it may be desirable to use small volume samples due to the difficulty of obtaining such samples, the discomfort of the patient when the sample is obtained, and/or other reasons. However, most conventional sensors are designed to test for analyte levels in samples larger than 3 microliters. It is desirable to have sensors that could be used for the in vitro monitoring of samples that may be as small as a microliter, or even 25 nanoliters or less. The use of such small samples reduces the inconvenience and pain associated with obtaining a sample, for example, by lancing a portion of the body to obtain a blood sample.

SUMMARY OF THE INVENTION

Generally, the present invention relates to an analyte sensor which can be used for the in vivo and/or in vitro determination of a level of an analyte in a fluid. Some embodiments of the invention are particularly useful for the continuous or automatic monitoring of a level of an analyte, such as glucose or lactate, in a patient. One embodiment of the invention is an electrochemical sensor. The electrochemical sensor includes a substrate, a recessed channel formed in a surface of the substrate, and a conductive material disposed in the recessed channel. The conductive material forms a working electrode.

Another embodiment of the invention is an electrochemical sensor that includes a substrate and a plurality of recessed channels formed in at least one surface of the substrate. Conductive material is disposed in each of the recessed channels. The conductive material in at least one of the recessed channels forms a working electrode.

A further embodiment of the invention is an analyte responsive electrochemical sensor that includes a working electrode and a mass transport limiting membrane. The mass transport limiting membrane preferably maintains a rate of permeation of the analyte through the mass transport limiting membrane with a variation of less than 3% per °C. at temperatures ranging from 30° C. to 40° C.

Yet another embodiment of the invention is a method of determining a level of an analyte in a fluid. The fluid is contacted by an electrochemical sensor that includes a substrate, a recessed channel in the substrate, and conductive material in the recessed channel forming a working electrode. An electrical signal is generated by the sensor in response to the presence of the analyte. The level of the analyte may be determined from the electrical signal.

A further embodiment of the invention is a temperature sensor. The temperature sensor includes a substrate, a recessed channel formed in the substrate, and a temperature probe disposed in the recessed channel. The temperature probe includes two probe leads that are disposed in spaced-apart portions of the recessed channel and a temperature-dependent element that is disposed in the recessed channel and is in contact with the two probe leads. The temperature-dependent element is formed using a material having a temperature-dependent characteristic that alters a signal from the temperature probe in response to a change in temperature.

One embodiment of the invention is a method of determining a level of an analyte in a fluid. The fluid is placed in contact with an electrochemical sensor. The electrochemical sensor has a substrate, a recessed channel formed in a surface of the substrate, conductive material disposed in the recessed channel to form a working electrode, and a catalyst proximally disposed to the working electrode. A level of a second compound in the fluid is changed by a reaction of the analyte catalyzed by the catalyst. A signal is generated in response to the level of the second electrode. The level of the analyte is determined from the signal.

Another embodiment of the invention is an electrochemical sensor having a substrate and a working electrode disposed on the substrate. The working electrode preferably includes a carbon material and has a width along at least a portion of the working electrode of 150 µm or less.

Another embodiment of the invention is an electrochemical sensor for determining a level of an analyte in a fluid. The electrochemical sensor includes a substrate, a recessed channel formed in a surface of the substrate, and conductive material disposed in the recessed channel to form a working electrode. A catalyst is positioned near the working electrode to catalyze a reaction of the analyte which results in a change in a level of a second compound. The electrochemical sensor produces a signal which is responsive to the level of the second compound.

Yet another embodiment of the invention is a sensor adapted for subcutaneous implantation. The sensor includes a substrate, and conductive carbon non-leachably disposed on the substrate to form a working electrode. An enzyme is non-leachably disposed in proximity to the working electrode.

Another embodiment of the invention is an electrochemical sensor including a substrate and conductive material disposed on the substrate. The conductive material forms a plurality of traces. At least one of the traces forms a working electrode. The plurality of conductive traces are preferably separated on the surface of the substrate by a distance of 150 µm or less.

One embodiment of the invention is an electrochemical sensor having a substrate and conductive material disposed on a surface of the substrate. The conductive material forms a plurality of conductive traces, at least one of which forms a working electrode. The plurality of conductive traces are disposed on the surface of the substrate at a preferred density, along a width of the substrate, of 667 µm/trace or less.

Another embodiment of the invention is an electrochemical sensor having a substrate, a conductive material disposed on the substrate to form a working electrode, and a contact pad disposed on the substrate and operatively connected to the working electrode. The contact pad is made of a non-metallic conductive material to avoid or reduce corrosion.

Yet another embodiment of the invention is an analyte monitoring system having a sensor and a control unit. The sensor includes a substrate, a working electrode disposed on the substrate, and a contact pad coupled to the working electrode. The control unit has a conductive contact coupled to the working electrode and is configured to apply a potential across the working electrode. At least one of the contact pad and the conductive contact is made using a non-metallic material to avoid or reduce corrosion.

A further embodiment of the invention is a method of determining a level of an analyte in an animal. A sensor is implanted in the animal. The sensor includes a substrate, a plurality of conductive traces disposed on the substrate, and a working electrode formed from one of the conductive traces. A signal is generated at the working electrode in response to the analyte. The level of the analyte is determined by analyzing the signal. If the level of the analyte exceeds a threshold amount, an electrical current is produced through a portion of the animal to warn the animal. The electrical current is produced by applying a potential between two of the conductive traces.

Another embodiment is an electrochemical sensor having a substrate, a conductive material disposed on the substrate to form a working electrode, and catalyst disposed in the conductive material. The catalyst catalyzes a reaction of the analyte to generate a signal at the working electrode.

The above summary of the present invention is not intended to describe each disclosed embodiment or every implementation of the present invention. The Figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
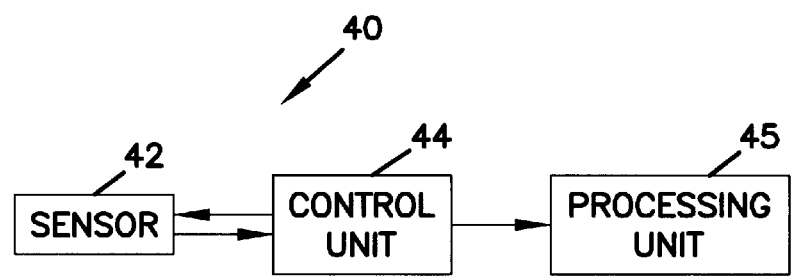
FIG. 1 is a block diagram of one embodiment of an analyte monitor using an analyte sensor, according to the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE PREFERRED EMBODIMENT

The present invention is applicable to an analyte sensor for the in vivo and/or in vitro determination of an analyte, such as glucose, lactate, or oxygen, in a fluid. The analyte sensors of the present invention can be utilized in a variety of contexts. For example, one embodiment of the analyte sensor can be subcutaneously implanted in the interstitial tissue of a patient for the continuous or periodic monitoring of a level of an analyte in a patient's interstitial fluid. This can then be used to infer the analyte level in the patient's bloodstream. Other in vivo analyte sensors can be made, according to the invention, for insertion into an organ, vein, artery, or other portion of the body containing fluid. The in vivo analyte sensors may be configured for obtaining a single measurement and/or for monitoring the level of the analyte over a time period which may range from hours to days or longer.

Another embodiment of the analyte sensor can be used for the in vitro determination of the presence and/or level of an analyte in a sample, and, particularly, in a small volume sample (e.g., 10 microliters to 50 nanoliters or less). While the present invention is not so limited, an appreciation of various aspects of the invention may be gained through a discussion of the examples provided below.

The following definitions are provided for terms used herein. A "counter electrode" refers to an electrode paired with the working electrode, through which passes a current equal in magnitude and opposite in sign to the current passing through the working electrode. In the context of the invention, the term "counter electrode" is meant to include counter electrodes which also function as reference electrodes (i.e., a counter/reference electrode).

An "electrochemical sensor" is a device configured to detect the presence and/or measure the level of an analyte in a sample via electrochemical oxidation and reduction reactions on the sensor. These reactions are transduced to an electrical signal that can be correlated to an amount, concentration, or level of an analyte in the sample.

"Electrolysis" is the electrooxidation or electroreduction of a compound either directly at an electrode or via one or more electron transfer agents.

A compound is "immobilized" on a surface when it is entrapped on or chemically bound to the surface.

A "non-leachable" or "non-releasable" compound or a compound that is "non-leachably disposed" is meant to define a compound that is affixed on the sensor such that it does not substantially diffuse away from the working surface of the working electrode for the period in which the sensor is used (e.g., the period in which the sensor is implanted in a patient or measuring a sample).

Components are "immobilized" within a sensor, for example, when the components are covalently, ionically, or coordinatively bound to constituents of the sensor and/or are entrapped in a polymeric or sol-gel matrix or membrane which precludes mobility.

An "electron transfer agent" is a compound that carries electrons between the analyte and the working electrode, either directly, or in cooperation with other electron transfer agents. One example of an electron transfer agent is a redox mediator.

A "working electrode" is an electrode at which the analyte (or a second compound whose level depends on the level of the analyte) is electrooxidized or electroreduced with or without the agency of an electron transfer agent.

A "working surface" is that portion of the working electrode which is coated with or is accessible to the electron transfer agent and configured for exposure to an analyte-containing fluid.

A "sensing layer" is a component of the sensor which includes constituents that facilitate the electrolysis of the analyte. The sensing layer may include constituents such as an electron transfer agent, a catalyst which catalyzes a reaction of the analyte to produce a response at the electrode, or both. In some embodiments of the sensor, the sensing layer is non-leachably disposed in proximity to or on the working electrode.

A "non-corroding" conductive material includes non-metallic materials, such as carbon and conductive polymers.

Analyte Sensor Systems

The sensors of the present invention can be utilized in a variety of devices and under a variety of conditions. The particular configuration of a sensor may depend on the use for which the sensor is intended and the conditions under which the sensor will operate (e.g., in vivo or in vitro). One embodiment of the analyte sensor is configured for implantation into a patient or user for in vivo operation. For example, implantation of the sensor may be made in the arterial or venous systems for direct testing of analyte levels in blood. Alternatively, a sensor may be implanted in the interstitial tissue for determining the analyte level in interstitial fluid. This level may be correlated and/or converted to analyte levels in blood or other fluids. The site and depth of implantation may affect the particular shape, components, and configuration of the sensor. Subcutaneous implantation may be preferred, in some cases, to limit the depth of implantation of the sensor. Sensors may also be implanted in other regions of the body to determine analyte levels in other fluids.

An implantable analyte sensor may be used as part of an analyte monitoring system to continuously and/or periodically monitor the level of an analyte in a body fluid of a patient. In addition to the sensor 42, the analyte monitoring system 40 also typically includes a control unit 44 for operating the sensor 42 (e.g., providing a potential to the electrodes and obtaining measurements from the electrodes) and a processing unit 45 for analyzing the measurements from the sensor 42. The control unit 44 and processing unit 45 may be combined in a single unit or may be separate.

Another embodiment of the sensor may be used for in vitro measurement of a level of an analyte. The in vitro sensor is coupled to a control unit and/or a processing unit to form an analyte monitoring system. In some embodiments, an in vitro analyte monitoring system is also configured to provide a sample to the sensor. For example, the analyte monitoring system may be configured to draw a sample from, for example, a lanced wound using a wicking and/or capillary action. The sample may then be drawn into contact with the sensor. Examples of such sensors may be found in U.S. patent application Ser. No. 08/795,767 and PCT patent application Ser. No. PCT/US98/02652, incorporated herein by reference.

Other methods for providing a sample to the sensor include using a pump, syringe, or other mechanism to draw a sample from a patient through tubing or the like either directly to the sensor or into a storage unit from which a sample is obtained for the sensor. The pump, syringe, or other mechanism may operate continuously, periodically, or when desired to obtain a sample for testing. Other useful devices for providing an analyte-containing fluid to the sensor include microfiltration and/or microdialysis devices. In some embodiments, particularly those using a microdialysis device, the analyte may be drawn from the body fluid through a microporous membrane, for example, by osmotic pressure, into a carrier fluid which is then conveyed to the sensor for analysis. Other useful devices for acquiring a sample are those that collect body fluids transported across the skin using techniques, such as reverse iontophoresis, to enhance the transport of fluid containing analyte across the skin.

The Sensor

Figure 2:
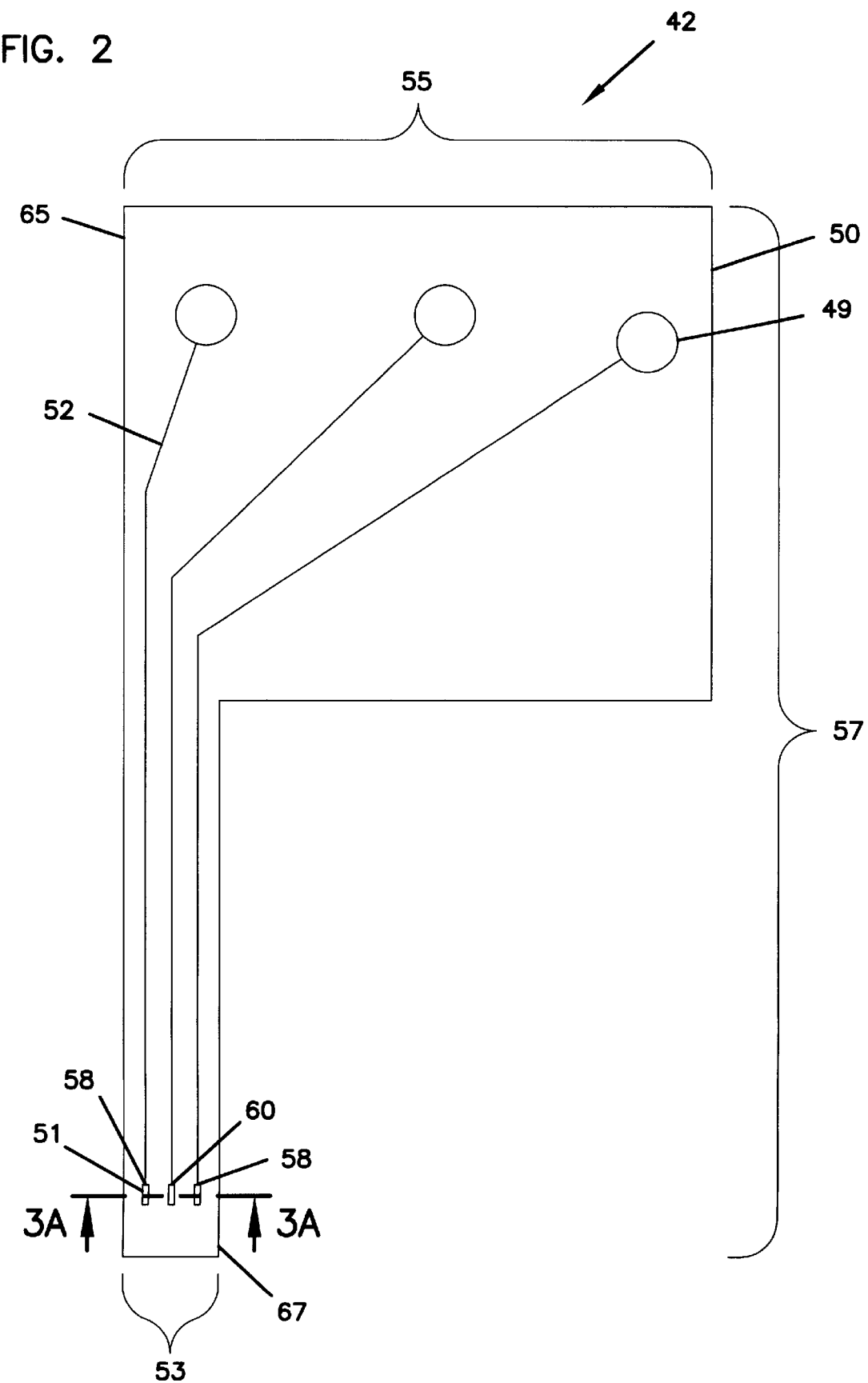
FIG. 2 is a top view of one embodiment of an analyte sensor, according to the invention.

A sensor 42, according to the invention, includes at least one working electrode 58 formed on a substrate 50, as shown in FIG. 2. The sensor 42 may also include at least one counter electrode 60 (or counter/reference electrode) and/or at least one reference electrode 62 (see FIG. 8). The counter electrode 60 and/or reference electrode 62 may be formed on the substrate 50 or may be separate units. For example, the counter electrode and/or reference electrode may be formed on a second substrate which is also implanted in the patient or, for some embodiments of the implantable sensors, the counter electrode and/or reference electrode may be placed on the skin of the patient with the working electrode or electrodes being implanted into the patient. The use of an on-the-skin counter and/or reference electrode with an implantable working electrode is described in U.S. Pat. No. 5,593,852, incorporated herein by reference.

The working electrode or electrodes 58 are formed using conductive traces 52 disposed on the substrate 50. The counter electrode 60 and/or reference electrode 62, as well as other optional portions of the sensor 42, such as a temperature probe 66 (see FIG. 8), may also be formed using conductive traces 52 disposed on the substrate 50. These conductive traces 52 may be formed over a smooth surface of the substrate 50 or within channels 54 formed by, for example, embossing, indenting or otherwise creating a depression in the substrate 50.

A sensing layer 64 (see FIGS. 3A and 3B) is often formed proximate to or on at least one of the working electrodes 58 to facilitate the electrochemical detection of the analyte and the determination of its level in the sample fluid, particularly if the analyte can not be electrolyzed at a desired rate and/or with a desired specificity on a bare electrode. The sensing layer 64 may include an electron transfer agent to transfer electrons directly or indirectly between the analyte and the working electrode 58. The sensing layer 64 may also contain a catalyst to catalyze a reaction of the analyte. The components of the sensing layer may be in a fluid or gel that is proximate to or in contact with the working electrode 58. Alternatively, the components of the sensing layer 64 may be disposed in a polymeric or sol-gel matrix that is proximate to or on the working electrode 58. Preferably, the components of the sensing layer 64 are non-leachably disposed within the sensor 42. More preferably, the components of the sensor 42 are immobilized within the sensor 42.

In addition to the electrodes 58, 60, 62 and the sensing layer 64, the sensor 42 may also include a temperature probe 66 (see FIGS. 6 and 8), a mass transport limiting layer 74 (see FIG. 9), a biocompatible layer 75 (see FIG. 9), and/or other optional components, as described below. Each of these items enhances the functioning of and/or results from the sensor 42, as discussed below.

The Substrate

The substrate 50 may be formed using a variety of non-conducting materials, including, for example, polymeric or plastic materials and ceramic materials. Suitable materials for a particular sensor 42 may be determined, at least in part, based on the desired use of the sensor 42 and properties of the materials.

In some embodiments, the substrate is flexible. For example, if the sensor 42 is configured for implantation into a patient, then the sensor 42 may be made flexible (although rigid sensors may also be used for implantable sensors) to reduce pain to the patient and damage to the tissue caused by the implantation of and/or the wearing of the sensor 42. A flexible substrate 50 often increases the patient's comfort and allows a wider range of activities. A flexible substrate 50 is also useful for an in vitro sensor 42, particularly for ease of manufacturing. Suitable materials for a flexible substrate 50 include, for example, non-conducting plastic or polymeric materials and other non-conducting, flexible, deformable materials. Examples of useful plastic or polymeric materials include thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate).

In other embodiments, the sensors 42 are made using a relatively rigid substrate 50 to, for example, provide structural support against bending or breaking. Examples of rigid materials that may be used as the substrate 50 include poorly conducting ceramics, such as aluminum oxide and silicon dioxide. One advantage of an implantable sensor 42 having a rigid substrate is that the sensor 42 may have a sharp point and/or a sharp edge to aid in implantation of a sensor 42 without an additional insertion device. In addition, rigid substrates 50 may also be used in sensors for in vitro analyte monitors.

It will be appreciated that for many sensors 42 and sensor applications, both rigid and flexible sensors will operate adequately. The flexibility of the sensor 42 may also be controlled and varied along a continuum by changing, for example, the composition and/or thickness of the substrate 50.

In addition to considerations regarding flexibility, it is often desirable that implantable sensors 42, as well as in vitro sensors which contact a fluid that is returned to a patient's body, should have a substrate 50 which is non-toxic. Preferably, the substrate 50 is approved by one or more appropriate governmental agencies or private groups for in vivo use.

Figure 12:
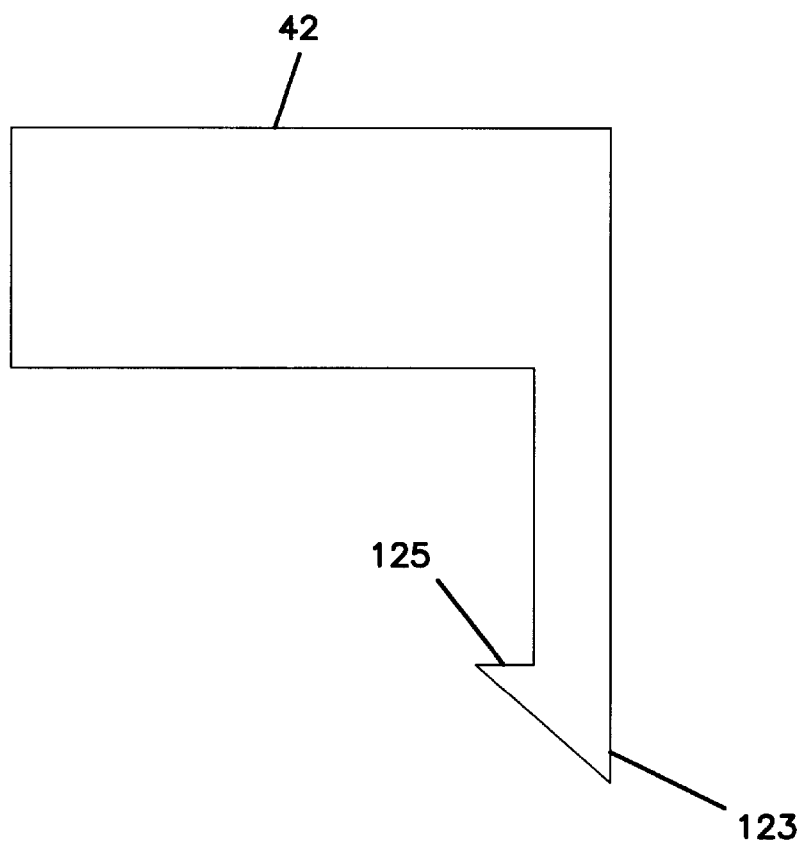
FIG. 12 is another embodiment of an analyte sensor according to the invention.

The sensor 42 may include optional features to facilitate insertion of an implantable sensor 42, as shown in FIG. 12. For example, the sensor 42 may be pointed at the tip 123 to ease insertion. In addition, the sensor 42 may include a barb 125 which assists in anchoring the sensor 42 within the tissue of the patient during operation of the sensor 42. However, the barb 125 is typically small enough that little damage is caused to the subcutaneous tissue when the sensor 42 is removed for replacement.

Although the substrate 50 in at least some embodiments has uniform dimensions along the entire length of the sensor 42, in other embodiments, the substrate 50 has a distal end 67 and a proximal end 65 with different widths 53, 55, respectively, as illustrated in FIG. 2. In these embodiments, the distal end 67 of the substrate 50 may have a relatively narrow width 53. For sensors 42 which are implantable into the subcutaneous tissue or another portion of a patient's body, the narrow width 53 of the distal end 67 of the substrate 50 may facilitate the implantation of the sensor 42. Often, the narrower the width of the sensor 42, the less pain the patient will feel during implantation of the sensor and afterwards.

For subcutaneously implantable sensors 42 which are designed for continuous or periodic monitoring of the analyte during normal activities of the patient, a distal end 67 of the sensor 42 which is to be implanted into the patient has a width 53 of 2 mm or less, preferably 1 mm or less, and more preferably 0.5 mm or less. If the sensor 42 does not have regions of different widths, then the sensor 42 will typically have an overall width of, for example, 2 mm, 1.5 mm, 1 mm, 0.5 mm, 0.25 mm, or less. However, wider or narrower sensors may be used. In particular, wider implantable sensors may be used for insertion into veins or arteries or when the movement of the patient is limited, for example, when the patient is confined in bed or in a hospital.

For sensors 42 which are designed for measuring small volume in vitro samples, the narrow width 53 may reduce the volume of sample needed for an accurate reading. The narrow width 53 of the sensor 42 results in all of the electrodes of the sensor 42 being closely congregated, thereby requiring less sample volume to cover all of the electrodes. The width of an in vitro sensor 42 may vary depending, at least in part, on the volume of sample available to the sensor 42 and the dimensions of the sample chamber in which the sensor 42 is disposed.

Returning to FIG. 2, the proximal end 65 of the sensor 42 may have a width 55 larger than the distal end 67 to facilitate the connection between contact pads 49 of the electrodes and contacts on a control unit. The wider the sensor 42 at this point, the larger the contact pads 49 can be made. This may reduce the precision needed to properly connect the sensor 42 to contacts on the control unit (e.g., sensor control unit 44 of FIG. 1). However, the maximum width of the sensor 42 may be constrained so that the sensor 42 remains small for the convenience and comfort of the patient and/or to fit the desired size of the analyte monitor. For example, the proximal end 65 of a subcutaneously implantable sensor 42, such as the sensor 42 illustrated in FIG. 1, may have a width 55 ranging from 0.5 mm to 15 mm, preferably from 1 mm to 10 mm, and more preferably from 3 mm to 7 mm. However, wider or narrower sensors may be used in this and other in vivo and in vitro applications.

The thickness of the substrate 50 may be determined by the mechanical properties of the substrate material (e.g., the strength, modulus, and/or flexibility of the material), the desired use of the sensor 42 including stresses on the substrate 50 arising from that use, as well as the depth of any channels or indentations formed in the substrate 50, as discussed below. Typically, the substrate 50 of a subcutaneously implantable sensor 42 for continuous or periodic monitoring of the level of an analyte while the patient engages in normal activities has a thickness of 50 to 500 $\mu$m and preferably 100 to 300 $\mu$m. However, thicker and thinner substrates 50 may be used, particularly in other types of in vivo and in vitro sensors 42.

The length of the sensor 42 may have a wide range of values depending on a variety of factors. Factors which influence the length of an implantable sensor 42 may include the depth of implantation into the patient and the ability of the patient to manipulate a small flexible sensor 42 and make connections between the sensor 42 and the sensor control unit 44. A subcutaneously implantable sensor 42 for the analyte monitor illustrated in FIG. 1 may have a length ranging from 0.3 to 5 cm, however, longer or shorter sensors may be used. The length of the narrow portion of the sensor 42 (e.g., the portion which is subcutaneously inserted into the patient), if the sensor 42 has narrow and wide portions, is typically about 0.25 to 2 cm in length. However, longer and shorter portions may be used. All or only a part of this narrow portion may be subcutaneously implanted into the patient.

The lengths of other implantable sensors 42 will vary depending, at least in part, on the portion of the patient into which the sensor 42 is to be implanted or inserted. The length of in vitro sensors may vary over a wide range depending on the particular configuration of the analyte monitoring system and, in particular, the distance between the contacts of the control unit and the sample.

Conductive Traces

At least one conductive trace 52 is formed on the substrate for use in constructing a working electrode 58. In addition, other conductive traces 52 may be formed on the substrate 50 for use as electrodes (e.g., additional working electrodes, as well as counter, counter/reference, and/or reference electrodes) and other components, such as a temperature probe. The conductive traces 52 may extend most of the distance along a length 57 of the sensor 50, as illustrated in FIG. 2, although this is not necessary. The placement of the conductive traces 52 may depend on the particular configuration of the analyte monitoring system (e.g., the placement of control unit contacts and/or the sample chamber in relation to the sensor 42). For implantable sensors, particularly subcutaneously implantable sensors, the conductive traces typically extend close to the tip of the sensor 42 to minimize the amount of the sensor that must be implanted.

The conductive traces 52 may be formed on the substrate 50 by a variety of techniques, including, for example, photolithography, screen printing, or other impact or non-impact printing techniques. The conductive traces 52 may also be formed by carbonizing conductive traces 52 in an organic (e.g., polymeric or plastic) substrate 50 using a laser. A description of some exemplary methods for forming the sensor 42 is provided in U.S. patent application Ser. No. 09/034,422, incorporated herein by reference.

Figure 3A:
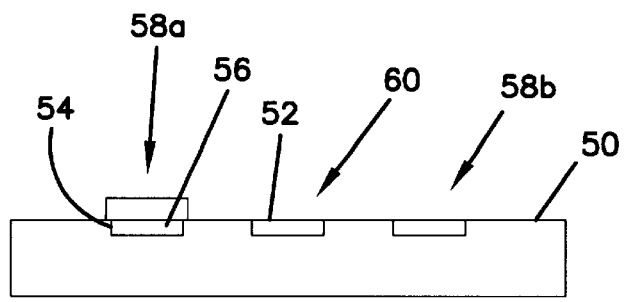
FIG. 3A is a cross-sectional view of the analyte sensor of FIG. 2.

Another method for disposing the conductive traces 52 on the substrate 50 includes the formation of recessed channels 54 in one or more surfaces of the substrate 50 and the subsequent filling of these recessed channels 54 with a conductive material 56, as shown in FIG. 3A. The recessed channels 54 may be formed by indenting, embossing, or otherwise creating a depression in the surface of the substrate 50. Exemplary methods for forming channels and electrodes in a surface of a substrate can be found in U.S. patent application Ser. No. 09/034,422, entitled "Process for the Manufacture of an Electrochemical Biosensor", filed on Mar. 4, 1998. The depth of the channels is typically related to the thickness of the substrate 50. In one embodiment, the channels have depths in the range of about 12.5 to 75 $\mu$m (0.5 to 3 mils), and preferably about 25 to 50 $\mu$m (1 to 2 mils).

The conductive traces are typically formed using a conductive material 56 such as carbon (e.g., graphite), a conductive polymer, a metal or alloy (e.g., gold or gold alloy), or a metallic compound (e.g., ruthenium dioxide or titanium dioxide). The formation of films of carbon, conductive polymer, metal, alloy, or metallic compound are well-known and include, for example, chemical vapor deposition (CVD), physical vapor deposition, sputtering, reactive sputtering, printing, coating, and painting. The conductive material 56 which fills the channels 54 is often formed using a precursor material, such as a conductive ink or paste. In these embodiments, the conductive material 56 is deposited on the substrate 50 using methods such as coating, painting, or applying the material using a spreading instrument, such as a coating blade. Excess conductive material between the channels 54 is then removed by, for example, running a blade along the substrate surface.

In one embodiment, the conductive material 56 is a part of a precursor material, such as a conductive ink, obtainable, for example, from Ercon, Inc. (Wareham, Mass.), Metech, Inc. (Elverson, Pa.), E. I. du Pont de Nemours and Co. (Wilmington, Del.), Emca-Remex Products (Montgomeryville, Pa.), or MCA Services (Melbourn, Great Britain). The conductive ink is typically applied as a semiliquid or paste which contains particles of the carbon, metal, alloy, or metallic compound and a solvent or dispersant. After application of the conductive ink on the substrate 50 (e.g., in the channels 54), the solvent or dispersant evaporates to leave behind a solid mass of conductive material 56.

In addition to the particles of carbon, metal, alloy, or metallic compound, the conductive ink may also contain a binder. The binder may optionally be cured to further bind the conductive material 56 within the channel 54 and/or on the substrate 50. Curing the binder increases the conductivity of the conductive material 56. However, this is typically not necessary as the currents carried by the conductive material 56 within the conductive traces 52 are often relatively low (usually less than 1 $\mu$A and often less than 100 nA). Typical binders include, for example, polyurethane resins, cellulose derivatives, elastomers, and highly fluorinated polymers. Examples of elastomers include silicones, polymeric dienes, and acrylonitrile-butadiene-styrene (ABS) resins. One example of a fluorinated polymer binder is Teflon® (DuPont, Wilmington, Del.). These binders are cured using, for example, heat or light, including ultraviolet (UV) light. The appropriate curing method typically depends on the particular binder which is used.

Often, when a liquid or semiliquid precursor of the conductive material 56 (e.g., a conductive ink) is deposited in the channel 54, the precursor fills the channel 54. However, when the solvent or dispersant evaporates, the conductive material 56 which remains may lose volume such that the conductive material 56 may or may not continue to fill the channel 54. Preferred conductive materials 56 do not pull away from the substrate 50 as they lose volume, but rather decrease in height within the channel 54. These conductive materials 56 typically adhere well to the substrate 50 and therefore do not pull away from the substrate 50 during evaporation of the solvent or dispersant. Other suitable conductive materials 56 either adhere to at least a portion of the substrate 50 and/or contain another additive, such as a binder, which adheres the conductive material 56 to the substrate 50. Preferably, the conductive material 56 in the channels 54 is non-leachable, and more preferably immobilized on the substrate 50. In some embodiments, the conductive material 56 may be formed by multiple applications of a liquid or semiliquid precursor interspersed with removal of the solvent or dispersant.

In another embodiment, the channels 54 are formed using a laser. The laser carbonizes the polymer or plastic material. The carbon formed in this process is used as the conductive material 56. Additional conductive material 56, such as a conductive carbon ink, may be used to supplement the carbon formed by the laser.

In a further embodiment, the conductive traces 52 are formed by pad printing techniques. For example, a film of conductive material is formed either as a continuous film or as a coating layer deposited on a carrier film. This film of conductive material is brought between a print head and the substrate 50. A pattern on the surface of the substrate 50 is made using the print head according to a desired pattern of conductive traces 52. The conductive material is transferred by pressure and/or heat from the film of conductive material to the substrate 50. This technique often produces channels (e.g., depressions caused by the print head) in the substrate 50. Alternatively, the conductive material is deposited on the surface of the substrate 50 without forming substantial depressions.

In other embodiments, the conductive traces 52 are formed by non-impact printing techniques. Such techniques include electrophotography and magnetography. In these processes, an image of the conductive traces 52 is electrically or magnetically formed on a drum. A laser or LED may be used to electrically form an image. A magnetic recording head may be used to magnetically form an image. A toner material (e.g., a conductive material, such as a conductive ink) is then attracted to portions of the drum according to the image. The toner material is then applied to the substrate by contact between the drum and the substrate. For example, the substrate may be rolled over the drum. The toner material may then be dried and/or a binder in the toner material may be cured to adhere the toner material to the substrate.

Another non-impact printing technique includes ejecting droplets of conductive material onto the substrate in a desired pattern. Examples of this technique include ink jet printing and piezo jet printing. An image is sent to the printer which then ejects the conductive material (e.g., a conductive ink) according to the pattern. The printer may provide a continuous stream of conductive material or the printer may eject the conductive material in discrete amounts at the desired points.

Yet another non-impact printing embodiment of forming the conductive traces includes an ionographic process. In the this process, a curable, liquid precursor, such as a photopolymerizable acrylic resin (e.g., Solimer 7501 from Cubital, Bad Kreuznach, Germany) is deposited over a surface of a substrate 50. A photomask having a positive or negative image of the conductive traces 52 is then used to cure the liquid precursor. Light (e.g., visible or ultraviolet light) is directed through the photomask to cure the liquid precursor and form a solid layer over the substrate according to the image on the photomask. Uncured liquid precursor is removed leaving behind channels 54 in the solid layer. These channels 54 can then be filled with conductive material 56 to form conductive traces 52.

Conductive traces 52 (and channels 54, if used) can be formed with relatively narrow widths, for example, in the range of 25 to 250 $\mu$m, and including widths of, for example, 250 $\mu$m, 150 $\mu$m, 100 $\mu$m, 75 $\mu$m, 50 $\mu$m, 25 $\mu$m or less by the methods described above. In embodiments with two or more conductive traces 52 on the same side of the substrate 50, the conductive traces 52 are separated by distances sufficient to prevent conduction between the conductive traces 52. The edge-to-edge distance between the conductive traces is preferably in the range of 25 to 250 $\mu$m and may be, for example, 150 $\mu$m, 100 $\mu$m, 75 $\mu$m, 50 $\mu$m, or less. The density of the conductive traces 52 on the substrate 50 is preferably in the range of about 150 to 700 $\mu$m/trace and may be as small as 667 $\mu$m/trace or less, 333 $\mu$m/trace or less, or even 167 $\mu$m/trace or less.

The working electrode 58 and the counter electrode 60 (if a separate reference electrode is used) are often made using a conductive material 56, such as carbon. Suitable carbon conductive inks are available from Ercon, Inc. (Wareham, Mass.), Metech, Inc. (Elverson, Pa.), E. I. du Pont de Nemours and Co. (Wilmington, Del.), Emca-Remex Products (Montgomeryville, Pa.), or MCA Services (Melbourn, Great Britain). Typically, the working surface 51 of the working electrode 58 is at least a portion of the conductive trace 52 that is in contact with the analyte-containing fluid (e.g., implanted in the patient or in the sample chamber of an in vitro analyte monitor).

The reference electrode 62 and/or counter/reference electrode are typically formed using conductive material 56 that is a suitable reference material, for example silver/silver chloride or a non-leachable redox couple bound to a conductive material, for example, a carbon-bound redox couple. Suitable silver/silver chloride conductive inks are available from Ercon, Inc. (Wareham, Mass.), Metech, Inc. (Elverson, Pa.), E. I. du Pont de Nemours and Co. (Wilmington, Del.), Emca-Remex Products (Montgomeryville, Pa.), or MCA Services (Melbourn, Great Britain). Silver/silver chloride electrodes illustrate a type of reference electrode that involves the reaction of a metal electrode with a constituent of the sample or body fluid, in this case, $Cl^-$.

Suitable redox couples for binding to the conductive material of the reference electrode include, for example, redox polymers (e.g., polymers having multiple redox centers.) It is preferred that the reference electrode surface be non-corroding so that an erroneous potential is not measured. Preferred conductive materials include less corrosive metals, such as gold and palladium. Most preferred are non-corrosive materials including non-metallic conductors, such as carbon and conducting polymers. A redox polymer can be adsorbed on or covalently bound to the conductive material of the reference electrode, such as a carbon surface of a conductive trace 52. Non-polymeric redox couples can be similarly bound to carbon or gold surfaces.

A variety of methods may be used to immobilize a redox polymer on an electrode surface. One method is adsorptive immobilization. This method is particularly useful for redox polymers with relatively high molecular weights. The molecular weight of a polymer may be increased, for example, by cross-linking.

Another method for immobilizing the redox polymer includes the functionalization of the electrode surface and then the chemical bonding, often covalently, of the redox polymer to the functional groups on the electrode surface. One example of this type of immobilization begins with a poly(4-vinylpyridine). The polymer's pyridine rings are, in part, complexed with a reducible/oxidizable species, such as $[Os(bpy)_2Cl]^{+/2+}$ where bpy is 2,2'-bipyridine. Part of the pyridine rings are quaternized by reaction with 2-bromoethylamine. The polymer is then crosslinked, for example, using a diepoxide, such as polyethylene glycol diglycidyl ether.

Carbon surfaces can be modified for attachment of a redox species or polymer, for example, by electroreduction of a diazonium salt. As an illustration, reduction of a diazonium salt formed upon diazotization of p-aminobenzoic acid modifies a carbon surface with phenylcarboxylic acid functional groups. These functional groups can then be activated by a carbodiimide, such as 1-ethyl-3-(3-dimethylaminopropyl)-carbodiimide hydrochloride. The activated functional groups are then bound with a amine-functionalized redox couple, such as the quaternized osmium-containing redox polymer described above or 2-aminoethylferrocene, to form the redox couple.

Similarly, gold can be functionalized by an amine, such as cystamine. A redox couple such as $[Os(bpy)_2(pyridine-4-carboxylate)Cl]^{0/+}$ is activated by 1-ethyl-3-(3-dimethylaminopropyl)-carbodiimide hydrochloride to form a reactive O-acylisourea which reacts with the gold-bound amine to form an amide.

In one embodiment, in addition to using the conductive traces 52 as electrodes or probe leads, two or more of the conductive traces 52 on the substrate 50 are used to give the patient a mild electrical shock when, for example, the analyte level exceeds a threshold level. This shock may act as a warning or alarm to the patient to initiate some action to restore the appropriate level of the analyte.

The mild electrical shock is produced by applying a potential between any two conductive traces 52 that are not otherwise connected by a conductive path. For example, two of the electrodes 58, 60, 62 or one electrode 58, 60, 62 and the temperature probe 66 may be used to provide the mild shock. Preferably, the working electrode 58 and the reference electrode 62 are not used for this purpose as this may cause some damage to the chemical components on or proximate to the particular electrode (e.g., the sensing layer on the working electrode or the redox couple on the reference electrode).

The current used to produce the mild shock is typically 0.1 to 1 mA. Higher or lower currents may be used, although care should be taken to avoid harm to the patient. The potential between the conductive traces is typically 1 to 10 volts. However, higher or lower voltages may be used depending, for example, on the resistance of the conductive traces 52, the distance between the conductive traces 52 and the desired amount of current. When the mild shock is delivered, potentials at the working electrode 58 and across the temperature probe 66 may be removed to prevent harm to those components caused by unwanted conduction between the working electrode 58 (and/or temperature probe 66, if used) and the conductive traces 52 which provide the mild shock.

Contact Pads

Typically, each of the conductive traces 52 includes a contact pad 49. The contact pad 49 may simply be a portion of the conductive trace 52 that is indistinguishable from the rest of the trace 52 except that the contact pad 49 is brought into contact with the conductive contacts of a control unit (e.g., the sensor control unit 44 of FIG. 1). More commonly, however, the contact pad 49 is a region of the conductive trace 52 that has a larger width than other regions of the trace 52 to facilitate a connection with the contacts on the control unit. By making the contact pads 49 relatively large as compared with the width of the conductive traces 52, the need for precise registration between the contact pads 49 and the contacts on the control unit is less critical than with small contact pads.

The contact pads 49 are typically made using the same material as the conductive material 56 of the conductive traces 52. However, this is not necessary. Although metal, alloys, and metallic compounds may be used to form the contact pads 49, in some embodiments, it is desirable to make the contact pads 49 from a carbon or other non-metallic material, such as a conducting polymer. In contrast to metal or alloy contact pads, carbon and other non-metallic contact pads are not easily corroded if the contact pads 49 are in a wet, moist, or humid environment. Metals and alloys may corrode under these conditions, particularly if the contact pads 49 and contacts of the control unit are made using different metals or alloys. However, carbon and non-metallic contact pads 49 do not significantly corrode, even if the contacts of the control device are metal or alloy.

One embodiment of the invention includes a sensor 42 having contact pads 49 and a control unit 44 having conductive contacts (not shown). During operation of the sensor 42, the contact pads 49 and conductive contacts are in contact with each other. In this embodiment, either the contact pads 49 or the conductive contacts are made using a non-corroding, conductive material. Such materials include, for example, carbon and conducting polymers. Preferred non-corroding materials include graphite and vitreous carbon. The opposing contact pad or conductive contact is made using carbon, a conducting polymer, a metal, such as gold, palladium, or platinum group metal, or a metallic compound, such as ruthenium dioxide. This configuration of contact pads and conductive contacts typically reduces corrosion. Preferably, when the sensor is placed in a 3 mM, and more preferably, in a 100 mM, NaCl solution, the signal arising due to the corrosion of the contact pads and/or conductive contacts is less than 3% of the signal generated by the sensor when exposed to concentration of analyte in the normal physiological range. For at least some subcutaneous glucose sensors, the current generated by analyte in a normal physiological range ranges from 3 to 500 nA.

Figure 10:
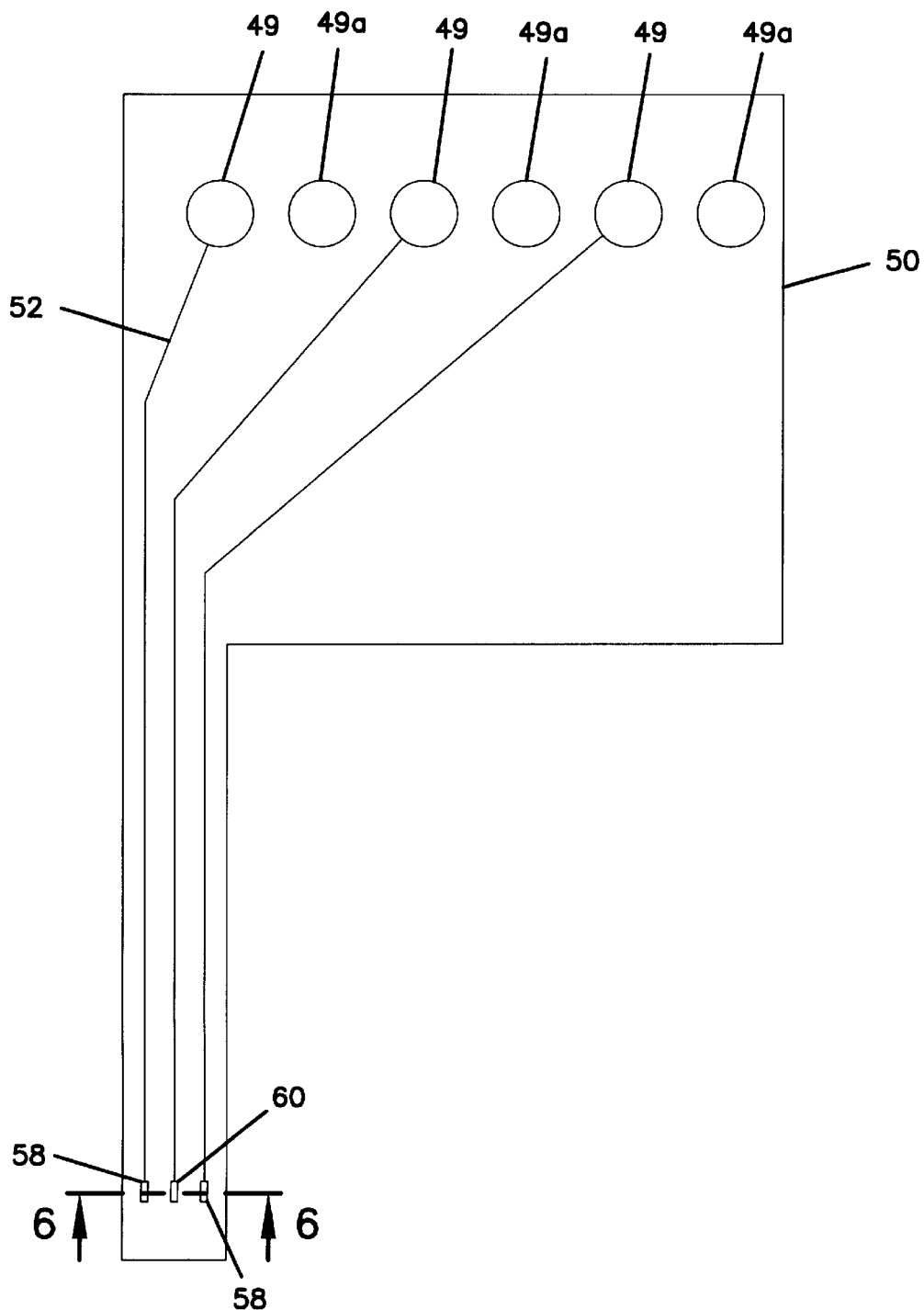
FIG. 10 is a top view of the analyte sensor of FIG. 6.
Figure 11:
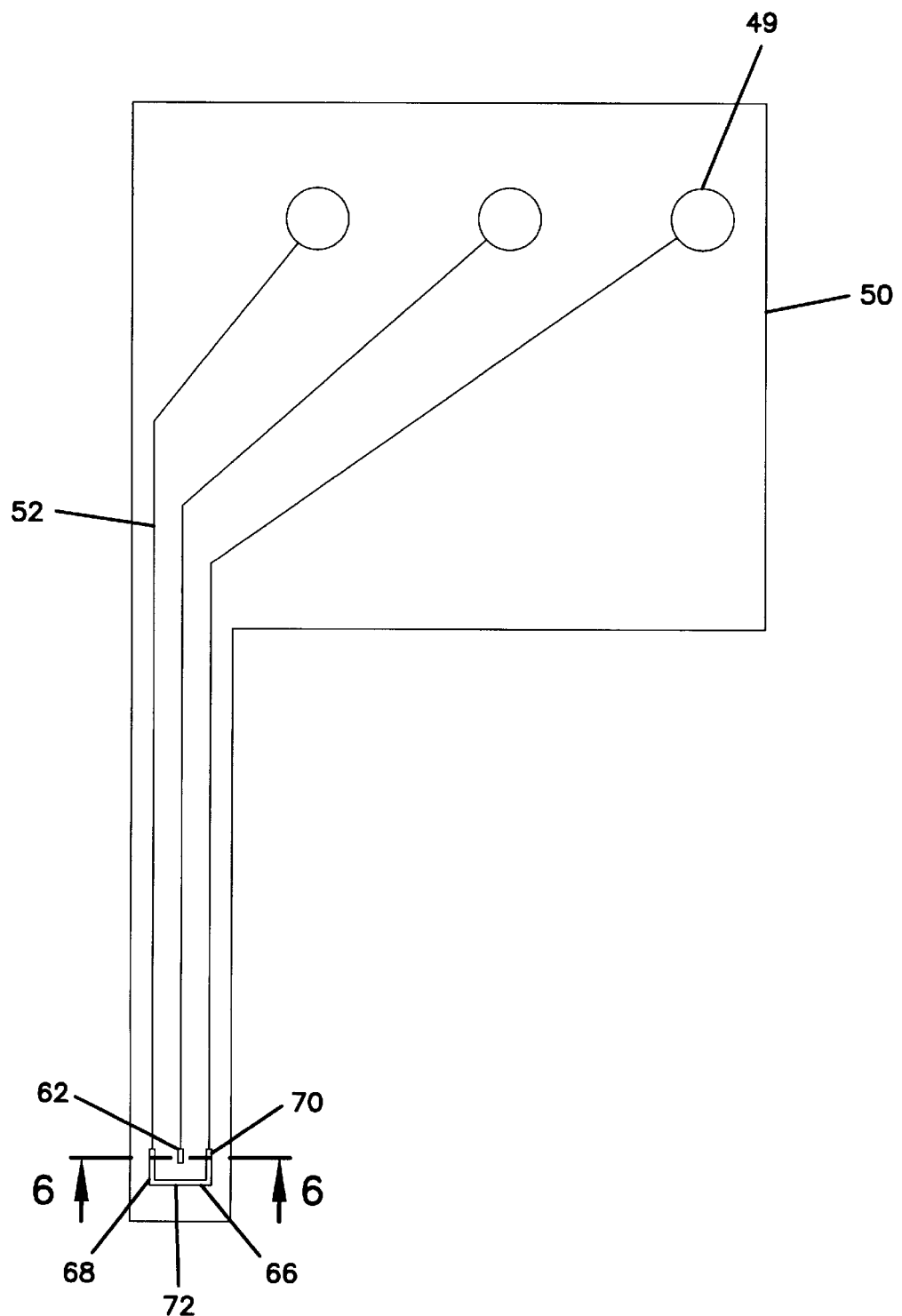
FIG. 11 is a bottom view of the analyte sensor of FIG. 6.

Each of the electrodes 58, 60, 62, as well as the two probe leads 68, 70 of the temperature probe 66 (described below), are connected to contact pads 49 as shown in FIGS. 10 and 11. In one embodiment (not shown), the contact pads 49 are on the same side of the substrate 50 as the respective electrodes or temperature probe leads to which the contact pads 49 are attached.

In other embodiments, the conductive traces 52 on at least one side are connected through vias in the substrate to contact pads 49a on the opposite surface of the substrate 50, as shown in FIGS. 10 and 11. An advantage of this configuration is that contact between the contacts on the control unit and each of the electrodes 58, 60, 62 and the probe leads 68,70 of the temperature probe 66 can be made from a single side of the substrate 50.

In yet other embodiments (not shown), vias through the substrate are used to provide contact pads on both sides of the substrate 50 for each conductive trace 52. The vias connecting the conductive traces 52 with the contact pads 49a can be formed by making holes through the substrate 50 at the appropriate points and then filling the holes with conductive material 56.

Exemplary Electrode Configurations

Figure 3B:
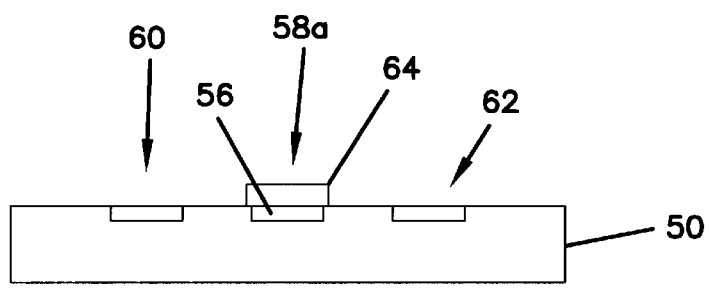
FIG. 3B is a cross-sectional view of another embodiment of an analyte sensor, according to the invention.

A number of exemplary electrode configurations are described below, however, it will be understood that other configurations may also be used. In one embodiment, illustrated in FIG. 3A, the sensor 42 includes two working electrodes 58a, 58b and one counter electrode 60, which also functions as a reference electrode. In another embodiment, the sensor includes one working electrode 58a, one counter electrode 60, and one reference electrode 62, as shown in FIG. 3B. Each of these embodiments is illustrated with all of the electrodes formed on the same side of the substrate 50.

Alternatively, one or more of the electrodes may be formed on an opposing side of the substrate 50. This may be convenient if the electrodes are formed using two different types of conductive material 56 (e.g., carbon and silver/silver chloride). Then, at least in some embodiments, only one type of conductive material 56 needs to be applied to each side of the substrate 50, thereby reducing the number of steps in the manufacturing process and/or easing the registration constraints in the process. For example, if the working electrode 58 is formed using a carbon-based conductive material 56 and the reference or counter/reference electrode is formed using a silver/silver chloride conductive material 56, then the working electrode and reference or counter/reference electrode may be formed on opposing sides of the substrate 50 for ease of manufacture.

Figure 6:
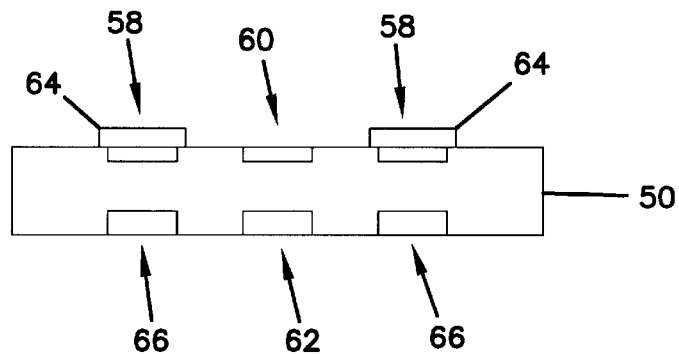
FIG. 6 is a cross-sectional view of a fifth embodiment of an analyte sensor, according to the invention.
Figure 7:
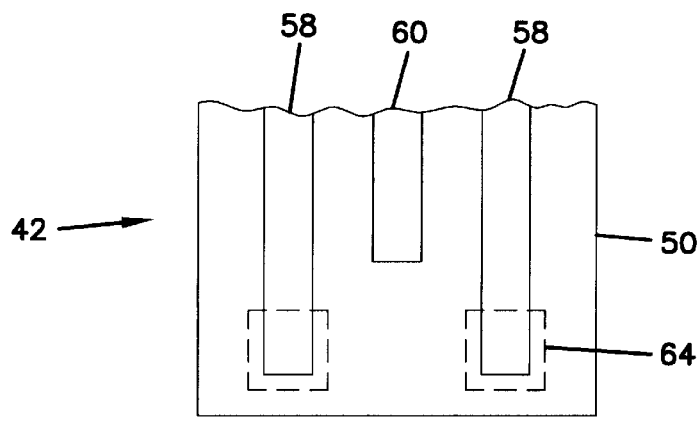
FIG. 7 is an expanded top view of a tip-portion of the analyte sensor of FIG. 6.
Figure 8:
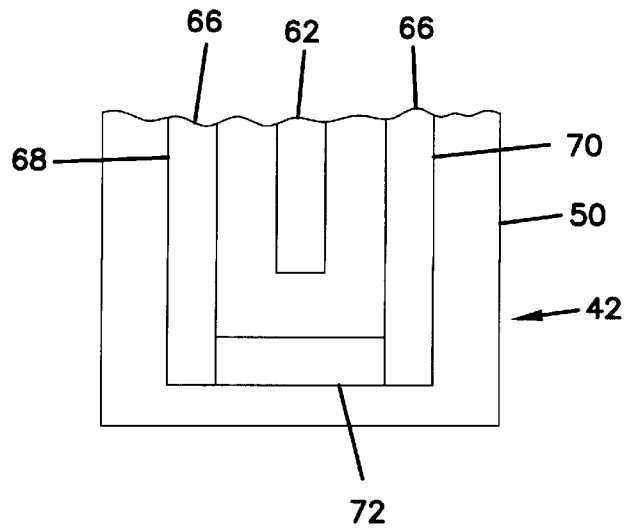
FIG. 8 is an expanded bottom view of a tip-portion of the analyte sensor of FIG. 6.

In another embodiment, two working electrodes 58 and one counter electrode 60 are formed on one side of the substrate 50 and one reference electrode 62 and a temperature probe 66 are formed on an opposing side of the substrate 50, as illustrated in FIG. 6. The opposing sides of the tip of this embodiment of the sensor 42 are illustrated in FIGS. 7 and 8.

Sensing Layer

Some analytes, such as oxygen, can be directly electrooxidized or electroreduced on the working electrode 58. Other analytes, such as glucose and lactate, require the presence of at least one electron transfer agent and/or at least one catalyst to facilitate the electrooxidation or electroreduction of the analyte. Catalysts may also be used for those analyte, such as oxygen, that can be directly electrooxidized or electroreduced on the working electrode 58. For these analytes, each working electrode 58 has a sensing layer 64 formed proximate to or on a working surface of the working electrode 58. Typically, the sensing layer 64 is formed near or on only a small portion of the working electrode 58, often near a tip of the sensor 42. This limits the amount of material needed to form the sensor 42 and places the sensing layer 64 in the best position for contact with the analyte-containing fluid (e.g., a body fluid, sample fluid, or carrier fluid).

The sensing layer 64 includes one or more components designed to facilitate the electrolysis of the analyte. The sensing layer 64 may include, for example, a catalyst to catalyze a reaction of the analyte and produce a response at the working electrode 58, an electron transfer agent to indirectly or directly transfer electrons between the analyte and the working electrode 58, or both.

The sensing layer 64 may be formed as a solid composition of the desired components (e.g., an electron transfer agent and/or a catalyst). These components are preferably non-leachable from the sensor 42 and more preferably are immobilized on the sensor 42. For example, the components may be immobilized on a working electrode 58. Alternatively, the components of the sensing layer 64 may be immobilized within or between one or more membranes or films disposed over the working electrode 58 or the components may be immobilized in a polymeric or sol-gel matrix. Examples of immobilized sensing layers are described in U.S. Pat. Nos. 5,262,035, 5,264,104, 5,264,105, 5,320,725, 5,593,852, and 5,665,222, U.S. patent application Ser. No. 08/540,789, and PCT patent application Ser. No. PCT/US98/02403, incorporated herein by reference.

In some embodiments, one or more of the components of the sensing layer 64 may be solvated, dispersed, or suspended in a fluid within the sensing layer 64, instead of forming a solid composition. The fluid may be provided with the sensor 42 or may be absorbed by the sensor 42 from the analyte-containing fluid. Preferably, the components which are solvated, dispersed, or suspended in this type of sensing layer 64 are non-leachable from the sensing layer. Non-leachability may be accomplished, for example, by providing barriers (e.g., the electrode, substrate, membranes, and/or films) around the sensing layer which prevent the leaching of the components of the sensing layer 64. One example of such a barrier is a microporous membrane or film which allows diffusion of the analyte into the sensing layer 64 to make contact with the components of the sensing layer 64, but reduces or eliminates the diffusion of the sensing layer components (e.g., a electron transfer agent and/or a catalyst) out of the sensing layer 64.

A variety of different sensing layer configurations can be used. In one embodiment, the sensing layer 64 is deposited on the conductive material 56 of a working electrode 58a, as illustrated in FIGS. 3A and 3B. The sensing layer 64 may extend beyond the conductive material 56 of the working electrode 58a. In some cases, the sensing layer 64 may also extend over the counter electrode 60 or reference electrode 62 without degrading the performance of the glucose sensor. For those sensors 42 which utilize channels 54 within which the conductive material 56 is deposited, a portion of the sensing layer 64 may be formed within the channel 54 if the conductive material 56 does not fill the channel 54.

A sensing layer 64 in direct contact with the working electrode 58a may contain an electron transfer agent to transfer electrons directly or indirectly between the analyte and the working electrode, as well as a catalyst to facilitate a reaction of the analyte. For example, a glucose, lactate, or oxygen electrode may be formed having a sensing layer which contains a catalyst, such as glucose oxidase, lactate oxidase, or laccase, respectively, and an electron transfer agent that facilitates the electrooxidation of the glucose, lactate, or oxygen, respectively.

Figure 4A:
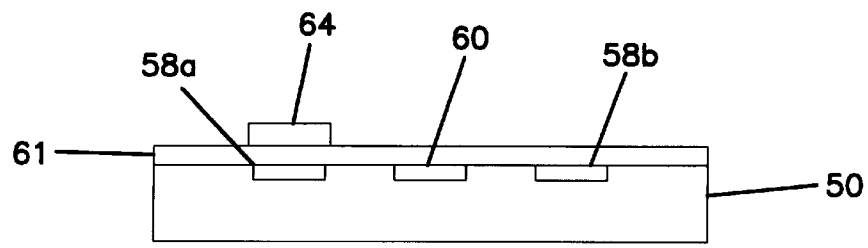
FIG. 4A is a cross-sectional view of yet another embodiment of an analyte sensor, according to the invention.

In another embodiment, the sensing layer 64 is not deposited directly on the working electrode 58a. Instead, the sensing layer 64 is spaced apart from the working electrode 58a, as illustrated in FIG. 4A, and separated from the working electrode 58a by a separation layer 61. The separation layer 61 typically includes one or more membranes or films. In addition to separating the working electrode 58a from the sensing layer 64, the separation layer 61 may also act as a mass transport limiting layer or an interferent eliminating layer, as described below.

Typically, a sensing layer 64, which is not in direct contact with the working electrode 58a, includes a catalyst that facilitates a reaction of the analyte. However, this sensing layer 64 typically does not include an electron transfer agent that transfers electrons directly from the working electrode 58a to the analyte, as the sensing layer 64 is spaced apart from the working electrode 58a. One example of this type of sensor is a glucose or lactate sensor which includes an enzyme (e.g., glucose oxidase or lactate oxidase, respectively) in the sensing layer 64. The glucose or lactate reacts with a second compound (e.g., oxygen) in the presence of the enzyme. The second compound is then electrooxidized or electroreduced at the electrode. Changes in the signal at the electrode indicate changes in the level of the second compound in the fluid and are proportional to changes in glucose or lactate level and, thus, correlate to the analyte level.

Figure 4B:
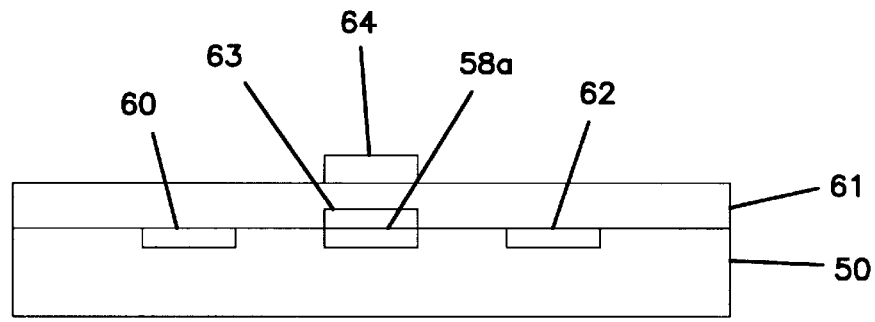
FIG. 4B is a cross-sectional view of a fourth embodiment of an analyte sensor, according to the invention.
Figure 5:
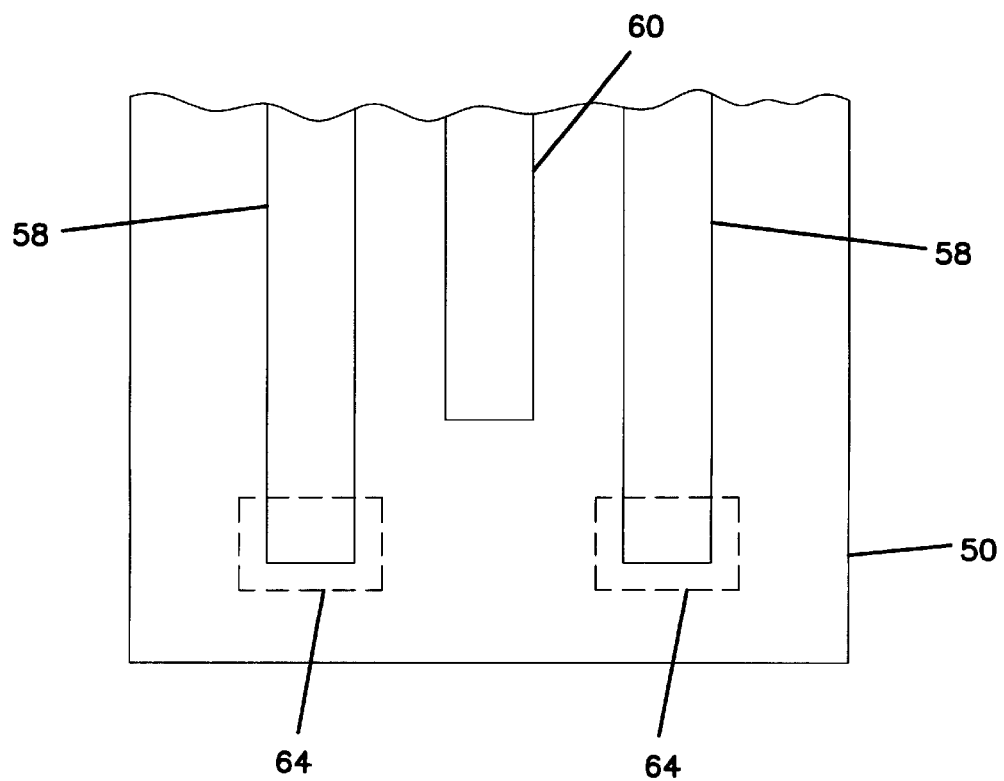
FIG. 5 is an expanded top view of a tip portion of the analyte sensor of FIG. 2.

In another embodiment, two sensing layers 63, 64 are used, as shown in FIG. 4B. Each of the two sensing layers 63, 64 may be independently formed on the working electrode 58a or in proximity to the working electrode 58a. One sensing layer 64 is typically, although not necessarily, spaced apart from the working electrode 58a. For example, this sensing layer 64 may include a catalyst which catalyzes a reaction of the analyte to form a product compound. The product compound is then electrolyzed in the second sensing layer 63 which may include an electron transfer agent to transfer electrons between the working electrode 58a and the product compound and/or a second catalyst to catalyze a reaction of the product compound to generate a signal at the working electrode 58a.

For example, a glucose or lactate sensor may include a first sensing layer 64 which is spaced apart from the working electrode and contains an enzyme, for example, glucose oxidase or lactate oxidase. The reaction of glucose or lactate in the presence of the appropriate enzyme forms hydrogen peroxide. A second sensing layer 63 is provided directly on the working electrode 58a and contains a peroxidase enzyme and an electron transfer agent to generate a signal at the electrode in response to the hydrogen peroxide. The level of hydrogen peroxide indicated by the sensor then correlates to the level of glucose or lactate. Another sensor which operates similarly can be made using a single sensing layer with both the glucose or lactate oxidase and the peroxidase being deposited in the single sensing layer. Examples of such sensors are described in U.S. Pat. No. 5,593,852, U.S. patent application Ser. No. 08/540,789, and PCT Patent application Ser. No. PCT/US98/02403, incorporated herein by reference.

In some embodiments, one or more of the working electrodes 58b do not have a corresponding sensing layer 64, as shown in FIGS. 3A and 4A, or have a sensing layer (not shown) which does not contain one or more components (e.g., an electron transfer agent or catalyst) needed to electrolyze the analyte. The signal generated at this working electrode 58b typically arises from interferents and other sources, such as ions, in the fluid, and not in response to the analyte (because the analyte is not electrooxidized or electroreduced). Thus, the signal at this working electrode 58b corresponds to a background signal. The background signal can be removed from the analyte signal obtained from other working electrodes 58a that are associated with fully-functional sensing layers 64 by, for example, subtracting the signal at working electrode 58b from the signal at working electrode 58a.

Sensors having multiple working electrodes 58a may also be used to obtain more precise results by averaging the signals or measurements generated at these working electrodes 58a. In addition, multiple readings at a single working electrode 58a or at multiple working electrodes may be averaged to obtain more precise data.

Electron Transfer Agent

In many embodiments, the sensing layer 64 contains one or more electron transfer agents in contact with the conductive material 56 of the working electrode 58, as shown in FIGS. 3A and 3B. In some embodiments, it is acceptable for the electron transfer agent to diffuse or leach away from the working electrode, particularly for in vitro sensors 42 that are used only once. Other in vitro sensors may utilize a carrier fluid which contains the electron transfer agent. The analyte is transferred to the carrier fluid from the original sample fluid by, for example, osmotic flow through a microporous membrane or the like.

In yet other embodiments of the invention, there is little or no leaching of the electron transfer agent away from the working electrode 58 during the period in which the sensor 42 is implanted in the patient or measuring an in vitro analyte-containing sample. A diffusing or leachable (i.e., releasable) electron transfer agent often diffuses into the analyte-containing fluid, thereby reducing the effectiveness of the electrode by reducing the sensitivity of the sensor over time. In addition, a diffusing or leaching electron transfer agent in an implantable sensor 42 may also cause damage to the patient. In these embodiments, preferably, at least 90%, more preferably, at least 95%, and, most preferably, at least 99%, of the electron transfer agent remains disposed on the sensor after immersion in the analyte-containing fluid for 24 hours, and, more preferably, for 72 hours. In particular, for an implantable sensor, preferably, at least 90%, more preferably, at least 95%, and most preferably, at least 99%, of the electron transfer agent remains disposed on the sensor after immersion in the body fluid at 37° C. for 24 hours, and, more preferably, for 72 hours.

In some embodiments of the invention, to prevent leaching, the electron transfer agents are bound or otherwise immobilized on the working electrode 58 or between or within one or more membranes or films disposed over the working electrode 58. The electron transfer agent may be immobilized on the working electrode 58 using, for example, a polymeric or sol-gel immobilization technique. Alternatively, the electron transfer agent may be chemically (e.g., ionically, covalently, or coordinatively) bound to the working electrode 58, either directly or indirectly through another molecule, such as a polymer, that is in turn bound to the working electrode 58.

Application of the sensing layer 64 on a working electrode 58a is one method for creating a working surface for the working electrode 58a, as shown in FIGS. 3A and 3B. The electron transfer agent mediates the transfer of electrons to electrooxidize or electroreduce an analyte and thereby permits a current flow between the working electrode 58 and the counter electrode 60 via the analyte. The mediation of the electron transfer agent facilitates the electrochemical analysis of analytes which are not suited for direct electrochemical reaction on an electrode.

In general, the preferred electron transfer agents are electroreducible and electrooxidizable ions or molecules having redox potentials that are a few hundred millivolts above or below the redox potential of the standard calomel electrode (SCE). Preferably, the electron transfer agents are not more reducing than about −150 mV and not more oxidizing than about +400 mV versus SCE.

The electron transfer agent may be organic, organometallic, or inorganic. Examples of organic redox species are quinones and species that in their oxidized state have quinoid structures, such as Nile blue and indophenol. Some quinones and partially oxidized quinhydrones react with functional groups of proteins such as the thiol groups of cysteine, the amine groups of lysine and arginine, and the phenolic groups of tyrosine which may render those redox species unsuitable for some of the sensors of the present invention because of the presence of the interfering proteins in an analyte-containing fluid. Usually substituted quinones and molecules with quinoid structure are less reactive with proteins and are preferred. A preferred tetrasubstituted quinone usually has carbon atoms in positions 1, 2, 3, and 4.

In general, electron transfer agents suitable for use in the invention have structures or charges which prevent or substantially reduce the diffusional loss of the electron transfer agent during the period of time that the sample is being analyzed. The preferred electron transfer agents include a redox species bound to a polymer which can in turn be immobilized on the working electrode. The bond between the redox species and the polymer may be covalent, coordinative, or ionic. Useful electron transfer agents and methods for producing them are described in U.S. Pat. Nos. 5,264,104; 5,356,786; 5,262,035; and 5,320,725, incorporated herein by reference. Although any organic or organometallic redox species can be bound to a polymer and used as an electron transfer agent, the preferred redox species is a transition metal compound or complex. The preferred transition metal compounds or complexes include osmium, ruthenium, iron, and cobalt compounds or complexes. The most preferred are osmium compounds and complexes. It will be recognized that many of the redox species described below may also be used, typically without a polymeric component, as electron transfer agents in a carrier fluid or in a sensing layer of a sensor where leaching of the electron transfer agent is acceptable.

One type of non-releasable polymeric electron transfer agent contains a redox species covalently bound in a polymeric composition. An example of this type of mediator is poly(vinylferrocene).

Another type of non-releasable electron transfer agent contains an ionically-bound redox species. Typically, this type of mediator includes a charged polymer coupled to an oppositely charged redox species. Examples of this type of mediator include a negatively charged polymer such as Nafion® (Dupont) coupled to a positively charged redox species such as an osmium or ruthenium polypyridyl cation. Another example of an ionically-bound mediator is a positively charged polymer such as quaternized poly(4-vinyl pyridine) or poly(1-vinyl imidazole) coupled to a negatively charged redox species such as ferricyanide or ferrocyanide. The preferred ionically-bound redox species is a highly charged redox species bound within an oppositely charged redox polymer.

In another embodiment of the invention, suitable non-releasable electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

The preferred electron transfer agents are osmium transition metal complexes with one or more ligands, each ligand having a nitrogen-containing heterocycle such as 2,2'-bipyridine, 1,10-phenanthroline, or derivatives thereof. Furthermore, the preferred electron transfer agents also have one or more ligands covalently bound in a polymer, each ligand having at least one nitrogen-containing heterocycle, such as pyridine, imidazole, or derivatives thereof. These preferred electron transfer agents exchange electrons rapidly between each other and the working electrodes 58 so that the complex can be rapidly oxidized and reduced.

One example of a particularly useful electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Preferred derivatives of 2,2'-bipyridine for complexation with the osmium cation are 4,4'-dimethyl-2,2'-bipyridine and mono-, di-, and polyalkoxy-2,2'-bipyridines, such as 4,4'-dimethoxy-2,2'-bipyridine. Preferred derivatives of 1,10-phenanthroline for complexation with the osmium cation are 4,7-dimethyl-1,10-phenanthroline and mono, di-, and polyalkoxy- 1,10-phenanthrolines, such as 4,7-dimethoxy- 1,10-phenanthroline. Preferred polymers for complexation with the osmium cation include polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole. Most preferred are electron transfer agents with osmium complexed to a polymer or copolymer of poly(1-vinyl imidazole).

The preferred electron transfer agents have a redox potential ranging from −100 mV to about +150 mV versus the standard calomel electrode (SCE). Preferably, the potential of the electron transfer agent ranges from −100 mV to +150 mV and more preferably, the potential ranges from −50 mV to +50 mV. The most preferred electron transfer agents have osmium redox centers and a redox potential ranging from +50 mV to −150 mV versus SCE.

Catalyst

The sensing layer 64 may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, such as a glucose oxidase, glucose dehydrogenase (e.g., pyrroloquinoline quinone glucose dehydrogenase (PQQ)), or oligosaccharide dehydrogenase, may be used when the analyte is glucose. A lactate oxidase or lactate dehydrogenase may be used when the analyte is lactate. Laccase may be used when the analyte is oxygen or when oxygen is generated or consumed in response to a reaction of the analyte.

Preferably, the catalyst is non-leachably disposed on the sensor, whether the catalyst is part of a solid sensing layer in the sensor or solvated in a fluid within the sensing layer. More preferably, the catalyst is immobilized within the sensor (e.g., on the electrode and/or within or between a membrane or film) to prevent unwanted leaching of the catalyst away from the working electrode 58 and into the patient. This may be accomplished, for example, by attaching the catalyst to a polymer, cross linking the catalyst with another electron transfer agent (which, as described above, can be polymeric), and/or providing one or more barrier membranes or films with pore sizes smaller than the catalyst.

As described above, a second catalyst may also be used. This second catalyst is often used to catalyze a reaction of a product compound resulting from the catalyzed reaction of the analyte. The second catalyst typically operates with an electron transfer agent to electrolyze the product compound to generate a signal at the working electrode. Alternatively, the second catalyst may be provided in an interferent-eliminating layer to catalyze reactions that remove interferents, as described below.

One embodiment of the invention is an electrochemical sensor in which the catalyst is mixed or dispersed in the conductive material 56 which forms the conductive trace 52 of a working electrode 58. This may be accomplished, for example, by mixing a catalyst, such as an enzyme, in a carbon ink and applying the mixture into a channel 54 on the surface of the substrate 50. Preferably, the catalyst is immobilized in the channel 53 so that it can not leach away from the working electrode 58. This may be accomplished, for example, by curing a binder in the carbon ink using a curing technique appropriate to the binder. Curing techniques include, for example, evaporation of a solvent or dispersant, exposure to ultraviolet light, or exposure to heat. Typically, the mixture is applied under conditions that do not substantially degrade the catalyst. For example, the catalyst may be an enzyme that is heat-sensitive. The enzyme and conductive material mixture should be applied and cured, preferably, without sustained periods of heating. The mixture may be cured using evaporation or UV curing techniques or by the exposure to heat that is sufficiently short that the catalyst is not substantially degraded.

Another consideration for in vivo analyte sensors is the thermostability of the catalyst. Many enzymes have only limited stability at biological temperatures. Thus, it may be necessary to use large amounts of the catalyst and/or use a catalyst that is thermostable at the necessary temperature (e.g., 37° C. or higher for normal body temperature). A thermostable catalyst may be defined as a catalyst which loses less than 5% of its activity when held at 37° C. for at least one hour, preferably, at least one day, and more preferably at least three days. One example of a thermostable catalyst is soybean peroxidase. This particular thermostable catalyst may be used in a glucose or lactate sensor when combined either in the same or separate sensing layers with glucose or lactate oxidase or dehydrogenase. A further description of thermostable catalysts and their use in electrochemical inventions is found in U.S. Pat. No. 5,665,222 U.S. patent application Ser. No. 08/540,789, and PCT application Ser. No. PCT/US98/02403.

Electrolysis of the Analyte

To electrolyze the analyte, a potential (versus a reference potential) is applied across the working and counter electrodes 58, 60. The minimum magnitude of the applied potential is often dependent on the particular electron transfer agent, analyte (if the analyte is directly electrolyzed at the electrode), or second compound (if a second compound, such as oxygen or hydrogen peroxide, whose level is dependent on the analyte level, is directly electrolyzed at the electrode). The applied potential usually equals or is more oxidizing or reducing, depending on the desired electrochemical reaction, than the redox potential of the electron transfer agent, analyte, or second compound, whichever is directly electrolyzed at the electrode. The potential at the working electrode is typically large enough to drive the electrochemical reaction to or near completion.

The magnitude of the potential may optionally be limited to prevent significant (as determined by the current generated in response to the analyte) electrochemical reaction of interferents, such as urate, ascorbate, and acetaminophen. The limitation of the potential may be obviated if these interferents have been removed in another way, such as by providing an interferent-limiting barrier, as described below, or by including a working electrode 58b (see FIG. 3A) from which a background signal may be obtained.

When a potential is applied between the working electrode 58 and the counter electrode 60, an electrical current will flow. The current is a result of the electrolysis of the analyte or a second compound whose level is affected by the analyte. In one embodiment, the electrochemical reaction occurs via an electron transfer agent and the optional catalyst. Many analytes B are oxidized (or reduced) to products C by an electron transfer agent species A in the presence of an appropriate catalyst (e.g., an enzyme). The electron transfer agent A is then oxidized (or reduced) at the electrode. Electrons are collected by (or removed from) the electrode and the resulting current is measured. This process is illustrated by reaction equations (1) and (2) (similar equations may be written for the reduction of the analyte B by a redox mediator A in the presence of a catalyst):

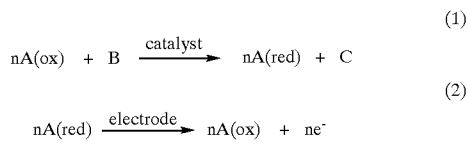

As an example, an electrochemical sensor may be based on the reaction of a glucose molecule with two non-leachable ferricyanide anions in the presence of glucose oxidase to produce two non-leachable ferrocyanide anions, two hydrogen ions, and gluconolactone. The amount of glucose present is assayed by electrooxidizing the non-leachable ferrocyanide anions to non-leachable ferricyanide anions and measuring the current.

In another embodiment, a second compound whose level is affected by the analyte is electrolyzed at the working electrode. In some cases, the analyte D and the second compound, in this case, a reactant compound E, such as oxygen, react in the presence of the catalyst, as shown in reaction equation (3).

$$D + E \xrightarrow{\text{catalyst}} F + G \qquad (3)$$

The reactant compound E is then directly oxidized (or reduced) at the working electrode, as shown in reaction equation (4)

$$nE(\text{red}) \xrightarrow{\text{electrode}} nE(\text{ox}) + ne^- \qquad (4)$$

Alternatively, the reactant compound E is indirectly oxidized (or reduced) using an electron transfer agent H (optionally in the presence of a catalyst), that is subsequently reduced or oxidized at the electrode, as shown in reaction equations (5) and (6).

$$nH(\text{ox}) + E \longrightarrow nH(\text{red}) + I \qquad (5)$$

$$nH(\text{red}) \xrightarrow{\text{electrode}} nH(\text{ox}) + ne^- \qquad (6)$$

In either case, changes in the concentration of the reactant compound, as indicated by the signal at the working electrode, correspond inversely to changes in the analyte (i.e., as the level of analyte increase then the level of reactant compound and the signal at the electrode decreases.)

In other embodiments, the relevant second compound is a product compound F, as shown in reaction equation (3). The product compound F is formed by the catalyzed reaction of analyte D and then be directly electrolyzed at the electrode or indirectly electrolyzed using an electron transfer agent and, optionally, a catalyst. In these embodiments, the signal arising from the direct or indirect electrolysis of the product compound F at the working electrode corresponds directly to the level of the analyte (unless there are other sources of the product compound). As the level of analyte increases, the level of the product compound and signal at the working electrode increases.

Those skilled in the art will recognize that there are many different reactions that will achieve the same result; namely the electrolysis of an analyte or a compound whose level depends on the level of the analyte. Reaction equations (1) through (6) illustrate non-limiting examples of such reactions.

Temperature Probe

A variety of optional items may be included in the sensor. One optional item is a temperature probe 66 (FIGS. 8 and 11). The temperature probe 66 may be made using a variety of known designs and materials. One exemplary temperature probe 66 is formed using two probe leads 68, 70 connected to each other through a temperature-dependent element 72 that is formed using a material with a temperature-dependent characteristic. An example of a suitable temperature-dependent characteristic is the resistance of the temperature-dependent element 72.

The two probe leads 68, 70 are typically formed using a metal, an alloy, a semimetal, such as graphite, a degenerate or highly doped semiconductor, or a small-band gap semiconductor. Examples of suitable materials include gold, silver, ruthenium oxide, titanium nitride, titanium dioxide, indium doped tin oxide, tin doped indium oxide, or graphite. The temperature-dependent element 72 is typically made using a fine trace (e.g., a conductive trace that has a smaller cross-section than that of the probe leads 68, 70) of the same conductive material as the probe leads, or another material such as a carbon ink, a carbon fiber, or platinum, which has a temperature-dependent characteristic, such as resistance, that provides a temperature-dependent signal when a voltage source is attached to the two probe leads 68, 70 of the temperature probe 66. The temperature-dependent characteristic of the temperature-dependent element 72 may either increase or decrease with temperature. Preferably, the temperature dependence of the characteristic of the temperature-dependent element 72 is approximately linear with temperature over the expected range of biological temperatures (about 25 to 45° C.), although this is not required.

Typically, a signal (e.g., a current) having an amplitude or other property that is a function of the temperature can be obtained by providing a potential across the two probe leads 68, 70 of the temperature probe 66. As the temperature changes, the temperature-dependent characteristic of the temperature-dependent element 72 increases or decreases with a corresponding change in the signal amplitude. The signal from the temperature probe 66 (e.g., the amount of current flowing through the probe) may be combined with the signal obtained from the working electrode 58 by, for example, scaling the temperature probe signal and then adding or subtracting the scaled temperature probe signal from the signal at the working electrode 58. In this manner, the temperature probe 66 can provide a temperature adjustment for the output from the working electrode 58 to offset the temperature dependence of the working electrode 58.

One embodiment of the temperature probe includes probe leads 68, 70 formed as two spaced-apart channels with a temperature-dependent element 72 formed as a cross-channel connecting the two spaced-apart channels, as illustrated in FIG. 8. The two spaced-apart channels contain a conductive material, such as a metal, alloy, semimetal, degenerate semiconductor, or metallic compound. The cross-channel may contain the same material (provided the cross-channel has a smaller cross-section than the two spaced-apart channels) as the probe leads 68, 70. In other embodiments, the material in the cross-channel is different than the material of the probe leads 68, 70.

One exemplary method for forming this particular temperature probe includes forming the two spaced-apart channels and then filling them with the metallic or alloyed conductive material. Next, the cross-channel is formed and then filled with the desired material. The material in the cross-channel overlaps with the conductive material in each of the two spaced-apart channels to form an electrical connection.

For proper operation of the temperature probe 66, the temperature-dependent element 72 of the temperature probe 66 can not be shorted by conductive material formed between the two probe leads 68, 70. In addition, to prevent conduction between the two probe leads 68, 70 by ionic species within the body or sample fluid, a covering may be provided over the temperature-dependent element 72, and preferably over the portion of the probe leads 68, 70 that is implanted in the patient. The covering may be, for example, a non-conducting film disposed over the temperature-dependent element 72 and probe leads 68, 70 to prevent the ionic conduction. Suitable non-conducting films include, for example, Kapton™ polyimide films (DuPont, Wilmington, Del.).

Another method for eliminating or reducing conduction by ionic species in the body or sample fluid is to use an ac voltage source connected to the probe leads 68, 70. In this way, the positive and negative ionic species are alternately attracted and repelled during each half cycle of the ac voltage. This results in no net attraction of the ions in the body or sample fluid to the temperature probe 66. The maximum amplitude of the ac current through the temperature-dependent element 72 may then be used to correct the measurements from the working electrodes 58.

The temperature probe can be placed on the same substrate as the electrodes. Alternatively, a temperature probe may be placed on a separate substrate. In addition, the temperature probe may be used by itself or in conjunction with other devices.

Biocompatible Layer

Figure 9:
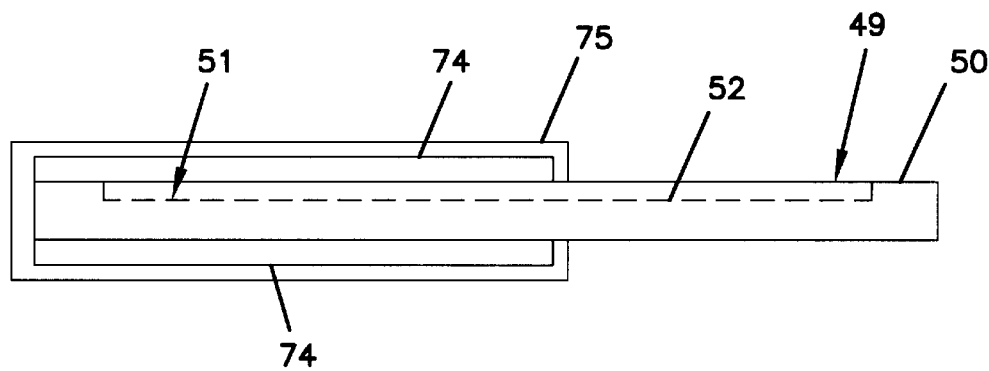
FIG. 9 is a side view of the analyte sensor of FIG. 2.

An optional film layer 75 is formed over at least that portion of the sensor 42 which is subcutaneously inserted into the patient, as shown in FIG. 9. This optional film layer 74 may serve one or more functions. The film layer 74 prevents the penetration of large biomolecules into the electrodes. This is accomplished by using a film layer 74 having a pore size that is smaller than the biomolecules that are to be excluded. Such biomolecules may foul the electrodes and/or the sensing layer 64 thereby reducing the effectiveness of the sensor 42 and altering the expected signal amplitude for a given analyte concentration. The fouling of the working electrodes 58 may also decrease the effective life of the sensor 42. The biocompatible layer 74 may also prevent protein adhesion to the sensor 42, formation of blood clots, and other undesirable interactions between the sensor 42 and body.

For example, the sensor may be completely or partially coated on its exterior with a biocompatible coating. A preferred biocompatible coating is a hydrogel which contains at least 20 wt. % fluid when in equilibrium with the analyte-containing fluid. Examples of suitable hydrogels are described in U.S. Pat. No. 5,593,852, incorporated herein by reference, and include crosslinked polyethylene oxides, such as polyethylene oxide tetraacrylate.

Interferent-Eliminating Layer

An interferent-eliminating layer (not shown) may be included in the sensor 42. The interferent-eliminating layer may be incorporated in the biocompatible layer 75 or in the mass transport limiting layer 74 (described below) or may be a separate layer. Interferents are molecules or other species that are electroreduced or electrooxidized at the electrode, either directly or via an electron transfer agent, to produce a false signal. In one embodiment, a film or membrane prevents the penetration of one or more interferents into the region around the working electrodes 58. Preferably, this type of interferent-eliminating layer is much less permeable to one or more of the interferents than to the analyte.

The interferent-eliminating layer may include ionic components, such as Nafion®, incorporated into a polymeric matrix to reduce the permeability of the interferent-eliminating layer to ionic interferents having the same charge as the ionic components. For example, negatively charged compounds or compounds that form negative ions may be incorporated in the interferent-eliminating layer to reduce the permeation of negative species in the body or sample fluid.

Another example of an interferent-eliminating layer includes a catalyst for catalyzing a reaction which removes interferents. One example of such a catalyst is a peroxidase. Hydrogen peroxide reacts with interferents, such as acetaminophen, urate, and ascorbate. The hydrogen peroxide may be added to the analyte-containing fluid or may be generated in situ, by, for example, the reaction of glucose or lactate in the presence of glucose oxidase or lactate oxidase, respectively. Examples of interferent eliminating layers include a peroxidase enzyme crosslinked (a) using gluteraldehyde as a crosslinking agent or (b) oxidation of oligosaccharide groups in the peroxidase glycoenzyme with $NaIO_4$, followed by coupling of the aldehydes formed to hydrazide groups in a polyacrylamide matrix to form hydrazones are describe in U.S. Pat. Nos. 5,262,305 and 5,356,786, incorporated herein by reference.

Mass Transport Limiting Layer

A mass transport limiting layer 74 may be included with the sensor to act as a diffusion-limiting barrier to reduce the rate of mass transport of the analyte, for example, glucose or lactate, into the region around the working electrodes 58. By limiting the diffusion of the analyte, the steady state concentration of the analyte in the proximity of the working electrode 58 (which is proportional to the concentration of the analyte in the body or sample fluid) can be reduced. This extends the upper range of analyte concentrations that can still be accurately measured and may also expand the range in which the current increases approximately linearly with the level of the analyte.

It is preferred that the permeability of the analyte through the film layer 74 vary little or not at all with temperature, so as to reduce or eliminate the variation of current with temperature. For this reason, it is preferred that in the biologically relevant temperature range from about 25° C. to about 45° C., and most importantly from 30° C. to 40° C., neither the size of the pores in the film nor its hydration or swelling change excessively. Preferably, the mass transport limiting layer is made using a film that absorbs less than 5 wt. % of fluid over 24 hours. This may reduce or obviate any need for a temperature probe. For implantable sensors, it is preferable that the mass transport limiting layer is made using a film that absorbs less than 5 wt. % of fluid over 24 hours at 37° C.

Particularly useful materials for the film layer 74 are membranes that do not swell in the analyte-containing fluid that the sensor tests. Suitable membranes include 3 to 20,000 nm diameter pores. Membranes having 5 to 500 nm diameter pores with well-defined, uniform pore sizes and high aspect ratios are preferred. In one embodiment, the aspect ratio of the pores is preferably two or greater and more preferably five or greater.

Well-defined and uniform pores can be made by track etching a polymeric membrane using accelerated electrons, ions, or particles emitted by radioactive nuclei. Most preferred are anisotropic, polymeric, track etched membranes that expand less in the direction perpendicular to the pores than in the direction of the pores when heated. Suitable polymeric membranes included polyearbonate membranes from Poretics (Livermore, Calif., catalog number 19401, 0.01 μm pore size polycarbonate membrane) and Corning Costar Corp. (Cambridge, Mass., Nucleopore™ brand membranes with 0.015 μm pore size). Other polyolefin and polyester films may be used. It is preferred that the permeability of the mass transport limiting membrane changes no more than 4%, preferably, no more than 3%, and, more preferably, no more than 2%, per °C. in the range from 30° C. to 40° C. when the membranes resides in the subcutaneous interstitial fluid.

In some embodiments of the invention, the mass transport limiting layer 74 may also limit the flow of oxygen into the sensor 42. This can improve the stability of sensors 42 that are used in situations where variation in the partial pressure of oxygen causes non-linearity in sensor response. In these embodiments, the mass transport limiting layer 74 restricts oxygen transport by at least 40%, preferably at least 60%, and more preferably at least 80%, than the membrane restricts transport of the analyte. For a given type of polymer, films having a greater density (e.g., a density closer to that of the crystalline polymer) are preferred. Polyesters, such as polyethylene terephthalate, are typically less permeable to oxygen and are, therefore, preferred over polycarbonate membranes.

Anticlotting agent

An implantable sensor may also, optionally, have an anticlotting agent disposed on a portion the substrate which is implanted into a patient. This anticlotting agent may reduce or eliminate the clotting of blood or other body fluid around the sensor, particularly after insertion of the sensor. Blood clots may foul the sensor or irreproducibly reduce the amount of analyte which diffuses into the sensor. Examples of useful anticlotting agents include heparin and tissue plasminogen activator (TPA), as well as other known anticlotting agents.

The anticlotting agent may be applied to at least a portion of that part of the sensor 42 that is to be implanted. The anticlotting agent may be applied, for example, by bath, spraying, brushing, or dipping. The anticlotting agent is allowed to dry on the sensor 42. The anticlotting agent may be immobilized on the surface of the sensor or it may be allowed to diffuse away from the sensor surface. Typically, the quantities of anticlotting agent disposed on the sensor are far below the amounts typically used for treatment of medical conditions involving blood clots and, therefore, have only a limited, localized effect.

Sensor Lifetime

The sensor 42 may be designed to be a replaceable component in an in vivo or in vitro analyte monitor, and particularly in an implantable analyte monitor. Typically, the sensor 42 is capable of operation over a period of days. Preferably, the period of operation is at least one day, more preferably at least three days, and most preferably at least one week. The sensor 42 can then be removed and replaced with a new sensor. The lifetime of the sensor 42 may be reduced by the fouling of the electrodes or by the leaching of the electron transfer agent or catalyst. These limitations on the longevity of the sensor 42 can be overcome by the use of a biocompatible layer 75 or non-leachable electron transfer agent and catalyst, respectively, as described above.

Another primary limitation on the lifetime of the sensor 42 is the temperature stability of the catalyst. Many catalysts are enzymes, which are very sensitive to the ambient temperature and may degrade at temperatures of the patient's body (e.g., approximately 37° C. for the human body). Thus, robust enzymes should be used where available. The sensor 42 should be replaced when a sufficient amount of the enzyme has been deactivated to introduce an unacceptable amount of error in the measurements.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. The claims are intended to cover such modifications and devices.

We claim:

1. An analyte responsive electrochemical sensor comprising a working electrode and a mass transport limiting membrane, which mass transport limiting membrane maintains a rate of permeation of the analyte through the mass transport limiting membrane with a variation of no more than 3% per ° C. at temperatures ranging from 30° C. to 40° C.

2. The electrochemical sensor of claim 1, wherein a rate of permeation of the analyte through the mass transport limiting layer varies by no more than 1% per °C. for temperatures ranging from 30° C. to 40° C.

3. The electrochemical sensor of claim 1, wherein the mass transport limiting layer comprises a membrane having a plurality of track etched pores.

4. The electrochemical sensor of claim 1, wherein the mass transport limiting layer absorbs 5 wt. % or less of water at 37° C. when in contact with interstitial fluid for 24 hours.

5. An electrochemical sensor, comprising:
a substrate; and
a working electrode disposed on the substrate, the working electrode comprising a carbon material and having a width along at least a portion of the working electrode of 150 µm or less.

6. The electrochemical sensor of claim 5, further comprising a catalyst for catalyzing a reaction of an analyte, the catalyst being disposed proximate to the working electrode.

7. The electrochemical sensor of claim 6, wherein the catalyst is disposed on the working electrode.

8. The electrochemical sensor of claim 6, further comprising an electron transfer agent disposed on the working electrode.

9. The electrochemical sensor of claim 8, wherein at least a portion of the catalyst is in contact with the electron transfer agent.

10. The electrochemical sensor of claim 6, wherein the catalyst is nonleachably disposed within the electrochemical sensor.

11. The electrochemical sensor of claim 6, wherein the catalyst is immobilized within the electrochemical sensor.

12. The electrochemical sensor of claim 6, wherein the catalyst comprises an enzyme.

13. The electrochemical sensor of claim 12, wherein the enzyme is an oxidase or a dehydrogenase.

14. The electrochemical sensor of claim 13, wherein the analyte is glucose and the enzyme is oligosaccharide dehydrogenase, PQQ-glucose dehydrogenase, or glucose oxidase.

15. The electrochemical sensor of claim 6, further comprising a second catalyst for catalyzing a reaction of a product compound formed in the reaction of the analyte.

16. The electrochemical sensor of claim 15, wherein the product compound comprises hydrogen peroxide and the second catalyst comprises a peroxidase.

17. The electrochemical sensor of claim 5, wherein the substrate is flexible.

18. The electrochemical sensor of claim 5, wherein a width along at least a portion of the working electrode is 75 µm or less.

19. The electrochemical sensor of claim 5, wherein a width along at least a portion of the working electrode is 25 µm or less.

20. The electrochemical sensor of claim 5, wherein the substrate is flexible.

21. The electrochemical sensor of claim 5, further comprising a second electrode disposed next to the working electrode, the second electrode and working electrode being disposed 150 µm or less apart.

22. The electrochemical sensor of claim 5, wherein the working electrode is disposed in a recessed channel formed on a surface of the substrate.

23. The electrochemical sensor of claim 5, wherein the working electrode is formed by transferring, to the substrate, carbon material electrically attracted to a drum in an image of the working electrode.

24. The electrochemical sensor of claim 5, wherein the working electrode is formed by transferring, to the substrate, carbon material magnetically attracted to a drum in an image of the working electrode.

25. The electrochemical sensor of claim 5, wherein the working electrode is formed by transferring the carbon material from a film onto the substrate using a print head.

26. The electrochemical sensor of claim 5, wherein the working electrode is formed by ejecting carbon material onto the substrate.

27. The electrochemical sensor of claim 5, wherein the working electrode is formed by depositing a curable coating on the substrate, curing portions of the curable coating to form a channel, and depositing carbon material in the channel to form the working electrode.

28. An electrochemical sensor, comprising:

a substrate;

a conductive material disposed on the substrate to form a working electrode;

catalyst dispersed in the conductive material, the catalyst catalyzing a reaction of the analyte to generate a signal at the working electrode; and a binder dispersed in the conductive material wherein the binder is cured so that the catalyst and conductive material are non-leachably disposed on the substrate.

29. An implantable electrochemical sensor, comprising:

a substrate having a longitudinal axis with a narrow distal region that is configured and arranged for implantation into an animal and a wider proximal region that extends in a single lateral direction from the longitudinal axis;

at least one working electrode disposed on the narrow distal region of the substrate; and at least one contact pad disposed on the wider proximal region of the substrate and in electrical communication with a one of the at least one working electrodes.

\* \* \* \* \*

UNITED STATES PATENT AND TRADEMARK OFFICE
CERTIFICATE OF CORRECTION

PATENT NO. : 6,134,461
DATED : October 17, 2000
INVENTOR(S) : Say et al.

It is certified that error appears in the above-identified patent and that said Letters Patent is hereby corrected as shown below:

On the title page, should be changed as follows: "Electrochemical Analyte" should read --ELECTRCHEMICAL ANALYTE SENSOR--.

Assignee should be changed as follows: "E. Heller & Company" should read-- TheraSense, Inc., Alameda, Calif.--

Signed and Sealed this

Twenty-ninth Day of May, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO. : 6,134,461  
DATED : October 17, 2000  
INVENTOR(S) : Say et al.

It is certified that error appears in the above-identified patent and that said Letters Patent is hereby corrected as shown below:

<u>Title page, Item [54] and Column 1, line 1</u>,  
Title, "ELECTRCHEMICAL ANALYTE SENSOR" should read  
-- ELECTROCHEMICAL ANALYTE SENSOR --

Signed and Sealed this

Sixth Day of July, 2004

JON W. DUDAS  
*Acting Director of the United States Patent and Trademark Office*

(12) EX PARTE REEXAMINATION CERTIFICATE (7582nd)
United States Patent
Say et al.

(10) Number: US 6,134,461 C1
(45) Certificate Issued: Jun. 29, 2010

(54) ELECTROCHEMICAL ANALYTE SENSOR

(75) Inventors: James Say, Alameda, CA (US); Michael F. Tomasco, Cupertino, CA (US); Adam Heller, Austin, TX (US); Yoram Gal, Kibbutz Yagur (IL); Behrad Aria, Alameda, CA (US); Ephraim Heller, Oakland, CA (US); Phillip John Plante, Sunnyvale, CA (US); Mark S. Vreeke, Alameda, CA (US)

(73) Assignee: Abbott Diabetes Care, Inc.

Reexamination Request:
No. 90/008,173, Aug. 16, 2006
No. 90/008,928, Nov. 16, 2007

Reexamination Certificate for:
Patent No.: 6,134,461
Issued: Oct. 17, 2000
Appl. No.: 09/034,372
Filed: Mar. 4, 1998

Certificate of Correction issued May 29, 2001.

Certificate of Correction issued Jul. 6, 2004.

(51) Int. Cl.
*C12Q 1/00* (2006.01)
*G01N 33/487* (2006.01)
*A61B 5/05* (2006.01)

(52) U.S. Cl. ...................................... 600/345; 600/309
(58) Field of Classification Search ................... 600/306, 600/308, 309, 352, 345–348, 354, 357, 358, 600/365, 372, 382, 384, 395–397
See application file for complete search history.

(56) References Cited

U.S. PATENT DOCUMENTS

| 498,929 A | 3/1893 | Colby |
|---|---|---|
| 1,564,641 A | 12/1925 | St. James |
| 2,402,306 A | 6/1946 | Turkel |
| 2,755,036 A | 7/1956 | Terho |
| 2,913,998 A | 11/1959 | Lich |
| 3,132,123 A | 5/1964 | Harris Jr., et al. |
| 3,210,578 A | 10/1965 | Sherer |
| 3,219,533 A | 11/1965 | Mullins |
| 3,260,656 A | 7/1966 | Ross, Jr. |
| 3,282,875 A | 11/1966 | Connolly et al. |

(Continued)

FOREIGN PATENT DOCUMENTS

DE 2903216 8/1979

(Continued)

OTHER PUBLICATIONS

US 5,998,179, 12/1999, Lantero et al. (withdrawn)
Shichiri et al. "Wearable Artificial Endocrine Pancreas with Needle–Type Glucose Sensor" The Lancet (Nov. 20, 1982) p. 1129–1131.*
Shichiri et al. "Glycaemic Control in Pancreatectomized Dogs with a Wearable Articficial Endocrine Pancreas" Diabetologia (1983) 24: 179–184.*

(Continued)

*Primary Examiner*—Sara S Clarke

(57) ABSTRACT

An electrochemical analyte sensor formed using conductive traces on a substrate can be used for determining and/or monitoring a level of analyte in in vitro or in vivo analyte-containing fluids. For example, an implantable sensor may be used for the continuous or automatic monitoring of a level of an analyte, such as glucose, lactate, or oxygen, in a patient. The electrochemical analyte sensor includes a substrate and conductive material disposed on the substrate, the conductive material forming a working electrode. In some sensors, the conductive material is disposed in recessed channels formed in a surface of the sensor. An electron transfer agent and/or catalyst may be provided to facilitate the electrolysis of the analyte or of a second compound whose level depends on the level of the analyte. A potential is formed between the working electrode and a reference electrode or counter/reference electrode and the resulting current is a function of the concentration of the analyte in the body fluid.

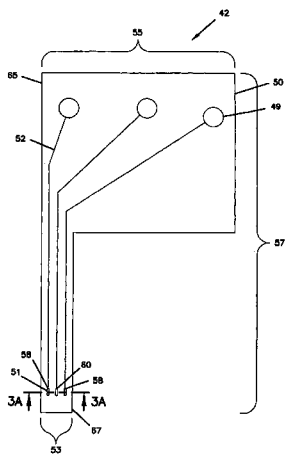

U.S. PATENT DOCUMENTS

| | | | |
|---|---|---|---|
| 3,304,413 A | 2/1967 | Lehmann et al. | |
| 3,310,606 A | 3/1967 | Fritz | |
| 3,397,191 A | 8/1968 | Beckerbauer | |
| 3,581,062 A | 5/1971 | Aston | |
| 3,635,926 A | 1/1972 | Gresham et al. | |
| 3,651,318 A | 3/1972 | Czekajewski | |
| 3,653,841 A | 4/1972 | Klein | |
| 3,698,386 A | 10/1972 | Fried | |
| 3,719,564 A | 3/1973 | Lilly, Jr. et al. | |
| 3,750,687 A | 8/1973 | Williams | |
| 3,768,014 A | 10/1973 | Smith et al. | |
| 3,770,607 A | 11/1973 | Williams | |
| 3,775,182 A | 11/1973 | Palton et al. | |
| 3,776,832 A | 12/1973 | Oswin et al. | |
| 3,785,939 A | 1/1974 | Hsu | |
| 3,826,244 A | 7/1974 | Salcman et al. | |
| 3,837,339 A | 9/1974 | Aisenberg et al. | |
| 3,851,018 A | 11/1974 | Kelly | |
| 3,898,984 A | 8/1975 | Mandel et al. | |
| 3,919,051 A | 11/1975 | Koch et al. | |
| 3,923,060 A | 12/1975 | Ellinwood, Jr. | |
| 3,926,760 A | 12/1975 | Allen et al. | |
| 3,929,971 A | 12/1975 | Roy | |
| 3,930,889 A | 1/1976 | Ruggiero et al. | |
| 3,933,593 A | 1/1976 | Sternberg | |
| 3,943,918 A | 3/1976 | Lewis | |
| 3,949,388 A | 4/1976 | Fuller | |
| 3,964,974 A | 6/1976 | Banauch et al. | |
| 3,966,580 A | 6/1976 | Janata et al. | |
| 3,972,320 A | 8/1976 | Kalman | |
| 3,979,274 A | 9/1976 | Newman | |
| 4,003,379 A | 1/1977 | Ellinwood, Jr. | |
| 4,008,717 A | 2/1977 | Kowarski | |
| 4,016,866 A | 4/1977 | Lawton | |
| 4,018,547 A | 4/1977 | Rogen | |
| 4,024,312 A | 5/1977 | Korpman | |
| 4,032,729 A | 6/1977 | Koistinen | |
| 4,036,749 A | 7/1977 | Anderson | |
| 4,040,908 A | 8/1977 | Clark, Jr. | |
| 4,055,175 A | 10/1977 | Clemens et al. | |
| 4,059,406 A | 11/1977 | Fleet | |
| 4,059,708 A | 11/1977 | Heiss, Jr. et al. | |
| 4,068,536 A | 1/1978 | Stackhouse | |
| 4,073,713 A | 2/1978 | Newman | |
| 4,076,182 A | 2/1978 | Stites | |
| 4,076,596 A | 2/1978 | Connery et al. | |
| 4,076,656 A | 2/1978 | White et al. | |
| 4,098,574 A | 7/1978 | Dappen | |
| 4,100,048 A | 7/1978 | Pompei et al. | |
| 4,101,814 A | 7/1978 | Haferl | |
| 4,120,292 A | 10/1978 | LeBlanc, Jr. et al. | |
| 4,121,282 A | 10/1978 | Ohsawa | |
| 4,129,128 A | 12/1978 | McFarlane | |
| 4,146,029 A | 3/1979 | Ellinwood, Jr. | |
| 4,151,845 A | 5/1979 | Clemens | |
| 4,154,231 A | 5/1979 | Russell | |
| 4,168,205 A | 9/1979 | Danninger et al. | |
| 4,172,770 A | 10/1979 | Semersky et al. | |
| 4,178,916 A | 12/1979 | McNamara | |
| 4,193,982 A | 3/1980 | Avrameas et al. | |
| 4,197,840 A | 4/1980 | Beck et al. | |
| 4,206,755 A | 6/1980 | Klein | |
| 4,215,703 A | 8/1980 | Willson | |
| 4,224,125 A | 9/1980 | Nakamura et al. | |
| 4,240,438 A | 12/1980 | Updike et al. | |
| 4,240,889 A | 12/1980 | Yoda et al. | |
| 4,241,438 A | 12/1980 | Kern | |
| 4,243,752 A | 1/1981 | Skinner et al. | |
| 4,245,634 A | 1/1981 | Albisser et al. | |
| 4,246,343 A | 1/1981 | Wilkins et al. | |
| 4,246,347 A | 1/1981 | Neidleman et al. | |
| 4,247,297 A | 1/1981 | Berti et al. | |
| 4,247,633 A | 1/1981 | Case et al. | |
| 4,247,636 A | 1/1981 | Schoenrock et al. | |
| 4,247,641 A | 1/1981 | Neidleman et al. | |
| 4,247,653 A | 1/1981 | Wagner | |
| 4,247,654 A | 1/1981 | Wagner | |
| 4,248,973 A | 2/1981 | Kallies | |
| 4,252,627 A | 2/1981 | Ohashi et al. | |
| 4,252,722 A | 2/1981 | Melillo et al. | |
| 4,252,903 A | 2/1981 | Kallies | |
| 4,255,500 A | 3/1981 | Hooke | |
| 4,256,832 A | 3/1981 | Findl et al. | |
| 4,259,358 A | 3/1981 | Duthie | |
| 4,259,442 A | 3/1981 | Gayral | |
| 4,259,443 A | 3/1981 | Danehy | |
| 4,259,540 A | 3/1981 | Sabia | |
| 4,260,680 A | 4/1981 | Muramatsu et al. | |
| 4,260,685 A | 4/1981 | Pilipski | |
| 4,260,725 A | 4/1981 | Keogh et al. | |
| 4,262,089 A | 4/1981 | Singh et al. | |
| 4,264,448 A | 4/1981 | Bodenrader | |
| 4,264,728 A | 4/1981 | Wilkins | |
| 4,268,628 A | 5/1981 | Klose et al. | |
| 4,271,001 A | 6/1981 | Imafuku et al. | |
| 4,271,449 A | 6/1981 | Grogan | |
| 4,272,619 A | 6/1981 | Balle et al. | |
| 4,275,225 A | 6/1981 | Krespan | |
| 4,276,379 A | 6/1981 | Heady | |
| 4,279,724 A | 7/1981 | Hearn et al. | |
| 4,282,325 A | 8/1981 | Rubenstein et al. | |
| 4,283,496 A | 8/1981 | Lee | |
| 4,284,722 A | 8/1981 | Tamuri et al. | |
| 4,284,723 A | 8/1981 | Neidleman et al. | |
| 4,284,763 A | 8/1981 | Thelwall et al. | |
| 4,285,841 A | 8/1981 | Barrat et al. | |
| 4,287,034 A | 9/1981 | Pieslak et al. | |
| 4,288,544 A | 9/1981 | Suzuki et al. | |
| 4,288,548 A | 9/1981 | Barrett et al. | |
| 4,290,773 A | 9/1981 | Magers et al. | |
| 4,294,258 A | 10/1981 | Bernard | |
| 4,296,242 A | 10/1981 | Nagabhushan et al. | |
| 4,297,173 A | 10/1981 | Hikuma et al. | |
| 4,298,441 A | 11/1981 | Seidel et al. | |
| 4,299,669 A | 11/1981 | Obana et al. | |
| 4,299,677 A | 11/1981 | Venkatasubramanian et al. | |
| 4,301,310 A | 11/1981 | Wagner | |
| 4,303,408 A | 12/1981 | Kim et al. | |
| 4,304,649 A | 12/1981 | Han et al. | |
| 4,304,854 A | 12/1981 | Nix et al. | |
| 4,305,802 A | 12/1981 | Koshiishi | |
| 4,307,195 A | 12/1981 | Karasawa et al. | |
| 4,308,349 A | 12/1981 | Foley et al. | |
| 4,313,884 A | 2/1982 | Arena | |
| 4,315,309 A | 2/1982 | Coli | |
| 4,316,747 A | 2/1982 | Rugg et al. | |
| 4,317,879 A | 3/1982 | Busby et al. | |
| 4,317,914 A | 3/1982 | Bernauer et al. | |
| 4,318,784 A | 3/1982 | Higgins et al. | |
| 4,318,927 A | 3/1982 | Marshall | |
| 4,318,989 A | 3/1982 | Marshall | |
| 4,321,057 A | 3/1982 | Buckles | |
| 4,322,471 A | 3/1982 | Miyakawa | |
| 4,322,523 A | 3/1982 | Wagner | |
| 4,324,257 A | 4/1982 | Albarda et al. | |
| 4,327,725 A | 5/1982 | Cortese et al. | |
| 4,331,869 A | 5/1982 | Rollo | |
| 4,332,622 A | 6/1982 | Hohnerlein, Jr. et al. | |
| 4,332,893 A | 6/1982 | Rosenberg | |
| 4,332,903 A | 6/1982 | Gong et al. | |
| 4,334,089 A | 6/1982 | Krass et al. | |

| Patent No. | Date | Inventor |
|---|---|---|
| 4,335,208 A | 6/1982 | Norman |
| 4,335,255 A | 6/1982 | Krespan |
| 4,336,028 A | 6/1982 | Tomibe et al. |
| 4,339,242 A | 7/1982 | Magers et al. |
| 4,339,243 A | 7/1982 | Magers et al. |
| 4,340,392 A | 7/1982 | Magers et al. |
| 4,340,393 A | 7/1982 | Magers et al. |
| 4,340,394 A | 7/1982 | Magers et al. |
| 4,340,395 A | 7/1982 | Magers et al. |
| 4,340,448 A | 7/1982 | Schiller et al. |
| 4,340,458 A | 7/1982 | Lerner et al. |
| 4,342,831 A | 8/1982 | Faber et al. |
| 4,344,438 A | 8/1982 | Schultz |
| 4,347,109 A | 8/1982 | Meshbesher |
| 4,348,480 A | 9/1982 | Brownewell |
| 4,349,481 A | 9/1982 | Lischewski et al. |
| 4,349,728 A | 9/1982 | Phillips et al. |
| 4,351,711 A | 9/1982 | Ambler |
| 4,351,937 A | 9/1982 | Stefanska et al. |
| 4,352,884 A | 10/1982 | Nakashima et al. |
| 4,352,960 A | 10/1982 | Dormer et al. |
| 4,353,867 A | 10/1982 | Luzzana |
| 4,353,888 A | 10/1982 | Sefton |
| 4,353,983 A | 10/1982 | Siddiqi |
| 4,354,308 A | 10/1982 | Shimada et al. |
| 4,354,913 A | 10/1982 | Pungor et al. |
| 4,355,105 A | 10/1982 | Lantero, Jr. |
| 4,355,117 A | 10/1982 | Antrim et al. |
| 4,356,074 A | 10/1982 | Johnson |
| 4,356,195 A | 10/1982 | Kahn et al. |
| 4,357,282 A | 11/1982 | Anderson et al. |
| 4,358,464 A | 11/1982 | Soehnlen |
| 4,358,619 A | 11/1982 | Stemmler et al. |
| 4,359,534 A | 11/1982 | Kurtzman et al. |
| 4,360,413 A | 11/1982 | Lee |
| 4,360,530 A | 11/1982 | Bernauer et al. |
| 4,363,671 A | 12/1982 | Rugg et al. |
| 4,364,385 A | 12/1982 | Lossef |
| 4,365,020 A | 12/1982 | Gado et al. |
| 4,365,637 A | 12/1982 | Johnson |
| 4,366,033 A | 12/1982 | Richter et al. |
| 4,366,040 A | 12/1982 | Marsoner et al. |
| 4,368,079 A | 1/1983 | Rugg et al. |
| 4,368,268 A | 1/1983 | Gong |
| 4,372,942 A | 2/1983 | Cimiluca |
| 4,374,013 A | 2/1983 | Enfors |
| 4,375,399 A | 3/1983 | Havas et al. |
| 4,376,023 A | 3/1983 | Venkatsubramanian et al. |
| 4,376,132 A | 3/1983 | Eguchi et al. |
| 4,376,824 A | 3/1983 | Hurst et al. |
| 4,376,825 A | 3/1983 | Rubenstein et al. |
| 4,377,522 A | 3/1983 | Branca et al. |
| 4,377,571 A | 3/1983 | Strobel |
| 4,377,637 A | 3/1983 | Weisrock |
| 4,378,016 A | 3/1983 | Loeb |
| 4,379,171 A | 4/1983 | Furda et al. |
| 4,379,749 A | 4/1983 | Roth |
| 4,379,862 A | 4/1983 | Wagner |
| 4,380,585 A | 4/1983 | Magers et al. |
| 4,380,624 A | 4/1983 | Wiesner et al. |
| 4,381,345 A | 4/1983 | Rohrbach et al. |
| 4,381,921 A | 5/1983 | Pierce et al. |
| 4,382,121 A | 5/1983 | Rohrbach et al. |
| 4,384,586 A | 5/1983 | Christiansen |
| 4,384,936 A | 5/1983 | Obana et al. |
| 4,388,166 A | 6/1983 | Suzuki et al. |
| 4,390,375 A | 6/1983 | Rugg et al. |
| 4,390,621 A | 6/1983 | Bauer |
| 4,392,933 A | 7/1983 | Nakamura et al. |
| 4,393,136 A | 7/1983 | Cheetham |
| 4,394,449 A | 7/1983 | Modrovich |
| 4,396,464 A | 8/1983 | Giner et al. |
| 4,396,520 A | 8/1983 | Payne et al. |
| 4,396,579 A | 8/1983 | Schroeder et al. |
| 4,397,949 A | 8/1983 | Peters et al. |
| 4,399,099 A | 8/1983 | Buckles |
| 4,399,224 A | 8/1983 | Flider et al. |
| 4,400,250 A | 8/1983 | Fairhurst |
| 4,400,467 A | 8/1983 | Bauer et al. |
| 4,401,122 A | 8/1983 | Clark, Jr. |
| 4,402,694 A | 9/1983 | Ash et al. |
| 4,404,066 A | 9/1983 | Johnson |
| 4,406,770 A | 9/1983 | Chan et al. |
| 4,407,288 A | 10/1983 | Langer et al. |
| 4,407,954 A | 10/1983 | Clyde |
| 4,407,955 A | 10/1983 | Muller et al. |
| 4,407,959 A | 10/1983 | Tsuji et al. |
| 4,409,032 A | 10/1983 | Paszner et al. |
| 4,410,627 A | 10/1983 | Lloyd et al. |
| 4,410,710 A | 10/1983 | Berkowitz et al. |
| 4,411,996 A | 10/1983 | Lloyd |
| 4,413,058 A | 11/1983 | Arcuri et al. |
| 4,414,329 A | 11/1983 | Wegner |
| 4,415,666 A | 11/1983 | D'Orazio et al. |
| 4,417,588 A | 11/1983 | Houghton et al. |
| 4,418,148 A | 11/1983 | Oberhardt |
| 4,419,210 A | 12/1983 | Wang |
| 4,420,559 A | 12/1983 | Zimmermann |
| 4,420,564 A | 12/1983 | Tsuji et al. |
| 4,420,566 A | 12/1983 | Jessop et al. |
| 4,423,149 A | 12/1983 | Amon, Jr. et al. |
| 4,423,150 A | 12/1983 | Heady |
| 4,425,920 A | 1/1984 | Bourland et al. |
| 4,426,449 A | 1/1984 | Geigert et al. |
| 4,427,004 A | 1/1984 | Miller |
| 4,427,584 A | 1/1984 | LeGrand et al. |
| 4,427,770 A | 1/1984 | Chen et al. |
| 4,427,778 A | 1/1984 | Zabriskie |
| 4,430,348 A | 2/1984 | Duncombe et al. |
| 4,430,436 A | 2/1984 | Koyama et al. |
| 4,431,004 A | 2/1984 | Bessman et al. |
| 4,431,507 A | 2/1984 | Nankai et al. |
| 4,432,801 A | 2/1984 | Tegiacchi et al. |
| 4,434,232 A | 2/1984 | Tabara |
| 4,436,094 A | 3/1984 | Cerami |
| 4,436,812 A | 3/1984 | Endoh et al. |
| 4,437,954 A | 3/1984 | Sammells et al. |
| 4,437,969 A | 3/1984 | Covington et al. |
| 4,440,175 A | 4/1984 | Wilkins |
| 4,440,620 A | 4/1984 | Ono et al. |
| 4,442,207 A | 4/1984 | Horwath et al. |
| 4,442,841 A | 4/1984 | Uehara et al. |
| 4,443,218 A | 4/1984 | DeCant, Jr. et al. |
| 4,444,794 A | 4/1984 | Whitehurst et al. |
| 4,444,878 A | 4/1984 | Paulus |
| 4,444,892 A | 4/1984 | Malmros |
| 4,445,888 A | 5/1984 | Osterholm |
| 4,447,531 A | 5/1984 | Horwath et al. |
| 4,447,535 A | 5/1984 | Zucker et al. |
| 4,449,480 A | 5/1984 | Ison et al. |
| 4,450,841 A | 5/1984 | Osterholm |
| 4,450,842 A | 5/1984 | Zick et al. |
| 4,451,251 A | 5/1984 | Osterholm |
| 4,451,629 A | 5/1984 | Tanaka et al. |
| 4,452,640 A | 6/1984 | Chen et al. |
| 4,452,682 A | 6/1984 | Takata et al. |
| 4,452,887 A | 6/1984 | Kitajima et al. |
| 4,453,537 A | 6/1984 | Spitzer |
| 4,454,007 A | 6/1984 | Pace |
| 4,458,686 A | 7/1984 | Clark, Jr. |
| 4,460,610 A | 7/1984 | Macfie, Jr. |
| 4,461,691 A | 7/1984 | Frank |

| | | | | | | |
|---|---|---|---|---|---|---|
| 4,461,832 A | 7/1984 | Tschang et al. | | 4,543,331 A | 9/1985 | Sonoyama et al. |
| 4,464,300 A | 8/1984 | Borer et al. | | 4,543,955 A | 10/1985 | Schroeppel |
| 4,467,811 A | 8/1984 | Clark, Jr. | | 4,544,869 A | 10/1985 | Pittaway |
| 4,469,110 A | 9/1984 | Slama | | 4,545,382 A | 10/1985 | Higgins et al. |
| 4,469,565 A | 9/1984 | Hampel | | 4,547,226 A | 10/1985 | Milch et al. |
| 4,472,113 A | 9/1984 | Rogen | | 4,547,280 A | 10/1985 | Karasawa et al. |
| 4,473,530 A | 9/1984 | Villa-Real | | 4,551,430 A | 11/1985 | Hafner |
| 4,473,638 A | 9/1984 | Auditore-Hargreaves | | 4,552,840 A | 11/1985 | Riffer |
| 4,474,777 A | 10/1984 | Cassal et al. | | 4,556,636 A | 12/1985 | Belly et al. |
| 4,476,003 A | 10/1984 | Frank et al. | | 4,559,037 A | 12/1985 | Franetzki et al. |
| 4,476,331 A | 10/1984 | Dubeck et al. | | 4,559,350 A | 12/1985 | Wehinger et al. |
| 4,477,314 A | 10/1984 | Richter et al. | | 4,560,534 A | 12/1985 | Kung et al. |
| 4,478,976 A | 10/1984 | Goertz et al. | | 4,560,655 A | 12/1985 | Baker |
| 4,479,796 A | 10/1984 | Kallok | | 4,560,881 A | 12/1985 | Briggs |
| 4,483,924 A | 11/1984 | Tsuji et al. | | 4,561,443 A | 12/1985 | Hogrefe et al. |
| 4,484,987 A | 11/1984 | Gough | | 4,563,249 A | 1/1986 | Hale |
| 4,486,291 A | 12/1984 | Schindler et al. | | 4,564,432 A | 1/1986 | Nagai et al. |
| 4,487,831 A | 12/1984 | Day et al. | | 4,567,142 A | 1/1986 | Lloyd |
| 4,488,912 A | 12/1984 | Milch et al. | | 4,568,444 A | 2/1986 | Nakamura et al. |
| 4,490,235 A | 12/1984 | Calzi | | 4,568,681 A | 2/1986 | Wehinger et al. |
| 4,490,465 A | 12/1984 | Limbach et al. | | 4,569,589 A | 2/1986 | Neufeld |
| 4,490,473 A | 12/1984 | Brunhouse | | 4,570,492 A | 2/1986 | Walsh |
| 4,492,622 A | 1/1985 | Kuypers | | 4,571,292 A | 2/1986 | Liu et al. |
| 4,494,950 A | 1/1985 | Fischell | | 4,573,994 A | 3/1986 | Fischell et al. |
| 4,496,479 A | 1/1985 | Hu et al. | | 4,576,687 A | 3/1986 | Hertl et al. |
| 4,497,821 A | 2/1985 | Wehinger et al. | | 4,576,817 A | 3/1986 | Montgomery et al. |
| 4,499,064 A | 2/1985 | Shive | | 4,577,642 A | 3/1986 | Stokes |
| 4,499,249 A | 2/1985 | Nakagawa et al. | | 4,578,352 A | 3/1986 | Katkocin et al. |
| 4,499,901 A | 2/1985 | Chang et al. | | 4,579,642 A | 4/1986 | Niiyama et al. |
| 4,502,938 A | 3/1985 | Covington et al. | | 4,579,734 A | 4/1986 | Hata et al. |
| 4,505,784 A | 3/1985 | Mund et al. | | 4,579,751 A | 4/1986 | Forster |
| 4,506,680 A | 3/1985 | Stokes | | 4,579,943 A | 4/1986 | Kamide et al. |
| 4,507,229 A | 3/1985 | Bohn | | 4,581,336 A | 4/1986 | Malloy et al. |
| 4,507,233 A | 3/1985 | Saito et al. | | 4,581,447 A | 4/1986 | Arena |
| 4,507,390 A | 3/1985 | Horiuchi et al. | | 4,581,846 A | 4/1986 | Stensaas |
| 4,508,822 A | 4/1985 | Taylor | | 4,582,719 A | 4/1986 | Kaetsu et al. |
| 4,508,894 A | 4/1985 | Omiya | | 4,582,803 A | 4/1986 | Knapik et al. |
| 4,509,531 A | 4/1985 | Ward | | 4,584,273 A | 4/1986 | Finkelman et al. |
| 4,511,656 A | 4/1985 | Gong | | 4,588,696 A | 5/1986 | Eskelson |
| 4,512,348 A | 4/1985 | Uchigaki et al. | | 4,590,541 A | 5/1986 | Takahashi et al. |
| 4,513,084 A | 4/1985 | Keller, Jr. et al. | | 4,591,386 A | 5/1986 | Rugg et al. |
| 4,514,276 A | 4/1985 | Covington et al. | | 4,591,550 A | 5/1986 | Hafeman et al. |
| 4,517,291 A | 5/1985 | Seago | | 4,593,091 A | 6/1986 | della Valle et al. |
| 4,519,912 A | 5/1985 | Kauffman et al. | | 4,595,011 A | 6/1986 | Phillips |
| 4,519,913 A | 5/1985 | Baldwin et al. | | 4,595,479 A | 6/1986 | Kimura et al. |
| 4,521,511 A | 6/1985 | Stout | | 4,596,776 A | 6/1986 | Nonaka et al. |
| 4,522,690 A | 6/1985 | Venkatasetty | | 4,596,816 A | 6/1986 | Meguro et al. |
| 4,522,723 A | 6/1985 | Kauffman et al. | | 4,597,848 A | 7/1986 | Oka et al. |
| 4,522,832 A | 6/1985 | Morrison | | 4,599,176 A | 7/1986 | Wittenberger |
| 4,524,114 A | 6/1985 | Samuels et al. | | 4,601,707 A | 7/1986 | Albisser et al. |
| 4,525,218 A | 6/1985 | Chen et al. | | 4,602,027 A | 7/1986 | Meguro et al. |
| 4,525,265 A | 6/1985 | Abe et al. | | 4,604,182 A | 8/1986 | Seago |
| 4,525,456 A | 6/1985 | Rohrbach | | 4,604,347 A | 8/1986 | Arai et al. |
| 4,526,661 A | 7/1985 | Steckhan et al. | | 4,604,354 A | 8/1986 | Katz et al. |
| 4,526,753 A | 7/1985 | Boger et al. | | 4,605,626 A | 8/1986 | Beck |
| 4,526,948 A | 7/1985 | Resnick | | 4,610,741 A | 9/1986 | Mase et al. |
| 4,526,986 A | 7/1985 | Fields et al. | | 4,612,096 A | 9/1986 | Lichtin et al. |
| 4,527,240 A | 7/1985 | Kvitash | | 4,612,284 A | 9/1986 | Pickens et al. |
| 4,529,401 A | 7/1985 | Leslie et al. | | 4,613,570 A | 9/1986 | Zeman |
| 4,529,495 A | 7/1985 | Marsoner | | 4,614,577 A | 9/1986 | Mund et al. |
| 4,530,696 A | 7/1985 | Bisera et al. | | 4,614,716 A | 9/1986 | Rohrback et al. |
| 4,531,235 A | 7/1985 | Brusen | | 4,614,760 A | 9/1986 | Homan et al. |
| 4,532,208 A | 7/1985 | Hafner et al. | | 4,615,742 A | 10/1986 | Wright |
| 4,534,355 A | 8/1985 | Potter | | 4,619,754 A | 10/1986 | Niki et al. |
| 4,534,356 A | 8/1985 | Papadakis | | 4,619,793 A | 10/1986 | Lee |
| 4,536,274 A | 8/1985 | Papadakis et al. | | 4,622,297 A | 11/1986 | Kappner et al. |
| 4,537,881 A | 8/1985 | Heiker et al. | | 4,625,730 A | 12/1986 | Fountain et al. |
| 4,538,616 A | 9/1985 | Rogoff | | 4,627,014 A | 12/1986 | Lo et al. |
| 4,540,665 A | 9/1985 | Hasegawa et al. | | 4,627,445 A | 12/1986 | Garcia et al. |
| 4,540,684 A | 9/1985 | Stoltefuss et al. | | 4,627,893 A | 12/1986 | Cormier et al. |
| 4,540,707 A | 9/1985 | Mardin et al. | | 4,627,908 A | 12/1986 | Miller |

| | | | | | | |
|---|---|---|---|---|---|---|
| 4,628,029 | A | 12/1986 | Eveleigh et al. | 4,698,582 A | 10/1987 | Braun et al. |
| 4,628,031 | A | 12/1986 | Zeikus et al. | 4,699,124 A | 10/1987 | Nagle |
| 4,628,928 | A | 12/1986 | Lowell | 4,700,709 A | 10/1987 | Kraig |
| 4,629,145 | A | 12/1986 | Graham | 4,702,732 A | 10/1987 | Powers et al. |
| 4,629,690 | A | 12/1986 | Weng et al. | 4,702,857 A | 10/1987 | Gosselink |
| 4,632,746 | A | 12/1986 | Bergman | 4,703,756 A | 11/1987 | Gough et al. |
| 4,633,878 | A | 1/1987 | Bombardieri | 4,704,193 A | 11/1987 | Bowers et al. |
| 4,633,881 | A | 1/1987 | Moore et al. | 4,704,353 A | 11/1987 | Humphries et al. |
| 4,635,467 | A | 1/1987 | Hoffa et al. | 4,705,616 A | 11/1987 | Andresen et al. |
| 4,637,403 | A | 1/1987 | Garcia et al. | 4,707,237 A | 11/1987 | Lepp et al. |
| 4,637,835 | A | 1/1987 | Nagle | 4,707,479 A | 11/1987 | Meyer et al. |
| RE32,361 | E | 2/1987 | Duggan | 4,710,370 A | 12/1987 | Macy |
| 4,643,967 | A | 2/1987 | Bryant | 4,711,245 A | 12/1987 | Higgins et al. |
| 4,645,541 | A | 2/1987 | DeLong | 4,711,251 A | 12/1987 | Stokes |
| 4,647,415 | A | 3/1987 | Schafft | 4,713,118 A | 12/1987 | Barker et al. |
| 4,647,538 | A | 3/1987 | Zeikus et al. | 4,713,165 A | 12/1987 | Conover et al. |
| 4,648,408 | A | 3/1987 | Hutcheson et al. | 4,714,462 A | 12/1987 | DiDomenico |
| 4,649,058 | A | 3/1987 | Schwengers | 4,714,673 A | 12/1987 | Kessler et al. |
| 4,650,547 | A | 3/1987 | Gough | 4,716,030 A | 12/1987 | Macy |
| 4,650,758 | A | 3/1987 | Shaked et al. | 4,717,673 A | 1/1988 | Wrighton et al. |
| 4,653,513 | A | 3/1987 | Dombrowski | 4,718,430 A | 1/1988 | Holzer |
| 4,654,197 | A | 3/1987 | Lilja et al. | 4,718,893 A | 1/1988 | Dorman et al. |
| 4,655,225 | A | 4/1987 | Dahne et al. | 4,719,272 A | 1/1988 | Tsai et al. |
| 4,655,880 | A | 4/1987 | Liu | 4,721,601 A | 1/1988 | Wrighton et al. |
| 4,655,885 | A | 4/1987 | Hill et al. | 4,721,677 A | 1/1988 | Clark, Jr. |
| 4,655,900 | A | 4/1987 | Neti et al. | 4,725,010 A | 2/1988 | Lothamer |
| 4,657,658 | A | 4/1987 | Sibbald | 4,725,542 A | 2/1988 | Barer et al. |
| 4,657,924 | A | 4/1987 | Mardin et al. | 4,726,378 A | 2/1988 | Kaplan |
| 4,658,463 | A | 4/1987 | Sugita et al. | 4,726,716 A | 2/1988 | McGuire |
| 4,659,732 | A | 4/1987 | Stegelmeier et al. | 4,728,608 A | 3/1988 | Roberts et al. |
| 4,663,006 | A | 5/1987 | Yao et al. | 4,731,051 A | 3/1988 | Fischell |
| 4,663,284 | A | 5/1987 | Jeffries | 4,731,726 A | 3/1988 | Allen, III |
| 4,663,448 | A | 5/1987 | Chiu | 4,732,855 A | 3/1988 | Zeikus et al. |
| 4,663,449 | A | 5/1987 | Barker et al. | 4,734,360 A | 3/1988 | Phillips |
| 4,663,824 | A | 5/1987 | Kenmochi | 4,734,368 A | 3/1988 | Schindler |
| 4,664,119 | A | 5/1987 | Bessman et al. | 4,735,895 A | 4/1988 | Kopelovich |
| 4,664,717 | A | 5/1987 | Young | 4,736,748 A | 4/1988 | Nakamura et al. |
| 4,665,025 | A | 5/1987 | Weidenbach et al. | 4,736,756 A | 4/1988 | Grollier |
| 4,668,523 | A | 5/1987 | Begleiter | 4,737,459 A | 4/1988 | Zeikus et al. |
| 4,670,460 | A | 6/1987 | Mardin et al. | 4,737,464 A | 4/1988 | McConnell et al. |
| 4,671,288 | A | 6/1987 | Gough | 4,738,850 A | 4/1988 | Thakur et al. |
| 4,671,937 | A | 6/1987 | Katsuyama et al. | 4,738,923 A | 4/1988 | Ammeraal |
| 4,673,633 | A | 6/1987 | Kelleher et al. | 4,742,006 A | 5/1988 | Bringer et al. |
| 4,673,643 | A | 6/1987 | Schwengers | 4,744,992 A | 5/1988 | Mitchell et al. |
| 4,673,707 | A | 6/1987 | Tsai et al. | 4,745,042 A | 5/1988 | Sasago et al. |
| 4,674,652 | A | 6/1987 | Aten et al. | 4,746,631 A | 5/1988 | Clagett |
| 4,675,191 | A | 6/1987 | Villettaz | 4,746,647 A | 5/1988 | Svenson |
| 4,675,292 | A | 6/1987 | Houtchens et al. | 4,747,828 A | 5/1988 | Tseo |
| 4,675,293 | A | 6/1987 | Gibs | 4,749,985 A | 6/1988 | Corsberg |
| 4,677,072 | A | 6/1987 | Orndorff | 4,750,496 A | 6/1988 | Reinhart et al. |
| 4,679,562 | A | 7/1987 | Luksha | 4,753,652 A | 6/1988 | Langer et al. |
| 4,680,268 | A | 7/1987 | Clark, Jr. | 4,755,472 A | 7/1988 | Ismail et al. |
| 4,680,270 | A | 7/1987 | Mitsumaki et al. | 4,756,912 A | 7/1988 | Mitchell et al. |
| 4,680,275 | A | 7/1987 | Wagner et al. | 4,757,008 A | 7/1988 | Reverman |
| 4,681,111 | A | 7/1987 | Silvian | 4,757,012 A | 7/1988 | Estell et al. |
| 4,681,639 | A | 7/1987 | Hinck | 4,757,022 A | 7/1988 | Shults et al. |
| 4,681,845 | A | 7/1987 | Mueller | 4,758,323 A | 7/1988 | Davis et al. |
| 4,682,602 | A | 7/1987 | Prohaska | 4,758,445 A | 7/1988 | Klusters |
| 4,684,537 | A | 8/1987 | Graetzel et al. | 4,759,371 A | 7/1988 | Franetzki |
| 4,685,463 | A | 8/1987 | Williams | 4,759,828 A | 7/1988 | Young et al. |
| 4,685,903 | A | 8/1987 | Cable et al. | 4,761,185 A | 8/1988 | Chornet et al. |
| 4,686,044 | A | 8/1987 | Behnke et al. | 4,763,658 A | 8/1988 | Jones |
| 4,686,624 | A | 8/1987 | Blum et al. | 4,764,364 A | 8/1988 | Heller et al. |
| 4,687,742 | A | 8/1987 | Skoet et al. | 4,764,416 A | 8/1988 | Ueyama et al. |
| 4,689,296 | A | 8/1987 | Chiang et al. | 4,764,516 A | 8/1988 | Franckowiak et al. |
| 4,689,309 | A | 8/1987 | Jones | 4,766,207 A | 8/1988 | Deger et al. |
| 4,695,011 | A | 9/1987 | Komatsubara et al. | 4,769,082 A | 9/1988 | Kumakura et al. |
| 4,695,539 | A | 9/1987 | Sakata et al. | 4,769,215 A | 9/1988 | Ehrenkranz |
| 4,695,540 | A | 9/1987 | Yamanishi et al. | 4,771,006 A | 9/1988 | Miller et al. |
| 4,696,183 | A | 9/1987 | Mitsumaki et al. | 4,771,772 A | 9/1988 | DeWitt |
| 4,696,897 | A | 9/1987 | Sonoyama et al. | 4,772,453 A | 9/1988 | Lisenbee |

| Patent | Date | Inventor |
|---|---|---|
| 4,772,612 A | 9/1988 | Goldmann et al. |
| 4,776,944 A | 10/1988 | Janata et al. |
| 4,777,953 A | 10/1988 | Ash et al. |
| 4,778,531 A | 10/1988 | Dobler et al. |
| 4,778,677 A | 10/1988 | Ebbesen |
| 4,778,753 A | 10/1988 | Yamanishi et al. |
| 4,778,769 A | 10/1988 | Forrest et al. |
| 4,779,618 A | 10/1988 | Mund et al. |
| 4,781,798 A | 11/1988 | Gough |
| 4,781,809 A | 11/1988 | Falcone, Jr. |
| 4,784,736 A | 11/1988 | Lonsdale et al. |
| 4,787,398 A | 11/1988 | Garcia et al. |
| 4,787,939 A | 11/1988 | Barker et al. |
| 4,787,940 A | 11/1988 | Kayane et al. |
| 4,788,140 A | 11/1988 | Findlay et al. |
| 4,791,122 A | 12/1988 | Stoltefuss et al. |
| 4,791,374 A | 12/1988 | Yodice et al. |
| 4,794,080 A | 12/1988 | Mays et al. |
| 4,795,542 A | 1/1989 | Ross et al. |
| 4,795,707 A | 1/1989 | Niiyama et al. |
| 4,796,634 A | 1/1989 | Huntsman et al. |
| 4,797,187 A | 1/1989 | Davis et al. |
| 4,797,360 A | 1/1989 | Doelle |
| 4,798,705 A | 1/1989 | Jakubowicz et al. |
| 4,803,170 A | 2/1989 | Stanton et al. |
| 4,803,243 A | 2/1989 | Fujimoto et al. |
| 4,803,625 A | 2/1989 | Fu et al. |
| 4,803,726 A | 2/1989 | Levine et al. |
| 4,804,455 A | 2/1989 | Matson |
| 4,804,543 A | 2/1989 | Dokuzovic et al. |
| 4,804,544 A | 2/1989 | Christen et al. |
| 4,804,667 A | 2/1989 | Goldmann et al. |
| 4,805,624 A | 2/1989 | Yao et al. |
| 4,805,625 A | 2/1989 | Wyler |
| 4,806,485 A | 2/1989 | Birks et al. |
| 4,806,650 A | 2/1989 | Schroder et al. |
| 4,810,183 A | 3/1989 | Place et al. |
| 4,810,470 A | 3/1989 | Burkhardt et al. |
| 4,810,827 A | 3/1989 | Mitsuhashi et al. |
| 4,812,398 A | 3/1989 | Kondo et al. |
| 4,813,424 A | 3/1989 | Wilkins |
| 4,814,166 A | 3/1989 | Vanlerberghe et al. |
| 4,814,267 A | 3/1989 | Zeikus et al. |
| 4,815,469 A | 3/1989 | Cohen et al. |
| 4,816,130 A | 3/1989 | Karakelle et al. |
| 4,816,131 A | 3/1989 | Bomsztyk |
| 4,818,554 A | 4/1989 | Giddey et al. |
| 4,818,710 A | 4/1989 | Sutherland et al. |
| 4,818,816 A | 4/1989 | Petitou et al. |
| 4,820,399 A | 4/1989 | Senda et al. |
| 4,820,490 A | 4/1989 | Morris |
| 4,820,630 A | 4/1989 | Taub |
| 4,821,733 A | 4/1989 | Peck |
| 4,822,336 A | 4/1989 | DiTraglia |
| 4,822,337 A | 4/1989 | Newhouse et al. |
| 4,822,776 A | 4/1989 | Cerami et al. |
| 4,823,808 A | 4/1989 | Clegg et al. |
| 4,824,529 A | 4/1989 | Thompson et al. |
| 4,824,779 A | 4/1989 | Aoyama et al. |
| RE32,920 E | 5/1989 | Matson et al. |
| 4,826,759 A | 5/1989 | Guire et al. |
| 4,826,768 A | 5/1989 | Chou |
| 4,828,882 A | 5/1989 | Tsezos et al. |
| 4,828,993 A | 5/1989 | Sridhar |
| 4,829,011 A | 5/1989 | Gibbons |
| 4,830,011 A | 5/1989 | Lim |
| 4,830,959 A | 5/1989 | McNeil et al. |
| 4,831,128 A | 5/1989 | Tsai et al. |
| 4,832,797 A | 5/1989 | Vadgama et al. |
| 4,834,988 A | 5/1989 | Karwowski et al. |
| 4,835,264 A | 5/1989 | Liav et al. |
| 4,835,372 A | 5/1989 | Gombrich et al. |
| RE32,947 E | 6/1989 | Dormer et al. |
| 4,836,904 A | 6/1989 | Armstrong et al. |
| 4,837,049 A | 6/1989 | Byers et al. |
| 4,837,395 A | 6/1989 | Leeder et al. |
| 4,838,887 A | 6/1989 | Idriss |
| 4,839,088 A | 6/1989 | Young |
| 4,840,893 A | 6/1989 | Hill et al. |
| 4,840,903 A | 6/1989 | Wu |
| 4,841,974 A | 6/1989 | Gumbrecht et al. |
| 4,842,987 A | 6/1989 | Elzer et al. |
| 4,843,021 A | 6/1989 | Noguchi et al. |
| 4,843,173 A | 6/1989 | Saito et al. |
| RE32,974 E | 7/1989 | Porat et al. |
| 4,844,076 A | 7/1989 | Lesho et al. |
| 4,844,814 A | 7/1989 | Jaeger |
| 4,845,035 A | 7/1989 | Fanta et al. |
| 4,846,950 A | 7/1989 | Yao et al. |
| 4,848,351 A | 7/1989 | Finch |
| 4,849,330 A | 7/1989 | Humphries et al. |
| 4,849,345 A | 7/1989 | Asano et al. |
| 4,849,458 A | 7/1989 | Reed et al. |
| 4,851,228 A | 7/1989 | Zentner et al. |
| 4,853,091 A | 8/1989 | Mund et al. |
| 4,854,322 A | 8/1989 | Ash et al. |
| 4,855,132 A | 8/1989 | Heller et al. |
| 4,856,340 A | 8/1989 | Garrison |
| 4,857,152 A | 8/1989 | Armstrong et al. |
| 4,857,339 A | 8/1989 | Maselli et al. |
| 4,857,713 A | 8/1989 | Brown |
| 4,858,617 A | 8/1989 | Sanders |
| 4,859,474 A | 8/1989 | Neidleman et al. |
| 4,861,482 A | 8/1989 | Frankenberger, Jr. et al. |
| 4,861,727 A | 8/1989 | Hauenstein et al. |
| 4,861,830 A | 8/1989 | Ward, Jr. |
| 4,863,016 A | 9/1989 | Fong et al. |
| 4,866,396 A | 9/1989 | Tamura |
| 4,868,767 A | 9/1989 | Colvin, Jr. et al. |
| 4,869,907 A | 9/1989 | Sasagawa |
| 4,870,022 A | 9/1989 | Fukuyasu et al. |
| 4,870,053 A | 9/1989 | Zalisz et al. |
| 4,870,060 A | 9/1989 | Muller |
| 4,870,561 A | 9/1989 | Love et al. |
| 4,871,351 A | 10/1989 | Feingold |
| 4,871,440 A | 10/1989 | Nagata et al. |
| 4,871,679 A | 10/1989 | Tanaka et al. |
| 4,873,187 A | 10/1989 | Taub |
| 4,874,499 A | 10/1989 | Smith et al. |
| 4,874,500 A | 10/1989 | Madou et al. |
| 4,874,700 A | 10/1989 | Seipenbusch |
| 4,875,486 A | 10/1989 | Rapoport et al. |
| 4,879,127 A | 11/1989 | Liu et al. |
| 4,879,229 A | 11/1989 | Sonoyama et al. |
| 4,880,631 A | 11/1989 | Haslam et al. |
| 4,880,635 A | 11/1989 | Janoff et al. |
| 4,882,013 A | 11/1989 | Turner et al. |
| 4,882,277 A | 11/1989 | Czytko et al. |
| 4,882,292 A | 11/1989 | Sudholter et al. |
| 4,882,492 A | 11/1989 | Schlager |
| 4,883,579 A | 11/1989 | Humphries et al. |
| 4,885,077 A | 12/1989 | Karakelle et al. |
| 4,886,668 A | 12/1989 | Haslam et al. |
| 4,886,735 A | 12/1989 | Boettcher et al. |
| 4,886,740 A | 12/1989 | Vadgama |
| 4,889,613 A | 12/1989 | McNeal et al. |
| 4,889,744 A | 12/1989 | Quaid |
| 4,890,620 A | 1/1990 | Gough |
| 4,890,621 A | 1/1990 | Hakky |
| 4,891,104 A | 1/1990 | Liston et al. |
| 4,894,137 A | 1/1990 | Takizawa et al. |
| 4,894,242 A | 1/1990 | Mitchell et al. |

| | | | | | | |
|---|---|---|---|---|---|---|
| 4,894,339 | A | 1/1990 | Hanazato et al. | 4,953,552 A | 9/1990 | DeMarzo |
| 4,895,147 | A | 1/1990 | Bodicky et al. | 4,954,129 A | 9/1990 | Giuliani et al. |
| 4,895,855 | A | 1/1990 | Goldmann et al. | 4,954,438 A | 9/1990 | Yoshimoto et al. |
| 4,896,142 | A | 1/1990 | Aycox et al. | 4,955,861 A | 9/1990 | Enegren et al. |
| 4,897,162 | A | 1/1990 | Lewandowski et al. | 4,956,301 A | 9/1990 | Ismail et al. |
| 4,897,173 | A | 1/1990 | Nankai et al. | 4,957,115 A | 9/1990 | Selker |
| 4,897,457 | A | 1/1990 | Nakamura et al. | 4,958,016 A | 9/1990 | Kerkenaar et al. |
| 4,899,839 | A | 2/1990 | Dessertine et al. | 4,958,632 A | 9/1990 | Duggan |
| 4,900,407 | A | 2/1990 | Saito et al. | 4,959,131 A | 9/1990 | Cook et al. |
| 4,900,423 | A | 2/1990 | Iida et al. | 4,959,324 A | 9/1990 | Ramel et al. |
| 4,900,666 | A | 2/1990 | Phillips | 4,959,465 A | 9/1990 | Klemann et al. |
| 4,902,294 | A | 2/1990 | Gosserez | 4,960,589 A | 10/1990 | Sasagawa |
| 4,908,114 | A | 3/1990 | Ayers | 4,962,021 A | 10/1990 | Meserol et al. |
| 4,908,115 | A | 3/1990 | Morita et al. | 4,963,245 A | 10/1990 | Weetall |
| 4,908,676 | A | 3/1990 | Bedell et al. | 4,963,498 A | 10/1990 | Hillman et al. |
| 4,909,908 | A | 3/1990 | Ross et al. | 4,963,595 A | 10/1990 | Ward et al. |
| 4,909,921 | A | 3/1990 | Ito | 4,963,815 A | 10/1990 | Hafeman |
| 4,911,794 | A | 3/1990 | Parce et al. | 4,966,784 A | 10/1990 | Tanaka et al. |
| 4,912,034 | A | 3/1990 | Kalra et al. | 4,968,400 A | 11/1990 | Shimomura et al. |
| 4,912,051 | A | 3/1990 | Zaromb | 4,969,468 A | 11/1990 | Byers et al. |
| 4,916,075 | A | 4/1990 | Malmros et al. | 4,970,145 A | 11/1990 | Bennetto et al. |
| 4,917,274 | A | 4/1990 | Asa et al. | 4,970,302 A | 11/1990 | Arena et al. |
| 4,917,800 | A | 4/1990 | Lonsdale et al. | 4,971,901 A | 11/1990 | Hayashi et al. |
| 4,918,170 | A | 4/1990 | Hasegawa et al. | 4,971,918 A | 11/1990 | Bouse et al. |
| 4,919,141 | A | 4/1990 | Zier et al. | 4,973,489 A | 11/1990 | Meyer et al. |
| 4,919,767 | A | 4/1990 | Vadgama et al. | 4,974,929 A | 12/1990 | Curry |
| 4,919,770 | A | 4/1990 | Preidel et al. | 4,975,165 A | 12/1990 | Brandley |
| 4,920,052 | A | 4/1990 | Byng | 4,975,175 A | 12/1990 | Karube et al. |
| 4,920,969 | A | 5/1990 | Suzuki et al. | 4,975,366 A | 12/1990 | Sudo et al. |
| 4,920,977 | A | 5/1990 | Haynes | 4,975,581 A | 12/1990 | Robinson et al. |
| 4,923,586 | A | 5/1990 | Katayama et al. | 4,976,590 A | 12/1990 | Baldwin |
| 4,924,127 | A | 5/1990 | Boireau et al. | 4,976,724 A | 12/1990 | Nieto et al. |
| 4,925,268 | A | 5/1990 | Iyer et al. | 4,976,994 A | 12/1990 | Matson |
| 4,925,544 | A | 5/1990 | Goldring | 4,978,503 A | 12/1990 | Shanks et al. |
| 4,925,545 | A | 5/1990 | Murel | 4,978,610 A | 12/1990 | Forrest et al. |
| 4,927,407 | A | 5/1990 | Dorman | 4,978,612 A | 12/1990 | Kobayashi et al. |
| 4,927,516 | A | 5/1990 | Yamaguchi et al. | 4,979,509 A | 12/1990 | Hakky |
| 4,927,756 | A | 5/1990 | Schwengers | 4,984,929 A | 1/1991 | Rock et al. |
| 4,927,757 | A | 5/1990 | Hatcher et al. | 4,985,125 A | 1/1991 | Watanabe et al. |
| 4,929,426 | A | 5/1990 | Bodai et al. | 4,986,271 A | 1/1991 | Wilkins |
| 4,929,542 | A | 5/1990 | Risley | 4,986,671 A | 1/1991 | Sun et al. |
| 4,931,172 | A | 6/1990 | Kobos et al. | 4,987,032 A | 1/1991 | Miyasaka et al. |
| 4,931,795 | A | 6/1990 | Gord | 4,987,075 A | 1/1991 | Nentwig et al. |
| 4,932,871 | A | 6/1990 | Bell et al. | 4,990,845 A | 2/1991 | Gord |
| 4,933,066 | A | 6/1990 | Osaka et al. | 4,991,582 A | 2/1991 | Byers et al. |
| 4,934,369 | A | 6/1990 | Maxwell | 4,994,068 A | 2/1991 | Hufnagle |
| 4,935,105 | A | 6/1990 | Churchouse | 4,994,167 A | 2/1991 | Shults et al. |
| 4,935,106 | A | 6/1990 | Liston et al. | 4,995,402 A | 2/1991 | Smith et al. |
| 4,935,345 | A | 6/1990 | Guilbeau et al. | 4,999,203 A | 3/1991 | Fukuyasu et al. |
| 4,935,346 | A | 6/1990 | Phillips et al. | 4,999,284 A | 3/1991 | Ward et al. |
| 4,935,360 | A | 6/1990 | Klemps et al. | 4,999,287 A | 3/1991 | Allen et al. |
| 4,936,956 | A | 6/1990 | Wrighton | 4,999,295 A | 3/1991 | Asakura et al. |
| 4,937,047 | A | 6/1990 | Kobayashi et al. | 4,999,582 A | 3/1991 | Parks et al. |
| 4,937,077 | A | 6/1990 | Deetz, III | 5,000,180 A | 3/1991 | Kuypers et al. |
| 4,937,328 | A | 6/1990 | Schmidt et al. | 5,001,048 A | 3/1991 | Taylor et al. |
| 4,938,860 | A | 7/1990 | Wogoman | 5,001,054 A | 3/1991 | Wagner |
| 4,938,989 | A | 7/1990 | Steeves et al. | 5,001,531 A | 3/1991 | Yamaguchi et al. |
| 4,939,304 | A | 7/1990 | Arena et al. | 5,002,054 A | 3/1991 | Ash et al. |
| 4,939,921 | A | 7/1990 | Carter et al. | 5,002,572 A | 3/1991 | Picha |
| 4,939,924 | A | 7/1990 | Johnson et al. | 5,004,459 A | 4/1991 | Peabody et al. |
| 4,940,065 | A | 7/1990 | Tanagho et al. | 5,004,532 A | 4/1991 | Hale |
| 4,940,945 | A | 7/1990 | Littlejohn et al. | 5,004,685 A | 4/1991 | Arai et al. |
| 4,942,251 | A | 7/1990 | Huey-Long | 5,006,262 A | 4/1991 | Weyls et al. |
| 4,944,299 | A | 7/1990 | Silvian | 5,006,551 A | 4/1991 | Groke et al. |
| 4,944,952 | A | 7/1990 | Kobayashi et al. | 5,007,427 A | 4/1991 | Suzuki et al. |
| 4,945,045 | A | 7/1990 | Forrest et al. | 5,007,929 A | 4/1991 | Quaid |
| 4,945,052 | A | 7/1990 | Hardy et al. | 5,008,190 A | 4/1991 | Lee et al. |
| 4,949,400 | A | 8/1990 | Leveen et al. | 5,008,193 A | 4/1991 | Anderson et al. |
| 4,950,378 | A | 8/1990 | Nagata | 5,009,230 A | 4/1991 | Hutchinson |
| 4,950,379 | A | 8/1990 | Young et al. | 5,012,667 A | 5/1991 | Kruse |
| 4,952,406 | A | 8/1990 | Brown et al. | 5,013,842 A | 5/1991 | Fleet et al. |

| | | | | | | |
|---|---|---|---|---|---|---|
| 5,015,344 | A | 5/1991 | Nidola et al. | 5,070,535 A | 12/1991 | Hochmair et al. |
| 5,015,586 | A | 5/1991 | Severn et al. | 5,071,762 A | 12/1991 | Shay et al. |
| 5,015,650 | A | 5/1991 | Stoltefuss et al. | 5,071,767 A | 12/1991 | Portenhauser et al. |
| 5,015,843 | A | 5/1991 | Seitz et al. | 5,072,732 A | 12/1991 | Rapoport et al. |
| 5,016,172 | A | 5/1991 | Dessertine | 5,073,500 A | 12/1991 | Saito et al. |
| 5,016,201 | A | 5/1991 | Bryan et al. | 5,073,713 A | 12/1991 | Smith et al. |
| 5,016,631 | A | 5/1991 | Hogrefe | 5,074,977 A | 12/1991 | Cheung et al. |
| 5,017,342 | A | 5/1991 | Haberzettl et al. | 5,076,898 A | 12/1991 | Nidola et al. |
| 5,017,485 | A | 5/1991 | Bringer-Meyer et al. | 5,077,206 A | 12/1991 | Cheetham et al. |
| 5,017,494 | A | 5/1991 | Karube et al. | 5,077,476 A | 12/1991 | Rosenthal |
| 5,018,855 | A | 5/1991 | Davison et al. | 5,078,854 A | 1/1992 | Burgess et al. |
| 5,019,232 | A | 5/1991 | Wilson et al. | 5,078,855 A | 1/1992 | Mochizuki et al. |
| 5,019,238 | A | 5/1991 | Cormier et al. | 5,080,771 A | 1/1992 | Novotny et al. |
| 5,019,974 | A | 5/1991 | Beckers | 5,080,911 A | 1/1992 | Saitou et al. |
| 5,022,967 | A | 6/1991 | Stieg | 5,081,014 A | 1/1992 | Brochot et al. |
| 5,023,176 | A | 6/1991 | Ducroo | 5,081,037 A | 1/1992 | Kariyone et al. |
| 5,025,798 | A | 6/1991 | Schindele | 5,082,550 A | 1/1992 | Rishpon et al. |
| 5,026,746 | A | 6/1991 | Floyd et al. | 5,082,629 A | 1/1992 | Burgess, Jr. et al. |
| D318,331 | S | 7/1991 | Phillips et al. | 5,082,786 A | 1/1992 | Nakamoto |
| 5,030,310 | A | 7/1991 | Wogoman | 5,084,828 A | 1/1992 | Kaufman et al. |
| 5,030,333 | A | 7/1991 | Clark, Jr. | 5,085,499 A | 2/1992 | Griffin et al. |
| 5,031,449 | A | 7/1991 | Kuwana et al. | 5,085,759 A | 2/1992 | Harker |
| 5,032,509 | A | 7/1991 | Matsumoto et al. | 5,087,556 A | 2/1992 | Ertinghausen |
| 5,032,512 | A | 7/1991 | Witholt et al. | 5,088,981 A | 2/1992 | Howson et al. |
| 5,032,514 | A | 7/1991 | Anderson et al. | 5,089,112 A | 2/1992 | Skotheim et al. |
| 5,034,112 | A | 7/1991 | Murase et al. | 5,089,181 A | 2/1992 | Hauser |
| 5,034,192 | A | 7/1991 | Wrighton et al. | 5,089,320 A | 2/1992 | Straus et al. |
| 5,034,212 | A | 7/1991 | Yokoyama et al. | 5,091,299 A | 2/1992 | Turner et al. |
| 5,034,330 | A | 7/1991 | Yamori et al. | 5,094,740 A | 3/1992 | Brandley et al. |
| 5,035,860 | A | 7/1991 | Kleingeld et al. | 5,094,947 A | 3/1992 | Nakajima et al. |
| 5,036,860 | A | 8/1991 | Leigh et al. | 5,094,951 A | 3/1992 | Rosenberg |
| 5,036,861 | A | 8/1991 | Sembrowich et al. | 5,095,904 A | 3/1992 | Seligman et al. |
| 5,037,527 | A | 8/1991 | Hayashi et al. | 5,096,560 A | 3/1992 | Takai et al. |
| 5,037,737 | A | 8/1991 | Liffmann et al. | 5,096,670 A | 3/1992 | Harris et al. |
| 5,041,378 | A | 8/1991 | Drummond et al. | 5,096,820 A | 3/1992 | Leleu et al. |
| 5,046,496 | A | 9/1991 | Betts et al. | 5,096,836 A | 3/1992 | Macho et al. |
| 5,047,044 | A | 9/1991 | Smith et al. | 5,097,834 A | 3/1992 | Skrabal |
| 5,047,152 | A | 9/1991 | Francis et al. | 5,099,123 A | 3/1992 | Harjunmaa |
| 5,047,332 | A | 9/1991 | Chahal | 5,100,778 A | 3/1992 | Rademacher et al. |
| 5,049,487 | A | 9/1991 | Phillips et al. | 5,100,791 A | 3/1992 | Spindler et al. |
| 5,049,499 | A | 9/1991 | Atlas et al. | 5,101,814 A | 4/1992 | Palti |
| 5,050,612 | A | 9/1991 | Matsumura | 5,102,795 A | 4/1992 | Rehr et al. |
| 5,051,161 | A | 9/1991 | Yamaguchi et al. | 5,104,508 A | 4/1992 | Williams et al. |
| 5,051,433 | A | 9/1991 | Stoltefuss et al. | 5,104,619 A | 4/1992 | de Castro et al. |
| 5,051,551 | A | 9/1991 | Doyle | 5,106,365 A | 4/1992 | Hernandez |
| 5,051,880 | A | 9/1991 | Harm et al. | 5,106,634 A | 4/1992 | Thacker et al. |
| 5,054,487 | A | 10/1991 | Clarke | 5,107,469 A | 4/1992 | Dodson |
| 5,054,651 | A | 10/1991 | Morane | 5,108,564 A | 4/1992 | Szuminsky et al. |
| 5,055,171 | A | 10/1991 | Peck | 5,108,576 A | 4/1992 | Malmros et al. |
| 5,055,267 | A | 10/1991 | Burroughs et al. | 5,108,889 A | 4/1992 | Smith et al. |
| 5,055,398 | A | 10/1991 | Fujie et al. | 5,109,850 A | 5/1992 | Blanco et al. |
| 5,056,521 | A | 10/1991 | Parsons et al. | 5,110,443 A | 5/1992 | Gregoli et al. |
| 5,057,197 | A | 10/1991 | Perry et al. | 5,110,724 A | 5/1992 | Hewett |
| 5,057,279 | A | 10/1991 | Inman et al. | 5,111,539 A | 5/1992 | Hiruta et al. |
| 5,058,592 | A | 10/1991 | Whisler | 5,111,818 A | 5/1992 | Suzuki et al. |
| 5,058,925 | A | 10/1991 | Dotson | 5,112,124 A | 5/1992 | Harjunmaa et al. |
| 5,059,290 | A | 10/1991 | Uchiyama et al. | 5,112,455 A | 5/1992 | Cozzette et al. |
| 5,059,394 | A | 10/1991 | Phillips et al. | 5,112,945 A | 5/1992 | Westermark et al. |
| 5,059,445 | A | 10/1991 | Arsem | 5,113,871 A | 5/1992 | Viljanto et al. |
| 5,059,526 | A | 10/1991 | Arai et al. | 5,114,678 A | 5/1992 | Crawford et al. |
| 5,059,654 | A | 10/1991 | Hou et al. | 5,114,859 A | 5/1992 | Kagenow |
| 5,061,497 | A | 10/1991 | Thacker et al. | 5,116,762 A | 5/1992 | Vogt et al. |
| 5,062,841 | A | 11/1991 | Siegel | 5,116,948 A | 5/1992 | Westermark et al. |
| 5,062,935 | A | 11/1991 | Schlag et al. | 5,118,404 A | 6/1992 | Saito |
| 5,063,081 | A | 11/1991 | Cozzette et al. | 5,118,472 A | 6/1992 | Tanaka et al. |
| 5,064,665 | A | 11/1991 | Klopfenstein et al. | 5,119,819 A | 6/1992 | Thomas et al. |
| 5,064,672 | A | 11/1991 | Mazur | 5,120,420 A | 6/1992 | Nankai et al. |
| 5,066,372 | A | 11/1991 | Weetall | 5,120,421 A | 6/1992 | Glass et al. |
| 5,066,582 | A | 11/1991 | Tsuruta et al. | 5,122,237 A | 6/1992 | Kim et al. |
| 5,067,491 | A | 11/1991 | Taylor, II et al. | 5,122,362 A | 6/1992 | Phillips et al. |
| 5,068,536 | A | 11/1991 | Rosenthal | 5,122,925 A | 6/1992 | Inpyn |

| | | | | | |
|---|---|---|---|---|---|
| 5,125,749 A | 6/1992 | Leugers et al. | 5,179,005 A | 1/1993 | Phillips et al. |
| 5,126,034 A | 6/1992 | Carter et al. | 5,179,288 A | 1/1993 | Miffitt et al. |
| 5,126,238 A | 6/1992 | Gebhard et al. | 5,180,480 A | 1/1993 | Manz |
| 5,126,247 A | 6/1992 | Palmer et al. | 5,182,004 A | 1/1993 | Kohno |
| 5,126,275 A | 6/1992 | Hatch et al. | 5,182,707 A | 1/1993 | Cooper et al. |
| 5,128,015 A | 7/1992 | Szuminsky et al. | 5,182,742 A | 1/1993 | Ohmori et al. |
| 5,130,009 A | 7/1992 | Marsoner et al. | 5,183,042 A | 2/1993 | Harjunmaa et al. |
| 5,130,231 A | 7/1992 | Kennedy et al. | 5,183,741 A | 2/1993 | Arai et al. |
| 5,131,441 A | 7/1992 | Simpson et al. | 5,183,742 A | 2/1993 | Omoto et al. |
| 5,131,999 A | 7/1992 | Gunasingham | 5,184,359 A | 2/1993 | Tsukamura et al. |
| 5,132,217 A | 7/1992 | Gabelman | 5,185,256 A | 2/1993 | Nankai et al. |
| 5,132,230 A | 7/1992 | Rosenthal et al. | 5,186,808 A | 2/1993 | Yamaguchi et al. |
| 5,132,452 A | 7/1992 | Deller et al. | 5,187,100 A | 2/1993 | Matzinger et al. |
| 5,133,856 A | 7/1992 | Yamaguchi et al. | 5,188,109 A | 2/1993 | Saito |
| 5,133,937 A | 7/1992 | Frackleton et al. | 5,190,041 A | 3/1993 | Palti |
| 5,133,976 A | 7/1992 | Rouy | 5,190,788 A | 3/1993 | Liang et al. |
| 5,134,391 A | 7/1992 | Okada | 5,190,869 A | 3/1993 | Rehr et al. |
| 5,135,003 A | 8/1992 | Souma | 5,192,415 A | 3/1993 | Yoshioka et al. |
| 5,137,818 A | 8/1992 | Harder et al. | 5,192,416 A | 3/1993 | Wang et al. |
| 5,138,251 A | 8/1992 | Koshiishi et al. | 5,192,502 A | 3/1993 | Attridge et al. |
| 5,139,023 A | 8/1992 | Stanley et al. | 5,193,539 A | 3/1993 | Schulman et al. |
| 5,140,161 A | 8/1992 | Hillman et al. | 5,193,540 A | 3/1993 | Schulman et al. |
| 5,140,393 A | 8/1992 | Hijikihigawa et al. | 5,194,130 A | 3/1993 | Byszewski et al. |
| 5,140,985 A | 8/1992 | Schroeder et al. | 5,196,219 A | 3/1993 | Hsu et al. |
| 5,141,604 A | 8/1992 | Ayers | 5,196,302 A | 3/1993 | Kidwell |
| 5,141,609 A | 8/1992 | Sweedler et al. | 5,196,340 A | 3/1993 | Miyamoto |
| 5,141,611 A | 8/1992 | Ford | 5,196,523 A | 3/1993 | Lee |
| 5,141,868 A | 8/1992 | Shanks et al. | 5,197,322 A | 3/1993 | Indravudh |
| 5,142,028 A | 8/1992 | Nagai et al. | 5,198,074 A | 3/1993 | Villavicencio et al. |
| 5,143,066 A | 9/1992 | Komives et al. | 5,198,367 A | 3/1993 | Aizawa et al. |
| 5,143,827 A | 9/1992 | Atlas et al. | 5,198,771 A | 3/1993 | Fidler et al. |
| 5,143,834 A | 9/1992 | Glassner et al. | 5,200,051 A | 4/1993 | Cozzette et al. |
| 5,147,725 A | 9/1992 | Pinchuk | 5,202,007 A | 4/1993 | Kozulic |
| 5,149,621 A | 9/1992 | McNally et al. | 5,202,010 A | 4/1993 | Guzman |
| 5,149,630 A | 9/1992 | Forrest et al. | 5,202,091 A | 4/1993 | Lisenbee |
| 5,151,354 A | 9/1992 | Strasser et al. | 5,202,261 A | 4/1993 | Musho et al. |
| 5,153,320 A | 10/1992 | Dasinger | 5,204,242 A | 4/1993 | Junius-Comer et al. |
| 5,153,827 A | 10/1992 | Coutre et al. | 5,204,267 A | 4/1993 | Sangha et al. |
| 5,154,808 A | 10/1992 | Miyasaka et al. | 5,204,922 A | 4/1993 | Weir et al. |
| 5,156,810 A | 10/1992 | Ribi | 5,205,297 A | 4/1993 | Montecalvo et al. |
| 5,156,972 A | 10/1992 | Issachar | 5,205,863 A | 4/1993 | Elion |
| 5,156,976 A | 10/1992 | Slovacek et al. | 5,205,920 A | 4/1993 | Oyama et al. |
| 5,157,116 A | 10/1992 | Ducep et al. | 5,205,925 A | 4/1993 | Shong et al. |
| 5,158,868 A | 10/1992 | Bergkuist et al. | 5,206,145 A | 4/1993 | Cattell |
| 5,158,887 A | 10/1992 | Hsu et al. | 5,207,218 A | 5/1993 | Carpentier et al. |
| 5,159,049 A | 10/1992 | Allen | 5,207,320 A | 5/1993 | Allen |
| 5,160,278 A | 11/1992 | Johnson | 5,208,151 A | 5/1993 | Usui et al. |
| 5,160,418 A | 11/1992 | Mullen | 5,208,154 A | 5/1993 | Weaver et al. |
| 5,160,436 A | 11/1992 | Hildenbrand et al. | 5,209,229 A | 5/1993 | Gilli |
| 5,160,597 A | 11/1992 | Colapicchioni et al. | 5,209,414 A | 5/1993 | Clemens et al. |
| 5,161,532 A | 11/1992 | Joseph | 5,211,371 A | 5/1993 | Coffee |
| 5,162,210 A | 11/1992 | Sierks et al. | 5,215,887 A | 6/1993 | Saito |
| 5,162,338 A | 11/1992 | Goldmann et al. | 5,216,597 A | 6/1993 | Beckers |
| 5,164,303 A | 11/1992 | Heefner et al. | 5,217,442 A | 6/1993 | Davis |
| 5,165,407 A | 11/1992 | Wilson et al. | 5,217,594 A | 6/1993 | Henkens et al. |
| 5,166,063 A | 11/1992 | Johnson | 5,217,595 A | 6/1993 | Smith et al. |
| 5,166,813 A | 11/1992 | Metz | 5,218,097 A | 6/1993 | Ernst |
| 5,168,046 A | 12/1992 | Hamamoto et al. | 5,220,920 A | 6/1993 | Gharib |
| 5,169,768 A | 12/1992 | Backman | 5,222,495 A | 6/1993 | Clarke et al. |
| 5,170,064 A | 12/1992 | Howe | 5,222,496 A | 6/1993 | Clarke et al. |
| 5,171,689 A | 12/1992 | Kawaguri et al. | 5,222,980 A | 6/1993 | Gealow |
| 5,173,160 A | 12/1992 | Rodkey et al. | 5,223,124 A | 6/1993 | Ege |
| 5,173,165 A | 12/1992 | Schmid et al. | 5,225,064 A | 7/1993 | Henkens et al. |
| 5,173,264 A | 12/1992 | Zaromb et al. | 5,225,321 A | 7/1993 | Hayashi et al. |
| 5,174,291 A | 12/1992 | Schoonen et al. | 5,226,902 A | 7/1993 | Bae et al. |
| 5,175,091 A | 12/1992 | Hannan | 5,227,042 A | 7/1993 | Zawodzinski et al. |
| 5,176,632 A | 1/1993 | Bernardi | 5,228,972 A | 7/1993 | Osaka et al. |
| 5,176,644 A | 1/1993 | Srisathapat et al. | 5,229,282 A | 7/1993 | Yoshioka et al. |
| 5,176,662 A | 1/1993 | Bartholomew et al. | 5,230,786 A | 7/1993 | Preidel |
| 5,177,012 A | 1/1993 | Kim et al. | 5,231,028 A | 7/1993 | Mullen |
| 5,178,142 A | 1/1993 | Harjunmaa et al. | 5,231,988 A | 8/1993 | Wernicke et al. |

| | | | | | |
|---|---|---|---|---|---|
| 5,231,993 A | 8/1993 | Haber et al. | 5,278,079 A | 1/1994 | Gubinski et al. |
| 5,232,668 A | 8/1993 | Grant et al. | 5,279,294 A | 1/1994 | Anderson et al. |
| 5,234,819 A | 8/1993 | Sonoyama et al. | 5,281,319 A | 1/1994 | Kaneko et al. |
| 5,235,003 A | 8/1993 | Ward et al. | 5,281,323 A | 1/1994 | Sugama et al. |
| 5,236,143 A | 8/1993 | Dragon | 5,281,539 A | 1/1994 | Schramm |
| 5,236,567 A | 8/1993 | Nanba et al. | 5,282,848 A | 2/1994 | Schmitt |
| 5,237,993 A | 8/1993 | Skrabal | 5,282,950 A | 2/1994 | Dietze et al. |
| 5,238,681 A | 8/1993 | Chang et al. | 5,283,525 A | 2/1994 | Lamerichs et al. |
| 5,238,826 A | 8/1993 | Leleu et al. | 5,284,140 A | 2/1994 | Allen et al. |
| 5,242,690 A | 9/1993 | Moechnig | 5,284,156 A | 2/1994 | Schramm et al. |
| 5,242,793 A | 9/1993 | Kariyone et al. | 5,284,558 A | 2/1994 | Linhardt et al. |
| 5,242,848 A | 9/1993 | Yeh | 5,284,570 A | 2/1994 | Savage et al. |
| 5,243,516 A | 9/1993 | White | 5,284,601 A | 2/1994 | Bouet et al. |
| 5,243,982 A | 9/1993 | Mostl et al. | 5,284,748 A | 2/1994 | Mroczkowski et al. |
| 5,243,983 A | 9/1993 | Tarr et al. | 5,285,513 A | 2/1994 | Kaufman et al. |
| 5,244,553 A | 9/1993 | Goldstein | 5,285,792 A | 2/1994 | Sjoquist et al. |
| 5,244,562 A | 9/1993 | Russell | 5,286,362 A | 2/1994 | Hoenes et al. |
| 5,246,552 A | 9/1993 | Kamiya et al. | 5,286,364 A | 2/1994 | Yacynych et al. |
| 5,246,558 A | 9/1993 | Chevigne et al. | 5,286,627 A | 2/1994 | Ueda et al. |
| 5,246,560 A | 9/1993 | Nekoksa et al. | 5,288,387 A | 2/1994 | Ito et al. |
| 5,246,867 A | 9/1993 | Lakowicz et al. | 5,288,636 A | 2/1994 | Pollmann et al. |
| 5,248,397 A | 9/1993 | Cawlfield et al. | 5,288,646 A | 2/1994 | Lundsgaard et al. |
| 5,248,597 A | 9/1993 | Hayashi et al. | 5,290,517 A | 3/1994 | Samuels et al. |
| 5,249,576 A | 10/1993 | Goldberger et al. | 5,291,887 A | 3/1994 | Stanley et al. |
| 5,250,168 A | 10/1993 | Tsukada et al. | 5,292,423 A | 3/1994 | Wang |
| 5,250,439 A | 10/1993 | Musho et al. | 5,292,663 A | 3/1994 | Yamazaki et al. |
| 5,251,126 A | 10/1993 | Kahn et al. | 5,292,899 A | 3/1994 | Tius et al. |
| 5,254,227 A | 10/1993 | Cawlfield et al. | 5,292,939 A | 3/1994 | Hollingsworth |
| 5,254,468 A | 10/1993 | Fournier et al. | 5,293,546 A | 3/1994 | Tadros et al. |
| 5,254,469 A | 10/1993 | Warren, III et al. | 5,293,770 A | 3/1994 | Hansen et al. |
| 5,256,271 A | 10/1993 | Ikariyama et al. | 5,293,877 A | 3/1994 | O'Hara et al. |
| 5,257,971 A | 11/1993 | Lord et al. | 5,296,122 A | 3/1994 | Katsube et al. |
| 5,257,980 A | 11/1993 | Van Antwerp et al. | 5,296,192 A | 3/1994 | Carroll et al. |
| 5,258,825 A | 11/1993 | Reed et al. | 5,296,356 A | 3/1994 | Mangold et al. |
| 5,259,769 A | 11/1993 | Cruise et al. | 5,298,022 A | 3/1994 | Bernardi |
| 5,260,195 A | 11/1993 | Azhar et al. | 5,298,144 A | 3/1994 | Spokane |
| 5,261,401 A | 11/1993 | Baker et al. | 5,299,141 A | 3/1994 | Hungerford et al. |
| 5,262,035 A | 11/1993 | Gregg et al. | 5,299,571 A | 4/1994 | Mastrototaro |
| 5,262,305 A | 11/1993 | Heller et al. | 5,300,779 A | 4/1994 | Hillman et al. |
| 5,262,429 A | 11/1993 | Stoltefuss et al. | 5,302,513 A | 4/1994 | Miike et al. |
| 5,262,430 A | 11/1993 | Borrevang et al. | 5,304,127 A | 4/1994 | Kawahara et al. |
| 5,264,092 A | 11/1993 | Skotheim et al. | 5,304,287 A | 4/1994 | Stieg |
| 5,264,103 A | 11/1993 | Yoshioka et al. | 5,304,293 A | 4/1994 | Tierney et al. |
| 5,264,104 A | 11/1993 | Gregg et al. | 5,304,295 A | 4/1994 | Kim et al. |
| 5,264,105 A | 11/1993 | Gregg et al. | 5,304,468 A | 4/1994 | Phillips et al. |
| 5,264,106 A | 11/1993 | McAleer et al. | 5,304,475 A | 4/1994 | Kim et al. |
| 5,265,888 A | 11/1993 | Yamamoto et al. | 5,304,492 A | 4/1994 | Klinkhammer |
| 5,266,179 A | 11/1993 | Nankai et al. | 5,306,413 A | 4/1994 | Hayashi et al. |
| 5,266,180 A | 11/1993 | Harnoncourt et al. | 5,306,623 A | 4/1994 | Kiser et al. |
| 5,266,475 A | 11/1993 | Lee et al. | 5,307,263 A | 4/1994 | Brown |
| 5,268,146 A | 12/1993 | Lawrence et al. | 5,308,459 A | 5/1994 | Herring |
| 5,268,285 A | 12/1993 | Rogers et al. | 5,308,460 A | 5/1994 | Mazid et al. |
| 5,268,301 A | 12/1993 | Potter | 5,308,836 A | 5/1994 | Sawai et al. |
| 5,269,212 A | 12/1993 | Peters et al. | 5,309,085 A | 5/1994 | Sohn |
| 5,269,891 A | 12/1993 | Colin | 5,309,919 A | 5/1994 | Snell et al. |
| 5,269,903 A | 12/1993 | Ikariyama et al. | 5,310,469 A | 5/1994 | Cunningham et al. |
| 5,269,929 A | 12/1993 | Sublette et al. | 5,310,540 A | 5/1994 | Giddey et al. |
| 5,271,736 A | 12/1993 | Picha | 5,310,665 A | 5/1994 | Lambeir et al. |
| 5,271,815 A | 12/1993 | Wong | 5,310,885 A | 5/1994 | Maier et al. |
| 5,272,060 A | 12/1993 | Hamamoto et al. | 5,312,361 A | 5/1994 | Zadini et al. |
| 5,272,073 A | 12/1993 | Frost et al. | 5,312,527 A | 5/1994 | Mikkelsen et al. |
| 5,272,077 A | 12/1993 | Warren, III et al. | 5,312,590 A | 5/1994 | Gunasingham |
| 5,272,087 A | 12/1993 | El Murr et al. | 5,314,450 A | 5/1994 | Thompson |
| 5,273,633 A | 12/1993 | Wang | 5,314,471 A | 5/1994 | Brauker et al. |
| 5,273,906 A | 12/1993 | Shultz et al. | 5,314,590 A | 5/1994 | Kamiya et al. |
| 5,274,240 A | 12/1993 | Mathies et al. | 5,314,594 A | 5/1994 | Chung et al. |
| 5,275,159 A | 1/1994 | Griebel | 5,314,595 A | 5/1994 | Fuller |
| 5,275,949 A | 1/1994 | Sakamoto et al. | 5,314,695 A | 5/1994 | Brown |
| 5,276,610 A | 1/1994 | Maeda et al. | 5,315,375 A | 5/1994 | Allen |
| 5,278,046 A | 1/1994 | Johnson et al. | 5,316,638 A | 5/1994 | Jackson |
| 5,278,047 A | 1/1994 | Lilja et al. | 5,318,521 A | 6/1994 | Slettenmark |

| | | | | | | |
|---|---|---|---|---|---|---|
| 5,319,110 | A | 6/1994 | Hollingsworth | 5,356,348 A | 10/1994 | Bellio et al. |
| 5,320,098 | A | 6/1994 | Davidson | 5,356,786 A | 10/1994 | Heller et al. |
| 5,320,725 | A | 6/1994 | Gregg et al. | 5,356,792 A | 10/1994 | Maeda et al. |
| 5,320,732 | A | 6/1994 | Nankai et al. | 5,357,113 A | 10/1994 | Liston et al. |
| 5,320,734 | A | 6/1994 | Yamasaki et al. | 5,358,135 A | 10/1994 | Robbins et al. |
| 5,320,939 | A | 6/1994 | Hashizume et al. | 5,358,514 A | 10/1994 | Schulman et al. |
| 5,321,265 | A | 6/1994 | Block | 5,358,619 A | 10/1994 | Suzuki et al. |
| 5,321,414 | A | 6/1994 | Alden et al. | 5,360,004 A | 11/1994 | Purdy et al. |
| 5,321,492 | A | 6/1994 | Detwiler et al. | 5,360,404 A | 11/1994 | Novacek et al. |
| 5,322,063 | A | 6/1994 | Allen et al. | 5,360,595 A | 11/1994 | Bell et al. |
| 5,322,608 | A | 6/1994 | Karger et al. | 5,361,758 A | 11/1994 | Hall et al. |
| 5,322,906 | A | 6/1994 | Rodkey et al. | 5,362,442 A | 11/1994 | Kent |
| 5,324,303 | A | 6/1994 | Strong et al. | 5,362,512 A | 11/1994 | Cabrera et al. |
| 5,324,316 | A | 6/1994 | Schulman et al. | 5,364,520 A | 11/1994 | Okuyama et al. |
| 5,324,322 | A | 6/1994 | Grill, Jr. et al. | 5,364,797 A | 11/1994 | Olson et al. |
| 5,324,436 | A | 6/1994 | John et al. | 5,364,851 A | 11/1994 | Joran |
| 5,324,599 | A | 6/1994 | Oyama et al. | 5,366,609 A | 11/1994 | White et al. |
| 5,324,658 | A | 6/1994 | Cox, deceased et al. | 5,366,903 A | 11/1994 | Lundsgaard et al. |
| 5,325,280 | A | 6/1994 | Tortola et al. | 5,368,028 A | 11/1994 | Palti |
| 5,326,356 | A | 7/1994 | Della Valle et al. | 5,368,562 A | 11/1994 | Blomquist et al. |
| 5,326,449 | A | 7/1994 | Cunningham | 5,368,707 A | 11/1994 | Henkens et al. |
| 5,326,450 | A | 7/1994 | Sugama et al. | 5,370,622 A | 12/1994 | Livingston et al. |
| 5,328,460 | A | 7/1994 | Lord et al. | 5,370,989 A | 12/1994 | Stern et al. |
| 5,328,847 | A | 7/1994 | Case et al. | 5,371,020 A | 12/1994 | Frischauf |
| 5,328,848 | A | 7/1994 | Fong et al. | 5,371,208 A | 12/1994 | Kozulic |
| 5,328,851 | A | 7/1994 | Zaromb | 5,371,687 A | 12/1994 | Holmes, II et al. |
| 5,329,931 | A | 7/1994 | Clauson et al. | 5,372,133 A | 12/1994 | Hogen Esch |
| 5,330,521 | A | 7/1994 | Cohen | 5,372,427 A | 12/1994 | Padovani et al. |
| 5,330,634 | A | 7/1994 | Wong et al. | 5,372,719 A | 12/1994 | Afeyan et al. |
| 5,330,901 | A | 7/1994 | Prevatt et al. | 5,372,939 A | 12/1994 | Lastick et al. |
| 5,331,966 | A | 7/1994 | Bennett et al. | 5,373,336 A | 12/1994 | Sugita |
| 5,332,479 | A | 7/1994 | Uenoyama et al. | 5,374,395 A | 12/1994 | Robinson et al. |
| 5,334,253 | A | 8/1994 | Berg | 5,374,563 A | 12/1994 | Maule |
| 5,334,296 | A | 8/1994 | Henkens et al. | 5,374,773 A | 12/1994 | Hollingsworth |
| 5,334,351 | A | 8/1994 | Heinze et al. | 5,375,604 A | 12/1994 | Kelly et al. |
| 5,336,387 | A | 8/1994 | Egen et al. | 5,376,070 A | 12/1994 | Purvis et al. |
| 5,337,018 | A | 8/1994 | Yamagishi | 5,376,251 A | 12/1994 | Kaneko et al. |
| 5,337,258 | A | 8/1994 | Dennis | 5,376,254 A | 12/1994 | Fisher |
| 5,337,745 | A | 8/1994 | Benaron | 5,376,536 A | 12/1994 | Quax et al. |
| 5,337,747 | A | 8/1994 | Neftel | 5,377,258 A | 12/1994 | Bro |
| 5,338,418 | A | 8/1994 | Hirayama et al. | 5,378,332 A | 1/1995 | Pandey |
| 5,338,420 | A | 8/1994 | Aga et al. | 5,378,628 A | 1/1995 | Gratzel et al. |
| 5,340,352 | A | 8/1994 | Nakanishi et al. | 5,379,238 A | 1/1995 | Stark |
| 5,340,453 | A | 8/1994 | Jackson | 5,379,764 A | 1/1995 | Barnes et al. |
| 5,340,461 | A | 8/1994 | Fukushige et al. | 5,380,411 A | 1/1995 | Schlief |
| 5,340,721 | A | 8/1994 | Goldblum et al. | 5,380,422 A | 1/1995 | Negishi et al. |
| 5,340,722 | A | 8/1994 | Wolfbeis et al. | 5,380,536 A | 1/1995 | Hubbell et al. |
| 5,341,805 | A | 8/1994 | Stavridi et al. | 5,382,331 A | 1/1995 | Banks |
| 5,342,409 | A | 8/1994 | Mullett | 5,382,346 A | 1/1995 | Uenoyama et al. |
| 5,342,498 | A | 8/1994 | Graves et al. | 5,383,452 A | 1/1995 | Buchert |
| 5,342,789 | A | 8/1994 | Chick et al. | 5,384,028 A | 1/1995 | Ito |
| 5,343,869 | A | 9/1994 | Pross et al. | 5,384,265 A | 1/1995 | Kidwell et al. |
| 5,344,454 | A | 9/1994 | Clarke et al. | 5,387,327 A | 2/1995 | Khan |
| 5,344,832 | A | 9/1994 | Cincotta et al. | 5,387,328 A | 2/1995 | Sohn |
| 5,348,002 | A | 9/1994 | Caro | 5,387,503 A | 2/1995 | Selmer et al. |
| 5,348,788 | A | 9/1994 | White | 5,389,534 A | 2/1995 | von Gentzkow et al. |
| 5,348,871 | A | 9/1994 | Scott et al. | 5,390,671 A | 2/1995 | Lord et al. |
| 5,350,407 | A | 9/1994 | McClure et al. | 5,391,250 A | 2/1995 | Cheney, II et al. |
| 5,350,688 | A | 9/1994 | Matsuno et al. | 5,391,272 A | 2/1995 | O'Daly et al. |
| 5,350,697 | A | 9/1994 | Swope et al. | 5,393,401 A | 2/1995 | Knoll |
| 5,352,348 | A | 10/1994 | Young et al. | 5,393,493 A | 2/1995 | Makino et al. |
| 5,352,349 | A | 10/1994 | Inamoto et al. | 5,393,615 A | 2/1995 | Corey et al. |
| 5,352,351 | A | 10/1994 | White et al. | 5,393,660 A | 2/1995 | Kitahata et al. |
| 5,352,574 | A | 10/1994 | Guiseppi-Elie | 5,393,903 A | 2/1995 | Gratzel et al. |
| 5,352,590 | A | 10/1994 | Kato et al. | 5,395,502 A | 3/1995 | Pawliszyn |
| 5,354,319 | A | 10/1994 | Wyborny et al. | 5,395,504 A | 3/1995 | Saurer et al. |
| 5,354,447 | A | 10/1994 | Uenoyama et al. | 5,395,623 A | 3/1995 | Kovach |
| 5,354,449 | A | 10/1994 | Band et al. | 5,395,924 A | 3/1995 | Blattler et al. |
| 5,354,654 | A | 10/1994 | Ligler et al. | 5,397,848 A | 3/1995 | Yang et al. |
| 5,354,679 | A | 10/1994 | Ohashi | 5,399,823 A | 3/1995 | McCusker |
| 5,356,217 | A | 10/1994 | Sheffield | 5,400,782 A | 3/1995 | Beaubiah |

| | | | | | |
|---|---|---|---|---|---|
| 5,401,376 A | 3/1995 | Foos et al. | 5,439,571 A | 8/1995 | Sammons et al. |
| 5,401,377 A | 3/1995 | Shieh et al. | 5,443,701 A | 8/1995 | Willner et al. |
| 5,401,639 A | 3/1995 | Saldivar, Jr. et al. | 5,443,710 A | 8/1995 | Broderick |
| 5,403,462 A | 4/1995 | Lev et al. | 5,443,961 A | 8/1995 | Prunieras et al. |
| 5,403,680 A | 4/1995 | Otagawa et al. | 5,445,611 A | 8/1995 | Eppstein et al. |
| 5,403,750 A | 4/1995 | Braatz et al. | 5,445,920 A | 8/1995 | Saito |
| 5,404,218 A | 4/1995 | Nave et al. | 5,445,942 A | 8/1995 | Rabin et al. |
| 5,405,510 A | 4/1995 | Betts et al. | 5,448,905 A | 9/1995 | Stetter et al. |
| 5,405,511 A | 4/1995 | White et al. | 5,448,992 A | 9/1995 | Kupershmidt |
| 5,406,829 A | 4/1995 | Ravel et al. | 5,449,625 A | 9/1995 | Kobayashi et al. |
| 5,407,554 A | 4/1995 | Saurer | 5,451,260 A | 9/1995 | Versteeg et al. |
| 5,407,658 A | 4/1995 | Hattner | 5,451,424 A | 9/1995 | Solomon et al. |
| 5,407,818 A | 4/1995 | von Gentzkow et al. | 5,452,173 A | 9/1995 | Brannon et al. |
| 5,409,583 A | 4/1995 | Yoshioka et al. | 5,452,716 A | 9/1995 | Clift |
| 5,409,719 A | 4/1995 | Cain et al. | 5,453,199 A | 9/1995 | Afeyan et al. |
| 5,410,471 A | 4/1995 | Alyfuku et al. | 5,453,278 A | 9/1995 | Chan et al. |
| 5,410,474 A | 4/1995 | Fox | 5,453,360 A | 9/1995 | Yu |
| 5,411,536 A | 5/1995 | Armstrong | 5,453,379 A | 9/1995 | Yamazaki et al. |
| 5,411,551 A | 5/1995 | Winston et al. | D363,543 S | 10/1995 | Van Funderburk et al. |
| 5,411,594 A | 5/1995 | Brelsford | 5,455,059 A | 10/1995 | McFeaters |
| 5,411,647 A | 5/1995 | Johnson et al. | 5,455,168 A | 10/1995 | Maruta et al. |
| 5,411,866 A | 5/1995 | Luong et al. | 5,456,692 A | 10/1995 | Smith, Jr. et al. |
| 5,411,892 A | 5/1995 | Bergamaschi | 5,456,932 A | 10/1995 | Fuisz et al. |
| 5,412,082 A | 5/1995 | Wittman et al. | 5,456,940 A | 10/1995 | Funderburk |
| 5,413,690 A | 5/1995 | Kost et al. | 5,458,140 A | 10/1995 | Eppstein et al. |
| 5,413,930 A | 5/1995 | Becwar et al. | 5,458,631 A | 10/1995 | Xavier |
| 5,413,939 A | 5/1995 | Gustafson et al. | 5,459,065 A | 10/1995 | Aust et al. |
| 5,415,758 A | 5/1995 | Comeau | 5,459,249 A | 10/1995 | Bergfeld et al. |
| 5,415,994 A | 5/1995 | Imrich et al. | 5,459,317 A | 10/1995 | Small et al. |
| 5,417,395 A | 5/1995 | Fowler et al. | 5,460,177 A | 10/1995 | Purdy et al. |
| 5,417,817 A | 5/1995 | Dammann et al. | 5,460,618 A | 10/1995 | Harreld |
| 5,417,824 A | 5/1995 | Greenbaum | 5,461,645 A | 10/1995 | Ishii |
| 5,417,837 A | 5/1995 | Suzuki et al. | 5,462,051 A | 10/1995 | Oka et al. |
| 5,418,136 A | 5/1995 | Miller et al. | 5,462,064 A | 10/1995 | D'Angelo et al. |
| 5,418,142 A | 5/1995 | Kiser et al. | 5,462,525 A | 10/1995 | Srisathapat et al. |
| 5,420,107 A | 5/1995 | Brooks | 5,462,645 A | 10/1995 | Albery et al. |
| 5,421,923 A | 6/1995 | Clarke et al. | 5,464,514 A | 11/1995 | Pluim et al. |
| 5,421,981 A | 6/1995 | Leader et al. | 5,464,760 A | 11/1995 | Tsai et al. |
| 5,421,982 A | 6/1995 | Ikeda et al. | 5,466,218 A | 11/1995 | Srisathapat et al. |
| 5,422,244 A | 6/1995 | Johnson-Wood et al. | 5,466,575 A | 11/1995 | Cozzette et al. |
| 5,422,246 A | 6/1995 | Koopal et al. | 5,468,355 A | 11/1995 | Shefer et al. |
| 5,422,495 A | 6/1995 | Cohn | 5,468,374 A | 11/1995 | Knoll |
| 5,424,193 A | 6/1995 | Pronovost et al. | 5,468,408 A | 11/1995 | Sugama et al. |
| 5,424,202 A | 6/1995 | Ingram et al. | 5,468,727 A | 11/1995 | Phillips et al. |
| 5,424,545 A | 6/1995 | Block et al. | 5,468,755 A | 11/1995 | Cincotta et al. |
| 5,425,361 A | 6/1995 | Fenzlein et al. | 5,469,846 A | 11/1995 | Khan |
| 5,426,032 A | 6/1995 | Phillips et al. | 5,472,317 A | 12/1995 | Field et al. |
| 5,426,042 A | 6/1995 | Maeda et al. | 5,472,582 A | 12/1995 | Jackson |
| 5,428,123 A | 6/1995 | Ward et al. | 5,474,552 A | 12/1995 | Palti |
| 5,429,129 A | 7/1995 | Lovejoy et al. | 5,476,094 A | 12/1995 | Allen et al. |
| 5,429,726 A | 7/1995 | Johnson et al. | 5,476,460 A | 12/1995 | Montalvo |
| 5,429,735 A | 7/1995 | Johnson et al. | 5,476,776 A | 12/1995 | Wilkins |
| 5,430,843 A | 7/1995 | Sato et al. | 5,477,321 A | 12/1995 | Johnson |
| 5,431,160 A | 7/1995 | Wilkins | 5,477,855 A | 12/1995 | Schindler et al. |
| 5,431,691 A | 7/1995 | Snell et al. | 5,478,460 A | 12/1995 | Sugama et al. |
| 5,431,793 A | 7/1995 | Wang et al. | 5,478,466 A | 12/1995 | Heilmann et al. |
| 5,431,806 A | 7/1995 | Suzuki et al. | 5,478,732 A | 12/1995 | Kunz et al. |
| 5,431,880 A | 7/1995 | Kramer | 5,480,415 A | 1/1996 | Cox et al. |
| 5,431,921 A | 7/1995 | Thombre | 5,482,473 A | 1/1996 | Lord et al. |
| 5,433,710 A | 7/1995 | VanAntwerp et al. | 5,482,830 A | 1/1996 | Bogart et al. |
| 5,433,793 A | 7/1995 | Herber et al. | 5,484,404 A | 1/1996 | Schulman et al. |
| 5,434,412 A | 7/1995 | Sodickson et al. | 5,486,458 A | 1/1996 | Kojima et al. |
| 5,436,342 A | 7/1995 | Goldman et al. | 5,486,459 A | 1/1996 | Burnham et al. |
| 5,436,718 A | 7/1995 | Fernandes et al. | 5,486,605 A | 1/1996 | Gatlin |
| 5,437,840 A | 8/1995 | King et al. | 5,487,751 A | 1/1996 | Radons et al. |
| 5,437,879 A | 8/1995 | Kabse et al. | D367,109 S | 2/1996 | Ryner et al. |
| 5,437,973 A | 8/1995 | Vadgama et al. | 5,489,515 A | 2/1996 | Hatschek et al. |
| 5,437,993 A | 8/1995 | Visuri | 5,491,090 A | 2/1996 | Handley, III et al. |
| 5,437,999 A | 8/1995 | Diebold et al. | 5,491,474 A | 2/1996 | Suni et al. |
| 5,438,271 A | 8/1995 | White et al. | 5,492,611 A | 2/1996 | Sugama et al. |
| 5,438,984 A | 8/1995 | Schoendorfer | 5,492,702 A | 2/1996 | Domingues |

| | | | | | | |
|---|---|---|---|---|---|---|
| 5,492,815 | A | 2/1996 | Nishidate et al. | 5,540,825 A | 7/1996 | Yeung et al. |
| 5,494,562 | A | 2/1996 | Maley et al. | 5,540,828 A | 7/1996 | Yacynych |
| 5,494,829 | A | 2/1996 | Sandstrom et al. | 5,541,057 A | 7/1996 | Bogart et al. |
| 5,496,453 | A | 3/1996 | Uenoyama et al. | 5,541,060 A | 7/1996 | Bell et al. |
| 5,496,741 | A | 3/1996 | Pawliszyn | 5,542,012 A | 7/1996 | Fernandes et al. |
| 5,497,772 | A | 3/1996 | Schulman et al. | 5,543,024 A | 8/1996 | Hanazato et al. |
| 5,498,528 | A | 3/1996 | King | 5,543,054 A | 8/1996 | Charkoudian et al. |
| 5,498,542 | A | 3/1996 | Corey et al. | 5,543,066 A | 8/1996 | Weissen et al. |
| 5,500,187 | A | 3/1996 | Deoms et al. | 5,543,299 A | 8/1996 | Diebold et al. |
| 5,500,188 | A | 3/1996 | Hafeman et al. | 5,543,326 A | 8/1996 | Heller et al. |
| 5,501,665 | A | 3/1996 | Jhuboo et al. | 5,543,576 A | 8/1996 | van Ooijen et al. |
| 5,501,956 | A | 3/1996 | Wada et al. | 5,545,152 A | 8/1996 | Funderburk et al. |
| 5,501,965 | A | 3/1996 | Iwata et al. | 5,545,191 A | 8/1996 | Mann et al. |
| 5,502,308 | A | 3/1996 | Wong | 5,545,220 A | 8/1996 | Andrews et al. |
| 5,502,396 | A | 3/1996 | Desarzens et al. | 5,545,223 A | 8/1996 | Neuenfeldt et al. |
| 5,503,721 | A | 4/1996 | Hearst et al. | 5,545,302 A | 8/1996 | Zhu et al. |
| 5,503,728 | A | 4/1996 | Kaneko et al. | 5,547,561 A | 8/1996 | Vadgama et al. |
| 5,505,709 | A | 4/1996 | Funderburk et al. | 5,547,874 A | 8/1996 | Terashima |
| 5,505,713 | A | 4/1996 | Van Antwerp | 5,547,955 A | 8/1996 | Silerman et al. |
| 5,505,828 | A | 4/1996 | Wong et al. | 5,549,113 A | 8/1996 | Halleck et al. |
| 5,505,847 | A | 4/1996 | Yamada et al. | 5,549,115 A | 8/1996 | Morgan et al. |
| 5,506,136 | A | 4/1996 | Becwar et al. | 5,549,675 A | 8/1996 | Neuenfeldt et al. |
| 5,506,205 | A | 4/1996 | Tajima et al. | 5,550,063 A | 8/1996 | Bogart |
| 5,507,288 | A | 4/1996 | Bocker et al. | 5,550,166 A | 8/1996 | Ostlund et al. |
| 5,507,936 | A | 4/1996 | Hatschek et al. | 5,551,427 A | 9/1996 | Altman |
| 5,508,171 | A | 4/1996 | Walling et al. | 5,552,027 A | 9/1996 | Birkle et al. |
| 5,508,183 | A | 4/1996 | Scott et al. | 5,552,267 A | 9/1996 | Stern et al. |
| 5,508,203 | A | 4/1996 | Fuller et al. | 5,552,272 A | 9/1996 | Bogart |
| 5,509,410 | A | 4/1996 | Hill et al. | 5,553,613 A | 9/1996 | Parker |
| 5,510,241 | A | 4/1996 | Thorns | 5,553,616 A | 9/1996 | Ham et al. |
| 5,510,266 | A | 4/1996 | Bonner et al. | 5,554,166 A | 9/1996 | Lange et al. |
| 5,511,547 | A | 4/1996 | Markle et al. | 5,554,531 A | 9/1996 | Zweig |
| 5,512,159 | A | 4/1996 | Yoshioka et al. | 5,554,623 A | 9/1996 | Cincotta et al. |
| 5,512,464 | A | 4/1996 | Spencer et al. | 5,554,742 A | 9/1996 | Wolf et al. |
| 5,514,103 | A | 5/1996 | Srisathapat et al. | 5,556,524 A | 9/1996 | Albers |
| 5,514,253 | A | 5/1996 | Davis et al. | 5,556,533 A | 9/1996 | Nozoe et al. |
| 5,515,170 | A | 5/1996 | Matzinger et al. | 5,556,760 A | 9/1996 | Nakamura et al. |
| 5,516,636 | A | 5/1996 | McCapra | 5,556,775 A | 9/1996 | Karube et al. |
| 5,518,006 | A | 5/1996 | Mawhirt et al. | 5,556,958 A | 9/1996 | Carroll et al. |
| 5,518,689 | A | 5/1996 | Dosmann et al. | 5,558,638 A | 9/1996 | Evers et al. |
| 5,518,841 | A | 5/1996 | Sotomura et al. | 5,559,219 A | 9/1996 | Wuest et al. |
| 5,518,891 | A | 5/1996 | Gibboni et al. | 5,560,357 A | 10/1996 | Faupel et al. |
| 5,520,786 | A | 5/1996 | Bloczynski et al. | 5,562,713 A | 10/1996 | Silvian |
| 5,520,787 | A | 5/1996 | Hanagan et al. | 5,563,031 A | 10/1996 | Yu |
| 5,520,788 | A | 5/1996 | Johnson | 5,563,042 A | 10/1996 | Phillips et al. |
| 5,521,074 | A | 5/1996 | Katsumata et al. | 5,563,067 A | 10/1996 | Sugihara et al. |
| D371,198 | S | 6/1996 | Savage et al. | 5,564,439 A | 10/1996 | Picha |
| 5,522,865 | A | 6/1996 | Schulman et al. | 5,565,085 A | 10/1996 | Ikeda et al. |
| 5,522,977 | A | 6/1996 | Shieh | 5,565,326 A | 10/1996 | Daiss et al. |
| 5,523,054 | A | 6/1996 | Switalski et al. | 5,567,290 A | 10/1996 | Vadgama et al. |
| 5,525,297 | A | 6/1996 | Dinger et al. | 5,567,302 A | 10/1996 | Song et al. |
| 5,525,511 | A | 6/1996 | D'Costa | 5,567,687 A | 10/1996 | Magda et al. |
| 5,525,518 | A | 6/1996 | Lundsgaard et al. | 5,568,400 A | 10/1996 | Stark et al. |
| 5,526,120 | A | 6/1996 | Jina et al. | 5,568,806 A | 10/1996 | Cheney, II et al. |
| 5,527,307 | A | 6/1996 | Srisathapat et al. | 5,569,186 A | 10/1996 | Lord et al. |
| 5,529,066 | A | 6/1996 | Palti | 5,569,212 A | 10/1996 | Brown |
| 5,529,676 | A | 6/1996 | Maley et al. | 5,569,366 A | 10/1996 | Chen et al. |
| 5,529,755 | A | 6/1996 | Higashio et al. | 5,569,462 A | 10/1996 | Martinson et al. |
| 5,529,920 | A | 6/1996 | Cole et al. | 5,569,591 A | 10/1996 | Kell et al. |
| 5,531,714 | A | 7/1996 | Dahn et al. | 5,571,132 A | 11/1996 | Mawhirt et al. |
| 5,531,871 | A | 7/1996 | Fauteux et al. | 5,571,292 A | 11/1996 | Sotomura et al. |
| 5,531,878 | A | 7/1996 | Vadgama et al. | 5,571,395 A | 11/1996 | Park et al. |
| 5,534,121 | A | 7/1996 | Merrick et al. | 5,571,410 A | 11/1996 | Swedberg et al. |
| 5,534,132 | A | 7/1996 | Vreeke et al. | 5,571,684 A | 11/1996 | Lawrence et al. |
| 5,534,998 | A | 7/1996 | Eastgate et al. | 5,572,140 A | 11/1996 | Lim et al. |
| 5,536,382 | A | 7/1996 | Sunzeri | 5,573,506 A | 11/1996 | Vasko |
| 5,538,007 | A | 7/1996 | Gorman | 5,573,647 A | 11/1996 | Maley et al. |
| 5,538,511 | A | 7/1996 | Van Antwerp | 5,573,649 A | 11/1996 | Sugama et al. |
| 5,538,883 | A | 7/1996 | Nishimoto et al. | 5,574,019 A | 11/1996 | Segall et al. |
| 5,540,709 | A | 7/1996 | Ramel | 5,575,403 A | 11/1996 | Charlton et al. |
| 5,540,734 | A | 7/1996 | Zabara | 5,575,895 A | 11/1996 | Ikeda et al. |

| | | | | | |
|---|---|---|---|---|---|
| 5,575,930 A | 11/1996 | Tietje-Girault et al. | 5,614,105 A | 3/1997 | Heilmann et al. |
| 5,578,179 A | 11/1996 | Demorest et al. | 5,614,361 A | 3/1997 | Webster, Jr. |
| 5,578,194 A | 11/1996 | Young et al. | 5,614,375 A | 3/1997 | Citri |
| 5,578,339 A | 11/1996 | Kunz et al. | 5,615,671 A | 4/1997 | Schoonen et al. |
| 5,578,463 A | 11/1996 | Berka et al. | 5,615,673 A | 4/1997 | Berger et al. |
| 5,580,434 A | 12/1996 | Robotti et al. | 5,616,139 A | 4/1997 | Okamoto |
| 5,580,527 A | 12/1996 | Bell et al. | 5,616,222 A | 4/1997 | Maley et al. |
| 5,580,714 A | 12/1996 | Polovina | 5,616,496 A | 4/1997 | Frost et al. |
| 5,580,764 A | 12/1996 | Holt et al. | 5,617,851 A | 4/1997 | Lipkovker |
| 5,580,794 A | 12/1996 | Allen | 5,618,664 A | 4/1997 | Kiessling |
| 5,580,857 A | 12/1996 | Oden | 5,618,681 A | 4/1997 | Friedman et al. |
| 5,582,184 A | 12/1996 | Erickson et al. | 5,618,686 A | 4/1997 | Kojima et al. |
| 5,582,497 A | 12/1996 | Noguchi | 5,618,708 A | 4/1997 | Shirai et al. |
| 5,582,593 A | 12/1996 | Hultman | 5,618,790 A | 4/1997 | Kennedy et al. |
| 5,582,696 A | 12/1996 | Sheehan | 5,620,579 A | 4/1997 | Genshaw et al. |
| 5,582,697 A | 12/1996 | Ikeda et al. | 5,620,853 A | 4/1997 | Smethers et al. |
| 5,582,698 A | 12/1996 | Flaherty et al. | 5,620,863 A | 4/1997 | Tomasco et al. |
| 5,583,006 A | 12/1996 | Storhoff et al. | 5,622,482 A | 4/1997 | Lee |
| 5,584,813 A | 12/1996 | Livingston et al. | 5,623,925 A | 4/1997 | Swenson et al. |
| 5,584,876 A | 12/1996 | Bruchman et al. | 5,624,537 A | 4/1997 | Turner et al. |
| 5,586,553 A | 12/1996 | Halili et al. | 5,625,209 A | 4/1997 | Appleton et al. |
| 5,587,273 A | 12/1996 | Yan et al. | 5,626,134 A | 5/1997 | Zuckerman |
| 5,589,045 A | 12/1996 | Hyodo | 5,628,309 A | 5/1997 | Brown |
| 5,589,047 A | 12/1996 | Coster et al. | 5,628,310 A | 5/1997 | Rao et al. |
| 5,589,326 A | 12/1996 | Deng et al. | 5,628,830 A | 5/1997 | Brink |
| 5,589,348 A | 12/1996 | Kaufman et al. | 5,628,890 A | 5/1997 | Carter et al. |
| 5,589,393 A | 12/1996 | Fiechtner et al. | 5,629,181 A | 5/1997 | Frost et al. |
| 5,589,563 A | 12/1996 | Ward et al. | 5,629,214 A | 5/1997 | Crosby |
| 5,590,651 A | 1/1997 | Shaffer et al. | 5,629,474 A | 5/1997 | Williams |
| 5,591,407 A | 1/1997 | Groger et al. | 5,629,981 A | 5/1997 | Nerlikar |
| 5,592,290 A | 1/1997 | Arai et al. | 5,630,923 A | 5/1997 | Aga et al. |
| 5,593,440 A | 1/1997 | Brauker et al. | 5,630,986 A | 5/1997 | Charlton et al. |
| 5,593,552 A | 1/1997 | Joshi et al. | 5,631,133 A | 5/1997 | Hanahan et al. |
| 5,593,852 A | 1/1997 | Heller et al. | 5,631,150 A | 5/1997 | Harkki et al. |
| 5,593,868 A | 1/1997 | Spencer et al. | 5,631,171 A | 5/1997 | Sandstrom et al. |
| 5,593,886 A | 1/1997 | Gaddy | 5,631,357 A | 5/1997 | Weuthen et al. |
| 5,594,243 A | 1/1997 | Weinberger et al. | 5,632,410 A | 5/1997 | Moulton et al. |
| 5,594,341 A | 1/1997 | Majidi-Ahy et al. | 5,633,359 A | 5/1997 | Beaulieu |
| 5,594,906 A | 1/1997 | Holmes, II et al. | D380,262 S | 6/1997 | Van Funderburk et al. |
| 5,595,726 A | 1/1997 | Magda et al. | 5,635,046 A | 6/1997 | Notsu et al. |
| 5,595,867 A | 1/1997 | Lin et al. | 5,635,512 A | 6/1997 | Cincotta et al. |
| 5,595,905 A | 1/1997 | Bishop et al. | 5,637,095 A | 6/1997 | Nason et al. |
| 5,596,150 A | 1/1997 | Arndt et al. | 5,637,502 A | 6/1997 | Scott et al. |
| 5,596,994 A | 1/1997 | Bro | 5,637,508 A | 6/1997 | Kidwell et al. |
| 5,597,595 A | 1/1997 | DeWille et al. | 5,637,683 A | 6/1997 | Usher et al. |
| 5,597,728 A | 1/1997 | Wyatt et al. | 5,640,470 A | 6/1997 | Iyer et al. |
| 5,597,730 A | 1/1997 | Aust et al. | 5,640,764 A | 6/1997 | Strojnik |
| 5,599,433 A | 2/1997 | Keo et al. | 5,640,954 A | 6/1997 | Pfeiffer et al. |
| 5,599,977 A | 2/1997 | Kiely et al. | 5,641,390 A | 6/1997 | Hawke et al. |
| 5,600,444 A | 2/1997 | Tong | 5,641,645 A | 6/1997 | Felder et al. |
| 5,601,435 A | 2/1997 | Quy | 5,641,759 A | 6/1997 | Patterson et al. |
| 5,601,694 A | 2/1997 | Maley et al. | 5,642,375 A | 6/1997 | King et al. |
| 5,603,820 A | 2/1997 | Malinski et al. | D381,591 S | 7/1997 | Rice et al. |
| 5,604,404 A | 2/1997 | Sahara | 5,643,212 A | 7/1997 | Coutre et al. |
| 5,604,587 A | 2/1997 | Che et al. | 5,643,791 A | 7/1997 | Warren et al. |
| 5,605,152 A | 2/1997 | Slate et al. | 5,645,709 A | 7/1997 | Birch et al. |
| 5,605,822 A | 2/1997 | Emerson et al. | 5,645,710 A | 7/1997 | Shieh |
| 5,605,837 A | 2/1997 | Karimi et al. | 5,645,878 A | 7/1997 | Breslin et al. |
| 5,606,164 A | 2/1997 | Price et al. | 5,646,001 A | 7/1997 | Terstappen et al. |
| D378,612 S | 3/1997 | Clark et al. | 5,647,853 A | 7/1997 | Feldmann et al. |
| 5,607,565 A | 3/1997 | Azarnia et al. | 5,648,271 A | 7/1997 | Kempe |
| 5,608,086 A | 3/1997 | Hemmerle | 5,650,062 A | 7/1997 | Ikeda et al. |
| 5,609,575 A | 3/1997 | Larson et al. | 5,650,846 A | 7/1997 | Yin et al. |
| 5,609,749 A | 3/1997 | Yamauchi et al. | 5,651,767 A | 7/1997 | Schulman et al. |
| 5,609,897 A | 3/1997 | Chandler et al. | 5,651,869 A | 7/1997 | Yoshioka et al. |
| 5,610,047 A | 3/1997 | Maruta et al. | 5,652,273 A | 7/1997 | Henry et al. |
| 5,610,076 A | 3/1997 | Founds et al. | 5,653,239 A | 8/1997 | Pompei et al. |
| 5,611,900 A | 3/1997 | Worden et al. | 5,653,735 A | 8/1997 | Chen et al. |
| 5,611,999 A | 3/1997 | Dosmann et al. | 5,653,756 A | 8/1997 | Clarke et al. |
| 5,612,203 A | 3/1997 | Maruo et al. | 5,653,862 A | 8/1997 | Parris |
| 5,614,062 A | 3/1997 | Schulte et al. | 5,653,863 A | 8/1997 | Genshaw et al. |

| | | | | | |
|---|---|---|---|---|---|
| 5,653,864 A | 8/1997 | Gotoh et al. | 5,696,580 A | 12/1997 | Kubo et al. |
| 5,654,313 A | 8/1997 | Cincotta et al. | 5,698,083 A | 12/1997 | Glass |
| 5,655,530 A | 8/1997 | Messerschmidt | 5,698,222 A | 12/1997 | Mazer et al. |
| 5,656,241 A | 8/1997 | Seifert et al. | 5,700,360 A | 12/1997 | Chan et al. |
| 5,657,754 A | 8/1997 | Rosencwaig | 5,700,447 A | 12/1997 | Bucala et al. |
| 5,658,250 A | 8/1997 | Blomquist et al. | 5,700,800 A | 12/1997 | Cincotta et al. |
| 5,658,330 A | 8/1997 | Carlisle et al. | 5,701,181 A | 12/1997 | Boiarski et al. |
| 5,658,443 A | 8/1997 | Yamamoto et al. | 5,701,894 A | 12/1997 | Cherry et al. |
| 5,658,444 A | 8/1997 | Black et al. | 5,702,575 A | 12/1997 | Foos et al. |
| 5,660,163 A | 8/1997 | Schulman et al. | 5,702,880 A | 12/1997 | Segall et al. |
| 5,660,692 A | 8/1997 | Nesburn et al. | 5,702,918 A | 12/1997 | Bannwarth et al. |
| 5,660,741 A | 8/1997 | Suzuki et al. | 5,704,354 A | 1/1998 | Preidel et al. |
| 5,660,791 A | 8/1997 | Brenneman et al. | 5,704,922 A | 1/1998 | Brown |
| 5,660,991 A | 8/1997 | Lakowicz et al. | 5,705,616 A | 1/1998 | Lehle et al. |
| 5,661,033 A | 8/1997 | Ho et al. | 5,706,807 A | 1/1998 | Picha |
| 5,661,643 A | 8/1997 | Blakely et al. | 5,707,502 A | 1/1998 | McCaffrey et al. |
| D383,550 S | 9/1997 | Larson et al. | 5,707,524 A | 1/1998 | Potter |
| 5,662,694 A | 9/1997 | Lidman et al. | 5,707,820 A | 1/1998 | Wilsey et al. |
| 5,662,781 A | 9/1997 | Denzinger et al. | 5,708,247 A | 1/1998 | McAleer et al. |
| 5,662,787 A | 9/1997 | Guttman et al. | 5,708,957 A | 1/1998 | Chuang et al. |
| 5,662,806 A | 9/1997 | Keshaviah et al. | 5,710,371 A | 1/1998 | Czernecki et al. |
| 5,662,813 A | 9/1997 | Sammons et al. | 5,710,630 A | 1/1998 | Essenpreis et al. |
| 5,662,904 A | 9/1997 | Ferguson et al. | 5,711,001 A | 1/1998 | Bussan et al. |
| 5,663,056 A | 9/1997 | Ollar et al. | 5,711,297 A | 1/1998 | Iliff |
| 5,665,065 A | 9/1997 | Colman et al. | 5,711,861 A | 1/1998 | Ward et al. |
| 5,665,215 A | 9/1997 | Bussmann et al. | 5,711,862 A | 1/1998 | Sakoda et al. |
| 5,665,222 A | 9/1997 | Heller et al. | 5,711,868 A | 1/1998 | Maley et al. |
| 5,665,492 A | 9/1997 | Sotomura | 5,711,915 A | 1/1998 | Siegmund et al. |
| 5,665,892 A | 9/1997 | Van Assche et al. | 5,713,888 A | 2/1998 | Neuenfeldt et al. |
| 5,667,964 A | 9/1997 | Ho | 5,714,123 A | 2/1998 | Sohrab |
| 5,667,983 A | 9/1997 | Abel et al. | 5,714,388 A | 2/1998 | Kusnetz |
| 5,668,010 A | 9/1997 | Felder et al. | 5,716,813 A | 2/1998 | Kubota et al. |
| 5,670,031 A | 9/1997 | Hintsche et al. | 5,716,932 A | 2/1998 | Meier et al. |
| 5,670,377 A | 9/1997 | Peterson et al. | 5,716,957 A | 2/1998 | Cincotta et al. |
| 5,672,513 A | 9/1997 | Terskikh et al. | 5,716,962 A | 2/1998 | Cincotta et al. |
| 5,672,515 A | 9/1997 | Furlong | 5,718,234 A | 2/1998 | Warden et al. |
| 5,672,875 A | 9/1997 | Block et al. | 5,718,694 A | 2/1998 | Rupp |
| 5,674,528 A | 10/1997 | Ogata et al. | 5,719,034 A | 2/1998 | Kiser et al. |
| 5,674,696 A | 10/1997 | Nakamura et al. | 5,719,160 A | 2/1998 | Cincotta et al. |
| 5,676,820 A | 10/1997 | Wang et al. | 5,720,733 A | 2/1998 | Brown |
| 5,676,849 A | 10/1997 | Sammons et al. | 5,720,862 A | 2/1998 | Hamamoto et al. |
| 5,677,169 A | 10/1997 | Ollar et al. | 5,721,783 A | 2/1998 | Anderson |
| 5,677,185 A | 10/1997 | Handley, III | D392,740 S | 3/1998 | Yung et al. |
| 5,678,571 A | 10/1997 | Brown | 5,722,397 A | 3/1998 | Eppstein |
| 5,679,231 A | 10/1997 | Alexander et al. | 5,723,284 A | 3/1998 | Ye |
| 5,679,690 A | 10/1997 | Andre et al. | 5,723,345 A | 3/1998 | Yamauchi et al. |
| 5,679,732 A | 10/1997 | Van Rheenen | 5,724,151 A | 3/1998 | Ryley et al. |
| 5,680,858 A | 10/1997 | Hansen et al. | 5,725,601 A | 3/1998 | Tajiri et al. |
| 5,681,572 A | 10/1997 | Seare, Jr. | 5,726,034 A | 3/1998 | Bryan et al. |
| 5,681,728 A | 10/1997 | Miao | 5,726,045 A | 3/1998 | Kagawa et al. |
| 5,682,233 A | 10/1997 | Brinda | 5,726,565 A | 3/1998 | Uchiyama et al. |
| 5,682,884 A | 11/1997 | Hill et al. | 5,727,548 A | 3/1998 | Hill et al. |
| 5,683,562 A | 11/1997 | Schaffar et al. | 5,728,225 A | 3/1998 | Duflot et al. |
| 5,683,563 A | 11/1997 | Mizutani et al. | 5,728,281 A | 3/1998 | Holmstrom et al. |
| 5,684,623 A | 11/1997 | King et al. | 5,728,290 A | 3/1998 | Xie et al. |
| 5,686,253 A | 11/1997 | Skold et al. | 5,728,352 A | 3/1998 | Poto et al. |
| 5,686,254 A | 11/1997 | Logan et al. | 5,730,124 A | 3/1998 | Yamauchi |
| 5,686,408 A | 11/1997 | Moses et al. | 5,730,149 A | 3/1998 | Nakayama et al. |
| 5,686,717 A | 11/1997 | Knowles et al. | 5,730,654 A | 3/1998 | Brown |
| 5,686,829 A | 11/1997 | Girault | 5,731,191 A | 3/1998 | Rutter et al. |
| 5,688,695 A | 11/1997 | Kramer | 5,731,203 A | 3/1998 | Handley, III |
| 5,691,701 A | 11/1997 | Wohlstein et al. | 5,731,204 A | 3/1998 | Rutter et al. |
| 5,692,504 A | 12/1997 | Essenpreis et al. | 5,731,312 A | 3/1998 | Cincotta et al. |
| 5,693,017 A | 12/1997 | Spears et al. | 5,733,336 A | 3/1998 | Neuenfeldt et al. |
| 5,693,349 A | 12/1997 | Scharfman et al. | 5,733,758 A | 3/1998 | Nguyen |
| 5,693,770 A | 12/1997 | Chen et al. | 5,733,762 A | 3/1998 | Midoux et al. |
| 5,694,932 A | 12/1997 | Michel | 5,734,587 A | 3/1998 | Backhaus et al. |
| 5,695,473 A | 12/1997 | Olsen | 5,735,273 A | 4/1998 | Kurnik et al. |
| 5,695,623 A | 12/1997 | Michel et al. | 5,735,285 A | 4/1998 | Albert et al. |
| 5,695,949 A | 12/1997 | Galen et al. | 5,735,916 A | 4/1998 | Lucas et al. |
| 5,696,314 A | 12/1997 | McCaffrey et al. | 5,736,050 A | 4/1998 | Pasternak et al. |

| | | |
|---|---|---|
| 5,736,103 A | 4/1998 | Pugh |
| 5,736,380 A | 4/1998 | Nishimoto et al. |
| 5,736,739 A | 4/1998 | Uber et al. |
| 5,738,244 A | 4/1998 | Charlton et al. |
| 5,738,992 A | 4/1998 | Cook et al. |
| 5,739,036 A | 4/1998 | Parris |
| 5,739,303 A | 4/1998 | Beck et al. |
| 5,741,211 A | 4/1998 | Renirie et al. |
| 5,741,330 A | 4/1998 | Brauker et al. |
| 5,741,634 A | 4/1998 | Nozoe et al. |
| 5,741,688 A | 4/1998 | Oxenb.o slashed.ll et al. |
| 5,743,250 A | 4/1998 | Gonda et al. |
| 5,743,262 A | 4/1998 | Lepper, Jr. et al. |
| 5,744,023 A | 4/1998 | Kakimoto et al. |
| 5,744,259 A | 4/1998 | Ohta et al. |
| 5,744,330 A | 4/1998 | Domingues |
| 5,746,217 A | 5/1998 | Erickson et al. |
| 5,746,898 A | 5/1998 | Preidel |
| 5,747,300 A | 5/1998 | Nishimoto et al. |
| 5,747,320 A | 5/1998 | Saha et al. |
| 5,747,666 A | 5/1998 | Willis |
| 5,747,669 A | 5/1998 | Suzuki |
| 5,747,809 A | 5/1998 | Eckstrom |
| 5,748,103 A | 5/1998 | Flach et al. |
| 5,748,308 A | 5/1998 | Lindberg et al. |
| 5,749,832 A | 5/1998 | Vadgama et al. |
| 5,749,907 A | 5/1998 | Mann |
| 5,750,363 A | 5/1998 | Ollar et al. |
| 5,750,389 A | 5/1998 | Elling et al. |
| 5,750,519 A | 5/1998 | Cincotta et al. |
| 5,750,926 A | 5/1998 | Schulman et al. |
| 5,752,512 A | 5/1998 | Gozani |
| 5,752,977 A | 5/1998 | Grevious et al. |
| 5,753,429 A | 5/1998 | Pugh |
| 5,753,452 A | 5/1998 | Smith |
| 5,753,454 A | 5/1998 | Lee |
| 5,754,722 A | 5/1998 | Melling |
| 5,755,953 A | 5/1998 | Henning et al. |
| 5,756,513 A | 5/1998 | Cincotta et al. |
| 5,756,632 A | 5/1998 | Ward et al. |
| 5,756,726 A | 5/1998 | Hemmi et al. |
| 5,759,364 A | 6/1998 | Charlton et al. |
| 5,759,610 A | 6/1998 | Nishimoto et al. |
| 5,759,764 A | 6/1998 | Polovina |
| 5,759,774 A | 6/1998 | Hackett et al. |
| 5,759,799 A | 6/1998 | Grosso |
| 5,760,047 A | 6/1998 | Cincotta et al. |
| 5,762,769 A | 6/1998 | Gotsu et al. |
| 5,762,770 A | 6/1998 | Pritchard et al. |
| 5,763,196 A | 6/1998 | Powell et al. |
| 5,763,277 A | 6/1998 | Zhu et al. |
| 5,766,439 A | 6/1998 | Eyal et al. |
| 5,766,473 A | 6/1998 | Strobel et al. |
| 5,766,515 A | 6/1998 | Jonas et al. |
| 5,766,839 A | 6/1998 | Johnson et al. |
| 5,766,934 A | 6/1998 | Guiseppi-Elie |
| 5,767,196 A | 6/1998 | Kozulic |
| 5,767,378 A | 6/1998 | Bojsen et al. |
| 5,770,028 A | 6/1998 | Maley et al. |
| 5,770,084 A | 6/1998 | Warner et al. |
| 5,770,389 A | 6/1998 | Ching et al. |
| 5,770,407 A | 6/1998 | Wong et al. |
| 5,770,439 A | 6/1998 | Bilitewski et al. |
| 5,770,454 A | 6/1998 | Essenpreis et al. |
| 5,770,571 A | 6/1998 | Cerami et al. |
| 5,771,001 A | 6/1998 | Cobb |
| 5,771,890 A | 6/1998 | Tamada |
| 5,771,891 A | 6/1998 | Gozani |
| 5,772,013 A | 6/1998 | Kunz et al. |
| 5,772,321 A | 6/1998 | Rhodes |
| 5,772,586 A | 6/1998 | Heinonen et al. |
| 5,772,606 A | 6/1998 | Ashibe et al. |
| 5,773,234 A | 6/1998 | Pronovost et al. |
| 5,773,270 A | 6/1998 | D'Orazio et al. |
| 5,773,606 A | 6/1998 | Vercauteren et al. |
| 5,776,324 A | 7/1998 | Usala |
| 5,777,060 A | 7/1998 | Van Antwerp |
| 5,779,665 A | 7/1998 | Mastrototaro et al. |
| 5,779,867 A | 7/1998 | Shieh |
| 5,780,038 A | 7/1998 | Bannwarth et al. |
| 5,780,251 A | 7/1998 | Klainer et al. |
| 5,780,304 A | 7/1998 | Matzinger et al. |
| 5,781,455 A | 7/1998 | Hyodo |
| 5,782,814 A | 7/1998 | Brown et al. |
| 5,782,880 A | 7/1998 | Lahtinen et al. |
| 5,782,912 A | 7/1998 | Brauker et al. |
| 5,783,054 A | 7/1998 | Raguse et al. |
| 5,783,056 A | 7/1998 | Hampp et al. |
| 5,784,154 A | 7/1998 | Pawliszyn |
| 5,785,681 A | 7/1998 | Indravudh |
| 5,785,830 A | 7/1998 | Foos et al. |
| 5,786,186 A | 7/1998 | Lancashire et al. |
| 5,786,226 A | 7/1998 | Bocker et al. |
| 5,786,439 A | 7/1998 | Van Antwerp et al. |
| 5,786,584 A | 7/1998 | Button et al. |
| 5,787,900 A | 8/1998 | Butler et al. |
| 5,788,632 A | 8/1998 | Pezzaniti et al. |
| 5,788,678 A | 8/1998 | Van Antwerp |
| 5,789,255 A | 8/1998 | Yu |
| 5,789,382 A | 8/1998 | Wellstein |
| 5,789,392 A | 8/1998 | Shibuya et al. |
| 5,791,344 A | 8/1998 | Schulman et al. |
| 5,792,117 A | 8/1998 | Brown |
| 5,792,473 A | 8/1998 | Gergely et al. |
| 5,792,621 A | 8/1998 | Verostko et al. |
| 5,792,920 A | 8/1998 | Bridges et al. |
| 5,795,305 A | 8/1998 | Cho et al. |
| 5,795,453 A | 8/1998 | Gilmartin |
| 5,795,751 A | 8/1998 | Apel |
| 5,795,774 A | 8/1998 | Matsumoto et al. |
| 5,798,031 A | 8/1998 | Charlton et al. |
| 5,798,032 A | 8/1998 | Khan et al. |
| 5,798,065 A | 8/1998 | Picha |
| 5,798,236 A | 8/1998 | Frost et al. |
| 5,798,265 A | 8/1998 | Springer et al. |
| 5,798,491 A | 8/1998 | Magda et al. |
| 5,800,387 A | 9/1998 | Duffy et al. |
| 5,800,420 A | 9/1998 | Gross et al. |
| 5,800,529 A | 9/1998 | Brauker et al. |
| 5,801,061 A | 9/1998 | Stephenson |
| 5,804,047 A | 9/1998 | Karube et al. |
| 5,804,048 A | 9/1998 | Wong et al. |
| 5,804,049 A | 9/1998 | Chan |
| 5,804,170 A | 9/1998 | Negishi et al. |
| 5,804,401 A | 9/1998 | Gardiol et al. |
| 5,804,411 A | 9/1998 | Tajima et al. |
| 5,804,599 A | 9/1998 | Tanaka et al. |
| 5,807,315 A | 9/1998 | Van Antwerp et al. |
| 5,807,375 A | 9/1998 | Gross et al. |
| 5,807,406 A | 9/1998 | Brauker et al. |
| 5,807,751 A | 9/1998 | Alajem et al. |
| 5,808,020 A | 9/1998 | Ferrieri et al. |
| 5,810,199 A | 9/1998 | Charlton et al. |
| 5,810,985 A | 9/1998 | Bao et al. |
| 5,811,253 A | 9/1998 | Friedman et al. |
| 5,811,280 A | 9/1998 | Visuri |
| 5,811,487 A | 9/1998 | Schulz, Jr. et al. |
| 5,811,812 A | 9/1998 | Williams et al. |
| 5,814,200 A | 9/1998 | Pethig et al. |
| 5,814,498 A | 9/1998 | Mani et al. |
| 5,814,599 A | 9/1998 | Mitragotri et al. |
| 5,815,278 A | 9/1998 | Johnston et al. |

| | | | | | | | |
|---|---|---|---|---|---|---|---|
| D399,566 | S | 10/1998 | Sohrab et al. | 5,856,191 | A | 1/1999 | Handley, III |
| 5,817,350 | A | 10/1998 | Rhode, Jr. et al. | 5,856,195 | A | 1/1999 | Charlton et al. |
| 5,817,780 | A | 10/1998 | Fleche et al. | 5,857,967 | A | 1/1999 | Frid et al. |
| 5,818,044 | A | 10/1998 | Sodickson et al. | 5,857,983 | A | 1/1999 | Douglas et al. |
| 5,818,048 | A | 10/1998 | Sodickson et al. | 5,858,186 | A | 1/1999 | Glass |
| 5,818,582 | A | 10/1998 | Fernandez et al. | 5,858,194 | A | 1/1999 | Bell |
| 5,820,551 | A | 10/1998 | Hill et al. | 5,858,195 | A | 1/1999 | Ramsey |
| 5,820,570 | A | 10/1998 | Erickson et al. | 5,858,644 | A | 1/1999 | Chen |
| 5,820,589 | A | 10/1998 | Torgerson et al. | 5,858,764 | A | 1/1999 | Osinga et al. |
| 5,820,622 | A | 10/1998 | Gross et al. | 5,859,271 | A | 1/1999 | Franson et al. |
| 5,821,093 | A | 10/1998 | Ingram et al. | 5,859,937 | A | 1/1999 | Nomura |
| 5,821,111 | A | 10/1998 | Grady et al. | 5,860,917 | A | 1/1999 | Comanor et al. |
| 5,821,399 | A | 10/1998 | Zelin | 5,861,009 | A | 1/1999 | Armstrong et al. |
| 5,822,472 | A | 10/1998 | Danielzik et al. | 5,861,019 | A | 1/1999 | Sun et al. |
| 5,822,715 | A | 10/1998 | Worthington et al. | 5,861,424 | A | 1/1999 | Chen et al. |
| 5,824,521 | A | 10/1998 | Nishimoto et al. | 5,861,948 | A | 1/1999 | Gilmutdinow et al. |
| 5,824,665 | A | 10/1998 | Henry et al. | 5,862,803 | A | 1/1999 | Besson et al. |
| 5,825,488 | A | 10/1998 | Kohl et al. | 5,863,400 | A | 1/1999 | Drummond et al. |
| 5,827,179 | A | 10/1998 | Lichter et al. | 5,864,014 | A | 1/1999 | Fasano |
| 5,827,183 | A | 10/1998 | Kurnik et al. | 5,865,738 | A | 2/1999 | Morcos et al. |
| 5,827,184 | A | 10/1998 | Netherly et al. | 5,866,004 | A | 2/1999 | Houck et al. |
| 5,827,685 | A | 10/1998 | Lindquist | 5,866,007 | A | 2/1999 | Whitson et al. |
| 5,827,748 | A | 10/1998 | Golden | 5,866,344 | A | 2/1999 | Georgiou |
| 5,828,943 | A | 10/1998 | Brown | 5,866,345 | A | 2/1999 | Wilding et al. |
| 5,830,341 | A | 11/1998 | Gilmartin | 5,866,349 | A | 2/1999 | Lilja et al. |
| 5,830,434 | A | 11/1998 | Taylor et al. | 5,866,352 | A | 2/1999 | Vorberg |
| 5,830,642 | A | 11/1998 | Fuller | 5,866,353 | A | 2/1999 | Berneth et al. |
| 5,830,715 | A | 11/1998 | Kubota et al. | 5,866,374 | A | 2/1999 | Kobayashi et al. |
| 5,832,448 | A | 11/1998 | Brown | 5,866,382 | A | 2/1999 | Hallborn et al. |
| 5,833,603 | A | 11/1998 | Kovacs et al. | 5,866,406 | A | 2/1999 | Wagner et al. |
| 5,833,757 | A | 11/1998 | Verhoff et al. | 5,866,531 | A | 2/1999 | Assmann et al. |
| 5,833,923 | A | 11/1998 | McClintock et al. | 5,866,584 | A | 2/1999 | Cincotta et al. |
| 5,833,924 | A | 11/1998 | McClintock et al. | 5,869,206 | A | 2/1999 | Sotomura |
| 5,834,224 | A | 11/1998 | Ruger et al. | 5,869,272 | A | 2/1999 | Bogart et al. |
| 5,834,258 | A | 11/1998 | Grifantini et al. | 5,869,273 | A | 2/1999 | Klock |
| 5,836,887 | A | 11/1998 | Oka et al. | 5,871,465 | A | 2/1999 | Vasko |
| 5,836,989 | A | 11/1998 | Shelton | 5,871,514 | A | 2/1999 | Wiklund et al. |
| 5,837,113 | A | 11/1998 | Suzuki et al. | 5,871,698 | A | 2/1999 | Laguna et al. |
| 5,837,199 | A | 11/1998 | Dumschat | 5,871,977 | A | 2/1999 | Kubota et al. |
| 5,837,446 | A | 11/1998 | Cozzette et al. | 5,872,245 | A | 2/1999 | Wilson |
| 5,837,454 | A | 11/1998 | Cozzette et al. | 5,872,713 | A | 2/1999 | Douglas et al. |
| 5,837,546 | A | 11/1998 | Allen et al. | 5,872,820 | A | 2/1999 | Upadrasta |
| 5,837,728 | A | 11/1998 | Purcell | 5,873,026 | A | 2/1999 | Reames |
| 5,840,020 | A | 11/1998 | Heinonen et al. | 5,873,358 | A | 2/1999 | Gonda et al. |
| 5,840,240 | A | 11/1998 | Stenoien et al. | 5,873,990 | A | 2/1999 | Wojciechowski et al. |
| 5,840,388 | A | 11/1998 | Karger et al. | 5,874,533 | A | 2/1999 | Bannwarth et al. |
| 5,840,777 | A | 11/1998 | Eagles et al. | 5,876,484 | A | 3/1999 | Raskin et al. |
| 5,840,877 | A | 11/1998 | Kozulic | 5,876,577 | A | 3/1999 | McAleer et al. |
| 5,842,983 | A | 12/1998 | Abel et al. | 5,876,621 | A | 3/1999 | Sapienza |
| 5,843,024 | A | 12/1998 | Brasile | 5,876,663 | A | 3/1999 | Laroussi |
| 5,843,140 | A | 12/1998 | Strojnik | 5,876,939 | A | 3/1999 | Reed et al. |
| 5,843,691 | A | 12/1998 | Douglas et al. | 5,879,163 | A | 3/1999 | Brown et al. |
| 5,843,692 | A | 12/1998 | Phillips et al. | 5,879,311 | A | 3/1999 | Duchon et al. |
| 5,846,392 | A | 12/1998 | Knoll | 5,879,373 | A | 3/1999 | Roper et al. |
| 5,846,486 | A | 12/1998 | Pugh | 5,879,878 | A | 3/1999 | Raguse et al. |
| 5,846,490 | A | 12/1998 | Yokota et al. | 5,880,107 | A | 3/1999 | Buenter |
| 5,846,492 | A | 12/1998 | Jacobs et al. | 5,880,829 | A | 3/1999 | Kauhaniemi et al. |
| 5,846,702 | A | 12/1998 | Deng et al. | 5,882,354 | A | 3/1999 | Brauker et al. |
| 5,846,744 | A | 12/1998 | Athey et al. | 5,882,494 | A | 3/1999 | Van Antwerp |
| 5,848,991 | A | 12/1998 | Gross et al. | 5,883,273 | A | 3/1999 | Miller et al. |
| 5,849,166 | A | 12/1998 | Fuller | 5,885,211 | A | 3/1999 | Eppstein et al. |
| 5,849,174 | A | 12/1998 | Sanghera et al. | 5,885,245 | A | 3/1999 | Lynch et al. |
| 5,849,293 | A | 12/1998 | Vargas et al. | 5,885,791 | A | 3/1999 | Cutler et al. |
| 5,849,984 | A | 12/1998 | Kim et al. | 5,887,133 | A | 3/1999 | Brown et al. |
| 5,851,197 | A | 12/1998 | Marano et al. | 5,888,365 | A | 3/1999 | Shih et al. |
| 5,853,994 | A | 12/1998 | Gopinathan et al. | 5,888,756 | A | 3/1999 | Ralston |
| 5,854,074 | A | 12/1998 | Charlton et al. | 5,889,025 | A | 3/1999 | Lohray et al. |
| 5,854,078 | A | 12/1998 | Asher et al. | 5,891,024 | A | 4/1999 | Jarman et al. |
| 5,854,189 | A | 12/1998 | Kruse et al. | 5,891,658 | A | 4/1999 | Klainer et al. |
| 5,854,255 | A | 12/1998 | Cincotta et al. | 5,891,971 | A | 4/1999 | Keoshkerian et al. |
| 5,856,146 | A | 1/1999 | Mitsuzumi et al. | 5,895,116 | A | 4/1999 | Kreinheder et al. |

| | | | | | |
|---|---|---|---|---|---|
| 5,895,371 A | 4/1999 | Levitas et al. | 5,938,903 A | 8/1999 | Broderick |
| 5,897,493 A | 4/1999 | Brown | 5,938,917 A | 8/1999 | Mulchandani |
| 5,897,578 A | 4/1999 | Wiklund et al. | 5,939,442 A | 8/1999 | Evans et al. |
| 5,897,995 A | 4/1999 | Vroemen et al. | 5,940,801 A | 8/1999 | Brown |
| 5,898,025 A | 4/1999 | Burg et al. | 5,941,821 A | 8/1999 | Chou |
| 5,899,855 A | 5/1999 | Brown | 5,941,906 A | 8/1999 | Barreras, Sr. et al. |
| 5,899,931 A | 5/1999 | Deschamp et al. | 5,942,102 A | 8/1999 | Hodges et al. |
| 5,900,362 A | 5/1999 | Eberz et al. | 5,942,388 A | 8/1999 | Willner et al. |
| 5,900,364 A | 5/1999 | Visuri | 5,942,754 A | 8/1999 | Yamaguchi et al. |
| 5,900,479 A | 5/1999 | Glasser et al. | 5,942,979 A | 8/1999 | Luppino |
| 5,902,577 A | 5/1999 | Asfari et al. | 5,944,661 A | 8/1999 | Swette et al. |
| 5,902,606 A | 5/1999 | Wunderlich et al. | 5,945,341 A | 8/1999 | Howard, III |
| 5,902,722 A | 5/1999 | Di Cesare et al. | 5,945,343 A | 8/1999 | Munkholm |
| 5,902,731 A | 5/1999 | Ouyang et al. | 5,945,345 A | 8/1999 | Blatt et al. |
| 5,902,939 A | 5/1999 | Ballard et al. | 5,946,083 A | 8/1999 | Melendez et al. |
| 5,904,708 A | 5/1999 | Goedeke | 5,946,431 A | 8/1999 | Fernandes |
| 5,904,798 A | 5/1999 | Bradford et al. | 5,947,749 A | 9/1999 | Rathburn |
| 5,906,724 A | 5/1999 | Sammons et al. | 5,947,921 A | 9/1999 | Johnson et al. |
| 5,906,921 A | 5/1999 | Ikeda et al. | 5,948,278 A | 9/1999 | Sammons et al. |
| 5,909,114 A | 6/1999 | Uchiyama et al. | 5,948,512 A | 9/1999 | Kubota et al. |
| 5,910,554 A | 6/1999 | Kempe et al. | 5,950,632 A | 9/1999 | Reber et al. |
| 5,911,862 A | 6/1999 | Chan | 5,951,300 A | 9/1999 | Brown |
| 5,912,323 A | 6/1999 | Fasano | 5,951,492 A | 9/1999 | Douglas et al. |
| 5,912,330 A | 6/1999 | Tabuchi et al. | 5,951,521 A | 9/1999 | Mastrototaro et al. |
| 5,912,398 A | 6/1999 | Goldstein et al. | 5,951,836 A | 9/1999 | McAleer et al. |
| 5,913,310 A | 6/1999 | Brown | 5,951,859 A | 9/1999 | Miura et al. |
| 5,913,827 A | 6/1999 | Gorman | 5,952,293 A | 9/1999 | Olsson et al. |
| 5,913,998 A | 6/1999 | Butler et al. | 5,954,643 A | 9/1999 | VanAntwerp et al. |
| 5,914,026 A | 6/1999 | Blubaugh, Jr. et al. | 5,954,685 A | 9/1999 | Tierney |
| 5,915,378 A | 6/1999 | Lloyd et al. | 5,954,700 A | 9/1999 | Kovelman |
| 5,916,156 A | 6/1999 | Hildenbrand et al. | 5,955,377 A | 9/1999 | Maul et al. |
| 5,916,445 A | 6/1999 | Hjerten et al. | 5,956,501 A | 9/1999 | Brown |
| 5,916,757 A | 6/1999 | Contestable et al. | 5,957,854 A | 9/1999 | Besson et al. |
| 5,916,780 A | 6/1999 | Foody et al. | 5,957,890 A | 9/1999 | Mann et al. |
| 5,916,869 A | 6/1999 | Croom, Jr. et al. | 5,957,903 A | 9/1999 | Mirzaee et al. |
| 5,917,068 A | 6/1999 | Barnicki et al. | 5,957,958 A | 9/1999 | Schulman et al. |
| 5,917,185 A | 6/1999 | Yeung et al. | 5,958,199 A | 9/1999 | Miyamoto et al. |
| 5,917,346 A | 6/1999 | Gord | 5,958,202 A | 9/1999 | Regnier et al. |
| 5,918,603 A | 7/1999 | Brown | 5,958,434 A | 9/1999 | Simon et al. |
| 5,919,215 A | 7/1999 | Wiklund et al. | 5,958,476 A | 9/1999 | Cain et al. |
| 5,919,216 A | 7/1999 | Houben et al. | 5,958,786 A | 9/1999 | Munkholm |
| 5,919,349 A | 7/1999 | Huber et al. | 5,959,050 A | 9/1999 | Mosbach et al. |
| 5,919,614 A | 7/1999 | Livesey et al. | 5,959,076 A | 9/1999 | Nagel et al. |
| 5,919,777 A | 7/1999 | Hansen et al. | 5,959,738 A | 9/1999 | Hafeman et al. |
| 5,922,183 A | 7/1999 | Rauh | 5,960,403 A | 9/1999 | Brown |
| 5,922,188 A | 7/1999 | Ikeda et al. | RE363,350 | 10/1999 | Sweldberg et al. |
| 5,922,285 A | 7/1999 | Melendez et al. | 5,961,451 A | 10/1999 | Reber et al. |
| 5,922,350 A | 7/1999 | Janoff et al. | 5,961,799 A | 10/1999 | Matsumoto et al. |
| 5,922,530 A | 7/1999 | Yu | 5,962,248 A | 10/1999 | Tadano et al. |
| 5,922,578 A | 7/1999 | Maruta et al. | 5,962,276 A | 10/1999 | Vercauteren et al. |
| 5,922,770 A | 7/1999 | Peschke et al. | 5,962,286 A | 10/1999 | Anastassiadis et al. |
| 5,923,421 A | 7/1999 | Rajic et al. | 5,962,287 A | 10/1999 | Suh et al. |
| 5,924,430 A | 7/1999 | Baldauf | 5,962,852 A | 10/1999 | Knuettel et al. |
| 5,924,996 A | 7/1999 | Cho et al. | 5,964,261 A | 10/1999 | Neuenfeldt et al. |
| 5,925,021 A | 7/1999 | Castellano et al. | 5,964,745 A | 10/1999 | Lyles et al. |
| 5,925,670 A | 7/1999 | Silverman et al. | 5,964,804 A | 10/1999 | Brauker et al. |
| 5,928,130 A | 7/1999 | Schmidt | 5,964,993 A | 10/1999 | Blubaugh, Jr. et al. |
| 5,928,886 A | 7/1999 | Logan et al. | 5,964,996 A | 10/1999 | Armstrong |
| RE36,268 E | 8/1999 | Szuminsky et al. | 5,964,999 A | 10/1999 | Guttman et al. |
| 5,931,791 A | 8/1999 | Saltzstein et al. | 5,965,380 A | 10/1999 | Heller et al. |
| 5,931,814 A | 8/1999 | Alex et al. | 5,965,411 A | 10/1999 | Nishimoto et al. |
| 5,932,075 A | 8/1999 | Strauss et al. | 5,967,975 A | 10/1999 | Ridgeway |
| 5,932,175 A | 8/1999 | Knute, deceased et al. | 5,968,726 A | 10/1999 | Segall et al. |
| 5,932,274 A | 8/1999 | Scharfmann et al. | 5,968,746 A | 10/1999 | Schneider |
| 5,932,455 A | 8/1999 | Viljava et al. | 5,968,760 A | 10/1999 | Phillips et al. |
| 5,932,462 A | 8/1999 | Harris et al. | 5,968,787 A | 10/1999 | Iwata et al. |
| 5,932,611 A | 8/1999 | Wuthier et al. | 5,968,836 A | 10/1999 | Matzinger et al. |
| 5,933,136 A | 8/1999 | Brown | 5,968,839 A | 10/1999 | Blatt et al. |
| 5,935,099 A | 8/1999 | Peterson et al. | 5,968,982 A | 10/1999 | Voss et al. |
| 5,935,636 A | 8/1999 | Nishimoto et al. | 5,971,922 A | 10/1999 | Arita et al. |
| 5,935,785 A | 8/1999 | Reber et al. | 5,971,941 A | 10/1999 | Simons et al. |

| | | | | | |
|---|---|---|---|---|---|
| 5,972,199 A | 10/1999 | Heller et al. | 6,013,491 A | 1/2000 | Martinez |
| 5,972,294 A | 10/1999 | Smith et al. | 6,013,527 A | 1/2000 | Kurrle-Weitenhiller et al. |
| 5,972,369 A | 10/1999 | Roorda et al. | 6,013,528 A | 1/2000 | Jacobs et al. |
| 5,972,710 A | 10/1999 | Weigl et al. | 6,013,529 A | 1/2000 | Munkholm |
| 5,972,715 A | 10/1999 | Celentano et al. | 6,013,658 A | 1/2000 | Lau et al. |
| 5,974,124 A | 10/1999 | Schlueter, Jr. et al. | 6,014,577 A | 1/2000 | Henning et al. |
| 5,976,085 A | 11/1999 | Kimball et al. | 6,015,466 A | 1/2000 | Maitre et al. |
| 5,976,465 A | 11/1999 | Luzzana et al. | 6,015,572 A | 1/2000 | Lin et al. |
| 5,977,178 A | 11/1999 | Hansen et al. | 6,015,703 A | 1/2000 | White et al. |
| 5,977,476 A | 11/1999 | Guha et al. | 6,016,448 A | 1/2000 | Busacker et al. |
| 5,977,545 A | 11/1999 | Haar et al. | 6,017,435 A | 1/2000 | Hassard et al. |
| 5,980,709 A | 11/1999 | Hodges et al. | 6,017,899 A | 1/2000 | Maruta et al. |
| 5,980,828 A | 11/1999 | McClintock et al. | 6,018,034 A | 1/2000 | Elseviers et al. |
| 5,981,129 A | 11/1999 | Akazawa et al. | 6,018,678 A | 1/2000 | Mitragotri et al. |
| 5,981,180 A | 11/1999 | Chandler et al. | 6,020,052 A | 2/2000 | Johnson |
| 5,981,203 A | 11/1999 | Meyerhoff et al. | 6,020,195 A | 2/2000 | Schmolke et al. |
| 5,981,268 A | 11/1999 | Kovacs et al. | 6,021,339 A | 2/2000 | Saito et al. |
| 5,981,294 A | 11/1999 | Blatt et al. | 6,022,316 A | 2/2000 | Eppstein et al. |
| 5,985,116 A | 11/1999 | Ikeda et al. | 6,022,713 A | 2/2000 | Noguchi et al. |
| 5,985,129 A | 11/1999 | Gough et al. | 6,023,540 A | 2/2000 | Walt et al. |
| 5,985,130 A | 11/1999 | Ikeda et al. | 6,023,629 A | 2/2000 | Tamada |
| 5,985,214 A | 11/1999 | Stylli et al. | 6,024,539 A | 2/2000 | Blomquist |
| 5,985,622 A | 11/1999 | Mattes et al. | 6,024,699 A | 2/2000 | Surwit et al. |
| 5,986,754 A | 11/1999 | Harding | 6,024,923 A | 2/2000 | Melendez et al. |
| 5,986,770 A | 11/1999 | Hein et al. | 6,024,925 A | 2/2000 | Little et al. |
| 5,987,352 A | 11/1999 | Klein et al. | 6,025,168 A | 2/2000 | Vercauteren et al. |
| 5,987,353 A | 11/1999 | Khatchatrian et al. | 6,025,203 A | 2/2000 | Vetter et al. |
| 5,989,409 A | 11/1999 | Kurnik et al. | 6,026,320 A | 2/2000 | Carlson et al. |
| 5,989,598 A | 11/1999 | Whalen et al. | 6,026,321 A | 2/2000 | Miyata et al. |
| 5,992,211 A | 11/1999 | Skrtic | 6,027,459 A | 2/2000 | Shain et al. |
| 5,994,091 A | 11/1999 | Attridge et al. | 6,027,570 A | 2/2000 | Farr et al. |
| 5,994,337 A | 11/1999 | Washburn et al. | 6,027,692 A | 2/2000 | Galen et al. |
| 5,994,476 A | 11/1999 | Shin et al. | 6,028,052 A | 2/2000 | Heyman et al. |
| 5,994,629 A | 11/1999 | Bojsen et al. | 6,028,311 A | 2/2000 | Sodickson et al. |
| 5,995,860 A | 11/1999 | Sun et al. | 6,029,500 A | 2/2000 | Tom |
| D417,504 S | 12/1999 | Love et al. | 6,030,399 A | 2/2000 | Ignotz et al. |
| 5,997,476 A | 12/1999 | Brown | 6,030,819 A | 2/2000 | Amaratunga et al. |
| 5,997,561 A | 12/1999 | Bocker et al. | 6,030,827 A | 2/2000 | Davis et al. |
| 5,997,817 A | 12/1999 | Crismore et al. | 6,030,973 A | 2/2000 | Lohray et al. |
| 5,998,157 A | 12/1999 | Schmitt et al. | 6,032,059 A | 2/2000 | Henning et al. |
| 5,998,701 A | 12/1999 | Kawchuk et al. | 6,032,199 A | 2/2000 | Lim et al. |
| 5,999,848 A | 12/1999 | Gord et al. | 6,033,546 A | 3/2000 | Ramsey |
| 5,999,849 A | 12/1999 | Gord et al. | 6,033,866 A | 3/2000 | Guo et al. |
| 6,001,067 A | 12/1999 | Shults et al. | 6,033,896 A | 3/2000 | Yang |
| 6,001,239 A | 12/1999 | Douglas et al. | 6,035,237 A | 3/2000 | Schulman et al. |
| 6,001,471 A | 12/1999 | Bries et al. | 6,036,919 A | 3/2000 | Thym et al. |
| 6,002,954 A | 12/1999 | Van Antwerp et al. | 6,036,922 A | 3/2000 | Kawamura et al. |
| 6,002,961 A | 12/1999 | Mitragotri et al. | 6,036,980 A | 3/2000 | Beck et al. |
| 6,004,391 A | 12/1999 | Letschert et al. | 6,040,151 A | 3/2000 | Douglas et al. |
| 6,004,441 A | 12/1999 | Fujiwara et al. | 6,040,194 A | 3/2000 | Chick et al. |
| 6,004,442 A | 12/1999 | Choulga et al. | 6,040,195 A | 3/2000 | Carroll et al. |
| 6,004,445 A | 12/1999 | Genders et al. | 6,041,253 A | 3/2000 | Kost et al. |
| 6,004,784 A | 12/1999 | Mobley et al. | 6,041,665 A | 3/2000 | Hussain |
| 6,004,938 A | 12/1999 | Frick et al. | 6,042,714 A | 3/2000 | Lin et al. |
| 6,004,972 A | 12/1999 | Cincotta et al. | 6,042,751 A | 3/2000 | Chan et al. |
| 6,006,753 A | 12/1999 | Efendic | 6,043,047 A | 3/2000 | Foote et al. |
| 6,007,845 A | 12/1999 | Domb et al. | 6,043,437 A | 3/2000 | Schulman et al. |
| 6,008,055 A | 12/1999 | Zhu et al. | D422,356 S | 4/2000 | Marano et al. |
| 6,008,345 A | 12/1999 | Dannoue et al. | 6,045,756 A | 4/2000 | Carr et al. |
| 6,009,339 A | 12/1999 | Bentsen et al. | 6,046,014 A | 4/2000 | Lagarias et al. |
| 6,009,632 A | 1/2000 | Douglas | 6,046,019 A | 4/2000 | Goumeniouk et al. |
| 6,010,607 A | 1/2000 | Ramsey | 6,046,804 A | 4/2000 | Kawamura et al |
| 6,010,608 A | 1/2000 | Ramsey | 6,046,805 A | 4/2000 | Kawamura et al. |
| 6,011,031 A | 1/2000 | Lohray et al. | 6,047,203 A | 4/2000 | Sackner et al. |
| 6,011,036 A | 1/2000 | Lohray et al. | 6,048,514 A | 4/2000 | Young et al. |
| 6,011,486 A | 1/2000 | Casey | 6,048,691 A | 4/2000 | Maracas |
| 6,011,984 A | 1/2000 | Van Antwerp et al. | 6,048,842 A | 4/2000 | Tsujihara et al. |
| 6,013,029 A | 1/2000 | Korf et al. | 6,049,004 A | 4/2000 | Kiely et al. |
| 6,013,113 A | 1/2000 | Mika | 6,049,727 A | 4/2000 | Crothall |
| 6,013,165 A | 1/2000 | Wiktorowicz et al. | 6,049,728 A | 4/2000 | Chou |
| 6,013,467 A | 1/2000 | Siedel et al. | 6,049,804 A | 4/2000 | Burgess et al. |

| | | | | | |
|---|---|---|---|---|---|
| 6,050,988 A | 4/2000 | Zuck | 6,090,595 A | 7/2000 | Foody et al. |
| 6,051,236 A | 4/2000 | Portman | 6,090,773 A | 7/2000 | Lukenbach et al. |
| 6,051,372 A | 4/2000 | Bayerl et al. | 6,090,792 A | 7/2000 | Nishimoto et al. |
| 6,051,392 A | 4/2000 | Ikeda et al. | 6,091,504 A | 7/2000 | Walker et al. |
| 6,051,393 A | 4/2000 | Jones et al. | 6,091,975 A | 7/2000 | Daddona et al. |
| 6,054,039 A | 4/2000 | Shieh | 6,091,976 A | 7/2000 | Pfeiffer et al. |
| 6,056,718 A | 5/2000 | Funderburk et al. | 6,093,156 A | 7/2000 | Cunningham et al. |
| 6,056,734 A | 5/2000 | Jacobsen et al. | 6,093,167 A | 7/2000 | Houben et al. |
| 6,057,120 A | 5/2000 | Heindl et al. | 6,093,172 A | 7/2000 | Funderburk et al. |
| 6,057,377 A | 5/2000 | Sasaki et al. | 6,093,546 A | 7/2000 | Ledden et al. |
| 6,057,493 A | 5/2000 | Willmitzer et al. | 6,096,319 A | 8/2000 | Seidel et al. |
| 6,059,946 A | 5/2000 | Yukawa et al. | 6,096,497 A | 8/2000 | Bauer |
| 6,060,327 A | 5/2000 | Keen | 6,097,188 A | 8/2000 | Sweedler et al. |
| 6,060,481 A | 5/2000 | LaNoue et al. | 6,097,831 A | 8/2000 | Wieck et al. |
| 6,060,640 A | 5/2000 | Pauley et al. | 6,098,615 A | 8/2000 | Lloyd et al. |
| 6,063,459 A | 5/2000 | Velte | 6,099,484 A | 8/2000 | Douglas et al. |
| 6,063,637 A | 5/2000 | Arnold et al. | 6,099,802 A | 8/2000 | Pugh et al. |
| 6,064,065 A | 5/2000 | Block et al. | 6,099,804 A | 8/2000 | Clausen et al. |
| 6,064,897 A | 5/2000 | Lindberg et al. | 6,100,045 A | 8/2000 | Van Es |
| 6,066,083 A | 5/2000 | Slater et al. | 6,101,478 A | 8/2000 | Brown |
| 6,066,243 A | 5/2000 | Anderson et al. | 6,102,872 A | 8/2000 | Doneen et al. |
| 6,066,249 A | 5/2000 | Manzoni et al. | 6,103,033 A | 8/2000 | Say et al. |
| 6,066,448 A | 5/2000 | Wohlstadter et al. | 6,103,199 A | 8/2000 | Bjornson et al. |
| 6,066,480 A | 5/2000 | Mobley et al. | 6,103,509 A | 8/2000 | Sode |
| 6,067,017 A | 5/2000 | Stewart et al. | 6,103,533 A | 8/2000 | Hassard et al. |
| 6,067,474 A | 5/2000 | Schulman et al. | 6,103,537 A | 8/2000 | Ullman et al. |
| 6,068,615 A | 5/2000 | Brown et al. | 6,103,703 A | 8/2000 | Renshaw et al. |
| 6,068,971 A | 5/2000 | Berry et al. | 6,104,940 A | 8/2000 | Watanabe et al. |
| 6,070,103 A | 5/2000 | Ogden | 6,106,692 A | 8/2000 | Kunimatsu et al. |
| 6,071,249 A | 6/2000 | Cunningham et al. | 6,106,780 A | 8/2000 | Douglas et al. |
| 6,071,251 A | 6/2000 | Cunningham et al. | 6,107,083 A | 8/2000 | Collins et al. |
| 6,071,294 A | 6/2000 | Simons et al. | 6,107,093 A | 8/2000 | Ingram et al. |
| 6,071,391 A | 6/2000 | Gotoh et al. | 6,107,099 A | 8/2000 | Munkholm |
| 6,071,392 A | 6/2000 | Yamamoto et al. | 6,107,358 A | 8/2000 | Harada et al. |
| 6,071,406 A | 6/2000 | Tsou | 6,110,148 A | 8/2000 | Brown et al. |
| 6,071,697 A | 6/2000 | Sosa-Pineda et al. | 6,110,152 A | 8/2000 | Kovelman |
| 6,071,739 A | 6/2000 | Vadgama et al. | 6,111,096 A | 8/2000 | Laugharn, Jr. et al. |
| 6,071,747 A | 6/2000 | Strosberg et al. | 6,111,251 A | 8/2000 | Hillenkamp |
| 6,073,031 A | 6/2000 | Helstab et al. | 6,113,578 A | 9/2000 | Brown |
| 6,073,049 A | 6/2000 | Alt et al. | 6,113,762 A | 9/2000 | Karube et al. |
| 6,074,385 A | 6/2000 | Klopotek | 6,113,763 A | 9/2000 | Henry et al. |
| 6,074,461 A | 6/2000 | Wilson | 6,115,634 A | 9/2000 | Donders et al. |
| 6,074,615 A | 6/2000 | Lewis et al. | 6,117,290 A | 9/2000 | Say et al. |
| 6,074,875 A | 6/2000 | Thorens | 6,117,391 A | 9/2000 | Mootz et al. |
| 6,075,177 A | 6/2000 | Bahia et al. | 6,117,643 A | 9/2000 | Simpson et al. |
| 6,077,408 A | 6/2000 | Miyamoto et al. | 6,117,658 A | 9/2000 | Dennis et al. |
| 6,077,411 A | 6/2000 | Nakamura | 6,119,026 A | 9/2000 | McNulty et al. |
| 6,077,660 A | 6/2000 | Wong et al. | 6,119,028 A | 9/2000 | Schulman et al. |
| 6,078,829 A | 6/2000 | Uchida et al. | 6,120,460 A | 9/2000 | Abreu |
| 6,080,385 A | 6/2000 | Clark et al. | 6,120,676 A | 9/2000 | Heller et al. |
| 6,080,538 A | 6/2000 | Segall et al. | 6,121,009 A | 9/2000 | Heller et al. |
| 6,081,104 A | 6/2000 | Kern | 6,121,011 A | 9/2000 | Douglas et al. |
| 6,081,182 A | 6/2000 | Tomozawa et al. | 6,121,050 A | 9/2000 | Han |
| 6,081,735 A | 6/2000 | Diab et al. | 6,121,055 A | 9/2000 | Hargreaves |
| 6,081,736 A | 6/2000 | Colvin et al. | 6,122,351 A | 9/2000 | Schlueter, Jr. et al. |
| 6,083,248 A | 7/2000 | Thompson | 6,122,536 A | 9/2000 | Sun et al. |
| 6,083,366 A | 7/2000 | Higson | 6,123,820 A | 9/2000 | Bergkuist et al. |
| 6,083,367 A | 7/2000 | Suzuki | 6,123,827 A | 9/2000 | Wong et al. |
| 6,083,523 A | 7/2000 | Dionne et al. | 6,124,134 A | 9/2000 | Stark |
| 6,083,635 A | 7/2000 | Jonas et al. | 6,125,290 A | 9/2000 | Miesel |
| 6,083,710 A | 7/2000 | Heller et al. | 6,125,291 A | 9/2000 | Miesel et al. |
| 6,083,908 A | 7/2000 | Ankersen | 6,125,292 A | 9/2000 | Uenoyama et al. |
| 6,084,660 A | 7/2000 | Shartle | 6,125,978 A | 10/2000 | Ando et al. |
| 6,085,753 A | 7/2000 | Gonda et al. | 6,126,800 A | 10/2000 | Caillat et al. |
| 6,085,871 A | 7/2000 | Karamata | 6,126,900 A | 10/2000 | Hildenbrand |
| 6,087,088 A | 7/2000 | Piran et al. | 6,127,341 A | 10/2000 | Hansen et al. |
| 6,087,131 A | 7/2000 | Gunata et al. | 6,127,354 A | 10/2000 | Peschke et al. |
| 6,087,182 A | 7/2000 | Jeng et al. | 6,127,391 A | 10/2000 | Hansen et al. |
| 6,088,608 A | 7/2000 | Schulman et al. | 6,128,519 A | 10/2000 | Say |
| 6,090,545 A | 7/2000 | Wohlstadter et al. | 6,130,214 A | 10/2000 | Lohray et al. |
| 6,090,568 A | 7/2000 | Belly et al. | 6,132,371 A | 10/2000 | Dempsey et al. |

| | | | | | | |
|---|---|---|---|---|---|---|
| 6,132,454 | A | 10/2000 | Fellows | 6,175,767 B1 | 1/2001 | Doyle, Sr. |
| 6,132,726 | A | 10/2000 | Daughenbaugh et al. | 6,176,119 B1 | 1/2001 | Kintzig |
| 6,132,955 | A | 10/2000 | Talley et al. | 6,176,988 B1 | 1/2001 | Kessler |
| 6,134,459 | A | 10/2000 | Roberts et al. | 6,177,553 B1 | 1/2001 | Hindsgaul et al. |
| 6,134,461 | A | 10/2000 | Say et al. | 6,179,979 B1 | 1/2001 | Hodges et al. |
| 6,134,504 | A | 10/2000 | Douglas et al. | 6,180,341 B1 | 1/2001 | Iverson et al. |
| 6,135,978 | A | 10/2000 | Houben et al. | 6,180,416 B1 | 1/2001 | Kurnik et al. |
| 6,136,293 | A | 10/2000 | Schneider et al. | 6,181,417 B1 | 1/2001 | Dosmann |
| 6,136,527 | A | 10/2000 | Fuchs et al. | 6,181,957 B1 | 1/2001 | Lambert et al. |
| 6,136,576 | A | 10/2000 | Diaz-Torres et al. | 6,181,958 B1 | 1/2001 | Steuer et al. |
| 6,136,607 | A | 10/2000 | Conlon et al. | 6,183,434 B1 | 2/2001 | Eppstein |
| 6,139,718 | A | 10/2000 | Kurnik et al. | 6,183,696 B1 | 2/2001 | Elkind et al. |
| 6,140,045 | A | 10/2000 | Wohlstadter et al. | 6,184,030 B1 | 2/2001 | Katoot et al. |
| 6,140,639 | A | 10/2000 | Gusev et al. | 6,185,452 B1 | 2/2001 | Schulman et al. |
| 6,141,573 | A | 10/2000 | Kurnik et al. | 6,186,145 B1 | 2/2001 | Brown |
| D434,142 | S | 11/2000 | Cheney, II et al. | 6,187,062 B1 | 2/2001 | Oweis et al. |
| 6,142,939 | A | 11/2000 | Eppstein et al. | 6,187,157 B1 | 2/2001 | Chen et al. |
| 6,142,972 | A | 11/2000 | Cheikh | 6,187,202 B1 | 2/2001 | Fish |
| 6,143,164 | A | 11/2000 | Heller et al. | 6,187,570 B1 | 2/2001 | Genders et al. |
| 6,143,326 | A | 11/2000 | Mockel et al. | 6,188,474 B1 | 2/2001 | Dussault et al. |
| 6,143,558 | A | 11/2000 | Kopelman et al. | 6,188,476 B1 | 2/2001 | Hafeman et al. |
| 6,144,837 | A | 11/2000 | Quy | 6,189,536 B1 | 2/2001 | Martinez et al. |
| 6,144,866 | A | 11/2000 | Miesel et al. | 6,190,522 B1 | 2/2001 | Haro |
| 6,144,869 | A | 11/2000 | Berner et al. | 6,190,612 B1 | 2/2001 | Berger et al. |
| 6,144,922 | A | 11/2000 | Douglas et al. | 6,190,892 B1 | 2/2001 | Weyler et al. |
| 6,146,497 | A | 11/2000 | Nguyen | 6,190,893 B1 | 2/2001 | Shastri et al. |
| 6,148,094 | A | 11/2000 | Kinsella | 6,190,906 B1 | 2/2001 | Schumacher et al. |
| 6,149,203 | A | 11/2000 | Hanlon | 6,190,914 B1 | 2/2001 | Grivell et al. |
| 6,150,128 | A | 11/2000 | Uretsky | 6,191,847 B1 | 2/2001 | Melendez et al. |
| 6,150,587 | A | 11/2000 | Guiltinan et al. | 6,192,891 B1 | 2/2001 | Gravel et al. |
| 6,150,812 | A | 11/2000 | Pinsky et al. | 6,193,873 B1 | 2/2001 | Ohara et al. |
| 6,151,586 | A | 11/2000 | Brown | 6,194,160 B1 | 2/2001 | Levin |
| 6,153,062 | A | 11/2000 | Saito et al. | 6,194,203 B1 | 2/2001 | Blum et al. |
| 6,153,069 | A | 11/2000 | Pottgen et al. | 6,195,582 B1 | 2/2001 | Scott |
| 6,153,419 | A | 11/2000 | Aisaka et al. | 6,196,970 B1 | 3/2001 | Brown |
| 6,154,675 | A | 11/2000 | Juran et al. | 6,197,172 B1 | 3/2001 | Dicks et al. |
| RE36,991 | E | 12/2000 | Yamamoto et al. | 6,197,257 B1 | 3/2001 | Raskas |
| 6,156,173 | A | 12/2000 | Gotoh et al. | 6,197,587 B1 | 3/2001 | Guiltinan et al. |
| 6,156,570 | A | 12/2000 | Hu et al. | 6,197,759 B1 | 3/2001 | Esswein et al. |
| 6,156,576 | A | 12/2000 | Allbritton et al. | 6,198,950 B1 | 3/2001 | Kraus |
| 6,157,442 | A | 12/2000 | Raskas | 6,198,952 B1 | 3/2001 | Miesel |
| 6,157,860 | A | 12/2000 | Hauser et al. | 6,198,957 B1 | 3/2001 | Green |
| 6,158,012 | A | 12/2000 | Watts, Jr. | 6,200,265 B1 | 3/2001 | Walsh et al. |
| 6,159,147 | A | 12/2000 | Lichter et al. | 6,200,459 B1 | 3/2001 | Vadgama et al. |
| 6,159,240 | A | 12/2000 | Sparer et al. | 6,200,772 B1 | 3/2001 | Vadgama et al. |
| 6,159,966 | A | 12/2000 | Lohray et al. | 6,200,773 B1 | 3/2001 | Ouyang et al. |
| 6,161,095 | A | 12/2000 | Brown | 6,200,783 B1 | 3/2001 | Chaen et al. |
| 6,161,437 | A | 12/2000 | Brennan et al. | 6,201,979 B1 | 3/2001 | Kurnik et al. |
| 6,162,397 | A | 12/2000 | Jurik et al. | 6,201,980 B1 | 3/2001 | Darrow et al. |
| 6,162,611 | A | 12/2000 | Heller et al. | 6,201,993 B1 | 3/2001 | Kruse et al. |
| 6,162,615 | A | 12/2000 | Zielenski | 6,203,680 B1 | 3/2001 | Cole |
| 6,162,639 | A | 12/2000 | Douglas | 6,204,431 B1 | 3/2001 | Prieto et al. |
| 6,162,825 | A | 12/2000 | Silverman et al. | 6,206,841 B1 | 3/2001 | Cunningham et al. |
| 6,163,723 | A | 12/2000 | Roberts et al. | 6,206,856 B1 | 3/2001 | Mahurkar |
| 6,165,981 | A | 12/2000 | Flaa et al. | 6,207,000 B1 | 3/2001 | Schwobel et al. |
| 6,166,807 | A | 12/2000 | Kawamura et al. | 6,207,098 B1 | 3/2001 | Nakanishi et al. |
| 6,167,362 | A | 12/2000 | Brown et al. | 6,207,110 B1 | 3/2001 | Sullivan et al. |
| 6,167,614 | B1 | 1/2001 | Tuttle et al. | 6,207,144 B1 | 3/2001 | Kurth et al. |
| 6,168,563 | B1 | 1/2001 | Brown | 6,207,369 B1 | 3/2001 | Wohlstadter et al. |
| 6,168,699 | B1 | 1/2001 | Frenkel et al. | 6,207,400 B1 | 3/2001 | Kwon |
| 6,168,957 | B1 | 1/2001 | Matzinger et al. | 6,208,894 B1 | 3/2001 | Schulman et al. |
| 6,170,318 | B1 | 1/2001 | Lewis | 6,210,272 B1 | 4/2001 | Brown |
| 6,171,238 | B1 | 1/2001 | Klimes et al. | 6,210,326 B1 | 4/2001 | Ehwald |
| 6,171,780 | B1 | 1/2001 | Pham et al. | 6,210,421 B1 | 4/2001 | Bocker et al. |
| 6,172,207 | B1 | 1/2001 | Damhaut et al. | 6,210,574 B1 | 4/2001 | Sammons et al. |
| 6,172,743 | B1 | 1/2001 | Kley et al. | 6,210,717 B1 | 4/2001 | Choi et al. |
| 6,173,160 | B1 | 1/2001 | Liimatainen | 6,210,976 B1 | 4/2001 | Sabbadini |
| 6,173,202 | B1 | 1/2001 | Eppstein | 6,212,416 B1 | 4/2001 | Ward et al. |
| 6,174,420 | B1 | 1/2001 | Hodges et al. | 6,212,417 B1 | 4/2001 | Ikeda et al. |
| 6,174,698 | B1 | 1/2001 | Miller | 6,212,424 B1 | 4/2001 | Robinson |
| 6,175,752 | B1 | 1/2001 | Say et al. | 6,214,185 B1 | 4/2001 | Offenbacher et al. |

| | | | | | | |
|---|---|---|---|---|---|---|
| 6,214,191 B1 | 4/2001 | Wiktorowicz et al. | | 6,251,584 B1 | 6/2001 | Unadkat |
| 6,214,205 B1 | 4/2001 | Willner et al. | | 6,251,626 B1 | 6/2001 | Stougaard et al. |
| 6,214,206 B1 | 4/2001 | Kriz | | 6,252,032 B1 | 6/2001 | Van Antwerp et al. |
| 6,214,560 B1 | 4/2001 | Yguerabide et al. | | 6,252,053 B1 | 6/2001 | Ohbayashi et al. |
| 6,214,612 B1 | 4/2001 | Yamamoto et al. | | 6,253,804 B1 | 7/2001 | Safabash |
| 6,216,023 B1 | 4/2001 | Holte et al. | | 6,254,586 B1 | 7/2001 | Mann et al. |
| 6,217,728 B1 | 4/2001 | Lehmann et al. | | 6,254,736 B1 | 7/2001 | Earl et al. |
| 6,217,744 B1 | 4/2001 | Crosby | | 6,254,831 B1 | 7/2001 | Barnard et al. |
| 6,217,969 B1 | 4/2001 | Takahashi et al. | | 6,255,061 B1 | 7/2001 | Mori et al. |
| 6,218,130 B1 | 4/2001 | Lamb | | 6,255,677 B1 | 7/2001 | Caillat et al. |
| 6,218,160 B1 | 4/2001 | Duan | | 6,256,522 B1 | 7/2001 | Schultz |
| 6,218,435 B1 | 4/2001 | Henry et al. | | 6,256,643 B1 | 7/2001 | Cork et al. |
| 6,218,546 B1 | 4/2001 | Watzele et al. | | 6,258,230 B1 | 7/2001 | Shen et al. |
| 6,218,556 B1 | 4/2001 | Pintauro | | 6,258,254 B1 | 7/2001 | Miyamoto et al. |
| 6,219,565 B1 | 4/2001 | Cupp et al. | | 6,258,586 B1 | 7/2001 | Jussila et al. |
| 6,219,574 B1 | 4/2001 | Cormier et al. | | 6,259,587 B1 | 7/2001 | Sheldon et al. |
| 6,221,225 B1 | 4/2001 | Mani | | 6,259,937 B1 | 7/2001 | Schulman et al. |
| 6,221,238 B1 | 4/2001 | Grundig et al. | | 6,260,022 B1 | 7/2001 | Brown |
| 6,221,608 B1 | 4/2001 | Middleton et al. | | 6,261,440 B1 | 7/2001 | Henning et al. |
| 6,221,625 B1 | 4/2001 | Ashihara et al. | | 6,261,519 B1 | 7/2001 | Harding et al. |
| 6,223,080 B1 | 4/2001 | Thompson | | 6,261,844 B1 | 7/2001 | Smith et al. |
| 6,223,083 B1 | 4/2001 | Rosar | | 6,262,264 B1 | 7/2001 | Buck, Jr. et al. |
| 6,223,471 B1 | 5/2001 | Barber | | 6,264,825 B1 | 7/2001 | Blackburn et al. |
| 6,224,550 B1 | 5/2001 | Ellingsen | | 6,266,459 B1 | 7/2001 | Walt et al. |
| 6,224,736 B1 | 5/2001 | Miyamoto | | 6,266,645 B1 | 7/2001 | Simpson |
| 6,224,745 B1 | 5/2001 | Baltruschat | | 6,267,722 B1 | 7/2001 | Anderson et al. |
| 6,224,909 B1 | 5/2001 | Opitz et al. | | 6,267,724 B1 | 7/2001 | Taylor |
| 6,225,078 B1 | 5/2001 | Ikeda et al. | | 6,267,987 B1 | 7/2001 | Park et al. |
| 6,226,082 B1 | 5/2001 | Roe | | 6,268,125 B1 | 7/2001 | Perkins |
| 6,228,574 B1 | 5/2001 | Rotman | | 6,268,161 B1 | 7/2001 | Han et al. |
| 6,228,581 B1 | 5/2001 | Acton et al. | | 6,268,162 B1 | 7/2001 | Phillips et al. |
| 6,230,059 B1 | 5/2001 | Duffin | | 6,268,214 B1 | 7/2001 | Bordignon et al. |
| 6,231,733 B1 | 5/2001 | Nilsson et al. | | 6,268,493 B1 | 7/2001 | Jefferson |
| 6,231,815 B1 | 5/2001 | Bainczyk et al. | | 6,268,913 B1 | 7/2001 | Rising |
| 6,231,879 B1 | 5/2001 | Li et al. | | 6,269,276 B1 | 7/2001 | Akhavan et al. |
| 6,231,920 B1 | 5/2001 | Guadalupe et al. | | D446,854 S | 8/2001 | Cheney, II et al. |
| 6,232,130 B1 | 5/2001 | Wolf | | 6,270,445 B1 | 8/2001 | Dean, Jr. et al. |
| 6,232,370 B1 | 5/2001 | Kubota et al. | | 6,270,455 B1 | 8/2001 | Brown |
| 6,232,609 B1 | 5/2001 | Snyder et al. | | 6,270,637 B1 | 8/2001 | Crismore et al. |
| 6,232,783 B1 | 5/2001 | Merrill | | 6,270,960 B1 | 8/2001 | Seidel et al. |
| 6,233,080 B1 | 5/2001 | Brenner et al. | | 6,271,045 B1 | 8/2001 | Douglas et al. |
| 6,233,471 B1 | 5/2001 | Berner et al. | | 6,272,364 B1 | 8/2001 | Kurnik |
| 6,233,539 B1 | 5/2001 | Brown | | 6,272,382 B1 | 8/2001 | Faltys et al. |
| 6,235,491 B1 | 5/2001 | Connolly | | 6,272,480 B1 | 8/2001 | Tresp et al. |
| 6,238,873 B1 | 5/2001 | Ames et al. | | 6,274,285 B1 | 8/2001 | Gries et al. |
| 6,238,914 B1 | 5/2001 | Boyce | | 6,274,565 B1 | 8/2001 | Katsumi |
| 6,239,161 B1 | 5/2001 | Tang et al. | | 6,274,584 B1 | 8/2001 | Peschke et al. |
| 6,239,925 B1 | 5/2001 | Ardrey et al. | | 6,274,686 B1 | 8/2001 | Mosbach et al. |
| 6,241,704 B1 | 6/2001 | Peterson et al. | | 6,274,726 B1 | 8/2001 | Laugharn, Jr. et al. |
| 6,241,862 B1 | 6/2001 | McAleer et al. | | 6,275,717 B1 | 8/2001 | Gross et al. |
| 6,241,863 B1 | 6/2001 | Monbouquette | | 6,277,489 B1 | 8/2001 | Abbott et al. |
| 6,241,948 B1 | 6/2001 | Watkins et al. | | 6,277,627 B1 | 8/2001 | Hellinga |
| 6,242,002 B1 | 6/2001 | Tritthart et al. | | 6,280,416 B1 | 8/2001 | Van Antwerp et al. |
| 6,242,207 B1 | 6/2001 | Douglas et al. | | 6,280,587 B1 | 8/2001 | Matsumoto |
| 6,242,267 B1 | 6/2001 | Herron et al. | | 6,281,006 B1 | 8/2001 | Heller et al. |
| 6,242,961 B1 | 6/2001 | Liu et al. | | 6,283,943 B1 | 9/2001 | Dy et al. |
| 6,245,215 B1 | 6/2001 | Douglas et al. | | 6,283,944 B1 | 9/2001 | McMullen et al. |
| 6,245,458 B1 | 6/2001 | Sotomura | | 6,284,113 B1 | 9/2001 | Bjornson et al. |
| 6,246,330 B1 | 6/2001 | Nielsen | | 6,284,125 B1 | 9/2001 | Hodges et al. |
| 6,246,893 B1 | 6/2001 | Gobeli | | 6,284,126 B1 | 9/2001 | Kurnik et al. |
| 6,246,966 B1 | 6/2001 | Perry | | 6,284,478 B1 | 9/2001 | Heller et al. |
| 6,246,992 B1 | 6/2001 | Brown | | 6,284,484 B1 | 9/2001 | Kopetzki et al. |
| 6,248,065 B1 | 6/2001 | Brown | | 6,284,550 B1 | 9/2001 | Carroll et al. |
| 6,248,067 B1 | 6/2001 | Causey, III et al. | | 6,285,448 B1 | 9/2001 | Kuenstner |
| 6,248,080 B1 | 6/2001 | Miesel et al. | | 6,285,454 B1 | 9/2001 | Douglas et al. |
| 6,248,093 B1 | 6/2001 | Moberg | | 6,285,807 B1 | 9/2001 | Walt et al. |
| 6,248,386 B1 | 6/2001 | Willibald-Ettle et al. | | 6,285,897 B1 | 9/2001 | Kilcoyne et al. |
| 6,251,246 B1 | 6/2001 | Chan | | 6,287,438 B1 | 9/2001 | Knoll |
| 6,251,260 B1 | 6/2001 | Heller et al. | | 6,287,796 B1 | 9/2001 | Jacobson et al. |
| 6,251,280 B1 | 6/2001 | Dai et al. | | 6,288,214 B1 | 9/2001 | Hook et al. |
| 6,251,428 B1 | 6/2001 | Yoo | | 6,289,238 B1 | 9/2001 | Besson et al. |

| Patent | Date | Name |
|---|---|---|
| 6,290,838 B1 | 9/2001 | Mifsud et al. |
| 6,290,839 B1 | 9/2001 | Kayyem et al. |
| 6,291,155 B1 | 9/2001 | Raguse et al. |
| 6,291,439 B1 | 9/2001 | Klock |
| 6,293,925 B1 | 9/2001 | Safabash et al. |
| 6,294,062 B1 | 9/2001 | Buck, Jr. et al. |
| 6,294,066 B1 | 9/2001 | Mani |
| 6,294,281 B1 | 9/2001 | Heller |
| 6,294,360 B1 | 9/2001 | Nishimoto et al. |
| 6,295,463 B1 | 9/2001 | Stenzler |
| 6,295,506 B1 | 9/2001 | Heinonen et al. |
| 6,297,009 B1 | 10/2001 | Demorest et al. |
| 6,297,025 B1 | 10/2001 | Sugihara et al. |
| 6,297,057 B1 | 10/2001 | Kawamura et al. |
| 6,298,254 B2 | 10/2001 | Tamada |
| 6,299,578 B1 | 10/2001 | Kurnik et al. |
| 6,299,583 B1 | 10/2001 | Eggers et al. |
| 6,299,757 B1 | 10/2001 | Feldman et al. |
| 6,300,002 B1 | 10/2001 | Webb et al. |
| 6,301,499 B1 | 10/2001 | Carlson et al. |
| 6,303,163 B1 | 10/2001 | Wu |
| 6,303,320 B1 | 10/2001 | Tajima et al. |
| 6,303,326 B1 | 10/2001 | Felton et al. |
| 6,303,351 B1 | 10/2001 | Anastassiadis et al. |
| 6,303,620 B1 | 10/2001 | Hansen et al. |
| 6,303,757 B1 | 10/2001 | Shigetou et al. |
| 6,303,758 B1 | 10/2001 | Shigetou et al. |
| 6,304,766 B1 | 10/2001 | Colvin, Jr. |
| 6,306,104 B1 | 10/2001 | Cunningham et al. |
| 6,306,285 B1 | 10/2001 | Narayanan et al. |
| 6,306,347 B1 | 10/2001 | Mason et al. |
| 6,306,427 B1 | 10/2001 | Annonier et al. |
| 6,306,432 B1 | 10/2001 | Shirley et al. |
| 6,306,579 B1 | 10/2001 | Seidel et al. |
| 6,306,642 B1 | 10/2001 | Nelson et al. |
| 6,307,029 B1 | 10/2001 | Shigetou et al. |
| 6,307,867 B1 | 10/2001 | Roobol et al. |
| 6,309,351 B1 | 10/2001 | Kurnik et al. |
| 6,309,384 B1 | 10/2001 | Harrington et al. |
| 6,309,427 B1 | 10/2001 | Korte |
| 6,309,526 B1 | 10/2001 | Fujiwara et al. |
| 6,309,535 B1 | 10/2001 | Williams et al. |
| 6,309,852 B1 | 10/2001 | Tazoe et al. |
| 6,309,878 B1 | 10/2001 | Chen et al. |
| 6,309,884 B1 | 10/2001 | Cooper et al. |
| 6,310,078 B1 | 10/2001 | Connolly et al. |
| 6,310,110 B1 | 10/2001 | Markowitz et al. |
| 6,312,393 B1 | 11/2001 | Abreu |
| 6,312,662 B1 | 11/2001 | Erion et al. |
| 6,313,113 B1 | 11/2001 | Lohray et al. |
| 6,315,721 B2 | 11/2001 | Schulman et al. |
| 6,315,738 B1 | 11/2001 | Nishikawa et al. |
| 6,316,274 B1 | 11/2001 | Herron et al. |
| 6,319,382 B1 | 11/2001 | Norddahl |
| 6,319,495 B1 | 11/2001 | Pollock et al. |
| 6,319,540 B1 | 11/2001 | Van Antwerp et al. |
| 6,319,566 B1 | 11/2001 | Polanyi et al. |
| 6,319,670 B1 | 11/2001 | Sigal et al. |
| 6,319,683 B1 | 11/2001 | James et al. |
| 6,320,357 B1 | 11/2001 | Peters et al. |
| 6,321,101 B1 | 11/2001 | Holmstrom |
| 6,322,682 B1 | 11/2001 | Arvidsson et al. |
| 6,322,963 B1 | 11/2001 | Bauer |
| 6,323,178 B1 | 11/2001 | Hale et al. |
| 6,323,214 B1 | 11/2001 | Baraldi |
| 6,323,309 B1 | 11/2001 | Swager et al. |
| 6,324,428 B1 | 11/2001 | Weinberg et al. |
| 6,325,066 B1 | 12/2001 | Hughes et al. |
| 6,325,917 B1 | 12/2001 | Maxwell et al. |
| 6,325,978 B1 | 12/2001 | Labuda et al. |
| 6,325,979 B1 | 12/2001 | Hahn et al. |
| 6,326,160 B1 | 12/2001 | Dunn et al. |
| 6,326,215 B1 | 12/2001 | Keen |
| 6,326,378 B1 | 12/2001 | Friebe et al. |
| 6,327,410 B1 | 12/2001 | Walt et al. |
| 6,328,891 B1 | 12/2001 | Gaudre-Longerinas et al. |
| 6,329,161 B1 | 12/2001 | Heller et al. |
| 6,329,192 B1 | 12/2001 | Ben-Bassat et al. |
| 6,329,208 B1 | 12/2001 | Jones et al. |
| 6,329,346 B1 | 12/2001 | Muhlegger et al. |
| 6,329,929 B1 | 12/2001 | Weijand et al. |
| 6,330,426 B2 | 12/2001 | Brown et al. |
| 6,330,464 B1 | 12/2001 | Colvin, Jr. et al. |
| 6,331,418 B1 | 12/2001 | Roth |
| 6,331,518 B2 | 12/2001 | Hemm et al. |
| 6,332,871 B1 | 12/2001 | Douglas et al. |
| 6,334,778 B1 | 1/2002 | Brown |
| 6,335,201 B1 | 1/2002 | Allbritton et al. |
| 6,335,203 B1 | 1/2002 | Patel et al. |
| 6,336,900 B1 | 1/2002 | Alleckson et al. |
| 6,337,199 B1 | 1/2002 | Yum et al. |
| 6,338,790 B1 | 1/2002 | Feldman et al. |
| 6,338,968 B1 | 1/2002 | Hefti |
| 6,340,421 B1 | 1/2002 | Vachon et al. |
| 6,340,428 B1 | 1/2002 | Ikeda et al. |
| 6,340,582 B1 | 1/2002 | Suzuki et al. |
| 6,340,588 B1 | 1/2002 | Nova et al. |
| 6,340,597 B1 | 1/2002 | Svorc et al. |
| 6,341,232 B1 | 1/2002 | Conn et al. |
| 6,342,346 B1 | 1/2002 | Raguse et al. |
| 6,342,948 B1 | 1/2002 | Gilby |
| 6,343,225 B1 | 1/2002 | Clark, Jr. |
| 6,348,143 B1 | 2/2002 | Serikawa et al. |
| 6,348,327 B1 | 2/2002 | Gorman et al. |
| 6,348,354 B1 | 2/2002 | Adolfsen et al. |
| 6,349,229 B1 | 2/2002 | Watanabe et al. |
| 6,349,230 B1 | 2/2002 | Kawanaka |
| 6,350,767 B1 | 2/2002 | Lau et al. |
| 6,352,505 B1 | 3/2002 | Bortz |
| 6,352,523 B1 | 3/2002 | Brown et al. |
| 6,352,824 B1 | 3/2002 | Buck, Jr. et al. |
| 6,355,166 B1 | 3/2002 | Amarasinghe et al. |
| 6,356,776 B1 | 3/2002 | Berner et al. |
| 6,358,237 B1 | 3/2002 | Paukovits et al. |
| 6,358,715 B1 | 3/2002 | Kumar |
| 6,359,176 B1 | 3/2002 | Nakamura et al. |
| 6,360,888 B1 | 3/2002 | McIvor et al. |
| 6,362,328 B1 | 3/2002 | Fisher et al. |
| 6,362,591 B1 | 3/2002 | Moberg |
| 6,363,282 B1 | 3/2002 | Nichols et al. |
| 6,365,109 B1 | 4/2002 | Jeng et al. |
| 6,365,628 B1 | 4/2002 | Berge |
| 6,365,670 B1 | 4/2002 | Fry |
| 6,366,793 B1 | 4/2002 | Bell et al. |
| 6,366,794 B1 | 4/2002 | Moussy et al. |
| 6,368,141 B1 | 4/2002 | VanAntwerp et al. |
| 6,368,274 B1 | 4/2002 | Van Antwerp et al. |
| 6,368,597 B1 | 4/2002 | Strassmann et al. |
| 6,368,795 B1 | 4/2002 | Hefti |
| 6,368,869 B2 | 4/2002 | Sullivan et al. |
| 6,370,410 B2 | 4/2002 | Kurnik et al. |
| 6,372,244 B1 | 4/2002 | Antanavich et al. |
| 6,372,461 B1 | 4/2002 | Frost |
| 6,372,499 B1 | 4/2002 | Midoux et al. |
| 6,375,998 B1 | 4/2002 | Wu |
| 6,377,896 B1 | 4/2002 | Sato et al. |
| 6,378,702 B1 | 4/2002 | Kintzig |
| 6,379,301 B1 | 4/2002 | Worthington et al. |
| 6,379,317 B1 | 4/2002 | Kintzig et al. |
| 6,379,513 B1 | 4/2002 | Chambers et al. |
| 6,379,691 B1 | 4/2002 | Tedeschi et al. |
| 6,379,706 B2 | 4/2002 | Opitz et al. |

| | | | | | | |
|---|---|---|---|---|---|---|
| 6,379,883 | B2 | 4/2002 | Davis et al. | 6,442,433 | B1 | 8/2002 | Linberg |
| 6,383,766 | B1 | 5/2002 | Warren et al. | 6,442,637 | B1 | 8/2002 | Hawkins et al. |
| 6,383,767 | B1 | 5/2002 | Polak | 6,443,942 | B2 | 9/2002 | Van Antwerp et al. |
| 6,384,132 | B1 | 5/2002 | Horley et al. | 6,445,938 | B1 | 9/2002 | Berman et al. |
| 6,387,048 | B1 | 5/2002 | Schulman et al. | 6,446,516 | B1 | 9/2002 | Sullivan |
| 6,387,232 | B1 | 5/2002 | Vadgama et al. | 6,447,448 | B1 | 9/2002 | Ishikawa et al. |
| 6,387,625 | B1 | 5/2002 | Eckhardt et al. | 6,447,542 | B1 | 9/2002 | Weadock |
| 6,387,709 | B1 | 5/2002 | Mason et al. | 6,447,656 | B1 | 9/2002 | Wieczorek |
| 6,391,633 | B1 | 5/2002 | Stern et al. | 6,448,029 | B1 | 9/2002 | Tazoe et al. |
| 6,391,643 | B1 | 5/2002 | Chen et al. | 6,451,369 | B1 | 9/2002 | Triantafyllou |
| 6,391,645 | B1 | 5/2002 | Huang et al. | 6,451,619 | B1 | 9/2002 | Catt et al. |
| 6,393,318 | B1 | 5/2002 | Conn et al. | 6,454,710 | B1 | 9/2002 | Ballerstadt et al. |
| 6,395,227 | B1 | 5/2002 | Kiser et al. | 6,454,921 | B1 | 9/2002 | Hodges et al. |
| 6,395,484 | B1 | 5/2002 | Brandt et al. | 6,454,945 | B1 | 9/2002 | Weigl et al. |
| 6,398,562 | B1 | 6/2002 | Butler et al. | 6,455,001 | B1 | 9/2002 | Knappe et al. |
| 6,398,727 | B1 | 6/2002 | Bui et al. | 6,455,303 | B1 | 9/2002 | Orwar et al. |
| 6,399,293 | B1 | 6/2002 | Pachl et al. | 6,458,570 | B1 | 10/2002 | Elseviers et al. |
| 6,399,333 | B1 | 6/2002 | Burg et al. | 6,458,600 | B1 | 10/2002 | Mirsky et al. |
| 6,399,381 | B1 | 6/2002 | Blum et al. | 6,459,917 | B1 | 10/2002 | Gowda et al. |
| 6,402,689 | B1 | 6/2002 | Scarantino et al. | 6,461,496 | B1 | 10/2002 | Feldman et al. |
| 6,402,691 | B1 | 6/2002 | Peddicord et al. | 6,461,870 | B2 | 10/2002 | Yatscoff et al. |
| 6,404,501 | B1 | 6/2002 | Hafeman et al. | 6,462,162 | B2 | 10/2002 | Van Antwerp et al. |
| 6,405,066 | B1 | 6/2002 | Essenpreis et al. | 6,463,312 | B1 | 10/2002 | Bergveld et al. |
| 6,406,066 | B1 | 6/2002 | Uegane | 6,464,635 | B1 | 10/2002 | Jimenez Cerrato et al. |
| 6,406,426 | B1 | 6/2002 | Reuss et al. | 6,464,687 | B1 | 10/2002 | Ishikawa et al. |
| 6,406,427 | B1 | 6/2002 | Williams et al. | 6,464,848 | B1 | 10/2002 | Matsumoto |
| 6,406,839 | B1 | 6/2002 | Segall et al. | 6,466,320 | B1 | 10/2002 | Kawamura et al. |
| 6,408,854 | B1 | 6/2002 | Gonda et al. | 6,466,810 | B1 | 10/2002 | Ward et al. |
| 6,409,674 | B1 | 6/2002 | Brockway et al. | 6,468,222 | B1 | 10/2002 | Mault et al. |
| 6,409,909 | B1 | 6/2002 | Spichiger-Keller et al. | 6,468,416 | B1 | 10/2002 | Nakamura et al. |
| 6,410,057 | B1 | 6/2002 | Kweon-Choi et al. | 6,468,657 | B1 | 10/2002 | Hou et al. |
| 6,410,251 | B2 | 6/2002 | Hoshino et al. | 6,468,800 | B1 | 10/2002 | Stylli et al. |
| 6,410,258 | B1 | 6/2002 | McTavish | 6,468,807 | B1 | 10/2002 | Svensson et al. |
| 6,410,270 | B1 | 6/2002 | Strittmatter et al. | 6,469,526 | B1 | 10/2002 | Franklin |
| 6,410,290 | B1 | 6/2002 | Robertson et al. | 6,471,645 | B1 | 10/2002 | Warkentin et al. |
| 6,411,832 | B1 | 6/2002 | Guthermann | 6,471,689 | B1 | 10/2002 | Joseph et al. |
| 6,413,393 | B1 | 7/2002 | Van Antwerp et al. | 6,472,122 | B1 | 10/2002 | Schulman et al. |
| 6,413,410 | B1 | 7/2002 | Hodges et al. | 6,472,218 | B1 | 10/2002 | Stylli et al. |
| 6,413,733 | B1 | 7/2002 | Nagel et al. | 6,475,180 | B2 | 11/2002 | Peterson et al. |
| 6,416,471 | B1 | 7/2002 | Kumar et al. | 6,475,360 | B1 | 11/2002 | Hodges et al. |
| 6,416,641 | B1 | 7/2002 | Ikeda et al. | 6,475,363 | B1 | 11/2002 | Ramsey |
| 6,416,643 | B1 | 7/2002 | Henry et al. | 6,475,745 | B1 | 11/2002 | Giulian |
| 6,416,646 | B2 | 7/2002 | Chan | 6,475,750 | B1 | 11/2002 | Han et al. |
| 6,418,332 | B1 | 7/2002 | Mastrototaro et al. | 6,475,764 | B1 | 11/2002 | Burtscher et al. |
| 6,418,346 | B1 | 7/2002 | Nelson et al. | 6,477,392 | B1 | 11/2002 | Honigs et al. |
| 6,420,604 | B1 | 7/2002 | Weber et al. | 6,477,395 | B2 | 11/2002 | Schulman et al. |
| 6,421,548 | B1 | 7/2002 | Berman et al. | 6,478,736 | B1 | 11/2002 | Mault |
| 6,421,633 | B1 | 7/2002 | Heinonen et al. | 6,479,015 | B1 | 11/2002 | Long et al. |
| 6,423,966 | B2 | 7/2002 | Hillenkamp et al. | 6,480,730 | B2 | 11/2002 | Darrow et al. |
| 6,424,847 | B1 | 7/2002 | Mastrototaro et al. | 6,481,440 | B2 | 11/2002 | Gielen et al. |
| 6,424,848 | B1 | 7/2002 | Berman et al. | 6,482,156 | B2 | 11/2002 | Iliff |
| 6,424,849 | B1 | 7/2002 | Berman et al. | 6,482,158 | B2 | 11/2002 | Mault |
| 6,424,851 | B1 | 7/2002 | Berman et al. | 6,482,596 | B1 | 11/2002 | Ueda et al. |
| 6,424,867 | B1 | 7/2002 | Snell et al. | 6,482,604 | B2 | 11/2002 | Kwon |
| 6,425,863 | B1 | 7/2002 | Werner et al. | 6,483,582 | B2 | 11/2002 | Modlin et al. |
| 6,426,045 | B1 | 7/2002 | Jeng et al. | 6,484,045 | B1 | 11/2002 | Holker et al. |
| 6,426,231 | B1 | 7/2002 | Bayley et al. | 6,484,046 | B1 | 11/2002 | Say et al. |
| 6,427,088 | B1 | 7/2002 | Bowman, IV et al. | 6,485,138 | B1 | 11/2002 | Kubota et al. |
| 6,428,972 | B2 | 8/2002 | Jacobson et al. | 6,485,439 | B1 | 11/2002 | Roe et al. |
| 6,429,002 | B1 | 8/2002 | Ben-Bassat et al. | 6,485,465 | B2 | 11/2002 | Moberg et al. |
| 6,430,424 | B1 | 8/2002 | Berman et al. | 6,485,703 | B1 | 11/2002 | Cote et al. |
| 6,432,629 | B1 | 8/2002 | Raguse et al. | 6,485,961 | B1 | 11/2002 | Meserol |
| 6,432,913 | B1 | 8/2002 | Tajima et al. | 6,485,980 | B1 | 11/2002 | Adolfsen et al. |
| 6,434,409 | B1 | 8/2002 | Pfeiffer et al. | 6,488,891 | B2 | 12/2002 | Mason et al. |
| 6,436,256 | B1 | 8/2002 | Williams et al. | 6,489,133 | B2 | 12/2002 | Phillips et al. |
| 6,436,349 | B1 | 8/2002 | Carey et al. | 6,489,286 | B1 | 12/2002 | Lukenbach et al. |
| 6,437,345 | B1 | 8/2002 | Bruno-Raimondi et al. | 6,491,870 | B2 | 12/2002 | Patel et al. |
| 6,437,692 | B1 | 8/2002 | Petite et al. | 6,494,830 | B1 | 12/2002 | Wessel |
| 6,438,414 | B1 | 8/2002 | Conn et al. | 6,496,260 | B1 | 12/2002 | Hafeman et al. |
| 6,440,068 | B1 | 8/2002 | Brown et al. | 6,496,728 | B2 | 12/2002 | Li et al. |
| 6,440,296 | B1 | 8/2002 | Stanzel et al. | 6,497,845 | B1 | 12/2002 | Sacherer |

| | | |
|---|---|---|
| 6,498,037 B1 | 12/2002 | Carey et al. |
| 6,498,043 B1 | 12/2002 | Schulman et al. |
| 6,498,241 B1 | 12/2002 | Seela et al. |
| 6,498,941 B1 | 12/2002 | Jackson |
| 6,500,211 B2 | 12/2002 | Fowler et al. |
| 6,500,661 B1 | 12/2002 | Sjoberg |
| 6,501,008 B1 | 12/2002 | Nevins et al. |
| 6,503,381 B1 | 1/2003 | Gotoh et al. |
| 6,503,382 B1 | 1/2003 | Bartlett et al. |
| 6,505,059 B1 | 1/2003 | Kollias et al. |
| 6,505,069 B2 | 1/2003 | Scott et al. |
| 6,506,583 B1 | 1/2003 | Stoddard |
| 6,508,785 B1 | 1/2003 | Eppstein |
| 6,509,148 B2 | 1/2003 | Cha et al. |
| 6,511,592 B1 | 1/2003 | Hill et al. |
| 6,511,820 B1 | 1/2003 | Stoddard |
| 6,512,939 B1 | 1/2003 | Colvin et al. |
| 6,513,532 B2 | 2/2003 | Mault et al. |
| 6,514,718 B2 | 2/2003 | Heller et al. |
| 6,515,593 B1 | 2/2003 | Stark et al. |
| 6,516,808 B2 | 2/2003 | Schulman |
| 6,517,482 B1 | 2/2003 | Elden et al. |
| 6,517,781 B1 | 2/2003 | Coassin et al. |
| 6,517,886 B1 | 2/2003 | Chau et al. |
| 6,518,485 B1 | 2/2003 | Connett-Porceddu et al. |
| 6,520,326 B2 | 2/2003 | McIvor et al. |
| 6,520,938 B1 | 2/2003 | Funderburk et al. |
| 6,520,997 B1 | 2/2003 | Pekkarinen et al. |
| 6,521,110 B1 | 2/2003 | Hodges et al. |
| 6,521,182 B1 | 2/2003 | Shartle et al. |
| 6,521,446 B2 | 2/2003 | Hellinga |
| 6,526,298 B1 | 2/2003 | Khalil et al. |
| 6,527,716 B1 | 3/2003 | Eppstein |
| 6,527,729 B1 | 3/2003 | Turcott |
| 6,528,584 B2 | 3/2003 | Kennedy et al. |
| 6,529,755 B2 | 3/2003 | Kurnik et al. |
| 6,529,772 B2 | 3/2003 | Carlson et al. |
| 6,530,915 B1 | 3/2003 | Eppstein et al. |
| 6,531,322 B1 | 3/2003 | Jurik et al. |
| 6,534,322 B1 | 3/2003 | Sabbadini |
| 6,534,323 B1 | 3/2003 | Sabbadini |
| 6,535,753 B1 | 3/2003 | Raskas |
| 6,537,243 B1 | 3/2003 | Henning et al. |
| 6,537,264 B1 | 3/2003 | Cormier et al. |
| 6,537,268 B1 | 3/2003 | Gibson et al. |
| 6,537,318 B1 | 3/2003 | Ita et al. |
| 6,537,496 B1 | 3/2003 | Knappe et al. |
| 6,537,800 B1 | 3/2003 | Karube et al. |
| 6,540,672 B1 | 4/2003 | Simonsen et al. |
| 6,540,675 B2 | 4/2003 | Aceti et al. |
| 6,540,891 B1 | 4/2003 | Stewart et al. |
| 6,541,107 B1 | 4/2003 | King et al. |
| 6,541,228 B1 | 4/2003 | Mazur et al. |
| 6,541,237 B1 | 4/2003 | Yu et al. |
| 6,542,765 B1 | 4/2003 | Guy et al. |
| 6,544,212 B2 | 4/2003 | Galley et al. |
| 6,544,393 B1 | 4/2003 | Künnecke |
| 6,544,475 B1 | 4/2003 | Douglas et al. |
| 6,544,748 B2 | 4/2003 | Stern et al. |
| 6,545,009 B1 | 4/2003 | Sugiyama et al. |
| 6,545,085 B2 | 4/2003 | Kilgour et al. |
| 6,545,280 B2 | 4/2003 | Weinberg |
| 6,546,268 B1 | 4/2003 | Ishikawa et al. |
| 6,546,269 B1 | 4/2003 | Kurnik |
| 6,547,839 B2 | 4/2003 | Zhang et al. |
| 6,547,954 B2 | 4/2003 | Ikeda et al. |
| 6,548,263 B1 | 4/2003 | Kapur et al. |
| 6,548,296 B1 | 4/2003 | Stern et al. |
| 6,549,796 B2 | 4/2003 | Sohrab |
| 6,549,804 B1 | 4/2003 | Osorio et al. |
| 6,551,276 B1 | 4/2003 | Mann et al. |
| 6,551,494 B1 | 4/2003 | Feldman et al. |
| 6,551,495 B1 | 4/2003 | Porter et al. |
| 6,551,496 B1 | 4/2003 | Moles et al. |
| 6,551,794 B1 | 4/2003 | Burton et al. |
| 6,552,165 B1 | 4/2003 | Nagel et al. |
| 6,553,244 B2 | 4/2003 | Lesho et al. |
| 6,554,798 B1 | 4/2003 | Mann et al. |
| 6,555,062 B1 | 4/2003 | Lewis et al. |
| 6,555,373 B1 | 4/2003 | Stern et al. |
| 6,555,570 B2 | 4/2003 | Hansen et al. |
| 6,555,986 B2 | 4/2003 | Moberg |
| 6,558,320 B1 | 5/2003 | Causey, III et al. |
| 6,558,321 B1 | 5/2003 | Burd et al. |
| 6,558,345 B1 | 5/2003 | Houben et al. |
| 6,558,351 B1 | 5/2003 | Steil et al. |
| 6,558,671 B1 | 5/2003 | Slingluff et al. |
| 6,558,917 B2 | 5/2003 | Schabert |
| 6,558,955 B1 | 5/2003 | Kristal et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,612 B2 | 5/2003 | Jones et al. |
| 6,564,105 B2 | 5/2003 | Starkweather et al. |
| 6,565,509 B1 | 5/2003 | Plante et al. |
| 6,565,811 B1 | 5/2003 | Zaromb |
| 6,566,337 B1 | 5/2003 | Ankersen et al. |
| 6,569,385 B1 | 5/2003 | Little et al. |
| 6,569,521 B1 | 5/2003 | Sheridan et al. |
| 6,569,654 B2 | 5/2003 | Shastri et al. |
| 6,571,128 B2 | 5/2003 | Lebel et al. |
| 6,571,200 B1 | 5/2003 | Mault |
| 6,572,545 B2 | 6/2003 | Knobbe et al. |
| 6,572,751 B1 | 6/2003 | De Boer et al. |
| 6,572,822 B2 | 6/2003 | Jurik et al. |
| 6,574,425 B1 | 6/2003 | Weiss et al. |
| 6,574,490 B2 | 6/2003 | Abbink et al. |
| 6,575,101 B2 | 6/2003 | Blute et al. |
| 6,575,905 B2 | 6/2003 | Knobbe et al. |
| 6,576,117 B1 | 6/2003 | Iketaki et al. |
| 6,577,885 B1 | 6/2003 | Braig et al. |
| 6,577,899 B2 | 6/2003 | Lebel et al. |
| 6,579,498 B1 | 6/2003 | Eglise |
| 6,579,690 B1 | 6/2003 | Bonnecaze et al. |
| 6,579,841 B1 | 6/2003 | Day et al. |
| 6,579,868 B1 | 6/2003 | Asano et al. |
| 6,582,365 B1 | 6/2003 | Hines et al. |
| 6,582,573 B2 | 6/2003 | Douglas et al. |
| 6,582,583 B1 | 6/2003 | Chen |
| 6,582,952 B1 | 6/2003 | Le Campion et al. |
| 6,583,164 B1 | 6/2003 | Horibe et al. |
| 6,584,335 B1 | 6/2003 | Haar et al. |
| 6,584,340 B1 | 6/2003 | Horiuchi et al. |
| 6,585,644 B2 | 7/2003 | Lebel et al. |
| 6,585,675 B1 | 7/2003 | O'Mahony et al. |
| 6,585,695 B1 | 7/2003 | Adair et al. |
| 6,585,763 B1 | 7/2003 | Keilman et al. |
| 6,587,705 B1 | 7/2003 | Berner et al. |
| 6,588,644 B2 | 7/2003 | Simon |
| 6,589,205 B1 | 7/2003 | Meadows |
| 6,589,229 B1 | 7/2003 | Connelly et al. |
| 6,591,125 B1 | 7/2003 | Buse et al. |
| 6,591,126 B2 | 7/2003 | Roeper et al. |
| 6,592,744 B1 | 7/2003 | Hodges et al. |
| 6,592,745 B1 | 7/2003 | Feldman et al. |
| 6,592,815 B1 | 7/2003 | Zimmer |
| 6,594,514 B2 | 7/2003 | Berner et al. |
| 6,595,919 B2 | 7/2003 | Berner et al. |
| 6,595,929 B2 | 7/2003 | Stivoric et al. |
| 6,599,406 B1 | 7/2003 | Kawanaka et al. |
| 6,599,408 B1 | 7/2003 | Chan et al. |
| 6,599,722 B2 | 7/2003 | Boston et al. |

| | | | |
|---|---|---|---|
| 6,599,750 B2 | 7/2003 | Yatscoff et al. | |
| 6,602,469 B1 | 8/2003 | Maus et al. | |
| 6,602,678 B2 | 8/2003 | Kwon et al. | |
| 6,602,691 B1 | 8/2003 | Ojamo et al. | |
| 6,602,909 B1 | 8/2003 | Jarowski | |
| 6,605,072 B2 | 8/2003 | Struys et al. | |
| 6,605,200 B1 | 8/2003 | Mao et al. | |
| 6,605,201 B1 | 8/2003 | Mao et al. | |
| 6,605,753 B1 | 8/2003 | Kennedy et al. | |
| 6,607,509 B2 | 8/2003 | Bobroff et al. | |
| 6,607,658 B1 | 8/2003 | Heller et al. | |
| 6,610,012 B2 | 8/2003 | Mault | |
| 6,610,699 B2 | 8/2003 | Cavazza et al. | |
| 6,611,634 B2 | 8/2003 | Herron et al. | |
| 6,612,306 B1 | 9/2003 | Mault | |
| 6,612,984 B1 | 9/2003 | Kerr, II | |
| 6,613,379 B2 | 9/2003 | Ward et al. | |
| 6,615,074 B2 | 9/2003 | Mickle et al. | |
| 6,615,078 B1 | 9/2003 | Burson et al. | |
| 6,616,819 B1 | 9/2003 | Liamos et al. | |
| 6,617,154 B1 | 9/2003 | Meserol | |
| 6,618,603 B2 | 9/2003 | Varalli et al. | |
| 6,618,934 B1 | 9/2003 | Feldman et al. | |
| 6,620,106 B2 | 9/2003 | Mault | |
| 6,620,880 B2 | 9/2003 | Horley et al. | |
| 6,627,058 B1 | 9/2003 | Chan | |
| 6,627,420 B1 | 9/2003 | Hols et al. | |
| 6,627,603 B1 | 9/2003 | Bibette et al. | |
| 6,629,776 B2 | 10/2003 | Bell et al. | |
| 6,629,934 B2 | 10/2003 | Mault et al. | |
| 6,632,349 B1 | 10/2003 | Hodges et al. | |
| 6,632,675 B1 | 10/2003 | Conlon et al. | |
| 6,633,772 B2 | 10/2003 | Ford et al. | |
| 6,635,014 B2 | 10/2003 | Starkweather et al. | |
| 6,635,167 B1 | 10/2003 | Richards et al. | |
| 6,635,222 B2 | 10/2003 | Kent | |
| 6,635,224 B1 | 10/2003 | Gui et al. | |
| 6,635,415 B1 | 10/2003 | Hodges et al. | |
| 6,638,772 B1 | 10/2003 | Douglas et al. | |
| RE38,323 E | 11/2003 | Sugihara et al. | |
| 6,641,533 B2 | 11/2003 | Causey, III et al. | |
| 6,642,007 B1 | 11/2003 | Saltarelli et al. | |
| 6,642,015 B2 | 11/2003 | Vachon et al. | |
| 6,642,057 B1 | 11/2003 | Zaromb | |
| 6,644,321 B1 | 11/2003 | Behm | |
| 6,645,142 B2 | 11/2003 | Braig et al. | |
| 6,645,181 B1 | 11/2003 | Lavi et al. | |
| 6,645,368 B1 | 11/2003 | Beaty et al. | |
| 6,648,821 B2 | 11/2003 | Lebel et al. | |
| 6,653,066 B1 | 11/2003 | Krutzik | |
| 6,653,091 B1 | 11/2003 | Dunn et al. | |
| 6,653,109 B1 | 11/2003 | Nilsson | |
| 6,654,625 B1 | 11/2003 | Say et al. | |
| 6,656,114 B1 | 12/2003 | Poulsen et al. | |
| 6,656,697 B1 | 12/2003 | Ouyang et al. | |
| 6,656,702 B1 | 12/2003 | Yugawa et al. | |
| 6,659,948 B2 | 12/2003 | Lebel et al. | |
| 6,660,141 B1 | 12/2003 | Minter et al. | |
| 6,660,276 B1 | 12/2003 | Slingluff et al. | |
| 6,660,765 B2 | 12/2003 | Wuthier et al. | |
| 6,662,030 B2 | 12/2003 | Khalil et al. | |
| 6,663,780 B2 | 12/2003 | Heikkila et al. | |
| 6,663,829 B1 | 12/2003 | Kjellstrand | |
| 6,664,284 B2 | 12/2003 | Gruber et al. | |
| 6,666,958 B2 | 12/2003 | Yoshikawa et al. | |
| 6,668,196 B1 | 12/2003 | Villegas et al. | |
| 6,670,192 B1 | 12/2003 | Galen et al. | |
| 6,671,554 B2 | 12/2003 | Gibson et al. | |
| 6,673,225 B1 | 1/2004 | Arnold | |
| 6,673,533 B1 | 1/2004 | Wohlstadter et al. | |
| 6,673,575 B1 | 1/2004 | Franze et al. | |
| 6,673,596 B1 | 1/2004 | Sayler et al. | |
| 6,673,625 B2 | 1/2004 | Satcher, Jr. et al. | |
| 6,676,947 B1 | 1/2004 | Gottschalk et al. | |
| 6,676,984 B1 | 1/2004 | Sharp et al. | |
| 6,678,577 B1 | 1/2004 | Stylli et al. | |
| 6,680,206 B1 | 1/2004 | McDevitt et al. | |
| 6,680,291 B1 | 1/2004 | Wiegand et al. | |
| 6,682,938 B1 | 1/2004 | Satcher, Jr. et al. | |
| 6,683,040 B2 | 1/2004 | Bragulla et al. | |
| 6,683,535 B1 | 1/2004 | Utke | |
| RE38,446 E | 2/2004 | Van Assche et al. | |
| 6,685,884 B2 | 2/2004 | Stylli et al. | |
| 6,685,943 B1 | 2/2004 | Höök et al. | |
| 6,687,522 B2 | 2/2004 | Tamada | |
| 6,687,546 B2 | 2/2004 | Lebel et al. | |
| 6,689,056 B1 | 2/2004 | Kilcoyne et al. | |
| 6,689,091 B2 | 2/2004 | Bui et al. | |
| 6,689,265 B2 | 2/2004 | Heller et al. | |
| 6,689,616 B1 | 2/2004 | Bosies et al. | |
| 6,692,974 B2 | 2/2004 | Perkins | |
| 6,693,069 B2 | 2/2004 | Merz et al. | |
| 6,694,158 B2 | 2/2004 | Polak | |
| 6,694,191 B2 | 2/2004 | Starkweather et al. | |
| 6,695,860 B1 | 2/2004 | Ward et al. | |
| 6,695,958 B1 | 2/2004 | Adam et al. | |
| 6,696,024 B1 | 2/2004 | Leichner et al. | |
| 6,699,218 B2 | 3/2004 | Flaherty et al. | |
| 6,699,382 B2 | 3/2004 | Yoshioka et al. | |
| 6,699,383 B2 | 3/2004 | Lemire et al. | |
| 6,699,667 B2 | 3/2004 | Keen | |
| 6,699,724 B1 | 3/2004 | West et al. | |
| 6,702,857 B2 | 3/2004 | Brauker et al. | |
| 6,703,539 B1 | 3/2004 | Keller et al. | |
| 6,704,587 B1 | 3/2004 | Kumar et al. | |
| 6,705,883 B1 | 3/2004 | Ku | |
| 6,706,160 B2 | 3/2004 | Kriz | |
| 6,706,532 B2 | 3/2004 | Vadgama et al. | |
| 6,707,554 B1 | 3/2004 | Miltner et al. | |
| 6,708,049 B1 | 3/2004 | Berson et al. | |
| 6,711,423 B2 | 3/2004 | Colvin, Jr. | |
| 6,714,815 B2 | 3/2004 | Guy et al. | |
| 6,719,888 B1 | 4/2004 | Zalenski et al. | |
| 6,721,587 B2 | 4/2004 | Gough | |
| 6,723,046 B2 | 4/2004 | Lichtenstein et al. | |
| 6,723,540 B1 | 4/2004 | Harkki et al. | |
| 6,727,258 B2 | 4/2004 | Baraldi | |
| 6,728,560 B2 | 4/2004 | Kollias et al. | |
| 6,730,028 B2 | 5/2004 | Eppstein et al. | |
| 6,730,200 B1 | 5/2004 | Stewart et al. | |
| 6,730,520 B2 | 5/2004 | Coassin et al. | |
| 6,731,976 B2 | 5/2004 | Penn et al. | |
| 6,733,446 B2 | 5/2004 | Lebel et al. | |
| 6,734,162 B2 | 5/2004 | Van Antwerp et al. | |
| 6,736,777 B2 | 5/2004 | Kim et al. | |
| 6,736,957 B1 | 5/2004 | Forrow et al. | |
| 6,737,401 B2 | 5/2004 | Kim et al. | |
| 6,738,654 B2 | 5/2004 | Sohrab | |
| 6,740,075 B2 | 5/2004 | Lebel et al. | |
| 6,740,214 B1 | 5/2004 | Dobson et al. | |
| 6,740,882 B2 | 5/2004 | Weinberg | |
| 6,741,163 B1 | 5/2004 | Roberts | |
| 6,741,876 B1 | 5/2004 | Scecina et al. | |
| 6,741,877 B1 | 5/2004 | Shults et al. | |
| 6,749,587 B2 | 6/2004 | Flaherty | |
| 6,750,311 B1 | 6/2004 | Van Antwerp et al. | |
| 6,752,962 B2 | 6/2004 | Carr et al. | |
| 6,752,964 B1 | 6/2004 | Grubbs et al. | |
| 6,756,360 B1 | 6/2004 | Erion et al. | |
| 6,756,361 B1 | 6/2004 | Fattom et al. | |
| 6,758,810 B2 | 7/2004 | Lebel et al. | |
| 6,761,816 B1 | 7/2004 | Blackburn et al. | |

| | | |
|---|---|---|
| 6,764,581 B1 | 7/2004 | Forrow et al. |
| 6,764,649 B2 | 7/2004 | Ammann |
| 6,766,183 B2 | 7/2004 | Walsh et al. |
| 6,766,191 B1 | 7/2004 | Billings et al. |
| 6,766,201 B2 | 7/2004 | Von Arx et al. |
| 6,767,887 B1 | 7/2004 | Hoffmann et al. |
| 6,768,425 B2 | 7/2004 | Flaherty et al. |
| 6,770,030 B1 | 8/2004 | Schaupp et al. |
| 6,770,729 B2 | 8/2004 | Van Antwerp |
| 6,771,995 B2 | 8/2004 | Kurnik et al. |
| 6,773,563 B2 | 8/2004 | Matsumoto |
| 6,773,564 B1 | 8/2004 | Yugawa et al. |
| 6,773,565 B2 | 8/2004 | Ono et al. |
| 6,773,922 B2 | 8/2004 | Jeng et al. |
| 6,777,176 B1 | 8/2004 | Erni et al. |
| 6,780,156 B2 | 8/2004 | Haueter et al. |
| 6,780,297 B2 | 8/2004 | Matsumoto et al. |
| 6,780,651 B2 | 8/2004 | Douglas et al. |
| 6,780,871 B2 | 8/2004 | Glick et al. |
| 6,783,537 B1 | 8/2004 | Kuhr et al. |
| 6,784,274 B2 | 8/2004 | Van Antwerp et al. |
| 6,790,178 B1 | 9/2004 | Mault et al. |
| 6,790,327 B2 | 9/2004 | Nankai et al. |
| 6,790,341 B1 | 9/2004 | Saban et al. |
| 6,790,470 B1 | 9/2004 | Kishishita et al. |
| 6,793,633 B2 | 9/2004 | Douglas et al. |
| 6,793,802 B2 | 9/2004 | Lee et al. |
| 6,794,124 B2 | 9/2004 | Steen |
| 6,794,195 B2 | 9/2004 | Colvin, Jr. |
| 6,796,941 B2 | 9/2004 | Williams et al. |
| 6,797,861 B2 | 9/2004 | Ulvskov et al. |
| 6,799,149 B2 | 9/2004 | Hartlaub |
| 6,800,059 B2 | 10/2004 | Muraki et al. |
| 6,800,071 B1 | 10/2004 | McConnell et al. |
| 6,800,451 B2 | 10/2004 | Nikolaitchik et al. |
| 6,801,041 B2 | 10/2004 | Karinka et al. |
| 6,801,420 B2 | 10/2004 | Talbot et al. |
| 6,802,957 B2 | 10/2004 | Jung et al. |
| 6,804,544 B2 | 10/2004 | Van Antwerp et al. |
| 6,806,077 B1 | 10/2004 | Deslys et al. |
| 6,808,854 B2 | 10/2004 | Imamura et al. |
| 6,808,918 B2 | 10/2004 | Kumar |
| 6,809,507 B2 | 10/2004 | Morgan et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,811,659 B2 | 11/2004 | Vachon et al. |
| 6,812,031 B1 | 11/2004 | Carlsson |
| 6,813,516 B2 | 11/2004 | Ujhelyi et al. |
| 6,813,519 B2 | 11/2004 | Lebel et al. |
| 6,815,186 B2 | 11/2004 | Clark, Jr. |
| 6,816,742 B2 | 11/2004 | Kim et al. |
| 6,816,743 B2 | 11/2004 | Moreno et al. |
| 6,817,990 B2 | 11/2004 | Yap et al. |
| 6,818,180 B2 | 11/2004 | Douglas et al. |
| 6,821,483 B2 | 11/2004 | McGarraugh et al. |
| 6,821,537 B2 | 11/2004 | Wu |
| 6,824,659 B2 | 11/2004 | Bayley et al. |
| 6,827,829 B2 | 12/2004 | Kawanaka et al. |
| 6,833,364 B1 | 12/2004 | Straub et al. |
| 6,835,553 B2 | 12/2004 | Han et al. |
| 6,835,571 B2 | 12/2004 | Conlon et al. |
| RE38,681 E | 1/2005 | Kurnik et al. |
| 6,840,912 B2 | 1/2005 | Kloepfer et al. |
| 6,844,023 B2 | 1/2005 | Schulman et al. |
| 6,846,657 B2 | 1/2005 | Heikkilä et al. |
| 6,846,673 B2 | 1/2005 | Brandt et al. |
| 6,846,824 B2 | 1/2005 | Lohray et al. |
| 6,849,237 B2 | 2/2005 | Housefield et al. |
| 6,850,790 B2 | 2/2005 | Berner et al. |
| 6,852,212 B2 | 2/2005 | Maxwell et al. |
| 6,852,337 B2 | 2/2005 | Gabel et al. |
| 6,852,500 B1 | 2/2005 | Hoss et al. |
| 6,852,694 B2 | 2/2005 | Van Antwerp et al. |
| 6,853,854 B1 | 2/2005 | Proniewicz et al. |
| 6,855,115 B2 | 2/2005 | Fonseca et al. |
| 6,855,516 B1 | 2/2005 | Nagai et al. |
| 6,855,546 B1 | 2/2005 | Strous et al. |
| 6,856,928 B2 | 2/2005 | Harmon |
| 6,858,401 B2 | 2/2005 | Phillips et al. |
| 6,858,403 B2 | 2/2005 | Han et al. |
| 6,859,570 B2 | 2/2005 | Walt et al. |
| 6,862,465 B2 | 3/2005 | Shults et al. |
| 6,862,466 B2 | 3/2005 | Ackerman |
| 6,863,801 B2 | 3/2005 | Hodges et al. |
| 6,866,183 B2 | 3/2005 | Purcell |
| 6,866,821 B2 | 3/2005 | Friedlander et al. |
| 6,867,002 B2 | 3/2005 | Miyashita et al. |
| 6,867,051 B1 | 3/2005 | Anderson et al. |
| 6,872,200 B2 | 3/2005 | Mann et al. |
| 6,872,539 B2 | 3/2005 | Rotman |
| 6,872,571 B1 | 3/2005 | Adolfsen et al. |
| 6,873,268 B2 | 3/2005 | Lebel et al. |
| 6,873,865 B2 | 3/2005 | Steuer et al. |
| 6,875,386 B1 | 4/2005 | Ward et al. |
| 6,878,120 B2 | 4/2005 | Roe et al. |
| 6,878,251 B2 | 4/2005 | Hodges et al. |
| 6,878,550 B2 | 4/2005 | Yatscoff et al. |
| 6,879,849 B2 | 4/2005 | Begic |
| 6,881,380 B1 | 4/2005 | Mootz et al. |
| 6,881,551 B2 | 4/2005 | Heller et al. |
| 6,882,940 B2 | 4/2005 | Potts et al. |
| 6,884,215 B1 | 4/2005 | Charash |
| 6,885,883 B2 | 4/2005 | Parris et al. |
| 6,890,762 B1 | 5/2005 | Sugihara et al. |
| 6,891,317 B2 | 5/2005 | Pei et al. |
| 6,892,085 B2 | 5/2005 | McIvor et al. |
| 6,893,545 B2 | 5/2005 | Gotoh et al. |
| 6,893,552 B1 | 5/2005 | Wang et al. |
| 6,895,263 B2 | 5/2005 | Shin et al. |
| 6,899,683 B2 | 5/2005 | Mault et al. |
| 6,899,684 B2 | 5/2005 | Mault et al. |
| 6,902,905 B2 | 6/2005 | Burson et al. |
| 6,904,301 B2 | 6/2005 | Raskas |
| 6,907,127 B1 | 6/2005 | Kravitz et al. |
| 6,908,770 B1 | 6/2005 | McDevitt et al. |
| 6,911,553 B1 | 6/2005 | Esswein et al. |
| 6,913,761 B1 | 7/2005 | Trigg et al. |
| 6,915,147 B2 | 7/2005 | Lebel et al. |
| 6,918,874 B1 | 7/2005 | Hatch et al. |
| 6,919,315 B1 | 7/2005 | Peschke et al. |
| 6,921,465 B2 | 7/2005 | Yoshikawa et al. |
| 6,922,576 B2 | 7/2005 | Raskas |
| 6,922,578 B2 | 7/2005 | Eppstein et al. |
| 6,922,584 B2 | 7/2005 | Wang et al. |
| RE38,775 E | 8/2005 | Kurnik et al. |
| 6,923,764 B2 | 8/2005 | Aceti et al. |
| 6,923,936 B2 | 8/2005 | Swanson et al. |
| 6,924,145 B1 | 8/2005 | Jorsboe et al. |
| 6,924,366 B2 | 8/2005 | Stougaard et al. |
| 6,927,070 B1 | 8/2005 | Bayley et al. |
| 6,927,246 B2 | 8/2005 | Noronha et al. |
| 6,931,327 B2 | 8/2005 | Goode, Jr. et al. |
| 6,932,084 B2 | 8/2005 | Estes et al. |
| 6,932,894 B2 | 8/2005 | Mao et al. |
| 6,934,572 B2 | 8/2005 | Schulman et al. |
| 6,936,006 B2 | 8/2005 | Sabra |
| 6,936,029 B2 | 8/2005 | Mann et al. |
| 6,936,476 B1 | 8/2005 | Anderson et al. |
| 6,939,880 B2 | 9/2005 | Hansen et al. |
| 6,940,590 B2 | 9/2005 | Colvin, Jr. et al. |

| | | | | | | |
|---|---|---|---|---|---|---|
| 6,941,163 B2 | 9/2005 | Ford et al. | | 7,049,277 B2 | 5/2006 | Bragulla et al. |
| 6,942,997 B2 | 9/2005 | Lantero et al. | | 7,052,472 B1 | 5/2006 | Miller et al. |
| 6,946,996 B2 | 9/2005 | Koyama | | 7,052,483 B2 | 5/2006 | Wojcik |
| 6,949,221 B2 | 9/2005 | Kiser et al. | | 7,056,302 B2 | 6/2006 | Douglas |
| 6,950,708 B2 | 9/2005 | Bowman IV et al. | | 7,064,190 B1 | 6/2006 | Endl et al. |
| 6,952,603 B2 | 10/2005 | Gerber et al. | | 7,066,900 B2 | 6/2006 | Botto et al. |
| 6,954,673 B2 | 10/2005 | Von Arx et al. | | 7,068,365 B2 | 6/2006 | Hansen et al. |
| 6,955,650 B2 | 10/2005 | Mault et al. | | 7,070,580 B2 | 7/2006 | Nielsen |
| 6,957,102 B2 | 10/2005 | Silver et al. | | 7,072,718 B2 | 7/2006 | Von Arx et al. |
| 6,957,107 B2 | 10/2005 | Rogers et al. | | 7,072,802 B2 | 7/2006 | Hartlaub |
| 6,958,129 B2 | 10/2005 | Galen et al. | | 7,074,307 B2 | 7/2006 | Simpson et al. |
| 6,958,705 B2 | 10/2005 | Lebel et al. | | 7,078,480 B2 | 7/2006 | Nagel et al. |
| 6,960,289 B2 | 11/2005 | Hodges et al. | | 7,079,881 B2 | 7/2006 | Schulman et al. |
| 6,965,791 B1 | 11/2005 | Hitchcock et al. | | 7,081,195 B2 | 7/2006 | Simpson et al. |
| 6,968,294 B2 | 11/2005 | Gutta et al. | | 7,082,334 B2 | 7/2006 | Boute et al. |
| 6,968,375 B1 | 11/2005 | Brown | | 7,087,148 B1 | 8/2006 | Blackburn et al. |
| 6,969,359 B2 | 11/2005 | Duchon et al. | | 7,094,609 B2 | 8/2006 | Demers |
| 6,973,706 B2 | 12/2005 | Say et al. | | 7,098,803 B2 | 8/2006 | Mann et al. |
| 6,974,437 B2 | 12/2005 | Lebel et al. | | 7,108,778 B2 | 9/2006 | Simpson et al. |
| 6,977,160 B2 | 12/2005 | Yanagawa et al. | | 7,109,005 B2 | 9/2006 | Eroma et al. |
| 6,978,182 B2 | 12/2005 | Mazar et al. | | 7,109,878 B2 | 9/2006 | Mann et al. |
| 6,979,326 B2 | 12/2005 | Mann et al. | | 7,110,803 B2 | 9/2006 | Shults et al. |
| 6,979,544 B2 | 12/2005 | Keen | | 7,112,265 B1 | 9/2006 | McAleer et al. |
| 6,985,767 B2 | 1/2006 | Horiuchi et al. | | 7,112,453 B2 | 9/2006 | Hutchens et al. |
| 6,986,869 B2 | 1/2006 | Tuohy et al. | | 7,113,821 B1 | 9/2006 | Sun et al. |
| 6,990,366 B2 | 1/2006 | Say et al. | | 7,115,362 B2 | 10/2006 | Douglas et al. |
| 6,991,096 B2 | 1/2006 | Gottlieb et al. | | 7,115,688 B1 | 10/2006 | Mirkin et al. |
| 6,995,835 B2 | 2/2006 | Samsoondar et al. | | 7,115,884 B1 | 10/2006 | Walt et al. |
| 6,995,844 B2 | 2/2006 | Hafeman et al. | | 7,118,919 B2 | 10/2006 | Yatscoff et al. |
| 6,997,907 B2 | 2/2006 | Safabash et al. | | 7,122,302 B2 | 10/2006 | Seidel et al. |
| 6,997,920 B2 | 2/2006 | Mann et al. | | 7,132,247 B1 | 11/2006 | Lyngberg et al. |
| 6,997,949 B2 | 2/2006 | Tuch | | 7,133,710 B2 | 11/2006 | Acosta et al. |
| 6,998,247 B2 | 2/2006 | Monfre et al. | | 7,134,999 B2 | 11/2006 | Brauker et al. |
| 6,999,808 B2 | 2/2006 | Gobeli et al. | | 7,136,689 B2 | 11/2006 | Shults et al. |
| 6,999,810 B2 | 2/2006 | Berner et al. | | 7,137,964 B2 | 11/2006 | Flaherty |
| 7,003,336 B2 | 2/2006 | Holker et al. | | 7,141,212 B2 | 11/2006 | Catt et al. |
| 7,003,340 B2 | 2/2006 | Say et al. | | 7,144,486 B1 | 12/2006 | Fritsch et al. |
| 7,003,341 B2 | 2/2006 | Say et al. | | 7,144,709 B2 | 12/2006 | Ouyang et al. |
| 7,004,901 B2 | 2/2006 | Fish | | 7,150,975 B2 | 12/2006 | Tamada et al. |
| 7,005,857 B2 | 2/2006 | Stiene et al. | | 7,160,321 B2 | 1/2007 | Shanley |
| 7,006,857 B2 | 2/2006 | Braig et al. | | 7,163,511 B2 | 1/2007 | Conn et al. |
| 7,008,764 B1 | 3/2006 | Honold et al. | | 7,166,074 B2 | 1/2007 | Reghabi et al. |
| 7,008,799 B1 | 3/2006 | Zimmer et al. | | 7,169,272 B2 | 1/2007 | Fritsch et al. |
| 7,010,336 B2 | 3/2006 | Lorenz et al. | | 7,171,274 B2 | 1/2007 | Starkweather et al. |
| 7,011,630 B2 | 3/2006 | Desai et al. | | 7,177,690 B2 | 2/2007 | Woods et al. |
| 7,011,954 B2 | 3/2006 | Ouyang et al. | | 7,179,288 B2 | 2/2007 | Shanley |
| 7,015,034 B2 | 3/2006 | Lawman et al. | | 7,182,912 B2 | 2/2007 | Carey et al. |
| 7,015,046 B2 | 3/2006 | Wohlstadter et al. | | 7,183,068 B2 | 2/2007 | Burson et al. |
| 7,016,721 B2 | 3/2006 | Lee et al. | | 7,183,102 B2 | 2/2007 | Monfre et al. |
| 7,018,366 B2 | 3/2006 | Easter | | 7,186,401 B2 | 3/2007 | Keller et al. |
| 7,018,568 B2 | 3/2006 | Tierney | | 7,186,529 B2 | 3/2007 | Stern et al. |
| 7,018,848 B2 | 3/2006 | Douglas et al. | | 7,187,528 B2 | 3/2007 | Talbot et al. |
| 7,019,112 B1 | 3/2006 | Slingluff et al. | | 7,189,341 B2 | 3/2007 | Li et al. |
| 7,021,309 B2 | 4/2006 | Gonda et al. | | 7,190,988 B2 | 3/2007 | Say et al. |
| 7,022,072 B2 | 4/2006 | Fox et al. | | 7,192,450 B2 | 3/2007 | Brauker et al. |
| 7,022,286 B2 | 4/2006 | Lemke et al. | | 7,192,772 B1 | 3/2007 | Ingram et al. |
| 7,024,236 B2 | 4/2006 | Ford et al. | | 7,193,521 B2 | 3/2007 | Moberg et al. |
| 7,024,245 B2 | 4/2006 | Lebel et al. | | 7,198,606 B2 | 4/2007 | Boecker et al. |
| 7,025,743 B2 | 4/2006 | Mann et al. | | 7,202,470 B1 | 4/2007 | Marriott |
| 7,026,142 B2 | 4/2006 | Sjoberg | | 7,203,549 B2 | 4/2007 | Schommer et al. |
| 7,029,444 B2 | 4/2006 | Shin et al. | | 7,207,974 B2 | 4/2007 | Safabash et al. |
| RE39,112 E | 5/2006 | Asano et al. | | 7,211,096 B2 | 5/2007 | Kuhr et al |
| 7,037,261 B2 | 5/2006 | Charash | | 7,214,514 B2 | 5/2007 | Brandt et al. |
| 7,037,277 B1 | 5/2006 | Smith et al. | | 7,214,532 B2 | 5/2007 | Stern et al. |
| 7,039,810 B1 | 5/2006 | Nichols | | 7,220,550 B2 | 5/2007 | Keen |
| 7,041,210 B2 | 5/2006 | Hodges et al. | | 7,223,236 B2 | 5/2007 | Brown |
| 7,041,468 B2 | 5/2006 | Drucker et al. | | 7,226,978 B2 | 6/2007 | Tapsak et al. |
| 7,043,287 B1 | 5/2006 | Khalil et al. | | 7,228,163 B2 | 6/2007 | Ackerman |
| 7,044,919 B1 | 5/2006 | Catt et al. | | 7,233,817 B2 | 6/2007 | Yen |
| 7,045,046 B2 | 5/2006 | Chambers et al. | | 7,235,056 B2 | 6/2007 | Duchon et al. |
| 7,045,310 B2 | 5/2006 | Buck, Jr. et al. | | 7,238,534 B1 | 7/2007 | Zimmer |

| Patent Number | Date | Inventor |
|---|---|---|
| 7,238,830 B2 | 7/2007 | Amino et al. |
| 7,247,144 B2 | 7/2007 | Douglas et al. |
| 7,247,456 B2 | 7/2007 | Sjoberg |
| 7,248,929 B2 | 7/2007 | Meadows et al. |
| 7,252,636 B2 | 8/2007 | Brown |
| 7,261,691 B1 | 8/2007 | Asomani |
| 7,265,087 B1 | 9/2007 | Göke et al. |
| 7,268,665 B2 | 9/2007 | Inagaki et al. |
| 7,270,970 B2 | 9/2007 | Anderson et al. |
| 7,276,029 B2 | 10/2007 | Goode, Jr. et al. |
| 7,282,029 B1 | 10/2007 | Poulsen et al. |
| 7,285,197 B2 | 10/2007 | Carlsson |
| 7,289,836 B2 | 10/2007 | Colvin, Jr. |
| 7,294,498 B2 | 11/2007 | Bylina et al. |
| 7,295,867 B2 | 11/2007 | Berner et al. |
| 7,297,109 B2 | 11/2007 | Brown |
| 7,303,922 B2 | 12/2007 | Jeng et al. |
| 7,310,544 B2 | 12/2007 | Brister et al. |
| 7,318,816 B2 | 1/2008 | Bobroff et al. |
| 7,320,030 B2 | 1/2008 | Brown |
| 7,323,314 B2 | 1/2008 | Curtis |
| 7,324,012 B2 | 1/2008 | Mann et al. |
| 7,329,239 B2 | 2/2008 | Safabash et al. |
| 7,335,292 B2 | 2/2008 | Hodges et al. |
| 7,335,294 B2 | 2/2008 | Heller et al. |
| 7,338,639 B2 | 3/2008 | Burke et al. |
| 7,344,499 B1 | 3/2008 | Prausnitz et al. |
| 7,347,971 B2 | 3/2008 | Knappe |
| 7,347,973 B2 | 3/2008 | Douglas et al. |
| 7,348,181 B2 | 3/2008 | Walt et al. |
| RE40,198 E | 4/2008 | Buck, Jr. et al. |
| RE40,209 E | 4/2008 | Sugihara et al. |
| RE40,316 E | 5/2008 | Gobeli et al. |
| 7,374,778 B2 | 5/2008 | Hoffman et al. |
| H2218 H | 6/2008 | Hwang et al. |
| 7,381,544 B2 | 6/2008 | Gilbert et al. |
| 7,381,571 B2 | 6/2008 | Woudenberg et al. |
| 7,384,600 B2 | 6/2008 | Burns et al. |
| 7,390,667 B2 | 6/2008 | Burke et al. |
| 7,401,111 B1 | 7/2008 | Batman et al. |
| 7,402,153 B2 | 7/2008 | Steil et al. |
| RE40,470 E | 8/2008 | Fitzpatrick et al. |
| 7,407,811 B2 | 8/2008 | Burke et al. |
| 7,419,696 B2 | 8/2008 | Berg et al. |
| 7,405,055 B2 | 9/2008 | Dunn et al. |
| 7,425,443 B2 | 9/2008 | Alam et al. |
| 7,431,814 B2 | 10/2008 | Hodges |
| 7,462,264 B2 | 12/2008 | Heller et al. |
| 7,476,548 B2 | 1/2009 | Blatt et al. |
| 7,477,053 B2 | 1/2009 | Pinsky |
| 7,479,253 B2 | 1/2009 | Knappe et al. |
| 7,494,816 B2 | 2/2009 | Burke et al. |
| 2001/0011224 A1 | 8/2001 | Brown |
| 2001/0016310 A1 | 8/2001 | Brown et al. |
| 2001/0016682 A1 | 8/2001 | Berner et al. |
| 2001/0016683 A1 | 8/2001 | Darrow et al. |
| 2001/0020124 A1 | 9/2001 | Tamada |
| 2001/0029340 A1 | 10/2001 | Mault et al. |
| 2001/0031931 A1 | 10/2001 | Cunningham et al. |
| 2001/0032278 A1 | 10/2001 | Brown et al. |
| 2001/0037060 A1 | 11/2001 | Thompson et al. |
| 2001/0037069 A1 | 11/2001 | Calrson et al. |
| 2001/0039504 A1 | 11/2001 | Linberg et al. |
| 2001/0041830 A1 | 11/2001 | Varalli et al. |
| 2001/0044581 A1 | 11/2001 | Mault |
| 2001/0044588 A1 | 11/2001 | Mault |
| 2001/0047125 A1 | 11/2001 | Quy |
| 2001/0049096 A1 | 12/2001 | Brown |
| 2001/0049470 A1 | 12/2001 | Mault et al. |
| 2001/0056255 A1 | 12/2001 | Kost et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0009810 A1 | 1/2002 | O'Connor et al. |
| 2002/0010414 A1 | 1/2002 | Coston et al. |
| 2002/0013538 A1 | 1/2002 | Teller |
| 2002/0016530 A1 | 2/2002 | Brown |
| 2002/0019022 A1 | 2/2002 | Dunn et al. |
| 2002/0019330 A1 | 2/2002 | Murray et al. |
| 2002/0019586 A1 | 2/2002 | Teller et al. |
| 2002/0019748 A1 | 2/2002 | Brown |
| 2002/0022883 A1 | 2/2002 | Burg |
| 2002/0023852 A1 | 2/2002 | McIvor et al. |
| 2002/0026111 A1 | 2/2002 | Ackerman |
| 2002/0026937 A1 | 3/2002 | Mault |
| 2002/0027164 A1 | 3/2002 | Mault et al. |
| 2002/0028995 A1 | 3/2002 | Mault |
| 2002/0040208 A1 | 4/2002 | Flaherty et al. |
| 2002/0042090 A1 | 4/2002 | Heller et al. |
| 2002/0042561 A1 | 4/2002 | Schulman et al. |
| 2002/0045808 A1 | 4/2002 | Ford et al. |
| 2002/0047867 A1 | 4/2002 | Mault et al. |
| 2002/0053637 A1 | 5/2002 | Conn et al. |
| 2002/0062069 A1 | 5/2002 | Mault |
| 2002/0063060 A1 | 5/2002 | Gascoyne et al. |
| 2002/0065453 A1 | 5/2002 | Lesho et al. |
| 2002/0068858 A1 | 6/2002 | Braig et al. |
| 2002/0068860 A1 | 6/2002 | Clark, Jr. |
| 2002/0072858 A1 | 6/2002 | Cheng |
| 2002/0077765 A1 | 6/2002 | Mault |
| 2002/0077766 A1 | 6/2002 | Mault |
| 2002/0081559 A1 | 6/2002 | Brown et al. |
| 2002/0082487 A1 | 6/2002 | Kollias et al. |
| 2002/0083461 A1 | 6/2002 | Hutcheson et al. |
| 2002/0087056 A1 | 7/2002 | Aceti et al. |
| 2002/0091312 A1 | 7/2002 | Berner et al. |
| 2002/0099282 A1 | 7/2002 | Knobbe et al. |
| 2002/0099997 A1 | 7/2002 | Piret |
| 2002/0103425 A1 | 8/2002 | Mault |
| 2002/0107433 A1 | 8/2002 | Mault |
| 2002/0107476 A1 | 8/2002 | Mann et al. |
| 2002/0109600 A1 | 8/2002 | Mault et al. |
| 2002/0111547 A1 | 8/2002 | Knobbe et al. |
| 2002/0119711 A1 | 8/2002 | Van Antwerp et al. |
| 2002/0124017 A1 | 9/2002 | Mault |
| 2002/0128594 A1 | 9/2002 | Das et al. |
| 2002/0130042 A1 | 9/2002 | Moerman et al. |
| 2002/0133378 A1 | 9/2002 | Mault et al. |
| 2002/0151796 A1 | 10/2002 | Koulik |
| 2002/0151816 A1 | 10/2002 | Rich et al. |
| 2002/0155615 A1 | 10/2002 | Novikov et al. |
| 2002/0156434 A1 | 10/2002 | Van Antwerp et al. |
| 2002/0161286 A1 | 10/2002 | Gerber et al. |
| 2002/0161288 A1 | 10/2002 | Shin et al. |
| 2002/0169394 A1 | 11/2002 | Eppstein et al. |
| 2002/0177764 A1 | 11/2002 | Sohrab |
| 2002/0182241 A1 | 12/2002 | Boerenstein et al. |
| 2002/0193679 A1 | 12/2002 | Malave et al. |
| 2002/0193885 A1 | 12/2002 | Legeay et al. |
| 2002/0198513 A1 | 12/2002 | Lebel et al. |
| 2003/0000834 A1 | 1/2003 | Yoshioka et al. |
| 2003/0004457 A1 | 1/2003 | Andersson |
| 2003/0006669 A1 | 1/2003 | Pei et al. |
| 2003/0023171 A1 | 1/2003 | Sato et al. |
| 2003/0023182 A1 | 1/2003 | Mault et al. |
| 2003/0023317 A1 | 1/2003 | Brauker et al. |
| 2003/0028089 A1 | 2/2003 | Galley et al. |
| 2003/0028120 A1 | 2/2003 | Mault et al. |
| 2003/0032077 A1 | 2/2003 | Itoh et al. |
| 2003/0032867 A1 | 2/2003 | Crothall et al. |
| 2003/0032868 A1 | 2/2003 | Graskov et al. |
| 2003/0032874 A1 | 2/2003 | Rhodes et al. |

| Pub. No. | Date | Inventor |
|---|---|---|
| 2003/0040683 A1 | 2/2003 | Rule et al. |
| 2003/0042137 A1 | 3/2003 | Mao et al. |
| 2003/0050537 A1 | 3/2003 | Wessel |
| 2003/0050546 A1 | 3/2003 | Dasai et al. |
| 2003/0059631 A1 | 3/2003 | All-Lamee |
| 2003/0065254 A1 | 4/2003 | Schulman et al. |
| 2003/0065257 A1 | 4/2003 | Mault et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0065308 A1 | 4/2003 | Lebel et al. |
| 2003/0076082 A1 | 4/2003 | Morgan et al. |
| 2003/0078481 A1 | 4/2003 | Melvor et al. |
| 2003/0078560 A1 | 4/2003 | Miller et al. |
| 2003/0088166 A1 | 5/2003 | Say et al. |
| 2003/0097082 A1 | 5/2003 | Purdy et al. |
| 2003/0100040 A1 | 5/2003 | Bonnecaze et al. |
| 2003/0100821 A1 | 5/2003 | Heller et al. |
| 2003/0105407 A1 | 6/2003 | Pearce et al. |
| 2003/0108976 A1 | 6/2003 | Braig et al. |
| 2003/0125612 A1 | 7/2003 | Fox et al. |
| 2003/0125613 A1 | 7/2003 | Enegren et al. |
| 2003/0125669 A1 | 7/2003 | Safabash et al. |
| 2003/0130616 A1 | 7/2003 | Steil et al. |
| 2003/0130619 A1 | 7/2003 | Safabash |
| 2003/0134347 A1 | 7/2003 | Heller et al. |
| 2003/0135100 A1 | 7/2003 | Kim et al. |
| 2003/0135333 A1 | 7/2003 | Aceti et al. |
| 2003/0153820 A1 | 8/2003 | Berner et al. |
| 2003/0153821 A1 | 8/2003 | Berner et al. |
| 2003/0158472 A1 | 8/2003 | Sohrab |
| 2003/0158520 A1 | 8/2003 | Safabach et al. |
| 2003/0158707 A1 | 8/2003 | Doi |
| 2003/0168338 A1 | 9/2003 | Gao et al. |
| 2003/0175806 A1 | 9/2003 | Rule et al. |
| 2003/0176183 A1 | 9/2003 | Drucker et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0188427 A1 | 10/2003 | Say et al. |
| 2003/0191376 A1 | 10/2003 | Samuels et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0199744 A1 | 10/2003 | Buse et al. |
| 2003/0199791 A1 | 10/2003 | Boecker et al. |
| 2003/0199823 A1 | 10/2003 | Bobroff et al. |
| 2003/0199903 A1 | 10/2003 | Boecker et al. |
| 2003/0201194 A1 | 10/2003 | Heller et al. |
| 2003/0208110 A1 | 11/2003 | Mault et al. |
| 2003/0208113 A1 | 11/2003 | Mault et al. |
| 2003/0208133 A1 | 11/2003 | Mault |
| 2003/0208409 A1 | 11/2003 | Mault |
| 2003/0211625 A1 | 11/2003 | Cohan |
| 2003/0212346 A1 | 11/2003 | Yuzhakov et al. |
| 2003/0212364 A1 | 11/2003 | Mann et al. |
| 2003/0212379 A1 | 11/2003 | Bylund et al. |
| 2003/0217966 A1 | 11/2003 | Tapsak et al. |
| 2003/0225373 A1 | 12/2003 | Bobroff et al. |
| 2003/0225437 A1 | 12/2003 | Ferguson |
| 2003/0226695 A1 | 12/2003 | Mault |
| 2003/0229514 A2 | 12/2003 | Brown |
| 2003/0232370 A1 | 12/2003 | Trifiro |
| 2003/0235817 A1 | 12/2003 | Bartkowiak et al. |
| 2004/0002682 A1 | 1/2004 | Kovelman et al. |
| 2004/0003493 A1 | 1/2004 | Adair et al. |
| 2004/0010207 A1 | 1/2004 | Flaherty et al. |
| 2004/0011671 A1 | 1/2004 | Shults et al. |
| 2004/0015134 A1 | 1/2004 | Lavi et al. |
| 2004/0018486 A1 | 1/2004 | Dunn et al. |
| 2004/0026244 A1 | 2/2004 | Hodges et al. |
| 2004/0030285 A1 | 2/2004 | Lavi et al. |
| 2004/0030294 A1 | 2/2004 | Mahurkar |
| 2004/0039256 A1 | 2/2004 | Kawatahara et al. |
| 2004/0039406 A1 | 2/2004 | Jessen |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0054267 A1 | 3/2004 | Feldman et al. |
| 2004/0055898 A1 | 3/2004 | Heller et al. |
| 2004/0059201 A1 | 3/2004 | Ginsberg |
| 2004/0068230 A1 | 4/2004 | Estes et al. |
| 2004/0069164 A1 | 4/2004 | Nakamura et al. |
| 2004/0069657 A1 | 4/2004 | Hodges et al. |
| 2004/0072357 A1 | 4/2004 | Stiene et al. |
| 2004/0073095 A1 | 4/2004 | Causey, III et al. |
| 2004/0074785 A1 | 4/2004 | Holker |
| 2004/0078219 A1 | 4/2004 | Kaylor |
| 2004/0085215 A1 | 5/2004 | Moberg et al. |
| 2004/0092873 A1 | 5/2004 | Moberg et al. |
| 2004/0096959 A1 | 5/2004 | Steine et al. |
| 2004/0106858 A1 | 6/2004 | Say et al. |
| 2004/0106859 A1 | 6/2004 | Say et al. |
| 2004/0106860 A1 | 6/2004 | Say et al. |
| 2004/0108226 A1 | 6/2004 | Polychronakos et al. |
| 2004/0122353 A1 | 6/2004 | Shahmirian et al. |
| 2004/0122489 A1 | 6/2004 | Mazar et al. |
| 2004/0133164 A1 | 7/2004 | Funderburk et al. |
| 2004/0138588 A1 | 7/2004 | Saikley et al. |
| 2004/0153585 A1 | 8/2004 | Kawatahara et al. |
| 2004/0158137 A1 | 8/2004 | Eppstein et al. |
| 2004/0162473 A1 | 8/2004 | Sohrab |
| 2004/0164961 A1 | 8/2004 | Bal et al. |
| 2004/0167383 A1 | 8/2004 | Kim et al. |
| 2004/0167801 A1 | 8/2004 | Say et al. |
| 2004/0171921 A1 | 9/2004 | Say et al. |
| 2004/0172284 A1 | 9/2004 | Sullivan et al. |
| 2004/0176913 A1 | 9/2004 | Kawatahara et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0199059 A1 | 10/2004 | Brauker et al. |
| 2004/0202576 A1 | 10/2004 | Aceti et al. |
| 2004/0210184 A1 | 10/2004 | Kost et al. |
| 2004/0219664 A1 | 11/2004 | Heller et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0248204 A1 | 12/2004 | Moerman |
| 2004/0249250 A1 | 12/2004 | Mcgee et al. |
| 2004/0249253 A1 | 12/2004 | Racchini et al. |
| 2004/0249254 A1 | 12/2004 | Racchini et al. |
| 2004/0249999 A1 | 12/2004 | Connolly et al. |
| 2004/0253736 A1 | 12/2004 | Stout et al. |
| 2004/0254429 A1 | 12/2004 | Yang |
| 2004/0254433 A1 | 12/2004 | Bandis et al. |
| 2004/0254434 A1 | 12/2004 | Goodnow et al. |
| 2004/0260363 A1 | 12/2004 | Von Arx et al. |
| 2004/0263354 A1 | 12/2004 | Mann et al. |
| 2005/0003470 A1 | 1/2005 | Nelson et al. |
| 2005/0010087 A1 | 1/2005 | Banet et al. |
| 2005/0010269 A1 | 1/2005 | Lebel et al. |
| 2005/0021000 A1 | 1/2005 | Adair et al. |
| 2005/0027177 A1 | 2/2005 | Shin et al. |
| 2005/0027179 A1 | 2/2005 | Berner et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |

| | | | | | | |
|---|---|---|---|---|---|---|
| 2005/0031689 A1 | 2/2005 | Shults et al. | | 2006/0001551 A1 | 1/2006 | Kraft et al. |
| 2005/0033126 A1 | 2/2005 | Charash | | 2006/0003398 A1 | 1/2006 | Heller et al. |
| 2005/0033132 A1 | 2/2005 | Shults et al. | | 2006/0004271 A1 | 1/2006 | Peyder et al. |
| 2005/0038680 A1 | 2/2005 | McMahon | | 2006/0007017 A1 | 1/2006 | Mann et al. |
| 2005/0043598 A1 | 2/2005 | Goode, Jr. et al. | | 2006/0015020 A1 | 1/2006 | Neale et al. |
| 2005/0043894 A1 | 2/2005 | Fernandez | | 2006/0015024 A1 | 1/2006 | Brister et al. |
| 2005/0049473 A1 | 3/2005 | Desai et al. | | 2006/0016700 A1 | 1/2006 | Brister et al. |
| 2005/0051427 A1 | 3/2005 | Brauker et al. | | 2006/0019327 A1 | 1/2006 | Brister et al. |
| 2005/0051440 A1 | 3/2005 | Simpson et al. | | 2006/0020186 A1 | 1/2006 | Brister et al. |
| 2005/0054909 A1 | 3/2005 | Petisce et al. | | 2006/0020187 A1 | 1/2006 | Brister et al. |
| 2005/0056552 A1 | 3/2005 | Simpson et al. | | 2006/0020188 A1 | 1/2006 | Kamath et al. |
| 2005/0059895 A1 | 3/2005 | Brown | | 2006/0020189 A1 | 1/2006 | Brister et al. |
| 2005/0077176 A1 | 4/2005 | Hodges et al. | | 2006/0020190 A1 | 1/2006 | Kamath et al. |
| 2005/0089573 A1 | 4/2005 | Moeckel et al. | | 2006/0020191 A1 | 1/2006 | Brister et al. |
| 2005/0090007 A1 | 4/2005 | Brandt et al. | | 2006/0020192 A1 | 1/2006 | Brister et al. |
| 2005/0090607 A1 | 4/2005 | Tapsak et al. | | 2006/0025663 A1 | 2/2006 | Talbot et al. |
| 2005/0098431 A1 | 5/2005 | Hodges et al. | | 2006/0031094 A1 | 2/2006 | Cohen et al. |
| 2005/0112169 A1 | 5/2005 | Brauker et al. | | 2006/0036139 A1 | 2/2006 | Brister et al. |
| 2005/0112712 A1 | 5/2005 | Ouyang | | 2006/0036140 A1 | 2/2006 | Brister et al. |
| 2005/0113657 A1 | 5/2005 | Alarcon et al. | | 2006/0036141 A1 | 2/2006 | Kamath et al. |
| 2005/0113658 A1 | 5/2005 | Jacobson et al. | | 2006/0036142 A1 | 2/2006 | Brister et al. |
| 2005/0118726 A1 | 6/2005 | Schultz et al. | | 2006/0036143 A1 | 2/2006 | Brister et al. |
| 2005/0121322 A1 | 6/2005 | Say et al. | | 2006/0036144 A1 | 2/2006 | Brister et al. |
| 2005/0124873 A1 | 6/2005 | Shultz et al. | | 2006/0036145 A1 | 2/2006 | Brister et al. |
| 2005/0131346 A1 | 6/2005 | Douglas | | 2006/0036187 A1 | 2/2006 | Vos et al. |
| 2005/0137471 A1 | 6/2005 | Haar et al. | | 2006/0040402 A1 | 2/2006 | Brauker et al. |
| 2005/0143635 A1 | 6/2005 | Kamath et al. | | 2006/0042080 A1 | 3/2006 | Say et al. |
| 2005/0143636 A1 | 6/2005 | Zhang et al. | | 2006/0052679 A1 | 3/2006 | Kotulla et al. |
| 2005/0148003 A1 | 7/2005 | Keith et al. | | 2006/0058602 A1 | 3/2006 | Kwiatkowski et al. |
| 2005/0154271 A1 | 7/2005 | Rasdal et al. | | 2006/0063218 A1 | 3/2006 | Bartkowiak et al. |
| 2005/0161346 A1 | 7/2005 | Simpson et al. | | 2006/0068208 A1 | 3/2006 | Tapsak et al. |
| 2005/0164322 A1 | 7/2005 | Heller et al. | | 2006/0069351 A9 | 3/2006 | Ssafabash et al. |
| 2005/0171503 A1 | 8/2005 | Van Den Berghe et al. | | 2006/0074564 A1 | 4/2006 | Bartowiak et al. |
| 2005/0171513 A1 | 8/2005 | Mann et al. | | 2006/0085064 A1 | 4/2006 | Tuch |
| 2005/0173245 A1 | 8/2005 | Feldman et al. | | 2006/0086624 A1 | 4/2006 | Tapsak et al. |
| 2005/0173246 A1 | 8/2005 | Hodges et al. | | 2006/0088945 A1 | 4/2006 | Douglas et al. |
| 2005/0176136 A1 | 8/2005 | Burd et al. | | 2006/0118415 A1 | 6/2006 | Say et al. |
| 2005/0177036 A1 | 8/2005 | Shultz et al. | | 2006/0155180 A1 | 7/2006 | Brister et al. |
| 2005/0181012 A1 | 8/2005 | Saint et al. | | 2006/0155316 A1 | 7/2006 | Perez et al. |
| 2005/0182306 A1 | 8/2005 | Sloan et al. | | 2006/0156796 A1 | 7/2006 | Burke et al. |
| 2005/0182451 A1 | 8/2005 | Griffin et al. | | 2006/0159981 A1 | 7/2006 | Heller |
| 2005/0187720 A1 | 8/2005 | Goode, Jr. et al. | | 2006/0163061 A1 | 7/2006 | Hodges et al. |
| 2005/0192557 A1 | 9/2005 | Brauker et al. | | 2006/0171954 A1 | 8/2006 | Endl et al. |
| 2005/0195930 A1 | 9/2005 | Spital et al. | | 2006/0173444 A1 | 8/2006 | Choy et al. |
| 2005/0197626 A1 | 9/2005 | Moberg et al. | | 2006/0184154 A1 | 8/2006 | Moberg et al. |
| 2005/0199494 A1 | 9/2005 | Say et al. | | 2006/0189856 A1 | 8/2006 | Petisce et al. |
| 2005/0203349 A1 | 9/2005 | Nanikashvili | | 2006/0189863 A1 | 8/2006 | Peyser et al. |
| 2005/0203360 A1 | 9/2005 | Brauker et al. | | 2006/0195029 A1 | 8/2006 | Shults et al. |
| 2005/0203707 A1 | 9/2005 | Tsutsui et al. | | 2006/0198864 A1 | 9/2006 | Shults et al. |
| 2005/0214892 A1 | 9/2005 | Kovatchev et al. | | 2006/0200019 A1 | 9/2006 | Petisce et al. |
| 2005/0215871 A1 | 9/2005 | Feldman et al. | | 2006/0200020 A1 | 9/2006 | Brister et al. |
| 2005/0215872 A1 | 9/2005 | Berner et al. | | 2006/0200022 A1 | 9/2006 | Brauker et al. |
| 2005/0239154 A1 | 10/2005 | Feldman et al. | | 2006/0201804 A1 | 9/2006 | Chambers et al. |
| 2005/0239156 A1 | 10/2005 | Drucker et al. | | 2006/0211921 A1 | 9/2006 | Brauker et al. |
| 2005/0242479 A1 | 11/2005 | Petisce et al. | | 2006/0222566 A1 | 10/2006 | Brauker et al. |
| 2005/0245795 A1 | 11/2005 | Goode, Jr. et al. | | 2006/0224108 A1 | 10/2006 | Brauker et al. |
| 2005/0245799 A1 | 11/2005 | Brauker et al. | | 2006/0235285 A1 | 10/2006 | Brister et al. |
| 2005/0251083 A1 | 11/2005 | Carr-Brendel et al. | | 2006/0247985 A1 | 11/2006 | Liamos et al. |
| 2005/0261563 A1 | 11/2005 | Zhou et al. | | 2006/0254932 A1 | 11/2006 | Hodges et al. |
| 2005/0261660 A1 | 11/2005 | Choi | | 2006/0258761 A1 | 11/2006 | Boock et al. |
| 2005/0266570 A1 | 12/2005 | Carey et al. | | 2006/0258929 A1 | 11/2006 | Goode, Jr. et al. |
| 2005/0267780 A1 | 12/2005 | Ray et al. | | 2006/0270922 A1 | 11/2006 | Brauker et al. |
| 2005/0271546 A1 | 12/2005 | Gerber et al. | | 2006/0270923 A1 | 11/2006 | Brauker et al. |
| 2005/0271547 A1 | 12/2005 | Gerber et al. | | 2007/0016381 A1 | 1/2007 | Kamath et al. |
| 2005/0272640 A1 | 12/2005 | Doyle, III et al. | | 2007/0017805 A1 | 1/2007 | Hodges et al. |
| 2005/0272985 A1 | 12/2005 | Kotulla et al. | | 2007/0027381 A1 | 2/2007 | Stafford |
| 2005/0277164 A1 | 12/2005 | Drucker et al. | | 2007/0027384 A1 | 2/2007 | Brister et al. |
| 2005/0278945 A1 | 12/2005 | Feldman et al. | | 2007/0027385 A1 | 2/2007 | Brister et al. |
| 2005/0287620 A1 | 12/2005 | Heller et al. | | 2007/0032706 A1 | 2/2007 | Kamath et al. |
| 2006/0001538 A1 | 1/2006 | Kraft et al. | | 2007/0032717 A1 | 2/2007 | Brister et al. |
| 2006/0001550 A1 | 1/2006 | Mann et al. | | 2007/0032718 A1 | 2/2007 | Shults et al. |

| Publication No. | Date | Inventor |
|---|---|---|
| 2007/0045902 A1 | 3/2007 | Brauker et al. |
| 2007/0060814 A1 | 3/2007 | Stafford |
| 2007/0066873 A1 | 3/2007 | Kamath et al. |
| 2007/0078320 A1 | 4/2007 | Stafford |
| 2007/0078321 A1 | 4/2007 | Mazza et al. |
| 2007/0093704 A1 | 4/2007 | Brister et al. |
| 2007/0106135 A1 | 5/2007 | Sloan et al. |
| 2007/0118589 A1 | 5/2007 | Brown |
| 2007/0142721 A1 | 6/2007 | Berner |
| 2007/0142776 A9 | 6/2007 | Kovelman |
| 2007/0149873 A1 | 6/2007 | Say et al. |
| 2007/0149874 A1 | 6/2007 | Say et al. |
| 2007/0149926 A1 | 6/2007 | Moberg et al. |
| 2007/0151869 A1 | 7/2007 | Heller et al. |
| 2007/0156033 A1 | 7/2007 | Causey, III et al. |
| 2007/0156094 A1 | 7/2007 | Safabash et al. |
| 2007/0161879 A1 | 7/2007 | Say et al. |
| 2007/0161880 A1 | 7/2007 | Say et al. |
| 2007/0163880 A1 | 7/2007 | Woo et al. |
| 2007/0179370 A1 | 8/2007 | Say et al. |
| 2007/0179372 A1 | 8/2007 | Say et al. |
| 2007/0191699 A1 | 8/2007 | Say et al. |
| 2007/0191700 A1 | 8/2007 | Say et al. |
| 2007/0191770 A1 | 8/2007 | Moberg et al. |
| 2007/0197889 A1 | 8/2007 | Brister et al. |
| 2007/0197890 A1 | 8/2007 | Boock et al. |
| 2007/0203408 A1 | 8/2007 | Say et al. |
| 2007/0203410 A1 | 8/2007 | Say et al. |
| 2007/0203411 A1 | 8/2007 | Say et al. |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0208247 A1 | 9/2007 | Say et al. |
| 2007/0213610 A1 | 9/2007 | Say et al. |
| 2007/0215491 A1 | 9/2007 | Heller et al. |
| 2007/0218097 A1 | 9/2007 | Heller et al. |
| 2007/0235331 A1 | 10/2007 | Simpson et al. |
| 2007/0244380 A1 | 10/2007 | Say et al. |
| 2007/0249919 A1 | 10/2007 | Say et al. |
| 2007/0249920 A1 | 10/2007 | Say et al. |
| 2007/0249922 A1 | 10/2007 | Peyster et al. |
| 2007/0293747 A1 | 12/2007 | Douglas et al. |
| 2008/0015425 A1 | 1/2008 | Brown |
| 2008/0017522 A1 | 1/2008 | Heller et al. |
| 2008/0021436 A1 | 1/2008 | Wolpert et al. |
| 2008/0030369 A1 | 2/2008 | Mann et al. |
| 2008/0033271 A1 | 2/2008 | Say et al. |
| 2008/0033357 A1 | 2/2008 | Mann et al. |
| 2008/0047129 A1 | 2/2008 | Say et al. |
| 2008/0051871 A1 | 2/2008 | Tuch |
| 2008/0064944 A1 | 3/2008 | VanAntwerp et al. |
| 2008/0076997 A1 | 3/2008 | Peyser et al. |
| 2008/0091096 A1 | 4/2008 | Say et al. |
| 2008/0097180 A1 | 4/2008 | Brown |
| 2008/0097181 A1 | 4/2008 | Brown |
| 2008/0103377 A1 | 5/2008 | Brown |
| 2008/0103379 A1 | 5/2008 | Brown |
| 2008/0103380 A1 | 5/2008 | Brown |
| 2008/0108888 A1 | 5/2008 | Brown |
| 2008/0114229 A1 | 5/2008 | Brown |
| 2008/0147004 A1 | 6/2008 | Mann et al. |
| 2008/0147050 A1 | 6/2008 | Mann et al. |
| 2008/0167543 A1 | 7/2008 | Say et al. |
| 2008/0194990 A1 | 8/2008 | Heller et al. |
| 2008/0208025 A1 | 8/2008 | Shults et al. |
| 2008/0210557 A1 | 9/2008 | Heller et al. |
| 2008/0214914 A1 | 9/2008 | Say et al. |
| 2008/0221522 A1 | 9/2008 | Moberg et al. |
| 2008/0221523 A1 | 9/2008 | Moberg et al. |
| 2008/0228051 A1 | 9/2008 | Shults et al. |
| 2008/0228054 A1 | 9/2008 | Shults et al. |
| 2008/0249470 A1 | 10/2008 | Malave et al. |
| 2008/0262329 A1 | 10/2008 | Say et al. |
| 2008/0262334 A1 | 10/2008 | Dunn et al. |
| 2008/0269672 A1 | 10/2008 | Say et al. |
| 2008/0272007 A1 | 11/2008 | Say et al. |
| 2008/0275323 A1 | 11/2008 | Say et al. |
| 2008/0275423 A1 | 11/2008 | Say et al. |
| 2008/0275544 A1 | 11/2008 | Berg et al. |
| 2008/0276455 A1 | 11/2008 | Say et al. |
| 2008/0281175 A1 | 11/2008 | Say et al. |
| 2008/0281176 A1 | 11/2008 | Say et al. |
| 2008/0281177 A1 | 11/2008 | Say et al. |
| 2008/0286280 A1 | 11/2008 | Kallmeyer et al. |
| 2008/0287759 A1 | 11/2008 | Say et al. |
| 2008/0287760 A1 | 11/2008 | Say et al. |
| 2008/0294028 A1 | 11/2008 | Brown |
| 2008/0295324 A1 | 12/2008 | Say et al. |
| 2008/0296155 A1 | 12/2008 | Shults et al. |
| 2008/0319292 A1 | 12/2008 | Say et al. |
| 2009/0000961 A1 | 1/2009 | Heller et al. |
| 2009/0062634 A1 | 3/2009 | Say et al. |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0089999 A1 | 4/2009 | Say et al. |
| 2009/0093696 A1 | 4/2009 | Say et al. |
| 2009/0099432 A1 | 4/2009 | Say et al. |
| 2009/0099435 A1 | 4/2009 | Say et al. |

FOREIGN PATENT DOCUMENTS

| Country | Number | Date |
|---|---|---|
| DE | 227029 | 9/1985 |
| DE | 3934299 | 10/1990 |
| DE | 4234553 | 1/1995 |
| DE | 44 01 400 A1 | 7/1995 |
| EP | 0010375 | 4/1980 |
| EP | 1579690 | 11/1980 |
| EP | 0026995 | 4/1981 |
| EP | 0048090 | 3/1982 |
| EP | 0078636 | 5/1983 |
| EP | 0080304 | 6/1983 |
| EP | 0096228 | 12/1983 |
| EP | 0096288 | 12/1983 |
| EP | 98592 | 1/1984 |
| EP | 0098592 | 1/1984 |
| EP | 0 098 592 | 1/1984 |
| EP | 0107634 | 5/1984 |
| EP | 107634 | 5/1984 |
| EP | 0125139 | 11/1984 |
| EP | 0127958 | 12/1984 |
| EP | 127958 | 12/1984 |
| EP | 0136362 | 4/1985 |
| EP | 136362 | 4/1985 |
| EP | 0170375 | 2/1986 |
| EP | 0177743 | 4/1986 |
| EP | 0184909 | 6/1986 |
| EP | 0206218 | 12/1986 |
| EP | 0230472 | 8/1987 |
| EP | 0241309 | 10/1987 |
| EP | 0245073 | 11/1987 |
| EP | 0255291 | 2/1988 |
| EP | 0278647 | 8/1988 |
| EP | 0 286 118 | 10/1988 |
| EP | 0 320 109 A1 | 6/1989 |
| EP | 0 353 328 A1 | 2/1990 |
| EP | 0359831 | 3/1990 |
| EP | 0368209 | 5/1990 |
| EP | 0368290 | 5/1990 |
| EP | 0 390 390 | 10/1990 |
| EP | 0390390 | 10/1990 |

| | | | | | |
|---|---|---|---|---|---|
| EP | 0 396 788 A1 | 11/1990 | EP | 1013219 | 6/2000 |
| EP | 0400918 | 12/1990 | EP | 1024358 | 8/2000 |
| EP | 429076 | 5/1991 | EP | 1034734 | 9/2000 |
| EP | 0453283 | 10/1991 | EP | 1 048 264 | 11/2000 |
| EP | 0470290 | 2/1992 | EP | 1075209 | 2/2001 |
| EP | 471986 | 2/1992 | EP | 1077634 | 2/2001 |
| EP | 497308 | 8/1992 | EP | 1078258 | 2/2001 |
| EP | 502504 | 9/1992 | EP | 1300670 | 9/2003 |
| EP | 0504835 | 9/1992 | EP | 1352969 | 10/2003 |
| EP | 0512122 | 11/1992 | EP | 1362920 | 11/2003 |
| EP | 0534074 | 3/1993 | EP | 1362921 | 11/2003 |
| EP | 0535898 | 4/1993 | EP | 1398621 | 3/2004 |
| EP | 537761 | 4/1993 | EP | 1598656 | 11/2005 |
| EP | 0539625 | 5/1993 | EP | 1845165 | 10/2007 |
| EP | 560336 | 9/1993 | FR | 2656423 | 6/1991 |
| EP | 590661 | 4/1994 | FR | 2760962 | 9/1998 |
| EP | 0561966 | 10/1994 | GB | 1394171 | 5/1975 |
| EP | 0 286 118 | 1/1995 | GB | 1442303 | 7/1976 |
| EP | 636879 | 2/1995 | GB | 1579690 | 11/1980 |
| EP | 636880 | 2/1995 | GB | 1599241 | 9/1981 |
| EP | 0653718 | 5/1995 | GB | 2073891 | 10/1981 |
| EP | 679720 | 11/1995 | GB | 2 149 918 | 6/1985 |
| EP | 685737 | 12/1995 | GB | 2149918 | 6/1985 |
| EP | 689051 | 12/1995 | GB | 2154003 | 8/1985 |
| EP | 730037 | 9/1996 | GB | 2194892 | 3/1988 |
| EP | 732406 | 9/1996 | GB | 2204408 | 11/1988 |
| EP | 735363 | 10/1996 | GB | 2225637 | 6/1990 |
| EP | 744781 | 11/1996 | GB | 2254436 | 10/1992 |
| EP | 0776628 | 6/1997 | JP | 54-041191 | 4/1979 |
| EP | 794429 | 9/1997 | JP | 55-010582 | 1/1980 |
| EP | 795601 | 9/1997 | JP | 55-010583 | 1/1980 |
| EP | 795748 | 9/1997 | JP | 55-010584 | 1/1980 |
| EP | 797264 | 9/1997 | JP | 55-012406 | 1/1980 |
| EP | 800080 | 10/1997 | JP | 56-163447 | 12/1981 |
| EP | 0800082 | 10/1997 | JP | 57-070448 | 4/1982 |
| EP | 805352 | 11/1997 | JP | 60-173457 | 9/1985 |
| EP | 0817809 | 1/1998 | JP | 60-173458 | 9/1985 |
| EP | 823483 | 2/1998 | JP | 60-173459 | 9/1985 |
| EP | 0838230 | 4/1998 | JP | 60-210243 | 10/1985 |
| EP | 845673 | 6/1998 | JP | 61-090050 | 5/1986 |
| EP | 851224 | 7/1998 | JP | 62-083849 | 4/1987 |
| EP | 856586 | 8/1998 | JP | 62-085855 | 4/1987 |
| EP | 868144 | 10/1998 | JP | 62-114747 | 5/1987 |
| EP | 872728 | 10/1998 | JP | 63-058149 | 3/1988 |
| EP | 0880936 | 12/1998 | JP | 62-128252 | 5/1988 |
| EP | 884392 | 12/1998 | JP | 63-139246 | 6/1988 |
| EP | 0885932 | 12/1998 | JP | 63-294799 | 12/1988 |
| EP | 894869 | 2/1999 | JP | 63-317757 | 12/1988 |
| EP | 897745 | 2/1999 | JP | 63-317758 | 12/1988 |
| EP | 901018 | 3/1999 | JP | 1-114746 | 5/1989 |
| EP | 902270 | 3/1999 | JP | 1-114747 | 5/1989 |
| EP | 905506 | 3/1999 | JP | 1-124060 | 5/1989 |
| EP | 909952 | 4/1999 | JP | 1-134244 | 5/1989 |
| EP | 918045 | 5/1999 | JP | 1-156658 | 6/1989 |
| EP | 923903 | 6/1999 | JP | 2-062958 | 3/1990 |
| EP | 955546 | 11/1999 | JP | 2-120655 | 5/1990 |
| EP | 957361 | 11/1999 | JP | 2-287145 | 11/1990 |
| EP | 957362 | 11/1999 | JP | 2-310457 | 12/1990 |
| EP | 964059 | 12/1999 | JP | 3-026956 | 2/1991 |
| EP | 964060 | 12/1999 | JP | 3-028752 | 2/1991 |
| EP | 964245 | 12/1999 | JP | 3-202764 | 9/1991 |
| EP | 965301 | 12/1999 | JP | 5-072171 | 3/1993 |
| EP | 0967788 | 12/1999 | JP | 5-196595 | 8/1993 |
| EP | 969097 | 1/2000 | JP | 6-190050 | 7/1994 |
| EP | 0970655 | 1/2000 | JP | 7-055757 | 3/1995 |
| EP | 984069 | 3/2000 | JP | 7-072585 | 3/1995 |
| EP | 987544 | 3/2000 | JP | 8-154903 | 6/1996 |
| EP | 988828 | 3/2000 | JP | 8-285184 | 11/1996 |
| EP | 992589 | 4/2000 | JP | 8-285815 | 11/1996 |
| EP | 995803 | 4/2000 | JP | 9-021778 | 1/1997 |
| EP | 0995805 | 4/2000 | JP | 9-101280 | 4/1997 |

| | | |
|---|---|---|
| JP | 9-285459 | 11/1997 |
| JP | 10-170471 | 6/1998 |
| JP | 2000-000231 | 1/2000 |
| JP | 2000-116628 | 4/2000 |
| JP | 2002-189015 | 7/2002 |
| SU | 1281988 | 1/1987 |
| WO | WO93014693 | 6/1983 |
| WO | WO-1985/005119 | 11/1985 |
| WO | WO-1986/000513 | 1/1986 |
| WO | WO-1987/000513 | 1/1987 |
| WO | WO-1987/006040 | 10/1987 |
| WO | WO-1989/002246 | 3/1989 |
| WO | WO-1989/005119 | 6/1989 |
| WO | WO-1989/008713 | 9/1989 |
| WO | WO-1990/000367 | 1/1990 |
| WO | WO-1990/000738 | 1/1990 |
| WO | WO-1990/005300 | 5/1990 |
| WO | WO-1990/005910 | 5/1990 |
| WO | WO-1990/013021 | 11/1990 |
| WO | WO-1991/001680 | 2/1991 |
| WO | WO-1991/004704 | 4/1991 |
| WO | WO 1991009302 | 6/1991 |
| WO | WO-1991/015993 | 10/1991 |
| WO | WO 1991016416 | 10/1991 |
| WO | WO1992004153 | 3/1992 |
| WO | WO-1992/007525 | 5/1992 |
| WO | WO-1992/010584 | 6/1992 |
| WO | WO-1992/013271 | 8/1992 |
| WO | WO1993005703 | 4/1993 |
| WO | WO-1993/019701 | 10/1993 |
| WO | WO-1994/020602 | 9/1994 |
| WO | WO1994022357 | 10/1994 |
| WO | WO-1994/022367 | 10/1994 |
| WO | WO-1994/027140 | 11/1994 |
| WO | WO-1995/006240 | 3/1995 |
| WO | WO-1995/007109 | 3/1995 |
| WO | WO-1996/001611 | 1/1996 |
| WO | WO-1996/007908 | 3/1996 |
| WO | WO9614026 | 5/1996 |
| WO | WO 96/14026 | 5/1996 |
| WO | WO 96/25089 | 8/1996 |
| WO | WO1996026668 | 9/1996 |
| WO | WO-1996/030431 | 10/1996 |
| WO | WO-1996/032076 | 10/1996 |
| WO | WO-1996/035370 | 11/1996 |
| WO | WO-1996/036296 | 11/1996 |
| WO | WO 97/01986 | 1/1997 |
| WO | WO-1997/002847 | 1/1997 |
| WO | WO-1997/019344 | 5/1997 |
| WO | WO-1997/020207 | 6/1997 |
| WO | WO-1997/041421 | 11/1997 |
| WO | WO-1997/042882 | 11/1997 |
| WO | WO-1997/042883 | 11/1997 |
| WO | WO-1997/042886 | 11/1997 |
| WO | WO-1997/042888 | 11/1997 |
| WO | WO1997043633 | 11/1997 |
| WO | WO-1997/043962 | 11/1997 |
| WO | WO-1997/046868 | 12/1997 |
| WO | WO-1998/009167 | 3/1998 |
| WO | WO1998010699 | 3/1998 |
| WO | WO-1998/024358 | 6/1998 |
| WO | WO-1998/024366 | 6/1998 |
| WO | WO1998038906 | 9/1998 |
| WO | WO1998046124 | 10/1998 |
| WO | WO-1998/052045 | 11/1998 |
| WO | WO-1998/052293 | 11/1998 |
| WO | WO-1999/005966 | 2/1999 |
| WO | WO1999013574 | 3/1999 |
| WO | WO-1999/032883 | 7/1999 |
| WO | WO-1999/048419 | 9/1999 |
| WO | WO 99/56613 | 11/1999 |
| WO | WO-1999/056613 | 11/1999 |
| WO | WO-1999/058051 | 11/1999 |
| WO | WO-1999/058973 | 11/1999 |
| WO | WO2000013003 | 3/2000 |
| WO | WO-2000/013580 | 3/2000 |
| WO | WO-2000/018294 | 4/2000 |
| WO | WO-2000/019887 | 4/2000 |
| WO | WO-2000/020626 | 4/2000 |
| WO | WO-2000/032098 | 6/2000 |
| WO | WO-2000/033065 | 6/2000 |
| WO | WO 00/49940 | 8/2000 |
| WO | WO-2000/059373 | 10/2000 |
| WO | WO-2000/062664 | 10/2000 |
| WO | WO-2000/062665 | 10/2000 |
| WO | WO-2000/078210 | 12/2000 |
| WO | WO-2000/078992 | 12/2000 |
| WO | WO-2001/012158 | 2/2001 |
| WO | WO-2001/020019 | 3/2001 |
| WO | WO-2001/020334 | 3/2001 |
| WO | WO-2001/024038 | 4/2001 |
| WO | WO-2001/033216 | 5/2001 |
| WO | WO-2001/043660 | 6/2001 |
| WO | WO-2001/052727 | 7/2001 |
| WO | WO-2001/052935 | 7/2001 |
| WO | WO-2001/054753 | 8/2001 |
| WO | WO-2001/057238 | 8/2001 |
| WO | WO-2001/057239 | 8/2001 |
| WO | WO-2001/05/8348 | 8/2001 |
| WO | WO-2001/067009 | 9/2001 |
| WO | WO-2001/068901 | 9/2001 |
| WO | WO-2001/069222 | 9/2001 |
| WO | WO-2001/088524 | 11/2001 |
| WO | WO-2001/088534 | 11/2001 |
| WO | WO-2002/016905 | 2/2002 |
| WO | WO-2002/017210 | 2/2002 |
| WO | WO-2002/024065 | 3/2002 |
| WO | WO-2002/058537 | 8/2002 |
| WO | WO-2002/078512 | 10/2002 |
| WO | WO-2002/082989 | 10/2002 |
| WO | WO-2003/072269 | 9/2003 |
| WO | WO-2003/076893 | 9/2003 |
| WO | WO-2003/082091 | 10/2003 |
| WO | WO-2003/101862 | 12/2003 |
| WO | WO-2004/061420 | 7/2004 |
| WO | WO-2005/089103 | 9/2005 |
| WO | WO-2006/119084 | 11/2006 |
| WO | WO-2007/002189 | 1/2007 |
| WO | WO-2007/016399 | 2/2007 |
| WO | WO-2007/027381 | 3/2007 |
| WO | WO-2007/027788 | 3/2007 |
| WO | WO 2007051139 | 5/2007 |
| WO | WO-2007/053832 | 5/2007 |
| WO | WO-2007/056638 | 5/2007 |
| WO | WO-2007/120363 | 10/2007 |

OTHER PUBLICATIONS

Wilson et al., "Progress toward the Development of an Implantable Sensor for Glucose" Clinical Chemistry (1992), vol. 38, No. 9, p. 1613–1617.*

Shichiri et al. "In Vivo Characteristics of Needle–Type Glucose Sensor—Measurements of Subcutaneous Glucose Concentrations in Human Volunteers—" Horm. Metab. Res. Suppl. (1988) 20: 17–20.*

Sakakida et al. "Development of ferrocene–mediated needle–type glucose sensor as a measure of true subcutaneous tissue glucose concentrations" Art. Organs Today (1992) vol. 2, No. 2. p. 145–158.*

Belluci et al., "Electrochemical behavior of graphite–epoxy composite materials (GECM) in aqueous sale solutions," Journal of Applied Electrochemistry, 16(1986) 15–22.

Brauker et al., "Local Inflammatory Response Around Diffusion Chambers Containing Xenografts", Transplantation, vol. 61, 1671–1677, No. 12, Jun. 27, 1996.

Brauker et al., "Neovascularization of Synthetic Membranes Directed by Membrane Microarcitecture," Journal of Biomedical Materials Research 29:1517 (1995).

Brauker, et al., Jun. 27, 1996. Local Inflammatory Response Around Diffusion Chambers Containing Xenografts Transplantation 61(12):1671–1677.

Brauker et al., Neovascularization of synthetic membranes directed by membrane microachitecture. J Biomed Mater Res 1995, 29, 1517–1524.

Brauker, J.H. Unraveling Mysteries at the Biointerface: Molecular Mediator of Inhibition of Blood Vessel Formation in the Foreign Body Capsule Revealed. Surfacts Biomaterials 2001,6, 1:5.

Brunner, et al. Validation of home blood glucose meters with respect to clinical and analytical approaches. Diabetes Care 1998, 21, 585–590.

Davies et al., "Polymer membranes in clinical sensor applications, I. An overview of membrane function," Biomaterials 1992, vol. 13, No. 14, 971–978.

Direct 30/30.RTM. meter (Markwell Medical) (Catalog).

DuPont' Dimension AR.RTM. (Catalog).

DuPont.sup.1 Dimension AR.RTM. (Catalog).

Fraser, et al. Biosensors in the Body, Continous in Vivo Monitoring, Wiley Series of Biomaterials Science and Engineering, 1997, Chapter 4, Principles of Long–term Fully Implantable Sensors with Emphasis on Radiotelemetric Monitoring of Blood Glucose from inside a Subcutaneous Foreign Body Capsule pp. 118–137.

Gross, Todd, "Letters to the Editor Re: Diabetes Technology & Therapeutics, 2000;2:49–56," vol. 3, No. 1, p. 130–131, 2001.

Hamilton Company, "Complete Guide to Selecting the Right Hamilton Gastight, Microliter, and Specialty Syringe for your Application," May 2006.

Hawley's Condensed Chemical Dictionary (14.sup.th.Edition), John Wiley & Sons, Richard J. Lewis, Sr. p. 1248.

Hicks, "In Situ Monitoring," Clin. Chem. 31/12, 1931–1935 (1985).

Hu et al., "A Needle–type enzyme–based lactate sensor for in vivo monitoring," Analytica Chimica Acta, 281 (1993) 503–511.

Hunter, I., Jones, L., Kanigan, T., Brenan, C., Sanbol, L. Sosnowski, L. 2000. Minimally Invasive Glucose Sensor and Insulin Delivery System. MIT Home Automation and Healthcare Consortium. Progress Report No. 25.

Jeong, et al. 2003 In vivo calibration of the subcutaneous amperometric glucose sensors using a non–enzyme electrode. Biosensors and Bioelectronics 19:313–319.

Kawagoe et al., "Enzyme–Modified Organic Conducting Salt Microelectrode," Anal. Chem. 1991, 63, 2961–2965.

Kemp, G. J., "Theoretical Aspects of One–Point Calibration: Causes and Effects of Some Potential Errors, and Their Dependence on Concentration," Clinical Chemistry, vol. 30, No. 7, 1984, pp. 1163–1167.

Kerner, W., et al., "The Function of a Hydrogen Peroxide–Detecting Electroenzymatic Glucose Electrode is Markedly Impaired in Human Subcutaneous Tissue and Plasma," Biosensors & Bioelectronics, vol. 8, 1993, pp. 473–482.

Kiechle, F.L. The impact of continous glucose monitoring on hospital point–of–care testing programs. Diabetes Technol Ther 2001, 3, 647–649.

Klueh, et al. Use of Vascular Endothelia Cell Growth Factor Gene Transfer to Enhance Implantable Sensor Function in vivo, Biosensor Function and Vegf–Gene Transfer, 2003. pp. 1072–1086.

Korf, J., et al., "Monitoring of Glucose and Lactate Using Microdialysis: Applications in Neonates and Rat Brain," Developmental Neuroscience, vol. 15, 1993, pp. 240–246.

Loffler P. et al. Separation and determination of traces of ammonia in air by means of chromatomembrane cells, Fresenius J. Anal. Chem., 1995, 352: 613–614, entire document.

Layman D. 1960. Polyurethanes. I. The Solution Polymerization of Diisocyanates with Ethylene Glycol. J. Polymer Sci XLV:45–49.

Matsumoto et al. 1998. A micro–planar amperometeric glucose sensor unsusceptible to interference species. Senors and Actuators B 49:68–72.

Matsumoto et al. 1998. A micro–planar amperometeric glucose sensor unsusceptible to interference species. Senors and Actuators B 49:68–72.

Matsumoto et al. 1998. A long–term lifetime amperometeric glucose sensor with a perfluorocarbon polymer coating. Biosens Bioelectron 16:271–276.

Moussy, et al. Biomaterials community examines biosensor biocompatability. Diabetes Technol Ther 2000, 2, 473–477.

Murphy et al. "Polymer membranes in clinical sensor application, II. The design and fabrication of permselective hydrogels for electrochemical devices," Biomaterials 1992, vol. 13, No. 14, 979–990.

Myler, et al. Ultra–thin–polysiloxane–film–composite membranes for the optimisation of amperometric oxidase enzyme electrodes. Biosens Bioelectron 2002, 17, 35–43.

Philips and Smith, "Biomedical Applications of Polyurethanes: Implications of Failure Mechanisms,"J. Biomat. Appl. 3:202–227 (1988).

Pineda L. M. et al. Bone regeneration with resorbable polymeric membranes, III Effect of poly(L–lactide) membrane pore size on bone healing process in large defects, J. Biomedical Materials Research, 1996, 31: 385–394, entire document.

Reusch, W., "Other Topics: Organometallic Chemistry: Organometallic Compounds: Main Group Organometallic Compounds," Virtual Textbook of Organic Chemistry, 1999, Rev. 2007, 25 pages.

Sachlos et al. Making Tissue Engineering Scaffolds Work. Review on the Application of Solid Freeform Fabrication Technology to the Production of Tissue Engineering Scaffolds, European Cells and Materials vol. 5, 2003 (29–40).

Sakakida, M., et al., "Development of Ferrocene–Mediated Needle–Type Glucse Sensor as a Measure of True Subcutaneous Tissue Glucose Concentrations", Artificial Organs Today, vol. 2, No. 2, 1992, pp. 145–158.

Sanders, et al. Fibrous Encapsulation of Single Polymer Microfibers Depends on their Vertical Dimension in subcutaneous Tissue, Polymer Microfibers (2003) pp. 1181–1187.

Schuler, R.; Wittkampf, M.; Chemniti , G. C. Modified gas–permeable silicone rubber membranes for covalent immobilisation of enzymes and their use in biosensor development. Analyst 1999, 124, 1181–1184.

Sesen, et al. "Glucose sensor with telemetry system," Ko, W. H. (Ed.). Implantable Sensors for Closed Loop Prosthetic Systems, Ch. 12, 167–175, Futura Publishing Co. (1985).

Shichiri, M., et al., "Needle–type Glucose Sensor for Wearable Artificial Endocrine Pancreas", Implantable Sensors for Closed–Loop Prosthetic Systems, Chapter 15, 1985, pp. 197–210.

Schichiri, et al., 1986, "Telementry Glucose Monitoring Device With Needle–Type Glucose Sensor: A Useful Tool For Blood Glucose Monitoring In Diabetic Individuals," Diabetic Care, vol. 9 No. 3: p. 298–301.

Skoog, D. A., et al., "Evaluation of Analytical Data," Fundamentals of Analytical Chemistry, 1996, pp. 55.

Sokol et al. 1980, Immobilized–enzyme rate–determination method for glucose analysis, Clin. Chem. 26(1):89–92.

Stokes, "Polyether Polyurethanes: Biotable or Not!," Biosmat. Appl. 3:228–259 (1988).

The term "acceleration", Merriam–Webster Online Dictionary—at the web—http://www.m–w.com.

The term "impending", Oxford English Dictionary Online—at the web—http://www.oed.com.

The term "system", Merriam–Webster Online Dictionary—at the web—http://www.m–w.com.

Tsalikian, E., et al., "Accuracy of the GlucoWatch G2® Biographer and the Continuous Glucose Monitoring System During Hypoglycemia: Experience of the Diabetes Research in Children Network", Diabetes Care, vol. 27, No. 3, 2004, pp. 722–726.

Tse and Gough, "Time–Dependent Inactivation of Immobilized Glucose Oxidase and Catalase," Biotechnol. Bioeng. 29:705–713 (1987).

Updike et al. 1988. Laboratory Evaluation of New Reusable Blood Glucose Sensor. Diabetes Care 11:801–807.

Van den Berghe 2004. Tight blood glucose control with insulin in "real–life" intensive care. Mayo Clin Proc 79(8):977–978.

Woodward, "How Fibroblasts and Giant Encapsulate Implants: Considerations in Design of Glucose Sensor," Diabetes Care 5:278–281 (1982).

Yang, C., et al., "A Comparison of Physical Properties and Fuel Cell Performance of Nafion and Zirconium Phosphate/Nafion Composite Membranes," Journal of Membrane Science, vol. 237, 2004, pp. 145–161.

Mastrototaro et al., Sensors and Actuators B (1991) 5:139–144.

Pishko et al., "Amperometric glucose microelectrodes prepared through immobilization of glucose oxidase in redox hydrogels," Anal. Chem. (1991) 63:2268–2272.

Zhu et al., "Fabrication and characterization of glucose sensors based on a a microarray H202 electrode," Sensors and Actuators B. (1994) 9:295–300.

Armour et al., Diabetes (1990) 39:1519–1526.

Ko et al., (ed.), Chapter 15 in "Implantable Sensors for Closed Loop Prosthetic Systems" Mount Sisco, NY: Futura Publishing Company, Inc. (1985) pp. 197–210.

McKean et al., IEEE Transactions On Biomedical Engineering (1988) 35 (7):526–532.

Shults et al., IEEE Transactions On Biomedical Engineering (1994) 41(10):937–942.

Updike et al., Chapter 4 in "Biosensors in the Body: Continuous in vivo Monitoring" John Wiley & Sons Ltd. (1997) pp. 117–137.

American Heritage Dictionary, 4th ed., Houghton Mifflin Company, 2000, p. 782.

Wiley Electrical and Electronics Engineering Dictionary, John Wiley & Sons, Inc. (2004), pp. 141, 142, 548, 549.

Pickup et al., "Responses and calibration of amperometric glucose sensors implanted in the subcutaneous tissue of man," Acta Diabetol. 30:143–148 (1993).

Aussedat et al., "A User–Friendly Method for Calibrating a Subcutaneous Glucose Sensor–Based Hypoglycaeemic Alarm," Biosensors & Bioelectronics, vol. 12, No. 11, pp. 1061–1071 (1997).

Armour, et al., 1990, "Application Of Chronic Intravascular Blood Glucose Sensor In Dogs," *Diabetes*, vol. 39:p. 1519–1526.

Irish Patent Application No. 970443, filed Jun. 16, 1997.

Kaplan, 2004 "Wiley Electrical And Electronics Engineering Dictionary," John Wiley & Sons, Hoboken, New Jersey: p. 141–142, 548–549.

McKean, et al., 1998, "A Telemetry–Instrumentation System For Chronically Implanted Glucose And Oxygen Sensors," *IEE Transactions on Biomedical Engineering*, vol. 35, No. 7: p. 526–532.

Merriam–Webster's Medical Desk Dictionary, 2005, Merriam–Webster, Incorporated, Sprinfield, Massachusetts, U.S.A.: p. 843.

Merriam–Webster Unabridged Medical Dictionary, Definition: Protocol, http:unbridged.merriam–webster.comm/cgi–bin/medical!va=protocol, Dec. 21, 2005.

Schichiri, et al., 1985, "Needle–Type Glucose Sensor For Wearable Artificial Endocrine Pancreas," *Implantable Sensors for Closed–Loop Prosthetic Systems*, Chapter 15: p. 197–210.

Schichiri, et al., 1986, "Telementry Gloucose Monitoring Device With Needle–Type Glucose Sensor: A Useful Tool For Blood Glucose Monitoring In Diabetic Individuals," *Diabetes Care*, vol. 9, No. 3: p. 298–301.

Shults, et al., 1994, "A Telemetry–Instrumentation System for Monitoring Multiple Subcutaneously Implanted Glucose Sensors," *IEE Transactions On Biomedical Engineering*, vol. 14, No. 10: p. 937–942.

Thompson et al., 1986, "In Vivo Probes: Problems And Perspectives," *Clinical Biochemistry*, vol. 19: p. 255–261.

Updike, et al., 1997, "Principles Of Long–Term Fully Implanted Sensors With Emphasis On Radiotelmetric Monitoring Of Blood Glucose From Inside A Subcutaneous Foreign Body Capsule (FBC)," *Biosensors In The Body: Continuous In Vivo Monitoring*, Chapter 4: p. 117–137.

Velho, et al., 1989, "Strategies For Calibrating A Subcutaneous Glucose Sensor," *Biomed.Biochim. Acia*, vol. 28, No. 11/12: p. 957–964.

Wilson, et al., 1992, "Progress Toward The Development Of An Implantable Sensor For Glucose," *Clinical Chemistry*, vol. 38, No. 9: p. 1613–1617.

Brooks et al., "Development of an On–line Glucose Sensor for Fermentation Monitoring," Biosensors 3 (1987/88) 45–56.

Dai et al., "Hydrogel Membranes with Mesh Size Asymmetry Based on the Gradient Crosslinking of Poly(vinyl alcohol)," Journal of Membrane Science, 156 (1999) 67–79.

Diabetes Research in Children Network (DirecNet) Study Group. "Accuracy of the Gluco Watch G2 Biographer and the continuous glucose monitoring system during hypoglycemia: experience of the Diabetes Research in Children Network," Diabetes Care. 2004 Mar. 27(3):722–6.

Flentge F. et al., "An Enzyme–Reactor for Electrochemical Monitoring of Choline and Acetylcholine: Applications in High–Performance Liquid Chromatography, Brain Tissue, Microdialysis and Cerebrospinal Fluid", Analytical Biochemistry, vol. 204, No. 2, pp. 305–310, (Aug. 1, 1992).

Godsland et al., "Maximizing the Success Rate of Minimal Model Insulin Sensitivity Measurement in Humans: The Importance of Basal Glucose Levels," Clinical Science, (2001) 101, 1–9.

Graham, "Poly(ethylene Oxide) and Related Hydrogels," Hydrogels in Medicine and Pharmacy, Chapter 4, CRC Press, 1987.

Hamilton Needle Gauge Index, www.hamiltoncompany.com, undated.

Johnson et al., "In vivo evaluation of an electroenzymatic glucose sensor implanted in subcutaneous tissue," Biosensors and Bioelectronics, (1992) 7:709–714.

Kemp, "Theoretical Aspects of One–Point Calibration," Clinical Chemistry, 30/7 1163–1167 (1984).

Kerner et al., "The function of a hydrogen peroxide–detecting electroenzymatic glucose electrode is markedly impaired in hum subcutaneous tissue and plasma," (1993) Biosensors & Bioelectronics 8:473–482.

Korf, J. et al., "Monitoring of Glucose and Lactate Using Microdialysis: Applications in Neonates and Rat Brain", Developmental Neuroscience, vol. 15, No. 3–5, pp. 240–46 (1993).

Laurell, T., "A Continuous Glucose Monitoring System Based on Microdialysis", Journal of Med. Eng. & Tech., vol. 16, No. 5, pp. 187–193 (Sep./Oct. 1992).

Marko–Varga, G. et al., "Enzyme–Based Biosensor as a Selective Detection Unit in Column Liquid Chromatography", Journal of Chromatography A, vol. 660, pp. 153–167 (1994).

Mauras et al., "Lack of accuracy of continuous glucose sensors in healthy, nondiabetic children: results of the Diabetes Research in Children Network (DirecNet) accuracy study," J Pediatr. Jun. 2004; 144(6):770–5.

Pickup et al., "Implantable glucose sensors: choosing the appropriate sensing strategy," Biosensors, 1:335–346 (1987/88).

Reusch et al., "Special Topics: Organometallic Compounds," Virtual Texbook of Organic Chemistry (1999, latest revision 2004).

Sacks, ed., "Guidelines and Recommendations for Laboratory Analysis in the Diagnosis and Management of Diabetes Mellitus," (2002) in "Lad. Med. Practice Guidelines," vol. 13, pub. by Nat. Acad. Clin. Biochem.

Scheller et al., "Second Generation Biosensors," Biosens Bioelectron. 1991;6(3):245–53.

Schmidt, F.J. et al., "Calibration of a Wearable Glucose Sensor", The International Journal of Artificial Organs, vol. 15, No. 1, pp. 55–61 (1992).

Shaw et al., "In vitro testing of a simply constructed, highly stable glucose sensor suitable for implantation of diabetic patients," Biosensors & Bioelectronics, (1991) 6:401–406.

Schichiri et al., "Membrane Design for Extending the Long–Life of an Implantable Glucose Sensor.:" Diab.Nutr. Metab., 2, 309–313, 1989.

Shichiri et al., "Needle–Type Glucose Sensor for Wearable Artificial Endocrine Pancreas," Ch. 15, Implantable Sensors for Closed–Loop Prosthetic Systems, Futura Publishing, 1985. pp. 197–210.

Shichiri et al., "Telemetry Glucose Monitoring Device With Needle–Type Glucose Sensor: A Useful Tool for Blood Glucose Monitoring in Diabetic Individuals," Diabetes Care, vol. 9, No. 3, May–Jun. 1986, pp. 298–301.

Skoog & West, "Fundamentals of Analytical Chemistry," Holt, Rinehart & Winston, Inc. New York (1966), pp. 55.

Takamura et al., Drug Release from Ploy(Vinyl Alcohol) Gel Prepared by Freeze–Thaw Procedure, J Controlled Release, 20 (1992) 21–28.

Thompson et al., "In Vivo Probes: Problems and Prospectives," Clinical Biochemistry vol. 19, Oct. 1986, pp. 255–261.

von Woedtke et al., "In Situ Calibration of Implanted Electrochemical Glucose Sensors," Biomed Biochim Acta, 48 (1989) 11/12, pp. 943–952.

Yang et al., "A comparison of physical properties and fuel cell performance for Nafion and zirconium phosphate/Nafion composite membranes," Journal of Membrane Science 237 (2004) 145–161.

Abel, P. U., et al., "Biosensors for In Vivo Glucose Measurement: Can We Cross the Experimental Stage", *Biosensors and Bioelectronics, vol. 17*, 2002, pp. 1059–1070.

Abruna, H. D., et al., "Rectifying Interfaces Using Two–Layer Films of Electrochemically Polymerized Vinylpyridine and Vinylbipyridine Complexes of Ruthenium and Iron on Electrodes", *Journal of the American Chemical Society, vol. 103, No. 1*, 1981, pp. 1–5.

Albery, W. J., et al., "Amperometric Enzyme Electrodes Part II: Conducting Salts as Electrode Materials for the Oxidation of Glucose Oxidase", *Journal of ElectroAnalytical Chemistry, vol. 194*, 1985, pp. 223–235.

Albery, W. J., et al., "Amperometric Enzyme Electrodes", *Philosophical Transactions of The Royal Society of London, vol. 316*, pp. 107–119.

Alcock, S. J., et al., "Continuous Analyte Monitoring to Aid Clinical Practice", *IEEE Engineering in Medicine and Biology Magazine*, 1994, pp. 319–325.

Anderson, L. B., et al., "Thin–Layer Electrochemistry: Steady–State Methods of Studying Rate Processes", *Journal of ElectroAnalytical Chemistry, vol. 10*, 1965, pp. 295–305.

Asberg, P., et al., "Hydrogels of a Conducting Conjugated Polymer as 3–D Enzyme Electrode", *Biosensors & Bioelectronics, vol. 19*, 2003, pp. 199–207.

Atansov, P., et al., "Biosensor for Continuous Glucose Monitoring", *Biotechnology and Bioengineering, vol. 43*, 1994, pp. 262–266.

Atanasov, P., et al., "Implantation of a Refillable Glucose Monitoring–Telemetry Device", *Biosensors & Bioelectronics, vol. 12, No. 7*, 1997, pp. 669–680.

Aussedat, B., et al., "A User–Friendly Method for Calibrating a Subcutaneous Glucose Sensor–Based Hypoglycaemic Alarm", *Biosensors & Bioelectronics, vol. 12, No. 11*, 1997, pp. 1061–1071.

Baker, D. A., et al., "Dynamic Concentration Challenges for Biosensor Characterization", *Biosensors & Bioelectronics, vol. 8*, 1993, pp. 433–441.

Baker, D. et al., "Dynamic Delay and Maximal Dynamic Error in Continuous Biosensors", *Analytical Chemistry, vol. 68, No. 8*, 1996, pp. 1292–1297.

Bani Amer, M. M., "An Accurate Amperometric Glucose Sensor Based Glucometer with Eliminated Cross–Sensivity", *Journal of Medical Engineering & Technology, vol. 26, No. 5*, 2002, pp. 208–213.

Bard, A. J., et al., *Electrochemical Methods*, 1980, pp. 173–175.

Bartlett, P. N., et al., "Covalent Binding of Electron Relays to Glucose Oxidase", *Journal of the Chemical Society, Chemical Communications*, 1987, pp. 1603–1604.

Bartlett, P. N., et al., "Modification of Glucose of Oxidase by Tetrathiafulvalene", *Journal of the Chemical Society, Chemical Communications*, 1990, pp. 1135–1136.

Bartlett, P. N., et al., "Strategies for the Development of Amperometric Enzyme Electrodes", *Biosensors*, vol. 3, 1987/88, pp. 359–379.

Beach, R. D., et al., "Subminiature Implantable Potentiostat and Modified Commercial Telemetry Device for Remote Glucose Monitoring", *IEEE Transactions on Instrumentation and Measurement*, vol. 28, No. 6,, 1999, pp. 1239–1245.

Beech, W. A., "AX.25 Link Access Protocol for Amateur packet Radio", *Tucson Amateur Packet Radio Corporation*, 1998, pp. 1–133.

Bennion, N., et al., "Alternate Site Glucose Testing: A Crossover Design", *Diabetes Technology & Therapuetics*, vol. 4, No. 1, 2002, pp. 25–33.

Bindra, D. S., et al., "Design and in Vitro Studies of a Needle–Type Glucose Sensor for Subcutaneous Monitoring", *Analytical Chemistry*, vol. 63, No. 17, pp. 1692–1696.

Bindra, D.S., et al., "Pulsed Amperometric Detection of Glucose in Biological Fluids at a Surface–Modified Gold Electrode", *Analytical Chemistry*, vol. 61, No. 22, 1989, pp. 2566–2570.

Bisenberger, M., et al., "A Triple–Step Potential Waveform at Enzyme Multisensors with Thick–Film Gold Electrodes for Detection of Glucose and Sucrose", *Sensors and Actuators B*, vol. 28, 1995, pp. 181–189.

Bland, J. M., et al., "A Note on the Use of the Intraclass Correlation Coefficient in the Evaluation of Agreement Between Two Methods of Measurement", *Computers in Biology and Medicine*, vol. 20, No. 5, 1990, pp. 337–340.

Bland, J. M., et al., "Statistical Methods fo Assessing Agreement Between Two Methods of Clinical Measurement", *The Lancet*, 1986, pp. 307–310.

Blank, T. B. et al., "Clinical Results From a Non–Invasive Blood Glucose Monitor", *Optical Diagnostics and Sensing of Biological Fluids and Glucose and Cholesterol Monitoring II, Proceedings of SPIE*, vol. 4624, 2002, pp. 1–10.

Bobbioni–Harsch, E., et al., "Lifespan of Subcutaneous Glucose Sensors and Their Performances During Dynamic Glycaemia Changes in Rats", *Journal of Biomedical Engineering*, vol. 15, 1993, pp. 457–463.

Bode, B. W., "Clinical Utility of the Continuous Glucose Monitoring System", *Diabetes Technology & Therapeutics*, vol. 2, Sup. 1, 2000, pp. S35–S48.

Bode, B. W., et al., "Continuous Glucose Monitoring Used to Adjust Diabetes Therapy Improves Glycosylated Hemoglobin: A Pilot Study", *Diabetes Research and Clinical Practice*, vol. 46, 1999, pp. 183–190.

Bolinder, J., et al., "Microdialysis Measurement of the Absolute Glucose Concentration in Subcutaneous Adipose Tissue Allowing Glucose Monitoring in Diabetic Patients", *Diabetologia*, vol. 35, 1992, pp. 1177–1180.

Boedeker Plastics, Inc., "Polyethylene Specifications", *Web Page of Boedeker.com*, 2007, pp. 1–3.

Bolinder, J., et al., "Microdialysis Measurement of the Absolute Glucoe Concentration in Subcutaneous Adipose Tissue Allowing Glucose Monitoring in Diabetic Patients", *Diabetologia*, vol. 35, 1992, pp. 1177–1180.

Bolinder, J., et al., "Self–Monitoring of Blood Glucose in Type I Diabetic Patients: Comparison with Continuous Microdialysis Measurements of Glucose in Subcutaneous Adipose Tissue During Ordinary Life Conditions", *Diabetes Care*, vol. 20, No. 1, 1997, pp. 64–70.

Bott, A. W., "A Comparison of Cyclic Voltammetry and Cyclic Staircase Voltammetry", *Current Separations*, vol. 16, No. 1, 1997, pp. 23–26.

Bott, A. W., "Electrochemical Methods for the Determination of Glucose", *Current Separations*, vol. 17, No. 1, 1998, pp. 25–31.

Bowman, L., et al., "The Packaging of Implantable Integrated Sensors", *IEEE Transactions on Biomedical Engineering*, vol. 33, No. 2, 1986, pp. 248–255.

Brandt, J., et al., "Covalent Attachment of Proteins to Polysaccharide Carriers by Means of Benzoquinone", *Biochimica et Biophysica Acta*, vol. 386, 1975, pp. 196–202.

Brauker, J. et al., "Sustained Expression of High Levels of Human Factor IX from Human Cells Implanted Within an Immunoisolation Device into Athymic Rodents", *Human Gene Therapy*, vol. 9, No. 6, 1998, pp. 879–888.

Bremer, T. M., et al., "Benchmark Data from the Literature for Evaluation of New Glucose Sensing Technologies", *Diabetes Technology & Therapeutics*, vol. 3, No. 3, 2001, pp. 409–418.

Bremer, T. et al., "Is Blood Glucose Predictable from Previous Values?", *Diabetes*, vol. 48, 1999, pp. 445–451.

Brownlee, M., et al., "A Glucose–Controlled Insulin–Delivery System: Semisynthetic Insulin Bound to Lectin", *Science*, vol. 206, 1979, 1190–1191.

Cai, Q., et al., "A Wireless, Remove Query Glucose Biosensor Based on a pH–Sensitive Polymer", *Analytical Chemistry*, vol. 76, No. 14, 2004, pp. 4038–4043.

Cass, A. E., et al., "Ferricinum Ion As An Electron Acceptor for Oxdio–Reductases", *Journal of ElectroAnalytical Chemistry*, vol. 190, 1985, pp. 117–127.

Cass, A. E., et al., "Ferrocene–Medicated Enzyme Electrode for Amperometric Determination of Glucose", *Analytical Chemistry*, vol. 56, No. 4, 1984, 667–671.

Castner, J. F., et al., "Mass Transport and Reaction Kinetic Parameters Determined Electrochemically for Immobilized Glucose Oxidase", *Biochemistry*, vol. 23 No. 10, 1984, 2203–2210.

Chen, J. C., et al., "A Comparison of MAC Protocols for Wireless Local Networks Based on battery Power Consumption", *IEEE*, 1998, pp. 150–157.

Chen, T., et al., "Defining the Period of Recovery of the Glucose Concentration After Its Local Perturbation by the Implantation of a Miniature Sensor", *Clinical Chemistry and Laboratory Medicine*, vol. 40, No. 8, 2002, pp. 486–489.

Chia, C. W., et al., "Glucose Sensors: Toward Closed Loop Insulin Delivery", *Endocrinology and Metabolism Clinics of North America*, vol. 33, 2004, pp. 175–195.

Choleau, C., et al., "Calibration of a Subcutaneous Amperometric Glucose Sensor Implanted for 7 Days in Diabetic Patients Part 2: Superiority of the One–Point Calibration Method", *Biosensors and Bioelectronics*, vol. 17, 2002, pp. 647–654.

Choleau, C., et al., "Calibration of a Subcutaneous Amperometric Glucose Sensor Part 1: Effect of Measurement Uncertainties on the Determination of Sensor Sensitivity and Background Current", *Biosensors and Bioelectroncis*, vol. 17, 2002, pp. 641–646.

Claremont, D. J., et al., "Biosensors for Continuous In Vivo Glucose Monitoring" *Proceedings of the Annual International Conference of the IEEE Engineering in Medicine and Biology Society, vol. 10,* 1988.

Clark Jr., L. C., et al., "Diffrential Anodic Enzyme Polarography for the Measurement of Glucose", *Oxygen Transport to Tissue: Instrumentation, Methods, and Physiology,* 1973, pp. 127–133.

Clark Jr., L. C., et al., "Electrode Systems for Continuous Monitoring in Cardiovascular Surgery", *Annals New York Academy of Sciences,* 1962, pp. 29–45.

Clark Jr., L. C., et al., "Long–term Stability of Electroenzymatic Glucose Sensors Implanted in Mice", *American Society of Artificial Internal Organs Transactions, vol. XXXIV,* 1988, pp. 259–265.

Clarke, W. L., et al., "Evaluating Clinical Accuracy of Systems for Self–Monitoring of Blood Glucose", *Diabetes Care, vol. 10, No. 5,* 1987, pp. 622–628.

Complaint, "*Abbott Diabetes Care, Inc. v. Dexcom, Inc.*", filed Aug. 11, 2005.

Complaint, Amended, "*Abbott Diabetes Care, Inc. v. Dexcom, Inc.*", filed Jun. 27, 2006.

Cox, D. J., et al., "Accuracy of Perceiving Blood Glucose in IDDM", *Diabetes Care, vol. 8, No. 6,* 1985, pp. 529–536.

Csoregi, E., et al., "Amperometric Microbiosensors for Detection of Hydrogen Peroxidase and Glucose Based on Peroxide–Modified Carbon Fibers", *Electroanalysis, vol. 6,* 1994, pp. 925–933.

Csoregi, E., et al., "Design and Optimization of a Selective Subcutaneously Implantable Glucose Electrode Based on 'Wired' Glucose Oxidase", *Analytical Chemistry, vol. 67, No. 7,* 1995, pp. 1240–1244.

Csoregi, E., et al., "Design Characterization, and One–Point in Vivo Calibration of a Subcutaneously Implanted Glucose Electrode", *Analytical Chemistry, vol. 66 No. 19,* 1994, pp. 3131–3138.

Csoregi, E., et al., "On–Line Glucose Monitoring by Using Microdialysis Sampling and Amperometric Detection Based on 'Wired' Glucose Oxidase in Carbon Paste", *Mikrochimica Acta, vol. 121,* 1995, pp. 31–40.

D'Arrigo, G., et al., "Porous–Si Based Bio Reactors for Glucose Monitoring and Drugs Production", *Proceedings of SPIE; Microfluids, BioMEMS, and Medical Microsystems, vol. 4982,* 2003, pp. 178–184.

Davis, G., "Electrochemical Techniques for the Development of Amperometric Biosensors", *Biosensors, vol. 1,* 1985, pp. 161–178.

Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", *The Journal of Physical Chemistry, vol. 91, No. 6,* 1987, pp. 1285–1289.

Degani, Y., et al., "Direct Electrical Communication Between Chemically Modified Enzymes and Metal Electrodes. 2. Methods for Bonding Electron–Transfer Relays to Glucose Oxidase and D–Amino–Acid Oxidase", *Journal of the American Chemical Society, vol. 110, No. 8,* 1988, pp. 2615–2620.

Degani Y. et al., "Electrical Communication Between Redox Centers of Glucose Oxidase and Electrodes via Electrostatically and Covalently Bound Redox Polymers", *Journal of the American Chemical Society, vol. 111,* 1989, pp. 2357–2358.

Denisevich, P., et al., "Unidirectional Current Flow and Charge State Trapping at Redox Polymer Interfaces on Bilayer Electrodes: Principles, Experimental Demonstration, and Theory", *Journal of the American Chemical Society, vol. 103,* 1981, pp. 4727–4737.

Dicks, J. M., et al., "Ferrocene Modified Polypyrrole with Immobilised Glucose Oxidase and its Application in Amperometric Glucose Microbiosensors", *Annales de Biologie Clinique, vol. 47,* 1989, pp. 607–619.

Dixon, B. M., et al., "Characterization In Vitro and In Vivo of the Oxygen Dependence of an Enzyme/Polymer Biosensors for Monitoring Brain Glucose", *Journal of Neuroscience Methods, vol. 119,* 2002, pp. 135–142.

Ellis, C. D., et al., "Selectivity and Directed Charge Transfer through an Electroactive Metallopolymer Film", *Journal of the American Chemical Society, vol. 103, No. 25,* 1981, pp. 7480–7483.

EL–SA'AD, L., et al., "Moisture Absorption by Epoxy Resins: The Reverse Thermal Effect", *Journal of Materials Science, vol. 25, No. 8,* 1990, pp. 3577–3582.

Engstrom, R. C., "Electrochemical Pretreatment of Glassy Carbon Electrodes", *Analytical Chemistry, vol. 54, No. 13,* 1982, pp. 2310–2314.

Engstrom, R. C., et al., "Characterization of Electrochemically Pretreated Glassy Carbon Electrodes", *Analytical Chemistry, vol. 56, No. 2,* 1984, pp. 136–141.

Ernst, H., et al., "Reliable Glucose Monitoring Through the Use of Microsystem Technology", *Analytical and Bioanalytical Chemistry, vol. 373,* 2002, pp. 758–761.

Fare, T. L., et al., "Functional Characterization of a Conducting Polymer–Based Immunoassay System", *Biosensors & Bioelectronics, vol. 13, No. 3–4,* 1998, pp. 459–470.

Feldman, B., et al., "A Continuous Glucose Sensor Based on Wired Enzyme™ Technology—Results from a 3–Day Trial in Patients with Type 1 Diabetes", *Diabetes Techonology & Therapeutics, vol. 5, No. 5,* 2003, pp. 769–779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet.*

Feldman, B., et al., "Electron Transfer Kinetics at Redox Polymer/Solution Interfaces Using Microelectrodes and Twin Electrode Thin Layer Cells", *Journal of ElectroAnalytical Chemistry, vol. 194,* 1985, pp. 63–81.

Fischer, H., et al., "Intramolecular Electron Transfer Medicated by 4,4'–Bypyridine and Related Bridging Groups", *Journal of the American Chemical Society, vol. 98, No. 18,* 1976, pp. 5512–5517.

Foulds, N. C., et al., "Enzyme Entrapment in Electrically Conducting Polymers: Immobilisation of Glucose Oxidase in Polypyrrole and its Application in Amperometric Glucose Sensors", *Journal of the Chemical Society, Faraday Transactions, 1, vol. 82,* 1986, pp. 1259–1264.

Foulds, N. C., et al., "Immobilization of Glucose Oxidase in Ferrocene–Modified Pyrrole Polymers", *Analytical Chemistry, vol. 60, No. 22,* 1988, pp. 2473–2478.

Frew, J. E., et al., "Electron–Transfer Biosensors", *Philosophical Transactions of The Royal Society of London, vol. 316,* 1987, pp. 95–106.

Frohnauer, M. K., et al., "Graphical Human Insulin Time–Activity Profiles Using Standardized Difinitions", *Diabetes Technology & Therapeutics, vol. 3, No. 3,* 2001, pp. 419–429.

Frost, M. C., et al., "Implantable Chemical Sensors for Real–Time Clinical Monitoring: Progress and Challenges", *Current Opinion in Chemical Biology, vol. 6*, 2002, pp. 633–641.

Garg, S. K., et al., "Correlation of Fingerstick Blood Glucose Measurements with Gluco Watch Biographer Glucose Results in Young Subjects with Type 1 Diabetes", *Diabetes Care, vol. 22, No. 10*, 1999, pp. 1708–1714.

Garg, S. K., et al., "Improved Glucose Excursions Using an Implantable Real–Time Continuous Glucose Sensor in Adults with Type 1 Diabetes", *Diabetes Care, vol. 27, No. 3*, 2004, pp. 734–738.

Geller, R. L., et al., "Use of an Immunoisolation Device for Cell Transplantation and Tumor Immunotheraphy", *Annals of the New York Academy of Sciences, vol. 831*, 1997, pp. 438–451.

Gerritsen, M., "Problems Associated with Subcutaneously Implanted Glucose Sensors", *Diabetes Care, vol. 23, No. 2*, 2000, pp. 143–145.

Gerritsen, M., et al., "Influence of Inflammatory Cells and Serum on the Performance of Implantable Glucose Sensors", *Journal of Biomedical materials Research, vol. 54*, 2001, pp. 69–75.

Gerritsen, M., "Performance of Subcutaneuously Implanted glucose Sensors for Continuous Monitoring", *The Netherlands Journal of Medicine, vol. 54*, 1999, pp. 167–179.

Gilligan, B. J., et al., "Evaluation of a Subcutaneous Glucose Sensor Out to 3 Months in a Dog Model", *Diabetes Care, vol. 17, No. 8*, 1994, pp. 882–887.

Gilligan, B. J., et al., "Feasibility of Continuous Long–Term Glucose Monitoring from a Subcutaneous Glucose Sensor in Humans", *Diabetes Technology & Therapeutics, vol. 6, No. 3*, 2004, pp. 378–386.

Gordon, L., et al., "Selective Detection in Flow Analysis Based on the Combination of Immobilized Enzymes and Chemically Modified Electrodes", *Analytica Chimica Acta, vol. 250*, 1991, pp. 203–248.

Gough, D. A., et al., "Immobilized Glucose Oxidase in Implantable Glucose Sensor Technology", Diabetes Technology & Therapeutics, vol. 2, No. 3, 2000, pp. 377–380.

Grant, R., et al., *Grant & Hackh's Chemical Dictionary*, 1987, pp. 88, 89, 389, 390, 398.

Gregg, B. A., "Cross–Linked Redox Gels Containing Glucose Oxidase for Amperometric Biosensor Applications", *Analytical Chemistry, vol. 62, No. 3*, 1990, pp. 258–263.

Gregg, B. A., et al., "Redox Polymer Films Containing Enzymes. 1. A Redox–Conducting Epoxy Cement: Synthesis, Characterization, and Electrocatalytic Oxidation of Hydroquinone", *Journal of Physical Chemistry, vol. 95, No. 15*, 1991, 5970–5975.

Gross , T. M., et al., "Efficacy and Reliability of the Continuous Glucose Monitoring System", *Diabetes Technology & Therapeutics, vol. 2, Sup. 1*, 2000, pp. S19–S29.

Gross, T. M., et al., "Performance Evaluation of the MiniMed® Continuous Glucose Monitoring System During Patient Home Use", *Diabetes Technology & Therapeutics, vol. 2, No. 1*, 2000, pp. 49–56.

Hale, P. D., et al., "A New Class of Amperometric Biosensor Incorporating a Polymeric Electron–Transfer Mediator", *Journal of the American Chemical Society, vol. 111, No. 9*, 1989, pp. 3482–3484.

Hall, S. B., et al., "Electrochemical Oxidation of Hydrogen Peroxide at Platinum Electrodes: Part I: An Absorption–Controlled Mechanism", *Electrochimica Acta, vol. 43, No. 5–6*, 1998, pp. 579–588.

Hall, S. B., et al., "Electrochemical Oxidation of Hydrogen Peroxide at Platinum Electrodes: Part II: Effect of Potential", *Electrochimica Acta, vol. 43, No. 14–15*, 1998, pp. 2015–2024.

Hall, S. B., et al., "Electrochimical Oxidation of Hydrogen Peroxide at Platinum Electrodes: Part III: Effect of Temperature"*Electrochimica Acta, vol. 44*, 1999, pp. 2455–2462.

Hall, S. B., "Electrochemical Oxidation of Hydrogen Peroxide at Platinum Electrodes: Part IV: Phosphate Buffer Dependence", *Electrochimica Acta, vol. 44*, 1999, pp. 4573–4582.

Hall, S. B., et al., "Electrochemical Oxidation of Hydrogen Peroxide at Platinum Electrodes: Part V: Inhibition By Chloride", *Electrochimica Acta 45*, 2000, pp. 3573–3579.

Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry, vol. 60, No. 19*, 1988, pp. 2002–2007.

Hawkridge, F. M., et al., "Indirect Coulometric Titration of Biological Electron Transport Components", *Analytical Chemistry, vol. 45, No. 7*, 1973, pp. 1021–1027.

Heise, T., et al., "Hypoglycemia Warning Signal and Glucose Sensors: Requirements and Concepts", *Diabetes Technology & Therapeutics, vol. 5, No. 4*, 2003, pp. 563–571.

Heller, A., "Electrical Connection Enzyme Redox Centers to Electrodes", *Journal of Physical Chemistry, vol. 96, No. 9*, 1990, pp. 3579–3587.

Heller, A., "Electrical Wiring of Redox Enzymes", *Accounts of Chemical Research vol. 23, No. 5*, 1990, 128–134.

Heller, A., "Implanted Electrochemical Glucose Sensors for the Management of Diabetes", *Annual Review of Biomedical Engineering, vol. 1*, 1999, pp. 153–175.

Heller, A., "Plugging Metal Connectors into Enzymes", *Nature Biotechnology, vol. 21, No. 6*, 2003, pp. 631–632.

Heller, A., et al., "Amperometric Biosensors Based on Three–Dimensional Hydrogel–Forming Epoxy Networks", *Sensors and Actuators B, vol. 13–14*, 1993, pp. 180–183.

Hitchman, M. L., "Measurement of Dissolved Oxygen: Chapter 3: Principles of Voltammetry", *Chemical Analysis, vol. 49*, 1978, pp. 34–123.

Hrapovic, S., et al., "Picoamperometric Detection of Glucose at Ultrasmall Platinum–Based Biosensors: Preparation and Characterization", *Analytical Chemistry, vol. 75, No. 14*, 2003, pp. 3308–3315.

Huang, C. J., et al., "Electrochemical Generation of Oxygen", *Electrochemistry Research laboratory*, 1972, pp. 1–115.

Ianniello, R. M., et al., "Differential Pulse Voltammetric Study of Direct Electron Tranfer in Glucose Oxidase Chemically Modified Graphite Electrodes", *Analytical Chemistry, vol. 54, No. 7*, 1982, pp. 1098–1101.

Ianniello, R. M., et al., "Immobilized Enzyme Chemically Modified Electrode as an Amperometric Sensor", *Analytical Chemistry, vol. 53, No. 13*, 1981, pp. 2090–2095.

Ikeda, T., et al., "Glucose Oxidase–Immobilized Benzoquinone–Carbon Paste Electrode as a Glucose Sensor", *Agricultural and Biological Chemistry, vol. 49, No. 2*, 1985, pp. 541–543.

Ikeda, T., et al., "Kinetics of Outer–Sphere Electron Transfers Between Metal Complexes in Solutions and Polymeric Films on Modified Electrodes", *Journal of the American Chemical Society, vol. 103, No. 25,* 1981, pp. 7422–7425.

Ishikawa, M., et al., "Initial Evaluation of a 290–µm Diameter Subcutaneous Glucose Sensor: Glucose Monitoring with a Biocompatible, Flexible–Wire, Enzyme–Based Amperometric Microsensor in Diabetic and Nondiabetic Humans", *Journal of Diabetes and Its Complications, vol. 12,* 1998, pp. 295–301.

Jablecki, M., et al., "Simulations of the Frequency Response of Implantable of Glucose Sensors", *Analytical Chemistry, vol. 72, No. 8,* 2000, pp. 1853–1859.

Jaremko, J., et al., "Adavances Toward the Implantable Artificial Pancreas for Treatment of Diabetes", *Diabetes Care, vol. 21, No. 3,* 1998, pp. 444–450.

Jensen, M. B., et al., "Fast Wave Forms for Pulsed Electrochemical Detection of Glucose by Incorporation of Reductive Desorption of Oxidation Products", *Analytical Chemistry, vol. 69, No. 9,* 1997, pp. 1176–1781.

Jeutter, D. C., "A Transcutaneous Implanted Battery Recharging and Biotelemeter Power Switching System", *IEEE Transactions on Biomedical Engineering, vol. 29, No. 5,* 1982, pp. 314–321.

Johnson, J. M., et al., "Potential–Dependent Enzymatic Activity in an Enzyme Thin–Layer Cell", *Analytical Chemistry, vol. 54, No. 8,* 1982, pp. 1377–1373.

Johnson, K. W., "Reproducible Electrodeposition of Biomolecules for the Fabrication of Miniature Electroenzymatic Biosensors", *Sensors and Actuators B, vol. 5,* 1991, pp. 85–89.

Johnson, P. C., "Peripheral Circulation", *John Wiley & Sons,* 1978, pp. 198.

Jonsson, G., et al., "An Amperometric Glucose Sensor Made by Modification of a Graphite Electrode Surface With Immobilized Glucose Oxidase and Adsorbed Mediator", *Biosensors, vol. 1,* 1985, pp. 355–368.

Josowicz, M., et al., "Electrochemical Pretreatment of Thin Film Platinum Electrodes", *Journal of the Electrochemical Society, vol. 135, No. 1,* 1988, pp. 112–115.

Jovanovic, L., "The Role of Continuous Glucose Monitoring in Gestational Diabetes Mellitus", *Diabetes Technology & Therapeutics, vol. 2, Sup. 1,* 2000, pp. S67–S71.

Jungheim, K., et al., "How Rapid Does Glucose Concentration Change in Daily Life of Patients with Type 1 Diabetes?", pp. 250.

Jungheim, K., et al., "Risky Delay of Hypoglycemia Detection by Glucose Monitoring at the Arm", *Diabetes Care, vol. 24, No. 7,* 2001, pp. 1303–1304.

Kang, S. K., et al., "In Vitro and Short–Term In Vivo Characteristics of a Kel–F Thin Film Modified Glucose Sensor", *Analytical Sciences, vol. 19,* 2003, pp. 1481–1486.

Kaplan, S. M., "Wiley Electrical and Electronics Engineering Dictionary", *IEEE Press,* 2004, pp. 141, 142, 548, 549.

Kargol, M., et al., "Studies on the Structural Properties of Porous Membranes: Measurement of Linear Dimensions of Solutes", *Biophysical Chemistry, vol. 91,* 2001, pp. 263–271.

Katakis, I., et al., "Electrostatic Control of the Electron Transfer Enabling Binding of Recombinant Glucose Oxidase and Redox Polyelectrolytes", *Journal of the American Chemical Society, vol. 116, No. 8,* 1994, pp. 3617–3618.

Katakis, I., et al., "L–α–Glycerophosphate and L–Lactate Electrodes Based on the Electrochemical 'Wiring' of Oxidases", *Analytical Chemistry, vol. 64, No. 9,* 1992, pp. 1008–1013.

Kaufman, F. R., "Role of the Continuous Glucose Monitoring System in Pediatric Patients", *Diabetes Technology & Therapeutics, vol. 2, Sup. 1,* 2000, pp. S49–S52.

Kenausis, G., et al., "'Wiring' of Glucose Oxidase and Lactate Oxidase Within a Hydrogel Made with Poly(vinyl pyridine) complexed with $[Os(4,4'-dimethoxy-2,2'-bipyridine)_2 Cl]^{+/2+}$"*Journal of the Chemical Society, Faraday Transactions, vol. 92, No. 20,* 1996, pp. 4131–4136.

Kerner, W., "Implantable Glucose Sensors: Present Status and Future Developments", *Experimental and Clinical Endocrinology & Diabetes, vol. 109, Supplement 2,* 2001, pp. S341–S346.

Koschinsky, T., et al., "New Approach to Technical and Clinical Evaluation of Devices for Self–Monitoring of Blood Glucose", *Diabetes Care, vol. 11, No. 9,* 1988, pp. 619–629.

Koschinsky, T., et al., "Sensors for Glucose Monitoring: Technical and Clinical Aspects" *Diabetes Metabolism Research and Reviews, vol. 17,* 2001, pp. 113–123.

Koudelka, M., et al., "In–Vivo Behaviour of Hypodermically Implanted Microfabricated Glucose Sensors", *Biosensors & Bioelectronics, vol. 6,* 1991, pp. 31–36.

Kovatchev, B. P., et al., "Evaluating the Accuracy of Continuous Glucose–Monitoring Sensors", *Diabetes Care, vol. 27, No. 8,* 2004, pp. 1922–1928.

Kraver, K. L., et al., "A Mixed–Signal Sensor Interface Microinstrument", *Sensors and Actuators A, vol. 91,* 2001, pp. 266–277.

Krouwer, J. S., "Setting Performance Goals and Evaluating Total Analytical error for Diganostic Assays", *Clinical Chemistry, vol. 48, No. 6,* 2002, pp. 919–927.

Kruger, D., et al., "Psychological Motivation and Patient Education: A Role for Continuous Glucose Monitoring", *Diabetes Technology & Therapeutics, vol. 2, Sup. 1,* 2000, pp. S93–S97.

Kulys, J., et al., "Mediatorless Peroxidase Electrode and Preparation of Bienzyme Sensors", *Bioelectrochemistry and Bioenergetics, vol. 24,* 1990, pp. 305–311.

Kurnik, R. T.,et al., "Application of the Mixtures of Experts Algorithm for Signal Processing in a Noninvasive Glucose Monitoring System" *Sensors and Actuators B, vol. 60,* 1990, pp. 19–26.

Lacourse, W. R., et al., "Optimization of Waveforms for Pulsed Amperometric Detection of Carbohydrates Based on Pulsed Voltammetry", *Analytical Chemistry, vol. 65, No. 1,* 1993, pp. 50–55.

Lager, W., et al., "Implantable Electrocatalytic Glucose Sensor", *Hormone Metabolic Research, vol. 26,* 1994, pp. 526–530.

Lee, E., et al., "Effects of Pore Size, Void Volume, and Pore Connectivity on Tissue Responses to Porous Silicone Implants", *Transactions on the Twenty–Fifth Annual Meeting of the Society for Biomaterials, vol. 22,* 1999, pp. 171.

Lerner, H., et al., "An Implantable Electrochemical Glucose Sensor", *Annals of the New York Academy of Sciences, vol. 428,* 1984, pp. 263–278.

Leypoldt, J. K., et al., "Model of a Two–Substrate Enzyme Electrode for Glucose", *Analytical Chemistry, vol. 56, No. 14,* 1984, pp. 2896–2904.

Lindner, E., et al., "Flexible (Kapton–Based) Microsensor Arrays of High Stability for Cardiovascular Applications", *Journal of the Chemical Society, Faraday Transactions, vol. 89, No. 2,* 1993, pp. 361–367.

Liu, W., et al., "A Neuro–Stimulus Chip with Telemetry Unit for Retinal Prosthetic Device", *IEEE Journal of Solid–State Circuits, vol. 35, No. 10,* 2000, pp. 1487–1497.

Lortz, J., et al., "What is Bluetooth? We Explain The Newest Short–Range Connectivity Technology", *Smart Computing Learning Series, Wireless Computing, vol. 8, Issue 5,* 2002, pp. 72–74.

Luong, J. H. T., et al., "Solubilization of Multiwall Carbon Nanotubes by 3–Aminopropyltriethoxysilane Towards the Fabrication of Electrochemical Biosensors with Promoted Electron Transfer", *Electroanalysis, vol, 16, No. 1–2,* 2004, pp. 132–139.

Lynch, S. M., et al., "Estimation–Based Model Predictive Control of Blood Glucose in Type 1 Diabetics: A Simulation Study", *Proceedings of the IEEE 27th Annual Northeast Bioengineering Conference,* 2001, pp. 79–80.

Lynn, P. A., "Recursive Digital Filters for Biological Signals", *Medical and Biological Engineering, vol. 9,* 1971, pp. 37–43.

Maidan, R., et al., "Elimination of Electrooxidizable Interferant–Produced Currents in Amperometric Biosensors", *Analytical Chemistry, vol. 64, No. 23,* 1992, pp. 2889–2896.

Makale, M. T., et al., "Tissue Window Chamber System for Validation of Implanted Oxygen Sensors", *American Journal of Physiology: Heart and Ciculatory Physiology, vol. 284,* 2003, pp. H2288–H2294.

Malin, S. F., et al., "Noninvasive Prediction of Glucose by Near–Infrared Diffuse Reflectance Spectoscopy", *Clinical Chemistry, vol. 45, No. 9,* 1999, pp. 1651–1658.

Mancy, K. H., et al., "A Galvanic Cell Oxygen Analyzer", *Journal of Electroanalytical Chemistry, vol. 4,* 1962, pp. 65–92.

Maran, A., et al., "Continuous Glucose Monitoring in Diabetic Patients", *Diabetes Care, vol. 25, No. 2,* 2002, pp. 347–352.

March, W. F., "Dealing with the Delay", *Diabetes Technology & Therapeutics, vol. 4, No. 1,* 2002, pp. 49–50.

Martin, R. F., "General Deming Regression for Estimating Systematic Bias and Its Confidence Interval in Method–Comparison Studies", *Clinical Chemistry, vol. 46, No. 1,* 2000, pp. 100–104.

Mastrototaro, J. J., "The MiniMed COntinuous Glucose Monitoring System", *Diabetes Technology & Therapeutics, vol. 2, Sup. 1,* 2000, pp. S13–S18.

Mastrototaro, J. J., et al., "An Electroenzymatic Glucose Sensor Fabricated on a Flexible Substrate", *Sensors and Actuators B, vol. 5,* 1991, pp. 139–144.

Mastrototaro, J. J., et al., "Reproducibility of the Continuous Glucose Monitoring System Matches Previous Reports and the Intended Use of the Product" and "Response to Mastrototaro and Gross", *Diabetes Care, vol. 26, No. 1,* 2003, pp. 256–257.

McCartney, L. J., et al., "Near–Infrared Fluorescence Lifetime Assay for Serum Glucose Based on Allophycocyanin–Labeled Concanavalin A", *Analytical Biochemistry, vol. 292,* 2001, pp. 216–221.

McGarraugh, G., et al., "Glucose Measurements Using Blood Extracted from the Forearm and the Finger", *TheraSense, Inc.,* 16 pages.

McGarraugh, G., et al., "Physiological Influences on Off–Finger Glucose Testing", *Diabetes Technology & Therapeutics, vol. 3, No. 3,* 2001, pp. 367–376.

McGrath, M. J., et al., "The Use of Differential Measurements with a Glucose Biosensor for Interference Compensation During Glucose Determinations by Flow Injection Analysis", *Biosensors & Bioelectronics, vol. 10,* 1995, pp. 937–943.

McNeil, C. J., et al., "Thermostable Reduced Nicotinamide Adenine Dinucletide Oxidase: Application to Amperometric Enzyme Assay", *Analytical Chemistry, vol. 61, No. 1,* 1989, pp. 25–29.

Memoli, A., et al., "A Comparison Between Different Immobilized Glucoseoxidase–Based Electrodes", *Journal of Pharmaceutical and Biomedical Analysis, vol. 29,* 2002, pp. 1045–1052.

Metzger, M., et al., "Reproducibility of Glucose Measurements Using the Glucose Sensor", *Diabetes Care, vol. 25, No. 6,* 2002, pp. 1185–1191.

Miller, K. M., et al., "Generation of ILI–like Activity in Response to Biomedical Polymer Implants: A Comparison of In Vitro and In Vivo Models", *Journal of Biomedical Materials Research, vol. 23,* 1989, pp. 1007–1026.

Miller, K. M., et al., "Human Monocyte/Macrophage Activation and Interleukin 1 Generation by Biomedical Polymers", *Journal of Biomedical Materials Research, vol. 22,* 1988, pp. 713–731.

Miller, K. M., et al., "In Vitro Stimulation of Fibroblast Activity by Factors Generated from Human Monocytes Activated by Biomedical Polymers", *Journal of Biomedical Materials Research, vol. 23,* 1989, pp. 911–930.

Miyawaki, O., et al., "Electrochemical and Glucose Oxidase Coenzyme Activity of Flavin Adenin Dinucleotide Covalently Attached to Glassy Carbon at the Adenine Amino Group", *Biochimica et Biophysica Acta, vol. 838,* 1985, pp. 60–68.

Moatti–Sirat, D. et al., et al., "Evaluating In Vitro and In Vivo the Interference of Ascorbate and Acetaminophen on Glucose Detection by a Needle–Type Glucose Sensor", *Biosensors & Bioelectronics, vol. 7,* 1992, pp. 345–352.

Moatti–Sirat, D., et al., "Reduction of Acetaminophen Interference in Glucose Sensors by a Composite Nafion Membrane: Demonstration in Rats and Man", *Diabetologia, vol. 37,* 1994, pp. 610–616.

Moatti–Sirat, D. et al., "Towards Continuous Glucose Monitoring: In Vivo Evaluation of a Miniaturized Glucose Sensor Implanted for Several Days in Rat Subcutaneous Tissue", *Diabetologia, vol. 35,* 1992, pp. 224–330.

Monsod, T. P., et al., "Do Sensor Glucose Levels Accurately Predict Plasma Glucose Concentrations During Hypoglycemia and Hyperinsulinemia?" *Diabetes Care, vol. 25, No. 5,* 2002, pp. 889–893.

Moussy, F., et al., "A Miniaturized Nafion–Based Glucose Sensor: In Vitro and In Vivo Evaluation in Dogs", *The International Journal of Artificial Organs, vol. 17, No. 2,* 1994, pp. 88–94.

Mowery, K. A., et al., "Preparation and Characterization of Hydrophobic Polymeric Films that are Thromboresistant via Nitric Oxide Release", *Biomaterials, vol. 21,* 2000, pp. 9–21.

Nagy, G., et al., "A New Type of Enzyme Electrode: The Ascorbic Acid Eliminator Elecrode", *Life Sciences, vol. 31, No. 23,* 1982, pp. 2611–2616.

Nakamura, S., et al., "Effect of Periodate Oxidation on the Structure and Properties of Glucose Oxidase", *Biochimica et Biophysica Acta.*, vol. 445, 1976, pp. 294–308.

Nam, Y.S., et al., "A Novel Fabrication Method of Macroporous Biodegradable Polymer Scaffolds Using Gas Foaming Salt as a Porogen Additive", *Journal of Biomedical Materials Research*, vol. 53, 2000, pp. 1–7.

Nappholz, T. A., "Programmers for Implants: A Need for Radical Change", *18th Annual International Conference of the IEEE Engineering in Medicine and Biology Society*, Amsterdam, 1996, pp. 1274–1275.

Narasimham, K., et al., "p–Benzoquinone Activation of Metal Oxide Electrodes for Attachment of Enzymes", *Enzyme and Microbial Technology*, vol. 7, 1985, pp. 283–286.

Neuburger, G. G., et al., "Pulsed Amperometric Detection of Carbohydrates at Gold Electrodes with a Two–Step Potential Waveform", *Analytical Chemistry*, vol. 59, No. 1, 1987, pp. 150–154.

Ohara, T. J., "Osmium Bipyridyl Redox Polymers Used in Enzyme Electrodes", *Platinum Metals Review*, vol. 39, No. 2, 1995, pp. 54–62.

Ohara, T. J., et al., "'Wired' Enzyme Electrodes for Amperometric Determination", *Platinum Metals Review*, vol. 39, No. 2, 1995, pp. 54–62.

Ohara, T. J., et al., "Glucose Electrodes Based on Cross–Linked [Os(bpy)$_2$Cl]$^{30/20+}$Complexed Poly(1–Vinylimidazole) Films", *Analytical Chemistry*, vol. 65, No. 23, 1993, pp. 3512–3517.

Okuda, J., et al., "Mutarotase Effect on Micro Determinations of D–Glucose and Its Anomers with β–D–Glucose Oxidase", *Analytical Biochemistry*, vol. 43, 1971, pp. 312–315.

Olievier, C. N., et al., "In Vivo Measurement of Carbon Dioxide Tension with a Miniature Electrodes", *Pluegers Archiv: European Journal of Pfhysiology*, vol. 373, 1978, pp. 269–272.

Paddock, R. M., et al., "Electrocatalytic Reduction of Hydrogen Peroxide via Direct Electron Transfer From Pyrolytic Graphite Electrodes to Irreversibly Adsorbed Cyctochroyme C Peroxidase", *Journal of ElectroAnalytical Chemistry*, vol. 260, 1989, pp. 487–494.

Palleschi, G., et al., "A Study of Interferences in Glucose Measurements in Blood by Hydrogen Peroxide Based Glucose Probes", *Analytical Biochemistry*, vol. 159, 1986, pp. 114–121.

Palmisano, F., et al., "Simultaneous Monitoring of Glucose and Lactate by an Interference and Cross–Talk Free Dual Electrode Amperometric Biosensor Based on Electropolymerized Thin Films", *Biosensors & Bioelectronics*, vol. 15, 2000, pp. 531–539.

Pankratov, I., et al., "Sol–Gel Derived Renewable–Surface Biosensors", *Journal of ElectroAnalytical Chemistry*, vol. 393, 1995, pp. 34–41.

Panteleon, A. E., et al., "The Role of the Independent Variable to Glucose Sensor Calibration", *Diabetes Technology & Therapeutics*, vol. 5, No. 3, 2003, pp. 401–410.

Parker, R. S., et al., "A Model–Based Algorithm for Blood Glucose Control in Type I Diabetic Patients", *IEEE Transactions on Biomedical Engineering*, vol. 46, No. 2, 1999, pp. 148–157.

Patel, H., et al., "Amperometric Glucose Sensors Based on Ferrocene Containing Polymeric Electron Transfer Systems—A Preliminary Report", *Biosensors and Bioelectronics*, vol. 18, 2003, pp. 1073–1076.

Pathak, C., et al., "Rapid Photopolymerization of Immunoprotective Gels in Contact with Cells and Tissue", *Journal of the American Chemical Society*, vol. 114, No. 21, 1992, pp. 8311–8312.

Pichert, J. W., et al., "Issues for the Coming Age of Continuous Glucose Monitoring", *The Diabetic Educator*, vol. 26, No. 6, 2000, pp. 969–980.

Pickup, J. C., et al., "Responses and Calibration of Amperometric Glucose Sensors Implanted in the Subcutaneous Tissue of Man", *Acta Diabetologica*, vol. 30, 1993, pp. 143–148.

Pickup, J., "Developing Glucose Sensors for In Vivo Use", *Tibtech*, vol. 11, 1993, pp. 285–291.

Pickup, J., et al., "In Vivo Molecular Sensing in Diabetes Mellitus: An Implantable Glucose Sensor with Direct Electron Transfer", *Diabetologia*, vol. 32, 1989, pp. 213–217.

Pickup, J., et al., "Potentially–Implantable, Amperometric Glucose Sensors with Mediated Electron Transfer: Improving the Operating Stability", *Biosensors*, vol. 4, 1989, pp. 109–119.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268–2272.

Pitzer, K. R., et al., "Detection of Hydpoglycemia with the Gluco Watch Biographer", *Diabetes Care*, vol. 24, No. 5, 2001, pp. 881–885.

Poirier, J. Y., et al., "Clinical and Statistical Evaluation of Self–Monitoring Blood Glucose Meters", *Diabetes Care*, vol. 21, No. 11, 1998, pp. 1919–1924.

Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", *Diabetolgia*, vol. 36, 1993, pp. 658–663.

Poitout, V., et al., "Calibration in Dogs of a Subcutaneous Miniaturized Glucose Sensor Using a Glucose Meter for Blood Glucose Determination", *Biosensors & Bioelectronics*, vol. 7, 1992, pp. 587–592.

Poitout, V., et al., "In Vitro and In Vivo Evaluation in Dogs of a Miniaturized Glucose Sensor", *ASAIO Transactions*, vol. 37, No. 3, 1991, pp. M298–M300.

Pollak, A., et al., "Enzyme Immobilization by Condensation Copolymerization into Cross–Linked Polyacrylamide Gels", *Journal of the American Chemical Society*, vol. 102, No. 20, 1980, pp. 6324–6336.

Postlethwaite, T. A., et al., "Interdigitated Array Electrode as an Alternative to the Rotated Ring—Disk Electrode for Determination of the Reaction Products of Dioxygen Reduction", *Analytical Chemistry*, vol. 68, No. 17, 1996, pp. 2951–2958.

Quinn, C. A. P., et al., "Biocompatible, Glucose–Permeable Hydrogel for In Situ Coating of Implantable Biosensors", *Biomaterials*, vol. 18 No. 24, 1997, pp. 1665–1670.

Quinn,, C. P., et al., "Kinetics of Glucose Delivery to Subcutaneous Tissue in Rats Measured with 0.3–mm Amperometric Microsensors", *The American Physiological Society*, 1995, E155–S161.

Ratner, B. D., "Reducing Capsular Thickness and Enhancing Angeiogenesis Around Implant Drug Release Systems", *Journal of Controlled Release*, vol. 78, 2002, pp. 211–218.

Reach, G., "Which Threshold to Detect Hypoglycemia?", *Diabetes Care*, vol. 24, No. 5, 2001, pp. 803–804.

Reach, G., et al., "A Method of Evaluating In Vivo the Functional Characteristics of Glucose Sensors", *Biosensors 2*, 1986, pp. 211–220.

Reach, G., et al., "Can Continuous Glucose Monitoring Be Used for the Treatment of Diabetes?", *Analytical Chemistry*, vol. 64, No. 6, 1992, pp. 381–386.

Reach, G., et al., "Letters to the Editor: Re: Diabetes Technology & Therapeutics, 2000; 2:49–56", *Diabetes Technology & Therapeutics*, vol. 3, No. 1, 2001, pp. 129–131.

Rebrin, K., et al., "Automated Feedbackk Control of Subcutaneous Glucose Concentration in Diabetic Dogs", *Diabetologia*, vol. 32, 1989, pp. 573–576.

Rebrin, K., et al., "Subcutaneous Glucose Predicts Plasma Glucose Independent of Insulin: Implications for Continuous Monitoring", *The American Physiological Society*, 1999, pp. E561–E571.

Rhodes, R. K., et al., "Prediction of Pocket–Portable and Implantable Glucose Enzyme Electrode Performance from Combined Species Permeability and Digital Simulation Analysis", *Analytical Chemistry*, vol. 66, No. 9, 1994, pp. 1520–1529.

Rinken, T., et al., "Calibration of Glucose Biosensors By Using Pre–Study State Kinetic Data", *Biosensors & Bioelectronics*, vol. 13, 1998, pp. 801–807.

Roe, J. N., et al., "Bloodless Glucose Measurements", *Critical Review in Therapeutic Drug Carrier Systems*, vol. 15, Issue 3, 1998, pp. 199–241.

Sakakida, M., et al., "Ferrocene–Mediated Needle–Type Glucose Sensor Covered with Newly Designed Biocompatible Membrane", *Sensors and Actuators B*, vol. 13–14, 1993, pp. 319–322.

Salehi, C., et al., "A Telemetry–Instrumentation System for Long–Term Implantable Glucose and Oxygen Sensors", *Analytical Letters*, vol. 29, No. 13, 1996, pp. 2289–2308.

Samuels, G. L., et al., "An Electrode–Supported Oxidation Catalyst Based Ruthenium (IV). pH 'Encapsulation' in a Polymer Film", *Journal of the American Chemical Society*, vol. 103, No. 2, 1981, pp. 307–312.

Sansen, W., et al., "A Smart Sensor for the Voltammetric Measurement of Oxygen or Glucose Concentrations", *Sensors and Actuators B1*, 1990, p. 298–302.

Sansen, W., et al., "Chapter 12: Glucose Sensor with Telemetry Systems", *Implantable Sensors for Closed–Loop Prosthetic System*, 1985, pp. 167–175.

Sasso, S. V., et al., "Electropolymerized 1,2–Diaminobenzene as a Means to Prevent Interferences and Fouling and to Stabilize Immobilized Enzyme in Electrochemical Biosensors", *Analytical Chemistry*, vol. 62, No. 11, 1990, pp. 1111–1117.

Scheller, F., et al., "Enzyme Electrodes and Their Application", *Philosophical Transactions of The Royal Society of London B*. vol. 316, 1987, pp. 85–94.

Schmehl, R. H., et al., "The Effect of Redox Site Concentration on the Rate of Mediated Oxidation of Solution Substrates by a Redox Copolymer Film", *Journal of ElectroAnalytical Chemistry*, vol. 152, 1983, pp. 97–109.

Schmidt, F. J., et al., "Glucose Concentration in Subcutaneous Extracellular Space", *Diabetes Care*, vol. 16, No. 5, 1993, pp. 695–700.

Schmidtke, D. W., et al., "Accuracy of the One–Point In Vivo Calibration of 'Wired' Glucose Oxidase Electrodes Implanted in Jugular Veins of Rats in Periods of Rapid Rise and Decline of the Glucose Concentration", *Analytical Chemistry*, vol. 70, No. 10, 1998, pp. 2149–2155.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294–299.

Schoemaker, M., et al., "The SCHMI System: Subcutaneous Continuous Glucose Monitoring Based on Microdialysis Technique", *Diabetes Technology & Therapeutics*, vol. 5, No. 4, 2003, pp. 599–608.

Schwarz, M., et al., "Micro Implantable Visual Prostheses", *1st Annual International IEEE–EMBS Special Topic Conference on Microtechnologies in Medicine & Biology, Lyon, France*, 2000, pp. 461–465.

Selam, J. L., "Management of Diabetes with Glucose Sensors and Implantable Insulin Pumps: From the Dream of the of the 60s to the Realities of the 90's ", *American Society for Artificial Internal Organs Journal*, 1997, pp. 137–142.

Service, R. F., "Can Sensors Make a Home in the Body?", *Science*, vol. 297, 2002, pp. 962–963.

Sieminski, A. L., et al., "Biomaterial–Microvasculature Interactions", *Biomaterials*, vol. 21, 2000, pp. 2233–2241.

Sittampalam, G., et al., "Surface–Modified Electrochemical Detector for Liquid Chromatography", *Analytical Chemistry*, vol. 55, No. 9, 1983, pp. 1608–1610.

Skyler, J. S., "The Economic Burden of Diabetes and the Benefits of Improved Glycemic Control: The Potential Role of a Continuous Glucose Monitoring System", *Diabetes Technology & Therapeutics*, vol. 2, Sup. 1, 2000, pp. S7–S12.

Soegijoko, S., et al., "External Artificial Pancreas: A New Control Unit Using Microprocessor", *Hormone and Metabolic Research Supplement Series*, vol. 12, 1982, pp. 165–169.

Sokolov, S., et al., "Metrological Opportunities of the Dynamic Mode of Operating an Enzyme Amperometric Biosensor", *Medical Engineering and Physics*, vol. 17, No. 6, 1995, pp. 471–476.

Sproule, B. A., et al., "Fuzzy Pharmacology: Theory and Applications", *Trends in Pharmacological Sciences* vol. 23, No. 9, 2002, pp. 412–417.

Sprules, S. D., et al., "Evaluation of a New Disposable Screen–Printed Sensor Strip for the Measurement of NADH and Its Modification to Produce a Lactate Biosensor Employing Microliter Volumes", *Electroanalysis*, vol. 8, No. 6, 1996, pp. 539–543.

Sriyudthsak, M., et al., "Enzyme–Epoxy Membrane Based Glucose Analyzing System and Medical Applications", *Biosensors & Bioelectronics*, vol. 11, No. 8, 1996, pp. 735–742.

Steil, G. M., et al., "Determination of Plasma Glucose During Rapid Glucose Excursions with a Subcutaneous Glucose Sensor", *Diabetes Technology & Therapeutics*, vol. 5, No. 1, 2003, pp. 27–31.

Sternberg, F., et al., "Calibration Problems of Subcutaneous Glucosensors when Applied 'In–Situ' in Man", *Hormone and Metabolic Research*, vol. 26, 1994, pp. 523–526.

Sternberg, F., et al., "Does Fall In Tissue Glucose Precede Fall In Blood Glucose?" *Diabetologia*, vol. 29, 1996, pp. 609–612.

Sternberg, R., et al., "Covalent Enzyme Coupling on Cellulose Acetate Mebranes for Glucose Sensor Development", *Analytical Chemistry, vol. 60, No. 24,* 1988, pp. 2781–2786.

Sternberg, R., et al., "Study and Development of Multilayer Neddle–Type Enzyme–Based Glucose Microsensors", *Biosensors, vol. 4,* 1988, pp. 27–40.

Street, J. O., et al., "A Note on Computing Robust Regression Estimates Via Interactively Reweighted Least Squares", *The American Statistician, vol. 42, No. 2,* 1988, pp. 152–154.

Suaning, G. J., et al., "CMOS Neurostimulation ASIC with 100 Channels, Scaleable Output, and Bidirectional Radio–Frequency Telemetry" *IEEE Transactions on Biomedical Engineering, vol. 48, No. 2,* 2001, pp. 248–260.

Suekane, M., "Immobilization of Glucose Isomerase", *Zettschrift Allgemeine Mikrobiologie, vol. 22, No. 8,* 1982, pp. 565–576.

Tajima, S., et al., "Simulataneous Determination of Glucose and 1,5–Anydroglucitol", *Chemical Abstracts, vol. 111, No. 25,* 1989, pp. 394.

Tamura, T., et al., "Preliminary Study of Continuous Glucose Monitoring with a Microdialysis Technique and a Null Method—a Numerical Analysis", *Frontiers Medical and Biological Engineering, vol. 10, No. 2,* 2000, pp. 147–156.

Tanenberg, R. J., et al., "Continuous Glucose Monitoring System: A New Approach to the Diagnosis of Diabetic Gastroparesis", *Diabetes Technology & Therapeutics, vol. 2, Sup. 1,* 2000, pp. S73–S80.

Tang, L. et al., "Fibrin(ogen) Mediates Acute Inflammatory Responses to Biomaterials", *Journal of Experimental Medicine, vol. 178,* 1993, pp. 2147–2156.

Tang, L., et al., "Inflammatory Responses to Biomaterials", *American Journal of Clinical Pathology, vol. 103, No. 4,* 1995, pp. 466–471.

Tang, L., et al., "Mast Cells Mediate Acute Inflammatory Responses to Implanted Biomaterials", *Proceedings of the National Academy of Sciences USA, vol. 95,* 1998, pp. 8841–8846.

Tang, L., et al., "Molecular Determinants of Acute Inflammatory Responses to Biomaterials", *Journal of Clinical Investigation, vol. 97, No. 5,* 1996, pp. 1329–1334.

Tang, Z., et al., "Data Transmission from an Implantable Biotelemeter by Load–Shift Keying Using Circuit Configuration Modular", *IEEE Transactions on Biomedical Engineering, vol. 42, No. 5,* 1995, pp. 524–528.

Tarasevich, M. R., "Bioelectrocatalysis", *Comprehensive Treatise of Electrochemistry, vol. 10,* 1985, pp. 231–295.

Tatsuma, T., et al., "Enzyme Monolayer–and Bilayer–Modified Tin Oxide Electrodes for the Determination of Hydrogen Peroxide and Glucose", *Analytical Chemistry, vol. 61, No. 21,* 1989, pp. 2352–2355.

Taylor, C., et al., "'Wiring' of Glucose Oxidase Within a Hydrogel Made with Polyvinyl Imidazole Complexed with [Os–4,4'–dimethoxy–2,2'–bipyridine)Cl]$^{+/2+}$", *Journal of ElectroAnalytical Chemistry, vol. 396,* 1995, pp. 511–515.

Thome–Duret, V., et al., "Continuous Glucose Monitoring in the Free–Moving Rat", *Metabolism, vol. 47, No. 7* 1998, pp. 799–803.

Thome–Duret, V., et al., "Modification of the Sensitivity of Glucose Sensor Implanted into Subcutaneous Tissue", *Diabetes & Metabolism, vol. 22, No. 3,* 1996, pp. 174–178.

Tibell, A., et al., "Survival of Macroencapsulated Allogeneic Parathyriod Tissue One Year After Tranplantation in Nonimmunosuppressed Humans", *Cell Transplantation, vol. 10, No. 7,* 2001, pp. 591–599.

Tierney, M. J., "The Gluco Watch® Biographer: A Frequent, Automatic and Noninvasive Glucose Monitor", *Annals of Medicine, vol. 32,* 2000, pp. 632–641.

Tierney, M. J., et al., "Effect of Acetaminophen on the Accuracy of Glucose Measurements Obtained with the Gluco Watch Biographer", *Diabetes Technology & Therapeutics, vol. 2, No. 2,* 2000, pp. 199–207.

Tilbury, J. B., et al., "Receiver Operating Characteristic Analysis for Intelligent Medical Systems—A New Approach for Finding Confidence Intervals", *IEEE Transactions on Biomedical Engineering, vol. 47, No. 7,* 2000, pp. 952–963

Trajanoski, Z., et al., "Neural Predictive Controller for Insulin Delivery Using the Subcutaneous Route", *IEEE Transactions on Biomedical Engineering, vol. 45, No. 9,* 1998, pp. 1122–1134.

Trecroci, D., "A Glimpse Into the Future: Continuous Monitoring of Glucose with a Microfiber", *Diabetes Interview,* 2002, pp. 42–43.

Trojanowicz, M., et al., "Enzyme Entrapped Polypyrrole Modified Electrode for Flow–Injection Determination of Glucose", *Biosensors & Bioelectronics, vol. 5,* 1990, pp. 149–156.

Turner, A., et al., "Diabetes Mellitus: Biosensors for Research and Management", *Biosensors, vol. 1,* 1985, pp. 85–115.

Turner, R. F., et al., "A Biocompatible Enzyme Electrode for Continuous in vivo Glucose Monitoring in Whole Blood", *Sensors and Actuators B, vol. 1,* 1990, pp. 561–564.

Tuzhi, P. et al., "Constant Potential Pretreatment of Carbon Fiber Electrodes for In Vivo Electrochemistry", *Analytical Letters, vol. 24, No. 6,* 1991, pp. 935–945.

U.S. Department of Health and Human Services, "Off–The–Shelf–Software Use in Medical Devices", *Guidance for Industry, FDA Reviewers and Compliance on,* 1999, pp. 1–26.

U.S. Patent Reexamination Application No. 90/008,172, Request for Reexamination of U.S. Patent No. 6,990,366, filed Aug. 16, 2006.

U.S. Patent Reexamination Application No. 90/008,909, Request for Reexamination of U.S. Patent No. 5,899,855, filed Dec. 11, 2007.

U.S. Patent Reexamination Application No. 90/008,928, Request for Reexamination of U.S. Patent No. 6,134,461, filed Nov. 16, 2007.

U.S. Patent Reexamination Application No. , Request for Reexamination of U.S. Patent No. 6,990,366, filed Apr. 8, 2008.

Umana, M., "Protein–Modified Electrochemically Active Biomaterial Surface", *U.S. Army Research Office, Analytical and Chemical Sciences Research Triangle Institute,* 1988, pp. 1–9.

Updike, S. J., et al., "A Subcutaneous Glucose Sensor with Improved Longevity, Dynamic Range, and Stability of Calibration", *Diabetes Care, vol. 23, No. 2,* 2000, pp. 208–214.

Updike, S. J., et al., "Continuous Glucose Monitor Based on an Immobilized Enzyme Electrode Detector", *The Journal of Laboratory and Clinical Medicine, vol. 93, No. 4,* 1979, pp. 518–527.

Updike, S. J., et al., "Enzymatic Glucose Sensors: Improved Long–Term Performance In Vitro and In Vivo", *American Society for Artificial Internal Organs Journal*, 1994, pp. 157–163.

Updike, S. J., et al., "Implanting the Glucose Enzyme Electrode: Problems, Progress, and Alternative Solutions", *Diabetes Care, vol. 5, No. 3*, 1982, pp. 207–212.

Updike, S. J., et al., "The Enzyme Electrode", *Nature, vol. 214*, 1967, pp. 986–988.

Urban, G., et al., "Miniaturized Thin–Film Biosensors Using Covalently Immobilized Glucose Oxidase", *Biosensors & Bioelectronics, vol. 6*, 1991, pp. 555–562.

Valdes, T. I., et al., "In Vitro and In Vivo Degradation of Glucose Oxidase Enxyme Used for an Implantable Glucose Biosensor", *Diabetes Technology & Therapeutics, vol. 2, No. 3*, 2000, pp. 367–376.

Velho, G., et al., "In Vitro and In Vivo Stability of Electrode Potentials in Needle–Type Glucose Sensors", *Diabetes, vol. 38, No. 2*, 1989, pp. 164–171.

Von Woedtke, T., et al., "In Situ Calibration of Implanted Electrochemical Glucose Sensors", *Biomedica Biochimica Acta, vol. 48*, 1989, pp. 943–952.

Vreeke, M. S., et al., "Hydrogen Peroxide Electrodes Based on Electrical Connection of Redox Centers of Various Peroxidases to Electrodes through a Three–Dimensional Electron–Relaying Polymer Network", *Diagnostic Biosensors Polymers, Chapter 15*, 1993, pp. 180–193.

Vreeke, M., et al., "Hydrogen Peroxide and β–Nicotinamide Adenine Dinucleotide Sensing Amperometric Electrodes Based on Electrical Connection of Horseradish Peroxidase Redox Centers to Electrodes through a Three–Dimensional Electron Relaying Polymer Network", *Analytical Chemistry, vol. 64, No. 24*, 1992, pp. 3084–3090.

Wade Jr., L. G., "Chapter 17: Reactions of Aromatic Compounds", *Organic Chemistry, Sixth Edition*, 2006, pp. 762–763.

Wagner, J. G., et al., "Continuous Amperometric Monitoring of Glucose in a Brittle Diabetic Chimpanzee with a Miniature Subcutaneous Electrode", *Proceedings of the National Academy of Sciences USA*, 1998, pp. 6379–6382.

Wang, D. L. et al., "Miniaturized Flexible Amperometric Lactate Probe", *Analytical Chemistry, vol. 65, No. 8, 1993*, pp. 1069–1073.

Wang, J., et al., "Activation of Glassy Carbon Electrodes by Alternating Current Electrochemical Treatment", *Analytica Chimica Acta, vol. 167*, 1985, pp. 325–334.

Wang, J., et al., "Amperometric Biosensing of Organic Peroxides with Peroxidase–Modified Electrodes", *Analytica Chimica Acta, vol. 254*, 1991, pp. 81–88.

Wang, J., et al., "Highly Selective Membrane–Free, Mediator–Free Glucose Biosensor", *Analytical Chemistry, vol. 66, No. 21*, 1994, pp. 3600–3606.

Wang, J., et al., "Screen–Printable Sol–Gel Enzyme–Containing Carbon Inks", *Analytical Chemistry, vol. 68, No. 15*, 1996, pp. 2705–2708.

Wang, J., et al. "Sol–Gel–Derived Metal–Dispersed Carbon Composite Amperometric Biosensors", *Electroanalysis, vol. 9, No. 1*, 1997, pp. 52–55.

Wang, X., et al., "Improved Ruggedness for Membrane–Based Amperometric Sensors Using a Pulsed Amperometric Method", *Analytical Chemistry, vol. 69, No. 21*, 1997, pp. 4482–4489.

Ward, W. K., et al., "A New Amperometric Glucose Microsensor: In Vitro and Short–Term In Vivo Evaluation", *Biosensors & Bioelectronics, vol. 17*, 2002, pp. 181–189.

Ward, W. K., et al., "Assesment of Chronically Implanted Subcutaneous Glucose Sensors in Dogs: The Effect of Surrounding Fluid Masses", *American Society for Artificial Internal Organs Journal*, 1999, pp. 555–561.

Ward, W. K., et al., "Rise in Background Current Over Time in a Subcutaneous Glucose Sensor in the Rabbit: Relevance to Calibration and Accuracy", *Biosensors & Bioelectronics, vol. 15*, 2000, pp. 53–61.

Ward, W. K., et al., "Understanding Spontaneous Output Fluctuations of an Amperometric Glucose Sensor: Effect of Inhalation Anesthesia and Use of a Nonenzyme Containing Electrode", *American Society for Artificial Internal Organs Journal*, 2000, pp. 540–546.

Wientjes, K. J. C., *Development of a Glucose Sensor for Diabetic Patients*, 2000, pp. vii–xiii.

Wilkins, E., et al., "Glucose Monitoring: State of the Art and Future Possibilities", *Medical Engineering and Physics, vol. 18, No. 4*, 1995, pp. 273–288.

Wilkins, E., et al., "Integrated Implantable Device for Long–Term Glucose Monitoring", *Biosensors & Bioelecronics, vol. 10*, 1995, pp. 485–494.

Williams, D. L., et al., "Electrochemical–Enzymatic Analysis of Blood Glucose and Lactate", *Analytical Chemistry, vol. 42, No. 1*, 1970, pp. 118–121.

Wilson, G.S., et al., "Enzyme–Based Biosensors for In Vivo Measurements", *Chemical Reviews, vol. 100, No. 7*, 2000, pp. 2693–2704.

Wilson, G. S., et al., "Progress Toward the Development of an Implantable Sensor for Glucose", *Clinical Chemistry, vol. 38, No. 9*, 1992, pp. 1613–1617.

Wood, W. D., et al., "Hermetic Sealing with Epoxy", *Mechanical Engineering*, 1990, pp. 46–48.

Wu, H., et al., "In Situ Electrochemical Oxygen Generation with an Immunoisolation Device", *Annals of the new York Academy of Sciences, vol. 875*, 1999, pp. 105–125.

Yabuki, S., et al., "Electro–Conductive Enzyme Membrane", *Journal of the Chemical Society, Chemical Communications*, 1989, pp. 945–946.

Yang, L., et al., "Determination of Oxidase Enzyme Substrates Using Cross–Flow Thin–Layer Amperometry", *Electroanalysis, vol. 8, No. 8–9*, 1996, pp. 716–721.

Yang, Q., et al., "Development of Needle–Type Glucose Sensor with High Selectivity", *Sensors and Actuators B, vol. 46*, 1998, pp. 249–256.

Yao, S. J., et al., "The Interference of Ascorbate and Urea in Low–Potential Electrochemical Glucose Sensing", *Proceedings of the Twelfth Annual International Conference of the IEEE Engineering in Medicine and Biology Society, vol. 12, Part 2*, 1990, pp. 487–489.

Yao, T., "A Chemically–Modified Enzyme Membrane Electrode as an Amperometric Glucose Sensor", *Analytica Chimica Acta, vol. 148*, 1983, pp. 27–33.

Ye, L., et al., "High Current Density 'Wired' Quinoprotein Glucose Dehydrogenase Electrode", *Analytical Chemistry, vol. 65, No. 3*, 1993, pp. 238–241.

Yildiz, A. et al., "Evaluation of an Improved Thin–Layer Electrode", *Analytical Chemistry, vol. 40, No.7*, 1968, pp. 1018–1024.

Zamzow, K., et al., "New Wearable Continuous Blood Glucose Monitor (BGM) and Artificial Pancreas (AP)", *Diabetes, vol. 39*, 1990, pp. 5A–20.

Zavalkoff, S. R., et al., "Evaluation of Conventional Blood Glucose Monitoring as an Indicator of Integrated Glucose Values Using a Continuous Subcutaneous Sensor", *Diabetes Care, vol. 25, No. 9,* 2002, pp.1603–1606.

Zhang, Y., et al., "Application of Cell Culture Toxicity Tests to the Development of Implantable Biosensors", *Biosensors & Bioelectronics, vol. 6,* 1991, pp. 653–661.

Zhang, Y., et al., "Elimination of the Acetaminophen Interference in an Implantable Glucose Sensor", *Anlytical Chemistry, vol. 66, No. 7,* 1994, pp. 1183–1188.

Zhu, J., et al., "Planar Amperometric Glucose Sensor Based on Glucose Oxidase Immobilized by Chitosan Film on Prussian Blue Layer", *Sensor, vol. 2,* 2002, pp. 127–136.

Johnson et al., Biosensors and Bioelectronics (1992) 7:709–714.

Shichiri et al., Diabetologia (1983) 24:179–184.

Shichiri et al., Horm. Metab, Res. Suppl. (1988) 20:17–20.

Shichiri et al., The Lancel (1982) 1129–1131.

Mastrototaro et al., Sensors and Actuators B (1991) 5:139–144.

Sakakida et al., Artif. Organs Today (1992) 2:145–158.

Hoel, Elementary Statistics, 4th ed., John Wiley & Sons, Inc (1976) pp. 113–114.

Freedman et al., Statistics, 2nd ed., W. W. Norton & Company (1991) p. 74.

Complaint, filed Aug. 11, 2005, Abbott Diabetes Care, Inc. V. Dexcom, Inc.

Amended Complaint, filed Jun. 27, 2006 in Abbott Diabetes Care, Inc. v. Dexcom, Inc.

Osmonics, Poretics Polycarbonate Membrane product insert, (2002).

\* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2–4, dependent on an amended claim, are determined to be patentable.

New claims 30–188 are added and determined to patentable.

Claims 5–29 were not reexamined.

1. An analyte responsive electrochemical sensor *capable of operating substantially continuously for a period of at least three days* comprising a working electrode and a mass transport limiting membrane, which mass transport limiting membrane maintains a rate of permeation of the analyte through the mass transport limiting membrane with a variation of no more than 3% per ° C. at temperatures ranging from 30° C. to 40 C.

*30. The electrochemical sensor of claim 1, wherein the working electrode has a width on at least a portion thereof between 150 µm and 25 µm.*

*31. The electrochemical sensor of claim 1, wherein the working electrode is a portion of a conductive trace.*

*32. The electrochemical sensor of claim 1, wherein the sensor is capable of periodic operation.*

*33. The electrochemical sensor of claim 1, wherein the sensor is capable of operation for a period of at least seven days.*

*34. The electrochemical sensor of claim 1, wherein the sensor is configured for at least partial implantation in the tissue of an animal.*

*35. The electrochemical sensor of claim 1, further comprising a sensing layer.*

*36. The electrochemical sensor of claim 35, wherein the sensing layer does not comprise an electron transfer agent.*

*37. The electrochemical sensor of claim 35, wherein the sensing layer comprises an electron transfer agent.*

*38. The electrochemical sensor of claim 37, wherein the electron transfer agent is a redox mediator.*

*39. The electrochemical sensor of claim 37, wherein the electron transfer agent comprises osmium transition metal complexes with one or more ligands.*

*40. The electrochemical sensor of claim 39, wherein at least one of said ligands comprises a nitrogen-containing heterocycle.*

*41. The electrochemical sensor of claim 40, wherein each said heterocycle is selected from the group consisting of pyridine, imidizole and derivatives thereof.*

*42. The electrochemical sensor of claim 39, wherein at least one of said ligands is bound in a polymer.*

*43. The electrochemical sensor of claim 37, wherein the electron transfer agent is configured to transfer electrons directly between the analyte and the working electrode.*

*44. The electrochemical sensor of claim 37, wherein the electron transfer agent is configured to transfer electrons indirectly between the analyte and the working electrode.*

*45. The electrochemical sensor of claim 35, wherein the sensing layer comprises a redox polymer.*

*46. The electrochemical sensor of claim 45, wherein the redox polymer comprises osmium.*

*47. The electrochemical sensor of claim 35, wherein the sensing layer comprises a catalyst.*

*48. The electrochemical sensor of claim 47, wherein the catalyst comprises an enzyme.*

*49. The electrochemical sensor of claim 48, wherein the catalyst acts as an electron transfer agent.*

*50. The electrochemical sensor of claim 48, wherein the enzyme comprises glucose oxidase.*

*51. The electrochemical sensor of claim 48, wherein the enzyme comprises glucose dehydrogenase.*

*52. The electrochemical sensor of claim 48, wherein the sensing layer is configured such that glucose reacts with a second reactant in the presence of the enzyme.*

*53. The electrochemical sensor of claim 52, wherein the second reactant is oxygen.*

*54. The electrochemical sensor of claim 48, wherein the sensing layer is configured such that the reaction of glucose in the presence of the enzyme forms hydrogen peroxide.*

*55. The electrochemical sensor of claim 54, wherein the level of hydrogen peroxide correlates to the level of glucose.*

*56. The electrochemical sensor of claim 35, wherein the sensing layer comprises both an electron transfer agent and a catalyst.*

*57. The electrochemical sensor of claim 35, wherein the sensing layer is immobilized within or between one or more membranes or films disposed over the working electrode.*

*58. The electrochemical sensor of claim 1, wherein the sensor is configured to couple with a control unit and/or a processing unit.*

*59. The electrochemical sensor of claim 58, wherein the control unit and processing unit are combined in a single unit.*

60. The electrochemical sensor of claim 58, wherein the control unit and processing unit are separate units.

61. The electrochemical sensor of claim 1, wherein the working electrode comprises carbon.

62. The electrochemical sensor of claim 1, wherein the working electrode comprises gold.

63. The electrochemical sensor of claim 1, wherein the mass transport limiting membrane does not comprise polycarbonate.

64. An analyte responsive electrochemical sensor capable of operating substantially continuously for a period of at least three days comprising a substrate, a first conductive material disposed on a surface of the substrate to form a first trace comprising a working electrode, a second conductive material disposed on a surface of the substrate to form a second trace comprising a second electrode, and a mass transport limiting membrane, which mass transport limiting membrane maintains a rate of permeation of the analyte through the mass transport limiting membrane with a variation of no more than 3% per ° C. at temperatures ranging from 30° C. to 40° C.

65. The electrochemical sensor of claim 64, wherein the first and second traces are disposed between 250 µm and 25 µm apart.

66. The electrochemical sensor of claim 64, wherein the first and second traces are disposed 150 µm or less apart.

67. The electrochemical sensor of claim 64, wherein the first and second traces are disposed between 150 µm and 25 µm apart.

68. The electrochemical sensor of claim 64, wherein the sensor is capable of periodic operation.

69. The electrochemical sensor of claim 64, wherein the sensor is capable of operation for a period of at least seven days.

70. The electrochemical sensor of claim 64, wherein the sensor is configured for at least partial implantation in the tissue of an animal.

71. The electrochemical sensor of claim 64, further comprising a sensing layer.

72. The electrochemical sensor of claim 71, wherein the sensing layer does not comprise an electron transfer agent.

73. The electrochemical sensor of claim 71, wherein the sensing layer comprises an electron transfer agent.

74. The electrochemical sensor of claim 73, wherein the electron transfer agent is a redox mediator.

75. The electrochemical sensor of claim 73, wherein the electron transfer agent comprises osmium transition metal complexes with one or more ligands.

76. The electrochemical sensor of claim 75, wherein at least one of said ligands comprises a nitrogen-containing heterocycle.

77. The electrochemical sensor of claim 76, wherein each said heterocycle is selected from the group consisting of pyridine, imidizole and derivatives thereof.

78. The electrochemical sensor of claim 75, wherein at least one of said ligands is bound in a polymer.

79. The electrochemical sensor of claim 73, wherein the electron transfer agent is configured to transfer electrons directly between the analyte and the working electrode.

80. The electrochemical sensor of claim 73, wherein the electron transfer agent is configured to transfer electrons indirectly between the analyte and the working electrode.

81. The electrochemical sensor of claim 71, wherein the sensing layer comprises a redox polymer.

82. The electrochemical sensor of claim 81, wherein the redox polymer comprises osmium.

83. The electrochemical sensor of claim 71, wherein the sensing layer comprises a catalyst.

84. The electrochemical sensor of claim 83, wherein the catalyst comprises an enzyme.

85. The electrochemical sensor of claim 84, wherein the catalyst acts as an electron transfer agent.

86. The electrochemical sensor of claim 84, wherein the enzyme comprises glucose oxidase.

87. The electrochemical sensor of claim 84, wherein the enzyme comprises glucose dehydrogenase.

88. The electrochemical sensor of claim 84, wherein the sensing layer is configured such that glucose reacts with a second reactant in the presence of the enzyme.

89. The electrochemical sensor of claim 88, wherein the second reactant is oxygen.

90. The electrochemical sensor of claim 84, wherein the sensing layer is configured such that the reaction of glucose in the presence of the enzyme forms hydrogen peroxide.

91. The electrochemical sensor of claim 90, wherein the level of hydrogen peroxide correlates to the level of glucose.

92. The electrochemical sensor of claim 71, wherein the sensing layer comprises both an electron transfer agent and a catalyst.

93. The electrochemical sensor of claim 71, wherein the sensing layer is immobilized within or between or more membranes or films disposed over the working electrode.

94. The electrochemical sensor of claim 64, wherein the sensor is configured to couple with a control unit and/or a processing unit.

95. The electrochemical sensor of claim 94, wherein the control unit and processing unit are combined in a single unit.

96. The electrochemical sensor of claim 94, wherein the control unit and processing unit are separate units.

97. The electrochemical sensor of claim 64, wherein the working electrode comprises carbon.

98. The electrochemical sensor of claim 64, wherein the working electrode comprises gold.

99. The electrochemical sensor of claim 64, wherein the mass transport limiting membrane does not comprise polycarbonate.

100. An analyte responsive electrochemical sensor capable of operating substantially continuously for a period of at least three days comprising a substrate, a conductive material disposed on a surface of the substrate to form a trace comprising a working electrode, and a mass transport limiting membrane, which mass transport limiting membrane maintains a rate of permeation of the analyte through the mass transport limiting membrane with a variation of no more than 3% per ° C. at temperature ranging from 30° C. to 40° C.

101. The electrochemical sensor of claim 100, wherein the trace having a width along at least a portion thereof between 150 µm and 25 µm.

102. The electrochemical sensor of claim 100, wherein the trace having a width along at least a portion thereof of 75 µm or less.

103. The electrochemical sensor of claim 100, wherein the trace having a width along at least a portion thereof of 75 µm and 25 µm.

104. The electrochemical sensor of claim 100, wherein the trace having a width along at least a portion thereof of 50 µm or less.

105. The electrochemical sensor of claim 100, wherein the trace having a width along at least a portion thereof of between 50 µm and 25 µm.

106. The electrochemical sensor of claim 100, wherein the sensor is capable of periodic operation.

107. The electrochemical sensor of claim 100, wherein the sensor is capable of operation for a period of at least seven days.

108. The electrochemical sensor of claim 100, wherein the sensor is configured for at least partial implantation in the tissue of an animal.

109. The electrochemical sensor of claim 100, further comprising a sensing layer.

110. The electrochemical sensor of claim 109, wherein the sensing layer does not comprise an electron transfer agent.

111. The electrochemical sensor of claim 109, wherein the sensing layer comprises an electron transfer agent.

112. The electrochemical sensor of claim 111, wherein the electron transfer agent is a redox mediator.

113. The electrochemical sensor of claim 111, wherein the electron transfer agent comprises osmium transition metal complexes with one or more ligands.

114. The electrochemical sensor of claim 113, wherein at least one of said ligands comprises a nitrogen-containing heterocycle.

115. The electrochemical sensor of claim 114, wherein each said heterocycle is selected from the group consisting of pyridine, imidizole and derivatives thereof.

116. The electrochemical sensor of claim 113, wherein at least one of said ligands is bound in a polymer.

117. The electrochemical sensor of claim 111, wherein the electron transfer agent is configured to transfer electrons directly between the analyte and the working electrode.

118. The electrochemical sensor of claim 111, wherein the electron transfer agent is configured to transfer electrons indirectly between the analyte and the working electrode.

119. The electrochemical sensor of claim 109, wherein the sensing layer comprises a redox polymer.

114. The electrochemical sensor of claim 119, wherein the redox polymer comprises osmium.

121. The electrochemical sensor of claim 109, wherein the sensing layer comprises a catalyst.

122. The electrochemical sensor of claim 121, wherein the catalyst comprises an enzyme.

123. The electrochemical sensor of claim 122, wherein the catalyst acts as an electron transfer agent.

124. The electrochemical sensor of claim 122, wherein the enzyme comprises glucose oxidase.

125. The electrochemical sensor of claim 122, wherein the enzyme comprises glucose dehydrogenase.

126. The electrochemical sensor of claim 122, wherein the sensing layer is configured such that glucose reacts with a second reactant in the presence of the enzyme.

127. The electrochemical sensor of claim 126, wherein the second reactant is oxygen.

128. The electrochemical sensor of claim 122, wherein the sensing layer is configured such that the reaction of glucose in the presence of the enzyme forms hydrogen peroxide.

129. The electrochemical sensor of claim 128, wherein the level of hydrogen peroxide correlates to the level of glucose.

130. The electrochemical sensor of claim 109, wherein the sensing layer comprises both an electron transfer agent and a catalyst.

131. The electrochemical sensor of claim 109, wherein the sensing layer is immobilized within or between one or more membranes or films disposed over the working electrode.

132. The electrochemical sensor of claim 100, wherein the sensor is configured to couple with a control unit and/or a processing unit.

133. The electrochemical sensor of claim 132, wherein the control unit and processing unit are combined in a single unit.

134. The electrochemical sensor of claim 132, wherein the control unit and processing unit are separate units.

135. The electrochemical sensor of claim 100, wherein the working electrode comprises carbon.

136. The electrochemical sensor of claim 100, wherein the working electrode comprises gold.

137. The electrochemical sensor of claim 100, wherein the mass transport limiting membrane does not comprise polycarbonate.

138. An analyte responsive electrochemical sensor, comprisng:
  a substrate having a longitudinal axis with a narrow distal region that is configured and arranged for implantation into an animal and a wider proximal region;
  at least one working electrode disposed on the narrow distal region of the substrate;
  at least one contact pad disposed on the wider proximal region of the substrate and in electrical communication with a one of the at least one working electrodes; and
  a mass transport limiting membrane, which mass transport limiting membrane maintains a rate of permeation of the analyte through the mass transport limiting membrane with a variation of no more than 3% per ° C. at temperatures ranging from 30° C. to 40° C.

139. The electrochemical sensor of claim 138, wherein the contact pad comprises carbon.

140. The electrochemical sensor of claim 138, wherein the contact pad comprises gold.

141. The electrochemical sensor of claim 138, wherein the contact pad comprises palladium.

142. The electrochemical sensor of claim 138, wherein the contact pad comprises platinum.

143. The electrochemical sensor of claim 138, wherein the sensor is capable of operation for a period of at least three days.

144. The electrochemical sensor of claim 138, wherein the sensor is capable of operation for a period of at least seven days.

145. The electrochemical sensor of claim 138, wherein the sensor is configured for at least partial implantation in the tissue of an animal.

146. The electrochemical sensor of claim 138, further comprising a sensing layer.

147. The electrochemical sensor of claim 146, wherein the sensing layer does not comprise an electron transfer agent.

148. The electrochemical sensor of claim 146, wherein the sensing layer comprises an electron transfer agent.

149. The electrochemical sensor of claim 148, wherein the electron transfer agent is a redox mediator.

150. The electrochemical sensor of claim 148, wherein the electron transfer agent comprises osmium transition metal complexes with one or more ligands.

151. The electrochemical sensor of claim 150, wherein at least one of said ligands comprises a nitrogen-containing heterocycle.

152. The electrochemical sensor of claim 151, wherein each said heterocycle is selected from the group consisting of pyridine, imidizole and derivatives thereof.

153. The electrochemical sensor of claim 150, wherein at least one of said ligands is bound in a polymer.

154. The electrochemical sensor of claim 148, wherein the electron transfer agent is configured to transfer electrons directly between the analyte and the working electrode.

155. The electrochemical sensor of claim 148, wherein the electron transfer agent is configured to transfer electrons indirectly between the analyte and the working electrode.

156. The electrochemical sensor of claim 146, wherein the sensing layer comprises a redox polymer.

157. The electrochemical sensor of claim 156, wherein the redox polymer comprises osmium.

158. The electrochemical sensor of claim 146, wherein the sensing layer comprises a catalyst.

159. The electrochemical sensor of claim 158, wherein the catalyst comprises an enzyme.

160. The electrochemical sensor of claim 159, wherein the catalyst acts as an electron transfer agent.

161. The electrochemical sensor of claim 159, wherein the enzyme comprises glucose oxidase.

162. The electrochemical sensor of claim 159, wherein the enzyme comprises glucose dehydrogenase.

163. The electrochemical sensor of claim 159, wherein the sensing layer is configured such that glucose reacts with a second reactant in the presence of the enzyme.

164. The electrochemical sensor of claim 163, wherein the second reactant is oxygen.

165. The electrochemical sensor of claim 159, wherein the sensing layer is configured such that the reaction of glucose in the presence of the enzyme forms hydrogen peroxide.

166. The electrochemical sensor of claim 165, wherein the level of hydrogen peroxide correlates to the level of glucose.

167. The electrochemical sensor of claim 146, wherein the sensing layer comprises both an electron transfer agent and a catalyst.

168. The electrochemical sensor of claim 146, wherein the sensing layer is immobilized within or between one or more membranes of films disposed over the working electrode.

169. The electrochemical sensor of claim 138, wherein at least one of the contact pads is configured to couple with a control unit and/or a processing unit.

170. The electrochemical sensor of claim 169, wherein the control unit and processing unit are combined in a single unit.

171. The electrochemical sensor of claim 169, wherein the control unit and processing unit are separate units.

172. The electrochemical sensor of claim 169, wherein the control unit is configured and arranged to communicate with a processing unit.

173. The electrochemical sensor of claim 138, wherein the mass transport limiting membrane does not comprise polycarbonate.

174. The electrochemical sensor of claim 138, wherein the working electrode has a width on at least a portion thereof of 150 μm or less.

175. The electrochemical sensor of claim 138, wherein the working electrode has a width on at least a portion thereof between 150 μm and 25 μm.

176. The electrochemical sensor of claim 138, wherein the working electrode is a portion of a conductive trace.

177. The electrochemical sensor of claim 138, further comprising a first conductive material disposed on a surface of the substrate to form a first trace coupled to the working electrode, a second conductive material disposed on a surface of the substrate to form a second trace coupled to a second electrode, the first and second traces being disposed 250 μm or less apart.

178. The electrochemical sensor of claim 177, wherein the first and second traces are disposed between 250 μm and 25 μm apart.

179. The electrochemical sensor of claim 177, wherein the first and second traces are disposed between 150 μm or less apart.

180. The electrochemical sensor of claim 177, wherein the first and second traces are disposed between 150 μm and 25 μm apart.

181. The electrochemical sensor of claim 138, further comprising a conductive material disposed on a surface of the substrate to form a trace comprising the working electrode, the trace having a width along at least a portion thereof of 150 μm or less.

182. The electrochemical sensor of claim 181, wherein the trace having a width along at least a portion thereof of between 180 μm and 25 μm.

183. The electrochemical sensor of claim 181, wherein the trace having a width along at least a portion thereof of 75 μm or less.

184. The electrochemical sensor of claim 181, wherein the trace having a width along at least a portion thereof of between 75 μm and 25 μm.

185. The electrochemical sensor of claim 181, wherein the trace having a width along at least a portion thereof of 50 μm or less.

186. The electrochemical sensor of claim 181, wherein the trace having a width along at least a portion thereof of between 50 μm and 25 μm.

187. The electrochemical sensor of claim 138, wherein the wider proximal region extends in a lateral direction from the longitudinal axis.

188. The electrochemical sensor of claim 187, wherein the wider proximal region extends in a single lateral direction from the longitudinal axis.

\* \* \* \* \*

(12) EX PARTE REEXAMINATION CERTIFICATE (10267th)
United States Patent
Say et al.

(10) Number: US 6,134,461 C2
(45) Certificate Issued: Aug. 21, 2014

(54) ELECTROCHEMICAL ANALYTE SENSOR

(75) Inventors: James Say, Alameda, CA (US); Michael F. Tomasco, Cupertino, CA (US); Adam Heller, Austin, TX (US); Yoram Gal, Kibbutz Yagur (IL); Behrad Aria, Alameda, CA (US); Ephraim Heller, Oakland, CA (US); Phillip John Plante, Sunnyvale, CA (US); Mark S. Vreeke, Alameda, CA (US)

(73) Assignee: Abbott Diabetes Care Inc., Alameda, CA (US)

Reexamination Request:
No. 90/010,835, Jan. 27, 2010
No. 90/009,763, Jun. 18, 2010

Reexamination Certificate for:
Patent No.: 6,134,461
Issued: Oct. 17, 2000
Appl. No.: 09/034,372
Filed: Mar. 4, 1998

Reexamination Certificate C1 6,134,461 issued Jun. 29, 2010

Certificate of Correction issued May 29, 2001
Certificate of Correction issued Jul. 6, 2004

(51) Int. Cl.
*A61B 5/05* (2006.01)

(52) U.S. Cl.
USPC .......................................... 600/345; 600/309

(58) Field of Classification Search
USPC ......................................................... 600/345
See application file for complete search history.

(56) References Cited

To view the complete listing of prior art documents cited during the proceedings for Reexamination Control Numbers 90/010,835 and 90/009,763, please refer to the USPTO's public Patent Application Information Retrieval (PAIR) system under the Display References tab.

*Primary Examiner* — Beverly M. Flanagan

(57) ABSTRACT

An electrochemical analyte sensor formed using conductive traces on a substrate can be used for determining and/or monitoring a level of analyte in in vitro or in vivo analyte-containing fluids. For example, an implantable sensor may be used for the continuous or automatic monitoring of a level of an analyte, such as glucose, lactate, or oxygen, in a patient. The electrochemical analyte sensor includes a substrate and conductive material disposed on the substrate, the conductive material forming a working electrode. In some sensors, the conductive material is disposed in recessed channels formed in a surface of the sensor. An electron transfer agent and/or catalyst may be provided to facilitate the electrolysis of the analyte or of a second compound whose level depends on the level of the analyte. A potential is formed between the working electrode and a reference electrode or counter/reference electrode and the resulting current is a function of the concentration of the analyte in the body fluid.

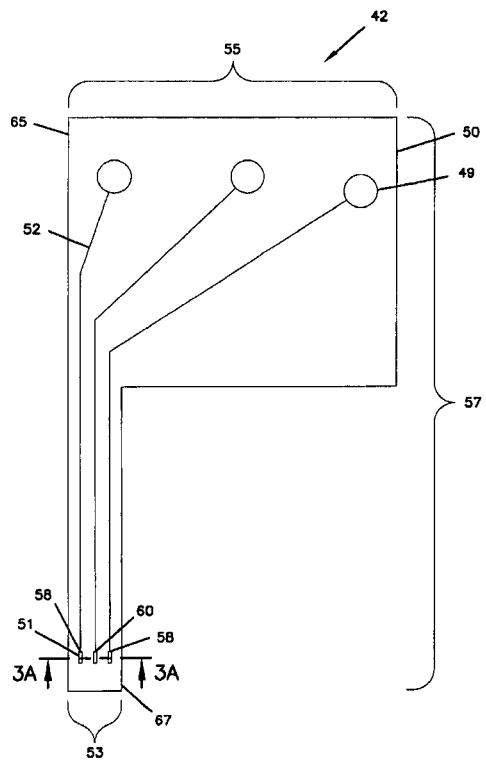

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 143 is cancelled.

Claims 1, 28, 64, 100 and 138 are determined to be patentable as amended.

Claims 2-4, 30-63, 65-99, 101-137, 139-142 and 144-188, dependent on an amended claim, are determined to be patentable.

Claims 5-27 and 29 were not reexamined.

1. [An] *A partially implantable* analyte responsive electrochemical sensor capable of operating substantially continuously *in vivo* for a period of at least three days, comprising *a portion comprising electrical contacts that remains outside an animal when used and a portion that remains in the tissue of the animal when used, the portion that remains in the tissue of the animal comprising a conductive material disposed on the sensor to form* a working electrode; *a catalyst catalyzing a reaction of the analyte to generate a signal at the working electrode, wherein the catalyst and conductive material are non-leachably disposed on the sensor* and a mass transport limiting membrane, which mass transport limiting membrane maintains a rate of permeation of the analyte through the mass transport limiting membrane with a variation of no more than 3% per ° C. at temperatures ranging from 30° C. to 40° C.

28. [An] *A partially implantable* analyte responsive electrochemical sensor *capable of operating substantially continuously in vivo for a period of at least three days* comprising:
    *a portion comprising electrical contacts that remains outside the animal when used; and*
    *a portion that remains in the tissue of the animal when used, the portion that remains in the tissue of the animal comprising:*
    a substrate;
    a conductive material disposed on the substrate to form a working electrode;
    catalyst dispersed in the conductive material, the catalyst catalyzing a reaction of the analyte to generate a signal at the working electrode; and
    a binder dispersed in the conductive material wherein the binder is cured so that the catalyst and conductive material are non-leachably disposed on the substrate.

64. [An] *A partially implantable* analyte responsive electrochemical sensor capable of operating substantially continuously *in vivo* for a period of at least three days, comprising a substrate *comprising a portion comprising electrical contacts that remains outside an animal when used and a portion that remains in the tissue of the animal when used*, a first conductive material disposed on a surface of the substrate to form a first trace comprising a working electrode, a second conductive material disposed on a surface of the substrate to form a second trace comprising a second electrode, and *the portion that remains in the tissue of the animal comprising a catalyst catalyzing a reaction of the analyte to generate a signal at the working electrode, wherein the catalyst and conductive material are non-leachably disposed on the substrate and* a mass transport limiting membrane which mass transport limiting membrane maintains a rate of permeation of the analyte through the mass transport limiting membrane with a variation of no more than 3% per ° C. at temperatures ranging from 30° C. to 40° C.

100. [An] *A partially implantable* analyte responsive electrochemical sensor capable of operating substantially continuously *in vivo* for a period of at least three days, comprising *a portion comprising electrical contacts that remains outside an animal when used and a portion that remains in the tissue of the animal when used*, a substrate, a conductive material disposed on a surface of the substrate to form a trace comprising a working electrode, and *the portion that remains in the tissue of the animal comprising a catalyst catalyzing a reaction of the analyte to generate a signal at the working electrode, wherein the catalyst and conductive material are non-leachably disposed on the substrate and* a mass transport limiting membrane, which mass transport limiting membrane maintains a rate of permeation of the analyte through the mass transport limiting membrane with a variation of no more than 3% per ° C. at temperatures ranging from 30° C. to 40° C.

138. An analyte responsive electrochemical sensor *capable of operating substantially continuously in vivo for a period of at least three days*, comprising:
    a substrate having a longitudinal axis with a narrow distal region that is configured and arranged for implantation into an animal and a wider proximal region;
    at least one working electrode disposed on the narrow distal region of the substrate;
    at least one contact pad disposed on the wider proximal region of the substrate and in electrical communication with a one of the at least one working electrodes; and
    a mass transport limiting membrane, which mass transport limiting membrane maintains a rate of permeation of the analyte through the mass transport limiting membrane with a variation of no more than 3% per ° C. at temperatures ranging from 30° C. to 40° C.

* * * * *